United States Patent
Zhang et al.

(10) Patent No.: US 11,999,979 B2
(45) Date of Patent: Jun. 4, 2024

(54) *LACHNOSPIRACEAE* SP. CAS12A MUTANTS WITH ENHANCED CLEAVAGE ACTIVITY AT NON-CANONICAL TTTT PROTOSPACER ADJACENT MOTIFS

(71) Applicant: INTEGRATED DNA TECHNOLOGIES, INC., Coralville, IA (US)

(72) Inventors: Liyang Zhang, North Liberty, IA (US); Christopher Anthony Vakulskas, North Liberty, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

(21) Appl. No.: 17/245,401

(22) Filed: Apr. 30, 2021

(65) Prior Publication Data

US 2021/0348144 A1    Nov. 11, 2021

Related U.S. Application Data

(60) Provisional application No. 63/090,912, filed on Oct. 13, 2020, provisional application No. 63/018,592, filed on May 1, 2020.

(51) Int. Cl.
   *C12N 9/22* (2006.01)

(52) U.S. Cl.
   CPC ..................... *C12N 9/22* (2013.01)

(58) Field of Classification Search
   CPC ..................................................... C12N 9/22
   See application file for complete search history.

(56) References Cited

U.S. PATENT DOCUMENTS

| | | | |
|---|---|---|---|
| 7,560,529 | B2 | 7/2009 | Gabibov et al. |
| 9,840,702 | B2 | 12/2017 | Collingwood et al. |
| 10,266,886 | B2 | 4/2019 | Abudayyeh et al. |
| 10,717,978 | B2 | 7/2020 | Vakulskas et al. |
| 10,767,176 | B2 | 9/2020 | Collingwood et al. |
| 2016/0177304 | A1 | 6/2016 | Collingwood et al. |
| 2016/0208243 | A1 | 7/2016 | Zhang et al. |
| 2017/0044536 | A1 | 2/2017 | Collingwood et al. |
| 2018/0179523 | A1 | 6/2018 | Collingwood et al. |
| 2018/0187176 | A1 | 7/2018 | Behlke et al. |
| 2018/0273938 | A1 | 9/2018 | Turk et al. |
| 2018/0320201 | A1 | 11/2018 | Vakulskas et al. |
| 2019/0010481 | A1 | 1/2019 | Joung et al. |
| 2019/0032131 | A1 | 1/2019 | Turk et al. |
| 2020/0080096 | A1 | 3/2020 | Flasinski et al. |
| 2020/0109382 | A1 | 4/2020 | Zhang et al. |

FOREIGN PATENT DOCUMENTS

| | | | | |
|---|---|---|---|---|
| WO | 2017127807 | A1 | 7/2017 | |
| WO | 2017184768 | A1 | 10/2017 | |
| WO | 2018195545 | A2 | 10/2018 | |
| WO | 2019138052 | A1 | 7/2019 | |
| WO | 2020172502 | A1 | 8/2020 | |
| WO | WO-2020172502 | A1 * | 8/2020 | ............ C12N 15/52 |
| WO | 2021093752 | A1 | 5/2021 | |
| WO | 2023097316 | A1 | 6/2023 | |

OTHER PUBLICATIONS

Studer. Residue mutations and their impact on protein structure and function: detecting beneficial and pathogenic changes. Biochem. J. (2013) 449, 581-594.*
Cebrian-Serrano et al., "CRISPR-Cas orthologues and variants: optimizing the repertoire, specificity and delivery of genome engineering tools", Mammalian Genome, 2017, vol. 28, No. 7, pp. 247-261.
Geneseq, "Lachnospiraceae bacterium Cpf1 gene (PL-LbCpf1-RR) encoded nuclease", Nov. 2017, EBI Accession No. GS_PROT:BEK39676, 1 pages.
International Search Report and Written Opinion for Application No. PCT/US2021/030089 dated May 20, 2022 (25 pages).
Abudayyeh et al., "C2c2 is a single component programmable RNA-guided RNA-targeting CRISPR effector", Science, vol. 353(6299), 2016.
Bowie et al., "Deciphering the Message in Protein Sequences: Tolerance to Amino Acid Substitutions", Science, vol. 247, 1990, pp. 1306-1310.
East-Seletsky et al., "Two distinct RNase activities of CRISPR-C2c2 enable guide-RNA processing and RNA detection", Nature, vol. 538 (7624), 2016, pp. 270-273.
Gao et al., "Engineered Cpf1 variants with altered PAM specificities increase genome targeting range", Nat Biotechnol., vol. 35, No. 8, 2017, pp. 789-792.
Gao et al., "Type V CRISPR-Cas Cas12a endonuclease employs a unique mechanism for crRNA-mediated target DNA recognition," Cell Research, vol. 26, 2016, pp. 901-913.
Gibson et al., "Enzymatic assembly of DNA molecules up to several hundred kilobases", Nature Methods, vol. 6, No. 5, 2009, pp. 343-334.
Gootenberg et al., "Nucleic acid detection with CRISPR-Cas13a/C2c2" Science, vol. 356(6336), 2017, pp. 438-442.
Hur et al., "Targeted mutagenesis in mice by electroporation of Cpf1 ribonucleoproteins," Nature Biotechnology 34(8): 807-808 (2016).
International Search Report and Written Opinion for Application No. PCT/US2020/19168 dated Jul. 23, 2020 (13 pages).
Jinek et al., "A programmable dual-RNA-guided DNA endonuclease in adaptive bacterial 5 immunity", Science, vol. 337, 2012, pp. 816-821.

(Continued)

*Primary Examiner* — Yong D Pak
(74) *Attorney, Agent, or Firm* — Michael Best & Friedrich LLP

(57) ABSTRACT

Described herein are CAS12A mutants from *Lachnospiraceae bacterium* and methods for use thereof. These mutants have enhanced DNA cleavage activities at non-canonical TTTT protospacer adjacent motifs (PAM) compared to the wild-type enzyme.

2 Claims, 8 Drawing Sheets

Specification includes a Sequence Listing.

(56) References Cited

OTHER PUBLICATIONS

Kim et al., "CRISPR/Cpf1-mediated DNA-free plant genome editing," Nature Commun., vol. 8(14406), 2017, pp. 1-7.
Kim et al., "Generation of knockdown mice by Cpf1-mediated gene targeting," Nature Biotechnology, vol. 34, No. 8, 2016, pp. 808-810.
Kim et al., "In vivo high-throughput profiling of CRISPR-Cpf1 activity," Nature Methods, vol. 14, No. 2, 2017, pp. 153-159.
Kleinstiver et al., "Engineered CRISPR-Cas 12a variants with increased activities and improved targerting ranges for gene, epigenetic and base editing", Nat. Biotechnol., vol. 37, 2019, pp. 276-282.
Kleinstiver et al., "Genome-wide specificities of CRISPR-Cas Cpf1 nucleases in human cells," Nature Biotechnology, vol. 34, No. 8, 2016, pp. 869-874.
Schindele et al., "Engineering CRISPR/LbCas12a for highly efficient, temperature tolerant plant gene editing", Plant Biotechnol J., vol. 18, No. 5, 2020, pp. 1118-1120.
Wrenbeck et al., "Plasmid-based one-pot saturation mutagenesis", Nat Methods, vol. 13, 2016, pp. 928-930.
Yamano et al., "Crystal Structure of Cpf1 in Complex with Guide RNA and Target RNA," Cell vol. 65, 2016, pp. 949-962.
Zetsche et al., "Cpf1 Is a Single RNA-Guided Endonuclease of a Class 2 CRISPR-Cas System", Cell, vol. 163, 2015, pp. 759-771.
Zetsche et al., "Multiplex gene editing by CRISPR-Cpf1 using a single rRNA array," Nature Biotechnology, vol. 35, No. 1, 2017, pp. 31-34.
Australian Patent Office Examination Report No. 1 for application 2020226864, dated Jan. 19, 2023 (4 pages).
Canadian Patent Office Action for application 3,130,087, dated Nov. 24, 2022 (6 pages).
Australian Patent Office Examination Report No. 2 for Application No. 2020226864, dated Jun. 26, 2023 (9 pages).
Carmignotto et al., "On the expression of recombinant Cas9 protein in E. coli BL21 (DE3) and BL21 (DE3) Rosetta strains," J Biotechnol. vol. 306:62-70 (epub Sep. 20, 2019) (Year: 2019).
Evans et al., "Concentration of proteins and removal of solutes," Methods Enzymol., vol. 463:97-120 (2009), PMID: 19892169 (Year: 2009).
Francis et al., "Strategies to Optimize Protein Expression in E. coli," Current Protocols in Protein Science, 5.24.1-5.24.29 (Aug. 2010) (Year: 2010).
Hi Trap SP HP cation exchange columns Protocol, SP Sepharose™ High Performance Ion Exchange Medium Instructions 18-1060-26-AG, GE Life Sciences, 20 pages (2014) (Year: 2014).
Livingstone et al., Protein sequence alignments, CABIOS, vol. 9(6):745-756 (1993) (Year: 1993).
PET System manual (Novagen, pET System Manual 10th Edition, 68 pages, published May 2003 (Year: 2003).
Rodrigues et al, Chapter 5: One-Step Isothermal Assembly of DNA Fragments, Synthetic Biology, Methods in Molecular Biology, vol. 1073:43-47 (2013) (Year: 2013).
Spriestersbach et al., "Purification of His-Tagged Proteins," Methods Enzymol., vol. 559:1-15, PMID: 26096499 (Epub May 4, 2015) ( Year: 2015).
Japanese Patent Office Notification of Reasons for Rejection for Application No. 2021-548687, dated Aug. 4, 2023, 14 pages with translation.
Chinese Patent Office Notification of First Office Action for Application No. 202080015167.9, dated Sep. 27, 2023, 17 pages with translation.
Lu Yifan et al., LbCpf1 "Prokaryotic Expression, Purification of LbCpf1 Protein Gene and in Vitro Cleavage Activity Assay." China Biotechnology 40.8 (2020): 41-48. With English Abstract.
Zhang, Y., et al. "Highly efficient genome editing in plant protoplasts by ribonucleoprotein delivery of CRISPR-Cas12a nucleases." Frontiers in Genome Editing 4 (2022): 780238.
Yamano T., "Structural basis for the canonical and non-canonical PAM recognition by CRISPR-Cpf1." Molecular cell 67.4 (2017): 633-645.
European Patent Office Extended European Search Report for Application No. 20760344.0, dated Feb. 26, 2024 (8 pages).
Canadian Patent Office Action for application 3,130,087, dated Feb. 19, 2024 (3 pages).
"SEQ ID No. 3 vs SEQ ID No. 109" Dowloaded from <https://blast.ncbi.nlm.nih.gov/Blast.cgi> Apr. 3, 2024 (Year: 2016) (2 pages).
"SEQ ID No. 6 vs SEQ ID No. 109" Dowloaded from <https://blast.ncbi.nlm.nih.gov/Blast.cgi> Apr. 3, 2024 (Year: 2016) (2 pages).

* cited by examiner

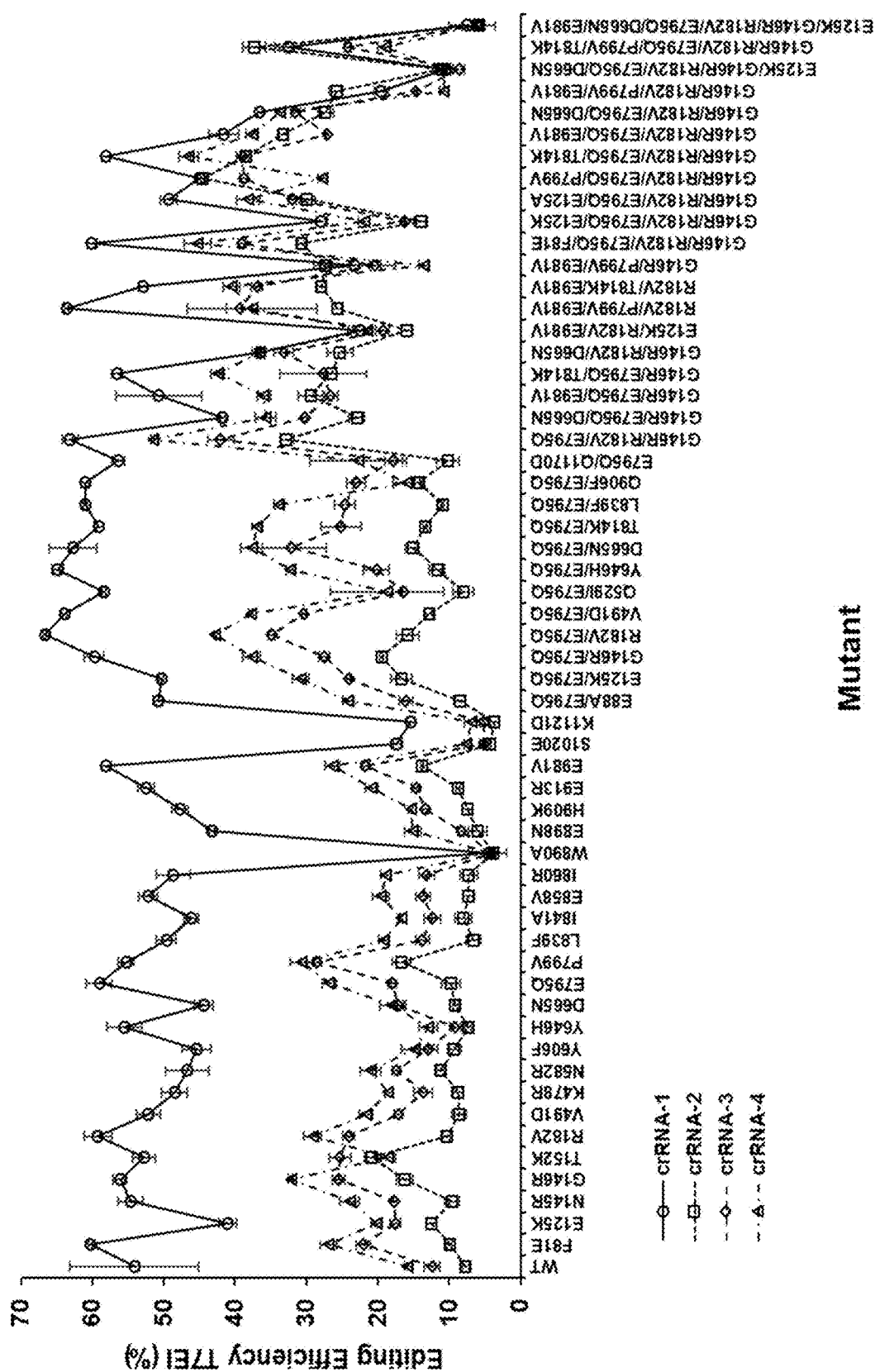

*LACHNOSPIRACEAE* SP. CAS12A MUTANTS WITH ENHANCED CLEAVAGE ACTIVITY AT NON-CANONICAL TTTT PROTOSPACER ADJACENT MOTIFS

CROSS-REFERENCE TO RELATED APPLICATIONS

This application claims priority to U.S. Provisional Patent Application No. 63/018,592, filed on May 1, 2020, and 63/090,912, filed on Oct. 13, 2020, the contents of each of which are incorporated by reference herein in its entirety. This application is related to International Application No. PCT/US2020/019168, filed on Feb. 21, 2020 and published as International Patent Application No. WO 202/0172502 A1 on Aug. 27, 2020, which is incorporated by reference herein in its entirety.

REFERENCE TO SEQUENCE LISTING

This application is filed with a Computer Readable Form of a Sequence Listing in accord with 37 C.F.R. § 1.821(c). The text file submitted by EFS, "013670-9067-US02_sequence_listing_27-APR-2021_ST25.K" was created on Apr. 27, 2021, contains 5320 sequences, has a file size of 30.2 Megabytes, and is hereby incorporated by reference in its entirety.

TECHNICAL FIELD

Described herein are Cas12a mutants from Lachnospiraceae bacterium and methods for use thereof. These mutants have enhanced DNA cleavage activities at non-canonical TTTT protospacer adjacent motifs (PAM) compared to the wild-type enzyme.

BACKGROUND

LbCas12a is an RNA-guided endonuclease from the Lachnospiraceae bacterium ND2006 (Lb) species Clustered Regularly Interspaced Short Palindromic Repeat (CRISPR) adaptive immune system. See Zetsche et al. *Cell* 163: 759-771 (2015). Cas12a nucleases are classified as a class 2 type V CRISPR system that provide a staggered DNA double-stranded break with a 5-nucleotide 5'-overhang when complexed with a CRISPR RNA (crRNA). The LbCas12a:crRNA complex is referred to as a CRISPR ribonucleoprotein (RNP) complex.

Cas12a is guided to a 21-24 nucleotide DNA target sequence, or commonly referred as protospacer, by a target site-specific 21-24 nucleotide complementary guide RNA (gRNA). The Cas12a-gRNA RNP complex mediates double-stranded DNA breaks (DSBs), which are then repaired by either the non-homologous end joining (NHEJ, typically introduces mutations or indels at the cut site), or the homology directed repair (HDR) system for precise editing if a suitable template nucleic acid is present.

The recognition of the correct DNA target by LbCas12a requires both crRNA and the canonical "TTTV" protospacer adjacent motif (PAM), which is a 4-bp sequence immediately upstream of the protospacer, in contrast to the 2-bp NGG PAM of Cas9 from *Streptococcus pyogenes*. See Jinek et al., *Science* 337: 816-821 (2012). Cas12a expanded the targetable loci in genome editing, particularly over the T-rich sites that are inaccessible to the Cas9 system. Although the occurrence of targetable sites of Cas12a on the genome is less frequent than Cas9, LbCas12a has gained significant popularity in the genome engineering of plants, owing to editing activity at ambient temperatures (20-30° C.). Improving the cleavage activity and associated genome editing efficiency of LbCas12a would greatly facilitate the development of agriculture products with enhanced properties.

It is desirable to further improve the utility of LbCas12a by enhancing its on-target activity through protein mutagenesis. Previous studies have been performed to improve the utility of Cas12a from Acidaminococcus sp. (also known as AsCas12a). See U.S. Patent App. Publication No. US 2020/0109382 A1, which is incorporated by reference herein. However, transferring the beneficial mutations identified in AsCas12a to the LbCas12a polypeptide sequence has not been simple. Despite significant structural and sequence similarity between the two homologous Cas12a enzymes, most point mutations that improved the activity of AsCas12a are detrimental to LbCas12a. See Schindele and Puchta, *Plant Biotechnol. J.* 18(5):1118-1120 (2020).

What are needed are novel LbCas12a mutants that enhance the activity of this enzyme at non-canonical TTTT protospacer adjacent motifs, particularly in human cells.

SUMMARY

One embodiment described herein is an isolated mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has 95% to 99% identity to a polypeptide sequence selected from the even numbered sequences of SEQ ID NO: 4-4022. In another aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from: (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence. In another aspect, the mutant LbCas12a polypeptide is selected from SEQ ID NO: 802, 428, 2902, 156, 694, 98, 954, 134, 1730, 642, 720, 1014, 930, 706, 834, 988, 114, 250, 3958, 48, 70, 1960, 880, 532, 598, 3960, 3962, 3964, 3966, 3968, 3970, 3972, 3974, 3976, 3978, 3980, 3982, 3984, 3986, 3988, 3990, 3992, 3994, 3996, 3998, 4000, 4002, 4004, 4006, 4008, 4010, 4012, 4014, 4016, 4018, 4020, or 4022. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is an isolated polynucleotide sequence encoding a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the encoded mutant LbCas12a polypeptide has 95% to 99% identity to a polypeptide sequence selected from the even numbered sequences of SEQ ID NO: 4-4022. In another aspect, the encoded mutant LbCas12a polypeptide has a polypeptide sequence selected from the even numbered sequences of SEQ ID NO: 4-4022. In another aspect, the mutant LbCas12a polynucleotide sequence has 95% to 99% identity to a nucleotide sequence selected from the odd numbered sequences of SEQ ID NO: 3-4021. In another aspect, the mutant LbCas12a polynucleotide has a nucleotide sequence selected from the odd numbered sequences of SEQ ID NO: 3-4021. In another aspect, the encoded mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the encoded mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D as compared to the wild-type LbCas12a polypeptide sequence of SEQ ID NO: 2. In another aspect, the mutant LbCas12a polynucleotide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960;

E981V, SEQ ID NO: 880; S1020E, SEQ ID NO: 532; V1083W, SEQ ID NO: 132; or K1121D, SEQ ID NO: 598. In another aspect, the encoded mutant LbCas12a polypeptide comprises a substitution mutation selected from: (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence. In another aspect, the encoded mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the encoded mutant LbCas12a polypeptide is G146R/R182V/E795Q (SEQ ID NO: 3984). In another aspect, the mutant LbCas12a polynucleotide is selected from SEQ ID NO: 801, 427, 2901, 155, 693, 97, 953, 133, 1729, 641, 719, 1013, 929, 705, 833, 987, 113, 249, 3957, 47, 69, 1959, 879, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, 4019, or 4021. In another aspect, the mutant LbCas12a polynucleotide is selected from SEQ ID NO: 801, 427, 2901, 155, 693, 97, 953, 133, 1729, 1013, 929, 705, 113, 249, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, or 4019, and encodes a mutant LbCas12a polypeptide that provides an improvement in CRISPR/LbCas12a-associated nuclease activity at non-canonical TTTT PAM sites as compared to the wild-type LbCas12a polypeptide sequence. In another aspect, the mutant LbCas12a polynucleotide is SEQ ID NO: 3983.

Another embodiment described herein is a vector or plasmid comprising any of the polynucleotide sequences described herein.

Another embodiment described herein is a cell comprising any of the polynucleotide sequences described herein or the vectors or plasmids described herein.

Another embodiment described herein is an isolated ribonucleoprotein complex comprising a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428;

N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a method for increasing efficiency of gene editing at non-canonical TTTT PAM sites in a cell with a CRISPR ribonucleoprotein complex, the method comprising contacting a cell with the CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/ E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/ R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/ R182V/E795Q/F81E (SEQ ID NO: 4002), G146R/R182V/ E795Q/E125K (SEQ ID NO: 4004), G146R/R182V/E795Q/ E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/ G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a kit for increasing efficiency of gene editing at non-canonical TTTT PAM sites in a cell, the kit comprising a CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/ E795Q, Q5291/E795Q, Y646H/E795Q, D665N/E795Q, T814K/E795Q, L839F/E795Q, Q906F/E795Q, E795Q/ Q1170D, G146R/R182V/E795Q, G146R/E795Q/D665N, G146R/E795Q/E981V, G146R/E795Q/T814K, G146R/ R182V/D665N, E125K/R182V/E981V, R182V/P799V/ E981V, R182V/T814K/E981V, G146R/P799V/E981V, G146R/R182V/E795Q/F81E, G146R/R182V/E795Q/ E125K, G146R/R182V/E795Q/E125A, G146R/R182V/ E795Q/P799V, G146R/R182V/E795Q/T814K, G146R/ R182V/E795Q/E981V, G146R/R182V/E795Q/D665N, G146R/R182V/P799V/E981V, E125K/G146R/R182V/ E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/ E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/ Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/ T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/ E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/ R182V/E795Q/P799V (SEQ ID NO: 4008), G146R/R182V/ E795Q/T814K (SEQ ID NO: 4010), G146R/R182V/E795Q/ E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is the use of a mutant LbCas12a polypeptide for improving CRISPR/ LbCas12a-associated nuclease activity at non-canonical TTTT PAM sites, wherein the mutant LbCas12a polypeptide comprises at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/T814K/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a method for expressing and purifying a mutant LbCas13a protein, the method comprising: (a) inserting a nucleotide sequence encoding a mutant LbCas12a polypeptide comprising at least one amino acid substitution compared to a wild-type LbCas12a polypeptide sequence and having 95-99% identity to any one of the even numbered polypeptide sequences of SEQ ID NO: 4-4022 into an expression plasmid; (b) transforming one or more cells with the expression plasmid; (c) inducing expression of the transformed plasmid; (d) isolating the cells; (e) extracting the mutant LbCas13a protein; and (f) purifying the mutant LbCas13a protein; wherein the mutant LbCas12a polypeptide provides an improvement in CRISPR/LbCas12a-associated nuclease activity at non-canonical TTTT PAM sites as compared to a wild-type LbCas12a polypeptide sequence.

Another embodiment described herein is a mutant LbCas12a polypeptide produced by a method described herein.

DESCRIPTION OF THE DRAWINGS

FIG. 3A shows exemplary phenotype scores of point mutations at position E795 of LbCas12a.

FIG. 5B). The cleavage activity of LbCas12a variants at TTTT PAM site was measured by bacterial-based activity assay. The survival of *E. coli* under arabinose selection is dependent on the successful cleavage of HPRT38346 protospacer on a toxin-expressing plasmid using TTTT PAM. The survival rate of *E. coli* dramatically reduced in the absence of HPRT38346 gRNA. See FIG. 5A (wild-type) vs. FIG. 5B (negative control). Compared to wild-type (FIG. 5A), all exemplary mutants increased the survival rate in the presence of gRNA (FIG. 5C-FIG. 5J, mutants: K478R; E898N; S396D; G146R; K595R; E795Q; T814G; and V1083W, respectively), reflecting an enhanced cleavage activity of LbCas12a variants at non-canonical TTTT PAM.

FIG. 6A-B show the performance evaluation of LbCas12a variants in human cells as RNP complexes. LbCas12a variants shown in Table 7 were purified and assembled as RNPs using four different crRNAs (Table 9). FIG. 6A shows the editing efficiency of LbCas12a variants using a T7 endonuclease I assay 48-hours post-delivery to human HEK293 cells. Three replicates were performed. The averaged data and standard deviation are shown in Table 10. FIG. 6B shows the normalized editing efficiency of each variant (normalized to wild-type LbCas12a) and presented as fold-improvement over the wild-type. The first quartile (Q1), median, and third quartile (Q3) are shown for each mutant. The dashed line represents the baseline activity of the wild-type LbCas12a protein. Two replicates were performed. The normalized data is shown in Table 11 for each crRNA.

DETAILED DESCRIPTION

Figure 1A:
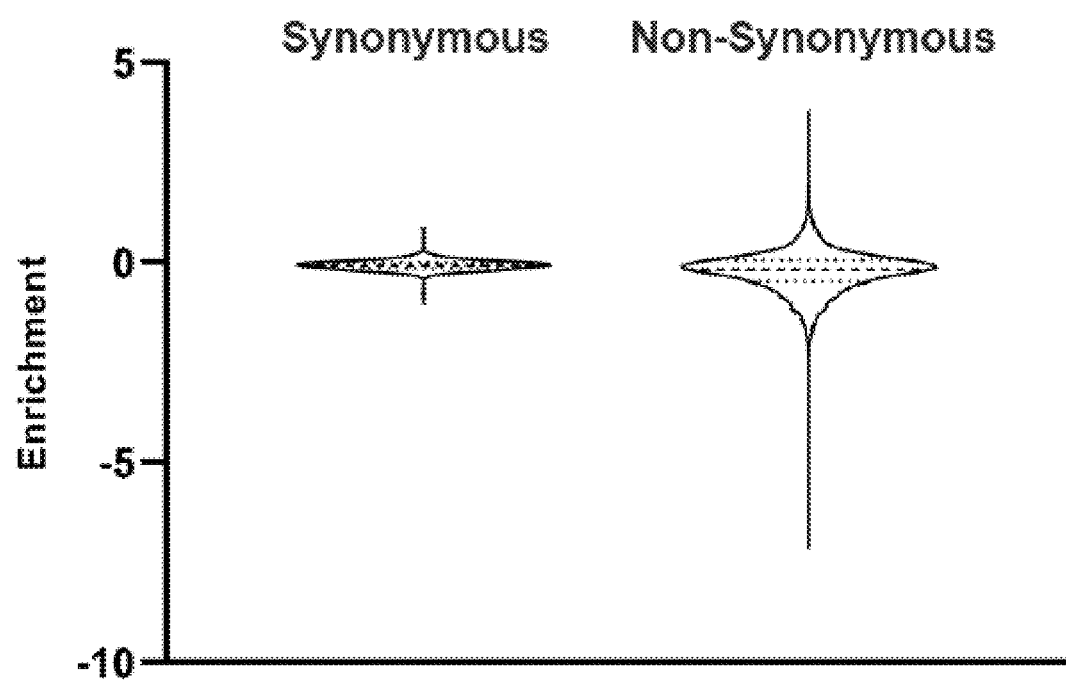
FIG. 1A shows exemplary phenotype distribution of all LbCas12a mutants covered by the bacteria screen. The averaged enrichment scores of point mutations over two biological replicates of selection were used for this analysis. The enrichment score of all synonymous changes (i.e., a different codon encoding the same amino acid as the wild-type amino acid) tightly clustered around 0, which enabled the quantification of phenotype of WT-LbCas12a in the selection.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the present invention.

As used herein, the terms "amino acid," "nucleotide," "polypeptide," "polynucleotide," and "vector" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or R) are used herein.

As used herein, the terms such as "include," "including," "contain," "containing," "having," and the like mean "comprising." The disclosure also contemplates other embodiments "comprising," "consisting of," and "consisting essentially of," the embodiments, aspects, or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the phrase "an effective amount" of a compound described herein refers to an amount of the compound described herein that will elicit the biological response, for example, reduction or inhibition of an enzyme or a protein activity, or ameliorate symptoms, alleviate conditions, slow or delay disease progression, or prevent a disease, etc.

As used herein, the terms "inhibit," "inhibition," or "inhibiting" refer to the reduction or suppression of a given condition, symptom, or disorder, or disease, or a significant decrease in the baseline activity of a biological activity or process.

As used herein, the terms "Lachnospiraceae bacterium Cas12a" or "LbCas12a" are used interchangeably and refer to the Lachnospiraceae bacterium ND2006 (Lb) Cas12a protein (previously named Cpf1), a class 2/type V CRISPR RNA-guided endonuclease.

The terms "LbCas12a," "wild-type LbCas12a," "wild-type Lb enzyme," or "WT LbCas12a" refer to a protein having the amino acid sequence of the naturally-occurring Lachnospiraceae bacterium ND2006 Cas12a (e.g., SEQ ID NO: 2, encoded by the nucleotide sequence of SEQ ID NO:

1) and that has biochemical activity when combined with a suitable crRNA to form an active CRISPR/Cas12a endonuclease system.

The term "mutant LbCas12a protein" or "variant LbCas12a protein" are used interchangeably and refer to LbCas12a protein forms having a different amino acid sequence form the wild-type Lachnospiraceae bacterium ND2006 Cas12a and that have biochemical activity when combined with a suitable crRNA to form an active CRISPR-Cas12a endonuclease system. This includes orthologs and Cas12a variants having different amino acid sequences from the wild-type Lachnospiraceae bacterium ND2006 Cas12a. The mutant LbCas12a proteins described herein have at least one amino acid substitution to the wild-type LbCas12a polypeptide sequence. In one aspect, the mutant LbCas12a polypeptides have at least one amino acid substitution to the wild-type LbCas12a polypeptide sequence and have an improvement in CRISPR/LbCas12a-associated nuclease activity at non-canonical TTTT PAM sites as compared to the wild-type LbCas12a enzyme.

As used herein, the phrase "the odd numbered sequences of SEQ ID NO: 3-4021" refers to nucleotide sequences of SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 851, 853, 855, 857, 859, 861, 863, 865, 867, 869, 871, 873, 875, 877, 879, 881, 883, 885, 887, 889, 891, 893, 895, 897, 899, 901, 903, 905, 907, 909, 911, 913, 915, 917, 919, 921, 923, 925, 927, 929, 931, 933, 935, 937, 939, 941, 943, 945, 947, 949, 951, 953, 955, 957, 959, 961, 963, 965, 967, 969, 971, 973, 975, 977, 979, 981, 983, 985, 987, 989, 991, 993, 995, 997, 999, 1001, 1003, 1005, 1007, 1009, 1011, 1013, 1015, 1017, 1019, 1021, 1023, 1025, 1027, 1029, 1031, 1033, 1035, 1037, 1039, 1041, 1043, 1045, 1047, 1049, 1051, 1053, 1055, 1057, 1059, 1061, 1063, 1065, 1067, 1069, 1071, 1073, 1075, 1077, 1079, 1081, 1083, 1085, 1087, 1089, 1091, 1093, 1095, 1097, 1099, 1101, 1103, 1105, 1107, 1109, 1111, 1113, 1115, 1117, 1119, 1121, 1123, 1125, 1127, 1129, 1131, 1133, 1135, 1137, 1139, 1141, 1143, 1145, 1147, 1149, 1151, 1153, 1155, 1157, 1159, 1161, 1163, 1165, 1167, 1169, 1171, 1173, 1175, 1177, 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, 1301, 1303, 1305, 1307, 1309, 1311, 1313, 1315, 1317, 1319, 1321, 1323, 1325, 1327, 1329, 1331, 1333, 1335, 1337, 1339, 1341, 1343, 1345, 1347, 1349, 1351, 1353, 1355, 1357, 1359, 1361, 1363, 1365, 1367, 1369, 1371, 1373, 1375, 1377, 1379, 1381, 1383, 1385, 1387, 1389, 1391, 1393, 1395, 1397, 1399, 1401, 1403, 1405, 1407, 1409, 1411, 1413, 1415, 1417, 1419, 1421, 1423, 1425, 1427, 1429, 1431, 1433, 1435, 1437, 1439, 1441, 1443, 1445, 1447, 1449, 1451, 1453, 1455, 1457, 1459, 1461, 1463, 1465, 1467, 1469, 1471, 1473, 1475, 1477, 1479, 1481, 1483, 1485, 1487, 1489, 1491, 1493, 1495, 1497, 1499, 1501, 1503, 1505, 1507, 1509, 1511, 1513, 1515, 1517, 1519, 1521, 1523, 1525, 1527, 1529, 1531, 1533, 1535, 1537, 1539, 1541, 1543, 1545, 1547, 1549, 1551, 1553, 1555, 1557, 1559, 1561, 1563, 1565, 1567, 1569, 1571, 1573, 1575, 1577, 1579, 1581, 1583, 1585, 1587, 1589, 1591, 1593, 1595, 1597, 1599, 1601, 1603, 1605, 1607, 1609, 1611, 1613, 1615, 1617, 1619, 1621, 1623, 1625, 1627, 1629, 1631, 1633, 1635, 1637, 1639, 1641, 1643, 1645, 1647, 1649, 1651, 1653, 1655, 1657, 1659, 1661, 1663, 1665, 1667, 1669, 1671, 1673, 1675, 1677, 1679, 1681, 1683, 1685, 1687, 1689, 1691, 1693, 1695, 1697, 1699, 1701, 1703, 1705, 1707, 1709, 1711, 1713, 1715, 1717, 1719, 1721, 1723, 1725, 1727, 1729, 1731, 1733, 1735, 1737, 1739, 1741, 1743, 1745, 1747, 1749, 1751, 1753, 1755, 1757, 1759, 1761, 1763, 1765, 1767, 1769, 1771, 1773, 1775, 1777, 1779, 1781, 1783, 1785, 1787, 1789, 1791, 1793, 1795, 1797, 1799, 1801, 1803, 1805, 1807, 1809, 1811, 1813, 1815, 1817, 1819, 1821, 1823, 1825, 1827, 1829, 1831, 1833, 1835, 1837, 1839, 1841, 1843, 1845, 1847, 1849, 1851, 1853, 1855, 1857, 1859, 1861, 1863, 1865, 1867, 1869, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2031, 2033, 2035, 2037, 2039, 2041, 2043, 2045, 2047, 2049, 2051, 2053, 2055, 2057, 2059, 2061, 2063, 2065, 2067, 2069, 2071, 2073, 2075, 2077, 2079, 2081, 2083, 2085, 2087, 2089, 2091, 2093, 2095, 2097, 2099, 2101, 2103, 2105, 2107, 2109, 2111, 2113, 2115, 2117, 2119, 2121, 2123, 2125, 2127, 2129, 2131, 2133, 2135, 2137, 2139, 2141, 2143, 2145, 2147, 2149, 2151, 2153, 2155, 2157, 2159, 2161, 2163, 2165, 2167, 2169, 2171, 2173, 2175, 2177, 2179, 2181, 2183, 2185, 2187, 2189, 2191, 2193, 2195, 2197, 2199, 2201, 2203, 2205, 2207, 2209, 2211, 2213, 2215, 2217, 2219, 2221, 2223, 2225, 2227, 2229, 2231, 2233, 2235, 2237, 2239, 2241, 2243, 2245, 2247, 2249, 2251, 2253, 2255, 2257, 2259, 2261, 2263, 2265, 2267, 2269, 2271, 2273, 2275, 2277, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2323, 2325, 2327, 2329, 2331, 2333, 2335, 2337, 2339, 2341, 2343, 2345, 2347, 2349, 2351, 2353, 2355, 2357, 2359, 2361, 2363, 2365, 2367, 2369, 2371, 2373, 2375, 2377, 2379, 2381, 2383, 2385, 2387, 2389, 2391, 2393, 2395, 2397, 2399, 2401, 2403, 2405, 2407, 2409, 2411, 2413, 2415, 2417, 2419, 2421, 2423, 2425, 2427, 2429, 2431, 2433, 2435, 2437, 2439, 2441, 2443, 2445, 2447, 2449, 2451, 2453, 2455, 2457, 2459, 2461, 2463, 2465, 2467, 2469, 2471, 2473, 2475, 2477, 2479, 2481, 2483, 2485, 2487, 2489, 2491, 2493, 2495, 2497, 2499, 2501, 2503, 2505, 2507, 2509, 2511, 2513, 2515, 2517, 2519, 2521, 2523, 2525, 2527, 2529, 2531, 2533, 2535, 2537, 2539, 2541, 2543, 2545, 2547, 2549, 2551, 2553, 2555, 2557, 2559, 2561, 2563, 2565, 2567, 2569, 2571, 2573, 2575, 2577, 2579, 2581, 2583, 2585, 2587, 2589, 2591, 2593, 2595, 2597, 2599, 2601, 2603, 2605, 2607, 2609, 2611, 2613, 2615, 2617, 2619, 2621, 2623, 2625, 2627, 2629, 2631, 2633, 2635, 2637, 2639, 2641, 2643, 2645, 2647, 2649, 2651, 2653, 2655, 2657, 2659, 2661, 2663, 2665, 2667, 2669, 2671, 2673, 2675, 2677, 2679, 2681, 2683, 2685, 2687, 2689, 2691, 2693, 2695, 2697, 2699, 2701, 2703, 2705, 2707, 2709, 2711, 2713, 2715, 2717, 2719, 2721, 2723, 2725, 2727, 2729, 2731, 2733, 2735, 2737, 2739, 2741, 2743, 2745, 2747, 2749, 2751, 2753, 2755, 2757, 2759, 2761, 2763, 2765, 2767, 2769, 2771, 2773, 2775, 2777, 2779, 2781, 2783, 2785, 2787, 2789, 2791, 2793, 2795, 2797, 2799, 2801, 2803, 2805, 2807, 2809, 2811, 2813, 2815, 2817, 2819, 2821, 2823, 2825, 2827, 2829, 2831, 2833, 2835, 2837, 2839, 2841, 2843, 2845, 2847, 2849, 2851, 2853, 2855, 2857, 2859, 2861, 2863, 2865, 2867, 2869, 2871, 2873, 2875, 2877, 2879, 2881, 2883, 2885, 2887, 2889, 2891, 2893, 2895, 2897, 2899, 2901, 2903, 2905, 2907, 2909, 2911, 2913, 2915, 2917, 2919, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, 2969, 2971, 2973, 2975, 2977, 2979, 2981, 2983, 2985, 2987, 2989, 2991, 2993, 2995, 2997, 2999, 3001, 3003, 3005, 3007, 3009, 3011, 3013, 3015, 3017, 3019, 3021, 3023, 3025, 3027, 3029, 3031, 3033, 3035, 3037, 3039, 3041, 3043, 3045, 3047, 3049, 3051, 3053, 3055, 3057, 3059, 3061, 3063, 3065, 3067, 3069, 3071, 3073, 3075, 3077, 3079, 3081, 3083, 3085, 3087, 3089, 3091, 3093, 3095, 3097, 3099, 3101, 3103, 3105, 3107, 3109, 3111, 3113, 3115, 3117, 3119, 3121, 3123, 3125, 3127, 3129, 3131, 3133, 3135, 3137, 3139, 3141, 3143, 3145, 3147, 3149, 3151, 3153, 3155, 3157, 3159, 3161, 3163, 3165, 3167, 3169, 3171, 3173, 3175, 3177, 3179, 3181, 3183, 3185, 3187, 3189, 3191, 3193, 3195, 3197, 3199, 3201, 3203, 3205, 3207, 3209, 3211, 3213, 3215, 3217, 3219, 3221, 3223, 3225, 3227, 3229, 3231, 3233, 3235, 3237, 3239, 3241, 3243, 3245, 3247, 3249, 3251, 3253, 3255, 3257, 3259, 3261, 3263, 3265, 3267, 3269, 3271, 3273, 3275, 3277, 3279, 3281, 3283, 3285, 3287, 3289, 3291, 3293, 3295, 3297, 3299, 3301, 3303, 3305, 3307, 3309, 3311, 3313, 3315, 3317, 3319, 3321, 3323, 3325, 3327, 3329, 3331, 3333, 3335, 3337, 3339, 3341, 3343, 3345, 3347, 3349, 3351, 3353, 3355, 3357, 3359, 3361, 3363, 3365, 3367, 3369, 3371, 3373, 3375, 3377, 3379, 3381, 3383, 3385, 3387, 3389, 3391, 3393, 3395, 3397, 3399, 3401, 3403, 3405, 3407, 3409, 3411, 3413, 3415, 3417, 3419, 3421, 3423, 3425, 3427, 3429, 3431, 3433, 3435, 3437, 3439, 3441, 3443, 3445, 3447, 3449, 3451, 3453, 3455, 3457, 3459, 3461, 3463, 3465, 3467, 3469, 3471, 3473, 3475, 3477, 3479, 3481, 3483, 3485, 3487, 3489, 3491, 3493, 3495, 3497, 3499, 3501, 3503, 3505, 3507, 3509, 3511, 3513, 3515, 3517, 3519, 3521, 3523, 3525, 3527, 3529, 3531, 3533, 3535, 3537, 3539, 3541, 3543, 3545, 3547, 3549, 3551, 3553, 3555, 3557, 3559, 3561, 3563, 3565, 3567, 3569, 3571, 3573, 3575, 3577, 3579, 3581, 3583, 3585, 3587, 3589, 3591, 3593, 3595, 3597, 3599, 3601, 3603, 3605, 3607, 3609, 3611, 3613, 3615, 3617, 3619, 3621, 3623, 3625, 3627, 3629, 3631, 3633, 3635, 3637, 3639, 3641, 3643, 3645, 3647, 3649, 3651, 3653, 3655, 3657, 3659, 3661, 3663, 3665, 3667, 3669, 3671, 3673, 3675, 3677, 3679, 3681, 3683, 3685, 3687, 3689, 3691, 3693, 3695, 3697, 3699, 3701, 3703, 3705, 3707, 3709, 3711, 3713, 3715, 3717, 3719, 3721, 3723, 3725, 3727, 3729, 3731, 3733, 3735, 3737, 3739, 3741, 3743, 3745, 3747, 3749, 3751, 3753, 3755, 3757, 3759, 3761, 3763, 3765, 3767, 3769, 3771, 3773, 3775, 3777, 3779, 3781, 3783, 3785, 3787, 3789, 3791, 3793, 3795, 3797, 3799, 3801, 3803, 3805, 3807, 3809, 3811, 3813, 3815, 3817, 3819, 3821, 3823, 3825, 3827, 3829, 3831, 3833, 3835, 3837, 3839, 3841, 3843, 3845, 3847, 3849, 3851, 3853, 3855, 3857, 3859, 3861, 3863, 3865, 3867, 3869, 3871, 3873, 3875, 3877, 3879, 3881, 3883, 3885, 3887, 3889, 3891, 3893, 3895, 3897, 3899, 3901, 3903, 3905, 3907, 3909, 3911, 3913, 3915, 3917, 3919, 3921, 3923, 3925, 3927, 3929, 3931, 3933, 3935, 3937, 3939, 3941, 3943, 3945, 3947, 3949, 3951, 3953, 3955, 3957, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, 4019, or 4021.

As used herein, the phrase "the even numbered sequences of SEQ ID NO: 4-4022" refers to polypeptide sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018, 3020, 3022, 3024, 3026, 3028, 3030, 3032, 3034, 3036, 3038, 3040, 3042, 3044, 3046, 3048, 3050, 3052, 3054, 3056, 3058, 3060, 3062, 3064, 3066, 3068, 3070, 3072, 3074, 3076, 3078, 3080, 3082, 3084, 3086, 3088, 3090, 3092, 3094, 3096, 3098, 3100, 3102, 3104, 3106, 3108, 3110, 3112, 3114, 3116, 3118, 3120, 3122, 3124, 3126, 3128, 3130, 3132, 3134, 3136, 3138, 3140, 3142, 3144, 3146, 3148, 3150, 3152, 3154, 3156, 3158, 3160, 3162, 3164, 3166, 3168, 3170, 3172, 3174, 3176, 3178, 3180, 3182, 3184, 3186, 3188, 3190, 3192, 3194, 3196, 3198, 3200, 3202, 3204, 3206, 3208, 3210, 3212, 3214, 3216, 3218, 3220, 3222, 3224, 3226, 3228, 3230, 3232, 3234, 3236, 3238, 3240, 3242, 3244, 3246, 3248, 3250, 3252, 3254, 3256, 3258, 3260, 3262, 3264, 3266, 3268, 3270, 3272, 3274, 3276, 3278, 3280, 3282, 3284, 3286, 3288, 3290, 3292, 3294, 3296, 3298, 3300, 3302, 3304, 3306, 3308, 3310, 3312, 3314, 3316, 3318, 3320, 3322, 3324, 3326, 3328, 3330, 3332, 3334, 3336, 3338, 3340, 3342, 3344, 3346, 3348, 3350, 3352, 3354, 3356, 3358, 3360, 3362, 3364, 3366, 3368, 3370, 3372, 3374, 3376, 3378, 3380, 3382, 3384, 3386, 3388, 3390, 3392, 3394, 3396, 3398, 3400, 3402, 3404, 3406, 3408, 3410, 3412, 3414, 3416, 3418, 3420, 3422, 3424, 3426, 3428, 3430, 3432, 3434, 3436, 3438, 3440, 3442, 3444, 3446, 3448, 3450, 3452, 3454, 3456, 3458, 3460, 3462, 3464, 3466, 3468, 3470, 3472, 3474, 3476, 3478, 3480, 3482, 3484, 3486, 3488, 3490, 3492, 3494, 3496, 3498, 3500, 3502, 3504, 3506, 3508, 3510, 3512, 3514, 3516, 3518, 3520, 3522, 3524, 3526, 3528, 3530, 3532, 3534, 3536, 3538, 3540, 3542, 3544, 3546, 3548, 3550, 3552, 3554, 3556, 3558, 3560, 3562, 3564, 3566, 3568, 3570, 3572, 3574, 3576, 3578, 3580, 3582, 3584, 3586, 3588, 3590, 3592, 3594, 3596, 3598, 3600, 3602, 3604, 3606, 3608, 3610, 3612, 3614, 3616, 3618, 3620, 3622, 3624, 3626, 3628, 3630, 3632, 3634, 3636, 3638, 3640, 3642, 3644, 3646, 3648, 3650, 3652, 3654, 3656, 3658, 3660, 3662, 3664, 3666, 3668, 3670, 3672, 3674, 3676, 3678, 3680, 3682, 3684, 3686, 3688, 3690, 3692, 3694, 3696, 3698, 3700, 3702, 3704, 3706, 3708, 3710, 3712, 3714, 3716, 3718, 3720, 3722, 3724, 3726, 3728, 3730, 3732, 3734, 3736, 3738, 3740, 3742, 3744, 3746, 3748, 3750, 3752, 3754, 3756, 3758, 3760, 3762, 3764, 3766, 3768, 3770, 3772, 3774, 3776, 3778, 3780, 3782, 3784, 3786, 3788, 3790, 3792, 3794, 3796, 3798, 3800, 3802, 3804, 3806, 3808, 3810, 3812, 3814, 3816, 3818, 3820, 3822, 3824, 3826, 3828, 3830, 3832, 3834, 3836, 3838, 3840, 3842, 3844, 3846, 3848, 3850, 3852, 3854, 3856, 3858, 3860, 3862, 3864, 3866, 3868, 3870, 3872, 3874, 3876, 3878, 3880, 3882, 3884, 3886, 3888, 3890, 3892, 3894, 3896, 3898, 3900, 3902, 3904, 3906, 3908, 3910, 3912, 3914, 3916, 3918, 3920, 3922, 3924, 3926, 3928, 3930, 3932, 3934, 3936, 3938, 3940, 3942, 3944, 3946, 3948, 3950, 3952, 3954, 3956, 3958, 3960, 3962, 3964, 3966, 3968, 3970, 3972, 3974, 3976, 3978, 3980, 3982, 3984, 3986, 3988, 3990, 3992, 3994, 3996, 3998, 4000, 4002, 4004, 4006, 4008, 4010, 4012, 4014, 4016, 4018, 4020, or 4022.

Described herein are nucleic acids encoding mutant LbCas12a polypeptides with enhanced editing activity at non-canonical TTTT protospacer adjacent motifs (PAM) compared to the wild-type LbCas12a enzyme.

Cas12a provides a useful complement to Cas9 by expanding the range of PAM sequences that can be targeted from GC-Rich areas (Cas9) to AT-rich areas of the genome (Cas12a), thereby expanding the range of sequences that can be modified using CRISPR genome engineering methods. In addition to having a T-rich PAM site, another advantage of the Cas12a system as compared with Cas9 is the use of a single short RNA molecule.

Described herein are isolated mutant Cas12a proteins comprising at least one point mutation to the wild-type Cas12a amino acid sequence. The isolated mutant Cas12a proteins are active in Clustered Regularly Interspaced Short Palindromic Repeats (CRISPR)/CRISPR-associated protein endonuclease system ("CRISPR/Cas12a endonuclease system"). The CRISPR/Cas12a endonuclease system displays maintained on-target editing activity relative to a wild-type CRISPR/Cas endonuclease system. In one aspect, the Cas12a protein is from Lachnospiraceae bacterium ND2006 (Lb). The wild-type LbCas12a protein (SEQ ID NO: 2) is encoded by the nucleotide sequence (SEQ ID NO: 1) shown below.

Wild-type LbCas12a DNA Sequence
(SEQ ID NO: 1; 3684 nt)

ATGAGCAAACTGGAAAAGTTCACCAACTGTTATAGCCT

GAGCAAAACCCTGCGTTTTAAAGCAATTCCGGTTGGTA

AAACCCAAGAGAACATTGATAATAAACGCCTGCTGGTC

GAAGATGAAAAACGCGCTGAAGATTATAAAGGCGTGAA

AAAACTGCTGGATCGCTATTATCTGAGCTTCATTAACG

ATGTGCTGCACAGCATTAAACTGAAGAACCTGAACAAC

TATATCAGCCTGTTTCGTAAAAAAACCCGCACCGAAAA

AGAAAACAAAGAGCTGGAAAACCTGGAAATCAATCTGC

GTAAAGAAATCGCCAAAGCGTTTAAAGGTAACGAGGGT

TATAAAAGCCTGTTCAAGAAAGACATCATCGAAACCAT

TCTGCCGGAATTTCTGGATGATAAAGATGAAATTGCCC

TGGTGAATAGCTTTAATGGCTTTACCACCGCATTTACC

GGCTTTTTTGATAATCGCGAAAACATGTTCAGCGAAGA

AGCAAAAAGCACCAGCATTGCATTTCGCTGCATTAATG

AAAATCTGACCCGCTACATTAGCAACATGGATATCTTT

GAAAAAGTGGACGCGATCTTCGATAAACACGAAGTGCA

AGAGATCAAAGAGAAAATCCTGAACAGCGATTATGACG

TCGAAGATTTTTTTGAAGGCGAGTTCTTTAACTTCGTT

CTGACCCAAGAAGGTATCGACGTTTATAACGCAATTAT

TGGTGGTTTTGTTACCGAAAGCGGTGAGAAAATCAAAG

GCCTGAATGAATATATCAACCTGTATAACCAGAAAACC

AAACAGAAACTGCCGAAATTCAAACCGCTGTATAAACA

GGTTCTGAGCGATCGTGAAAGCCTGAGCTTTTATGGTG

AAGGTTATACCAGTGATGAAGAGGTTCTGGAAGTTTTT

CGTAACACCCTGAATAAAAACAGCGAGATCTTTAGCAG

CATCAAAAAGCTTGAGAAACTGTTCAAAAACTTTGATG

AGTATAGCAGCGCAGGCATCTTTGTTAAAAATGGTCCG

GCAATTAGCACCATCAGCAAAGATATTTTTGGCGAATG

GAATGTGATCCGCGATAAATGGAATGCCGAATATGATG

ATATCCACCTGAAAAAAAAGGCCGTGGTGACCGAGAAA

TATGAAGATGATCGTCGTAAAAGCTTCAAGAAAATTGG

TAGCTTTAGCCTGGAACAGCTGCAAGAATATGCAGATG

CAGATCTGAGCGTTGTGGAAAAACTGAAAGAAATCATC

ATTCAGAAGGTGGACGAGATCTATAAAGTTTATGGTAG

CAGCGAAAAACTGTTCGATGCAGATTTTGTTCTGGAAA

AAAGCCTGAAAAAGAATGATGCCGTTGTGGCCATTATG

AAAGATCTGCTGGATAGCGTTAAGAGCTTCGAGAATTA

CATCAAAGCCTTTTTTGGTGAGGGCAAAGAAACCAATC

GTGATGAAAGTTTCTATGGCGATTTTGTGCTGGCCTAT

GATATTCTGCTGAAAGTGGACCATATTTATGATGCCAT

-continued

```
TCGCAATTATGTTACCCAGAAACCGTATAGCAAAGACA
AGTTCAAACTGTACTTTCAGAACCCGCAGTTTATGGGT
GGTTGGGATAAAGATAAAGAAACCGATTATCGTGCCAC
CATCCTGCGTTATGGTAGTAAATACTATCTGGCCATCA
TGGACAAAAAATACGCAAAATGCCTGCAGAAAATCGAC
AAAGATGATGTGAATGGCAACTATGAAAAAATCAACTA
CAAACTGCTGCCTGGTCCGAATAAAATGCTGCCGAAAG
TGTTCTTTAGCAAGAAATGGATGGCCTATTATAACCCG
AGCGAGGATATTCAAAAGATCTACAAAAATGGCACCTT
TAAAAAGGGCGACATGTTCAATCTGAACGATTGCCACA
AACTGATCGATTTCTTCAAAGATTCAATTTCGCGTTAT
CCGAAATGGTCCAATGCCTATGATTTTAACTTTAGCGA
AACCGAAAAATACAAAGACATTGCCGGTTTTTATCGCG
AAGTGGAAGAACAGGGCTATAAAGTGAGCTTTGAAAGC
GCAAGCAAAAAGAGGTTGATAAGCTGGTTGAAGAGGG
CAAACTGTATATGTTCCAGATTTACAACAAAGATTTTA
GCGACAAAAGCCATGGCACCCCGAATCTGCATACCATG
TACTTTAAACTGCTGTTCGACGAAAATAACCATGGTCA
GATTCGTCTGAGCGGTGGTGCCGAACTGTTTATGCGTC
GTGCAAGTCTGAAAAAGAAGAACTGGTTGTTCATCCG
GCAAATAGCCCGATTGCAAACAAAAATCCGGACAATCC
GAAAAAAACCACGACACTGAGCTATGATGTGTATAAAG
ACAAACGTTTTAGCGAGGATCAGTATGAACTGCATATC
CCGATTGCCATCAATAAATGCCCGAAAAACATCTTTAA
GATCAACACCGAAGTTCGCGTGCTGCTGAAACATGATG
ATAATCCGTATGTGATTGGCATTGATCGTGGTGAACGT
AACCTGCTGTATATTGTTGTTGATGGTAAAGGCAA
CATCGTGGAACAGTATAGTCTGAACGAAATTATCAACA
ACTTTAACGGCATCCGCATCAAAACCGACTATCATAGC
CTGCTGGACAAGAAAGAAAAAGAACGTTTTGAAGCACG
TCAGAACTGGACCAGTATTGAAAACATCAAGAACTGA
AAGCCGGTTATATTAGCCAGGTGGTTCATAAAATCTGT
GAGCTGGTAGAAAAATACGATGCAGTTATTGCACTGGA
AGATCTGAATAGCGGTTTCAAAAATAGCCGTGTGAAAG
TCGAAAAACAGGTGTATCAGAAATTCGAGAAAATGCTG
ATCGACAAACTGAACTACATGGTCGACAAAAAAAGCAA
TCCGTGTGCAACCGGTGGTGCACTGAAAGGTTATCAGA
TTACCAACAAATTTGAAAGCTTTAAAAGCATGAGCACC
CAGAACGGCTTTATCTTCTATATTCCGGCATGGCTGAC
CAGCAAAATTGATCCGAGCACCGGTTTTGTGAACCTGC
TGAAAACAAAATATACCTCCATTGCCGACAGCAAGAAG
TTTATTAGCAGCTTTGATCGCATTATGTATGTTCCGGA
AGAGGACCTGTTTGAATTCGCACTGGATTACAAAAATT
TCAGCCGTACCGATGCCGACTACATCAAAAAAATGGAAA
CTGTACAGCTATGGTAACCGCATTCGCATTTTTCGCAA
CCCGAAGAAAAACAATGTGTTCGATTGGGAAGAAGTTT
GTCTGACCAGCGCATATAAGAACTTTTCAACAAATAC
GGCATCAACTATCAGCAGGGTGATATTCGTGCACTGCT
GTGTGAACAGAGCGATAAAGCGTTTTATAGCAGTTTTA
TGGCACTGATGAGCCTGATGCTGCAGATGCGTAATAGC
ATTACCGGTCGCACCGATGTGGATTTTCTGATTAGTCC
GGTGAAAAATTCCGATGGCATCTTTTATGATAGCCGCA
ATTACGAAGCACAAGAAAATGCAATTCTGCCGAAAAAC
GCAGATGCAAATGGTGCATATAACATTGCACGTAAAGT
TCTGTGGGCAATTGGCCAGTTTAAGAAAGCAGAAGATG
AGAAGCTGGACAAAGTGAAAATTGCGATCAGCAATAAA
GAGTGGCTGGAATACGCACAGACCAGCGTTAAACAT
```

WT LbCas12a Amino Acid Sequence
(SEQ ID NO: 2; 1228 AA)

```
MSKLEKFTNCYSLSKTLRFKAIPVGKTQENIDNKRLLV
EDEKRAEDYKGVKKLLDRYYLSFINDVLHSIKLKNLNN
YISLFRKKTRTEKENKELENLEINLRKEIAKAFKGNEG
YKSLFKKDIIETILPEFLDDKDEIALVNSENGETTAFT
GFEDNRENMESEEAKSTSIAFRCINENLTRYISNMDIF
EKVDAIFDKHEVQEIKEKILNSDYDVEDFFEGEFFNEV
LTQEGIDVYNAIIGGFVTESGEKIKGLNEYINLYNQKT
KQKLPKFKPLYKQVLSDRESLSFYGEGYTSDEEVLEVF
RNTLNKNSEIFSSIKKLEKLFKNFDEYSSAGIFVKNGP
AISTISKDIFGEWNVIRDKWNAEYDDIHLKKKAVVTEK
YEDDRRKSFKKIGSFSLEQLQEYADADLSVVEKLKEII
IQKVDEIYKVYGSSEKLFDADFVLEKSLKKNDAVVAIM
KDLLDSVKSFENYIKAFFGEGKETNRDESFYGDFVLAY
DILLKVDHIYDAIRNYVTQKPYSKDKFKLYFQNPQFMG
GWDKDKETDYRATILRYGSKYYLAIMDKKYAKCLQKID
KDDVNGNYEKINYKLLPGPNKMLPKVFFSKKWMAYYNP
SEDIQKIYKNGTFKKGDMFNLNDCHKLIDFFKDSISRY
PKWSNAYDENFSETEKYKDIAGFYREVEEQGYKVSFES
ASKKEVDKLVEEGKLYMFQIYNKDFSDKSHGTPNLHTM
YFKLLFDENNHGQIRLSGGAELFMRRASLKKEELVVHP
ANSPIANKNPDNPKKTTTLSYDVYKDKRFSEDQYELHI
PIAINKCPKNIFKINTEVRVLLKHDDNPYVIGIDRGER
NLLYIVVVDGKGNIVEQYSLNEIINNENGIRIKTDYHS
```

-continued

LLDKKEKERFEARQNWTSIENIKELKAGYISQVVHKIC

ELVEKYDAVIALEDLNSGFKNSRVKVEKQVYQKFEKML

IDKLNYMVDKKSNPCATGGALKGYQITNKFESFKSMST

QNGFIFYIPAWLTSKIDPSTGFVNLLKTKYTSIADSKK

FISSFDRIMYVPEEDLFEFALDYKNFSRTDADYIKKWK

LYSYGNRIRIFRNPKKNNVFDWEEVCLTSAYKELFNKY

GINYQQGDIRALLCEQSDKAFYSSFMALMSLMLQMRNS

ITGRTDVDFLISPVKNSDGIFYDSRNYEAQENAILPKN

ADANGAYNIARKVLWAIGQFKKAEDEKLDKVKIAISNK

EWLEYAQTSVKH

Described herein is the phenotype of select point mutations of LbCas12a in the bacterial screening of the DNA cleavage activity at non-canonical TTTT PAM. A bacterial-based directed evolution of LbCas12a was performed to identify mutations with enhanced cleavage activity. A deep-scanning mutagenesis library was created that contains all possible amino acid point mutations over the entire coding sequence of LbCas12a, with most clones containing only a single mutation. Wrenbeck et al., *Nat. Methods* 13: 928-930 (2016). This type of library allows the direct evaluation of the phenotype of each point mutation by measuring their relative survival rates over the wild-type LbCas12a protein in the bacterial screen.

The screen works by transforming a screening strain harboring a toxin plasmid with the mutant LbCas12a library and crRNA targeting the HPRT38346 site on the toxin plasmid. After recovery and IPTG induction, cells were plated on LB-chloramphenicol media with arabinose and incubated at 37° C. overnight. Functional LbCas12 enzymes are capable of CRISPR activity and deactivate the toxin plasmid. If the mutant LbCas12a enzyme is not functional the transformed screening *E. coli* cells do not survive. LbCas12a expression plasmids carried by the surviving *E. coli* cells were extracted and purified. Both input and selected plasmid libraries were amplified by PCR, randomly fragmented by Nextera library prep kit, and sequenced on Illumina NextSeq™ with ~40 million reads per library. The frequencies of mutations at each position of LbCas12a in both libraries were measured and normalized to the total coverage of each codon. The relative survival rate of each point mutation was calculated as the ratio of normalized frequency between selected and input library. Since the degree of cell survival under the arabinose selection is indicative of the cleavage activity of LbCas12a variant at HPRT38346 protospacer, any variants that enriched during the selection over WT are those with enhanced activity at the TTTT PAM.

Figure 2:
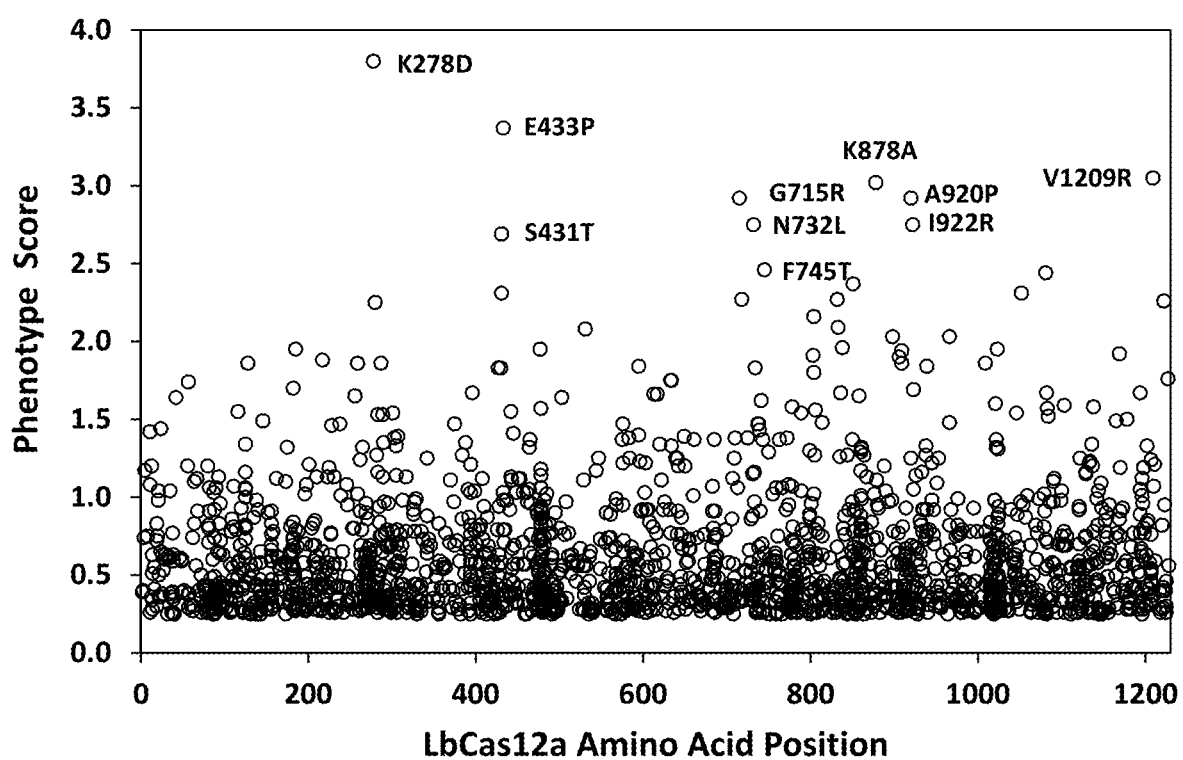
FIG. 2 shows the phenotype (activity) score of all mutations across the LbCas12a polypeptide sequence. The ten most active mutants are indicated.

The phenotype of 17,278 point-mutations of LbCas12a in the bacterial screening measures the cleavage activity at the non-canonical TTTT PAM. Two biological replicates were performed with phenotype measurements, which enabled the isolation of a large collection of novel LbCas12a variants with enhanced cleavage activity. The mutated residues in the library are shown in Table 1; the wild-type mutated amino acids are listed above the wild-type sequence (the actual mutated residues are not shown, e.g., only S2 is shown, not S2H). The specific mutations and activity levels are shown in Table 2. FIG. 2 shows the activity score of the mutations across the wild-type LbCas12a amino acid sequence and the top-ten mutants are indicated. The phenotype score (or activity score) is calculated as the natural logarithm of the ratio of normalized frequency between selected (Round 4) and Input Library (Round 3), where the normalized frequency of each mutant at each position is calculated as the ratio of mutant and synonyms change at each position.

The phenotypes of specific mutations were evaluated in *E. coli* as the colony formation unit (CFU) of each mutant. Those mutants with enhanced CFU upon selection indicated an improved editing efficiency in *E. coli*, regardless of the actual mechanism.

TABLE 1

Mutated LbCas12a Residues

|     | | |
|---|---|---|
| 1   | SKLE  T   YLS   T FKA I V KT  N DNR  LVED K    D   G   K    RYYS<br>MSKLEKFTNCYSLSKTLRFKAIPVGKTQENIDNKRLLVEDEKRAEDYKGVKKLLDRYYLS | 60 |
| 61  |    IND LHSIK    NNYISLFRKKTRTEKENKELE LEL   R  E   KAFKG  GYKS FK<br>FINDVLHSIKLKNLNNYISLFRKKTRTEKENKELENLEINLRKEIAKAFKGNEGYKSLFK | 120 |
| 121 |    D  IE  L EFLD KDEIAL    SFNG   AFT    DNR    FSE AKS    AFRC   ENL<br>KDIIETILPEFLDDKDEIALVNSFNGFITAFTGFFDNRENMFSEEAKSTSIAFRCINENL | 180 |
| 181 |    TRYISNMDI   VD IFDKHE QEIKEKIL SDY VE   FEGEFFNFV TQE I VYNAI<br>TRYISNMDIFEKVDAIFDKHEVQEIKEKILNSDYDVEDFFEGEFFNFVLTQEGIDVYNAI | 240 |
| 241 |     G    TES  K  GLN   I LYNQKTK K PKFK   KQVLSDRESLSFYGEGYTSDEEV<br>IGGFVTESGEKIKGLNEYINLYNQKTKQKLPKFKPLYKQVLSDRESLSFYGEGYTSDEEV | 300 |
| 301 | LEVFRNTLNKNSEI  SI KL  L KNFDE SSAG F   GPI  T   KD  G WNV R<br>LEVFRNTLNKNSEIFSSIKKLEKLFKNFDEYSSAGIFVKNGPAISTISKDIFGEWNVIRD | 360 |
| 361 | KWA      IH KKKAV TE YED   KS KKIGS S  EQLQ  ADADLSVVEKLKEIII<br>KWNAEYDDIHLKKKAVVTEKYEDDRRKSFKKIGSFSLEQLQEYADADLSVVEKLKEIIIQ | 420 |
| 421 | KVD IYKVYGSSEKLFD  FVLEKSL KNDA V  MKDL DS KSFENYI  FFG GKET<br>KVDEIYKVYGSSEKLFDADFVLEKSLKKNDAVVAIMKDLLDSVKSFENYIKAFFGEGKET | 480 |
| 481 | NR ES  YGDFVLAYDILLK DHI DA RN V  KPY K KY    F   PQFMG   DKDKET<br>NRDESFYGDFVLAYDILLKVDHIYDAIRNYVTQKPYSKDKFKLYFQNPQFMGGWDKDKET | 540 |

TABLE 1-continued

Mutated LbCas12a Residues

```
            D  A  L       YYLAIMD KYAK LQKI   DVNGNY  INYKLLPGPNKML KVF S
541         DYRATILRYGSKYYLAIMDKKYAKCLQKIDKDDVNGNYEKINYKLLPGPNKMLPKVFFSK          600

WMAYY  PS DIQK YK   TK  GDMF LNDCHK IDF DS ISRYPKWSNA  DFN S  T
601         KWMAYYNPSEDIQKIYKNGTFKKGDMFNLNDCHKLIDFFKDSISRYPKWSNAYDFNFSET          660

EK  D  AGFY  VE    Y  SFESASKK  V  KL  EGKLY  FQ  YNKDFS   SHGT  N
661         EKYKDIAGFYREVEEQGYKVSFESASKKEVDKLVEEGKLYMFQIYNKDFSDKSHGTPNLH          720

M   KL  FD  NNHGQIRLSGGAELFMR  ASLK    ELVVH  A  S  IA           DNKKTTTLS
721         TMYFKLLFDENNHGQIRLSGGAELFMRRASLKKEELVVHPANSPIANKNPDNPKKTTTLS          780

YDV  K  FSED   E   IPIA  NKCPKNIFK  TEV         D  PYVIGIDR  ERNLLY
781         YDVYKDKRFSEDQYELHIPIAINKCPKNIFKINTEVRVLLKHDDNPYVIGIDRGERNLLY          840

IVV   G  GNIVEQYSLNEIINN  N  IRI   DYH  LLDKKEK  RFE  RQNWT  I    KEL
841         IVVVDGKGNIVEQYSLNEIINNFNGIRIKTDYHSLLDKKEKERFEARQNWTSIENIKELK          900

AGYISQVVHKI  EL   KYDAVIA  EDLNS  FKNSR  KVEKQV   K  EKM  I  KLNY  V
901         AGYISQVVHKICELVEKYDAVIALEDLNSGFKNSRVKVEKQVYQKFEKMLIDKLNYMVDK          960

P  ATG  A  KGYQIT  KFES  KSMST   GF   YIPAW    K D    GF       KTKYTS
961         KSNPCATGGALKGYQITNKFESFKSMSTQNGFIFYIPAWLTSKIDPSTGFVNLLKTKYTS          1020

IADSKKF  S   DRIM  V   ED  FEFAL  YKNFSR  DA  Y  K  WKLY  YGNRIR    NKK
1021        IADSKKFISSFDRIMYVPEEDLFEFALDYKNFSRTDADYIKKWKLYSYGNRIRIFRNPKK          1080

NNVF  W   VCLTSA  KELFNKYGINY       IRA  LC    SDKAFY   FMA  MSLM  QMRS
1081        NNVFDWEEVCLTSAYKELFNKYGINYQQGDIRALLCEQSDKAFYSSFMALMSLMLQMRNS          1140

ITGRTDVDFL  SPVKNS  G   YD  RNY  AQ   A   PKN  DANGA  N  A     L  AIGQFK
1141        ITGRTDVDFLISPVKNSDGIFYDSRNYEAQENAILPKNADANGAYNIARKVLWAIGQFKK          1200

AEDEK  D  VKIA      EW  EYAQTS  KH
1201        AEDEKLDKVKIAISNKEWLEYAQTSVKH                                          1228
```

The top line shows the wild-type amino acid residues that were mutated; the bottom line has the wild-type LbCas12a sequence. The 10 bolded residues had the greatest average scores for the mutations K278D, S431T, E433P, F745T, G715R, N732L, K878A, A920P, I922R, and V1209R (see FIG. 2). The bold italicized residues indicate the position for the G146R, S396D, K478R, K595R, E795Q, T814G, E898N, V1083W, F81E, E125K, N145R, T152K, R182V, V491D, N582R, Y606F, Y646H, D665N, P799V, L839F, I841A, E858V, I860R, W890A, H909K, E913R, E981V, S1020E, or K1121D mutations.

In the wild-type LbCas12a polypeptide sequence shown above, bolded italicized amino acids indicate wild-type amino acids that are substituted as described herein either individually or in combination. The LbCas12a mutants described herein are useful as research tools or for therapeutic use for any CRISPR/Cas12a DNA cleavage or gene editing experiments or treatments. The superior activity of these mutants could potentially enhance the editing efficiency of LbCas12a, and directly replace the WT-LbCas12a in the application of genome editing.

One embodiment described herein is an isolated mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has 95% to 99% identity to a polypeptide sequence selected from the even numbered sequences of SEQ ID NO: 4-4022. In another aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from: (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence. In another aspect, the mutant LbCas12a polypeptide is selected from SEQ ID NO: 802, 428, 2902, 156, 694, 98, 954, 134, 1730, 642, 720, 1014, 930, 706, 834, 988, 114, 250, 3958, 48, 70, 1960, 880, 532, 598, 3960, 3962, 3964, 3966, 3968, 3970, 3972, 3974, 3976, 3978, 3980, 3982, 3984, 3986, 3988, 3990, 3992, 3994, 3996, 3998, 4000, 4002, 4004, 4006, 4008, 4010, 4012, 4014, 4016, 4018, 4020, or 4022. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is an isolated polynucleotide sequence encoding a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the encoded mutant LbCas12a polypeptide has 95% to 99% identity to a polypeptide sequence selected from the even numbered sequences of SEQ ID NO: 4-4022. In another aspect, the encoded mutant LbCas12a polypeptide has a polypeptide sequence selected from the even numbered sequences of SEQ ID NO: 4-4022. In another aspect, the mutant LbCas12a polynucleotide sequence has 95% to 99% identity to a nucleotide sequence selected from the odd numbered sequences of SEQ ID NO: 3-4021. In another aspect, the mutant LbCas12a polynucleotide has a nucleotide sequence selected from the odd numbered sequences of SEQ ID NO: 3-4021. In another aspect, the encoded mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the encoded mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D as compared to the wild-type LbCas12a polypeptide sequence of SEQ ID NO: 2. In another aspect, the mutant LbCas12a polynucleotide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the encoded mutant LbCas12a polypeptide comprises a substitution mutation selected from: (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence. In another aspect, the encoded mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the encoded mutant LbCas12a polypeptide is G146R/R182V/E795Q (SEQ ID NO: 3984). In another aspect, the mutant LbCas12a polynucleotide is selected from SEQ ID NO: 801, 427, 2901, 155, 693, 97, 953, 133, 1729, 641, 719, 1013, 929, 705, 833, 987, 113, 249, 3957, 47, 69, 1959, 879, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, 4019, or 4021. In another aspect, the mutant LbCas12a polynucleotide is selected from SEQ ID NO: 801, 427, 2901, 155, 693, 97, 953, 133, 1729, 1013, 929, 705, 113, 249, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, or 4019, and encodes a mutant LbCas12a polypeptide that provides an improvement in CRISPR/LbCas12a-associated nuclease activity at non-canonical TTTT PAM sites as compared to the wild-type LbCas12a polypeptide sequence. In another aspect, the mutant LbCas12a polynucleotide is SEQ ID NO: 3983.

Another embodiment described herein is a vector or plasmid comprising any of the polynucleotide sequences described herein.

Another embodiment described herein is a cell comprising any of the polynucleotide sequences described herein or the vectors or plasmids described herein.

Another embodiment described herein is an isolated ribonucleoprotein complex comprising a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930;

P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q529I/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a method for increasing efficiency of gene editing at non-canonical TTTT PAM sites in a cell with a CRISPR ribonucleoprotein complex, the method comprising contacting a cell with the CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q529I/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q529I/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO:

3998), G146R/P799V/E981V (SEQ ID NO: 4000), G146R/ R182V/E795Q/F81E (SEQ ID NO: 4002), G146R/R182V/ E795Q/E125K (SEQ ID NO: 4004), G146R/R182V/E795Q/ E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/ G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a kit for increasing efficiency of gene editing at non-canonical TTTT PAM sites in a cell, the kit comprising a CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/ E795Q, Q529I/E795Q, Y646H/E795Q, D665N/E795Q, T814K/E795Q, L839F/E795Q, Q906F/E795Q, E795Q/ Q1170D, G146R/R182V/E795Q, G146R/E795Q/D665N, G146R/E795Q/E981V, G146R/E795Q/T814K, G146R/ R182V/D665N, E125K/R182V/E981V, R182V/P799V/ E981V, R182V/T814K/E981V, G146R/P799V/E981V, G146R/R182V/E795Q/F81E, G146R/R182V/E795Q/ E125K, G146R/R182V/E795Q/E125A, G146R/R182V/ E795Q/P799V, G146R/R182V/E795Q/T814K, G146R/ R182V/E795Q/E981V, G146R/R182V/E795Q/D665N, G146R/R182V/P799V/E981V, E125K/G146R/R182V/ E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/ E795Q (SEQ ID NO: 3966), V491D/E795Q (SEQ ID NO: 3968), Q529I/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/ Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/ T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/ E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/ R182V/E795Q/P799V (SEQ ID NO: 4008), G146R/R182V/ E795Q/T814K (SEQ ID NO: 4010), G146R/R182V/ E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is the use of a mutant LbCas12a polypeptide for improving CRISPR/ LbCas12a-associated nuclease activity at non-canonical TTTT PAM sites, wherein the mutant LbCas12a polypeptide comprises at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence. In one aspect, the mutant LbCas12a polypeptide has a polypeptide sequence selected from the even numbered sequences of SEQ ID NO: 4-4022. In another aspect, the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2. In another aspect, the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2. In another aspect, the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598. In another aspect, the mutant LbCas12a polypeptide comprises a substitution mutation selected from (a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121. In another aspect, the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K. In another aspect, the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020). In another aspect, the mutant LbCas12a polypeptide is G146R/R182V/E795Q (SEQ ID NO: 3984).

Another embodiment described herein is a method for expressing and purifying a mutant LbCas13a protein, the method comprising: (a) inserting a nucleotide sequence encoding a mutant LbCas12a polypeptide comprising at least one amino acid substitution compared to a wild-type LbCas12a polypeptide sequence and having 95-99% identity to any one of the even numbered polypeptide sequences of SEQ ID NO: 4-4022 into an expression plasmid; (b) transforming one or more cells with the expression plasmid; (c) inducing expression of the transformed plasmid; (d) isolating the cells; (e) extracting the mutant LbCas13a protein; and (f) purifying the mutant LbCas13a protein; wherein the mutant LbCas12a polypeptide provides an improvement in CRISPR/LbCas12a-associated nuclease activity at non-canonical TTTT PAM sites as compared to a wild-type LbCas12a polypeptide sequence.

Another embodiment described herein is a mutant LbCas12a polypeptide produced by a method described herein.

Another embodiment described herein is a process for manufacturing one or more of the nucleotide sequences described herein or a polypeptide encoded by the nucleotide sequences described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence described herein; isolating the polypeptide encoded by a nucleotide described herein.

Another embodiment described herein is a means for manufacturing one or more of the nucleotide sequences described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence described herein; isolating the polypeptide encoded by a nucleotide described herein.

Another embodiment described herein is a nucleotide sequence or a polypeptide encoded by the nucleotide sequence produced by the method or the means described herein.

Another embodiment described herein is the use of an effective amount of a polypeptide encoded by one or more of the nucleotide sequences described herein in a CRISPR/Cas12a system.

Another embodiment described herein is a research tool comprising a polypeptide encoded by a nucleotide sequence described herein.

Another embodiment described herein is a biochemical reagent or therapeutic comprising a polypeptide encoded by a nucleotide sequence described herein.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions that do not alter the activity.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% identical to (a) nucleotide sequences, or degenerate, homologous, or codon-optimized variants thereof, encoding polypeptides having the amino acid sequences in the even numbered sequences of SEQ ID NO: 4-4022; (b) nucleotide sequences, or degenerate, homologous, or codon-optimized variants thereof, encoding polypeptides having the amino acid sequences in the even numbered sequences of SEQ ID NO: 4-4022; and (c) nucleotide sequences capable of hybridizing to the complement of any of the nucleotide sequences in (a) or (b) above and capable of expressing functional polypeptides of amino acid sequences in the even numbered sequences of SEQ ID NO: 4-4022.

By a polynucleotide having a nucleotide sequence at least, for example, 90-99% "identical" to a reference nucleotide sequence encoding a mutant LbCas12a is intended that the nucleotide sequence of the polynucleotide be identical to the reference sequence except that the polynucleotide sequence can include up to about 10 to 1 point mutations, additions, or deletions per each 100 nucleotides of the reference nucleotide sequence encoding the mutant LbCas12a.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981).

Due to the degeneracy of the genetic code, a large number of the nucleic acid molecules having a sequence at least 50%, 55%, 60%, 65%, 70%, 75%, 80%, 85%, 90%, 91%, 92%, 93%, 94%, 95%, 96%, 97%, 98%, or 99% identical to the nucleic acid sequences shown in odd numbered sequences of SEQ ID NO: 3-4021, or degenerate, homologous, or codon-optimized variants thereof, will encode a mutant LbCas12a.

The polynucleotides described herein include those encoding mutations, variations, substitutions, additions, deletions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of the even numbered sequences of SEQ ID NO: 4-4022 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of the even numbered sequences of SEQ ID NO: 4-4022 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, or 99% identical to the polypeptide sequence shown in the even numbered sequences of SEQ ID NO: 4-4022 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

The applications of Cas12a and LbCas12a based tools are many and varied. The applications include, but are not limited to: plant gene editing, yeast gene editing, mammalian gene editing, editing of cells in the organs of live animals, editing of embryos, rapid generation of knockout/knock-in animal lines, generating an animal model of disease state, correcting a disease state, inserting a reporter gene, and whole genome functional screening.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. An isolated mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 2. The isolated mutant LbCas12a polypeptide of clause 1, wherein the mutant LbCas12a polypeptide has 95% to 99% identity to a polypeptide sequence selected from the even numbered sequences of SEQ ID NO: 4-4022.

Clause 3. The isolated mutant LbCas12a polypeptide of clause 1 or 2, wherein the mutant LbCas12a polypeptide has a polypeptide sequence selected from the even numbered sequences of SEQ ID NO: 4-4022.

Clause 4. The isolated mutant LbCas12a polypeptide of any one of clauses 1-3, wherein the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 5. The isolated mutant LbCas12a polypeptide of any one of clauses 1-4, wherein the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2.

Clause 6. The isolated mutant LbCas12a polypeptide of any one of clauses 1-5, wherein the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 7. The isolated mutant LbCas12a polypeptide of any one of clauses 1-6, wherein the mutant LbCas12a polypeptide comprises a substitution mutation selected from:

(a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121.

Clause 8. The isolated mutant LbCas12a polypeptide of any one of clauses 1-7, wherein the multiple substitution mutations comprise: E88A/E795Q, E125K/E795Q, G146R/E795Q, R182V/E795Q, V491D/E795Q, Q529I/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V.

Clause 9. The isolated mutant LbCas12a polypeptide of any one of clauses 1-8, wherein the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence.

Clause 10. The isolated mutant LbCas12a polypeptide of any one of clauses 1-9, wherein the mutant LbCas12a polypeptide is selected from SEQ ID NO: 802, 428, 2902, 156, 694, 98, 954, 134, 1730, 642, 720, 1014, 930, 706, 834, 988, 114, 250, 3958, 48, 70, 1960, 880, 532, 598, 3960, 3962, 3964, 3966, 3968, 3970, 3972, 3974, 3976, 3978, 3980, 3982, 3984, 3986, 3988, 3990, 3992, 3994, 3996, 3998, 4000, 4002, 4004, 4006, 4008, 4010, 4012, 4014, 4016, 4018, 4020, or 4022.

Clause 11. The isolated mutant LbCas12a polypeptide of any one of clauses 1-10, wherein the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 12. The isolated mutant LbCas12a polypeptide of any one of clauses 1-11, wherein the mutant LbCas12a polypeptide is G146R/R182V/E795Q (SEQ ID NO: 3984).

Clause 13. An isolated polynucleotide sequence encoding a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 14. The isolated polynucleotide sequence of clause 13, wherein the encoded mutant LbCas12a polypeptide has 95% to 99% identity to a polypeptide sequence selected from the even numbered sequences of SEQ ID NO: 4-4022.

Clause 15. The isolated polynucleotide sequence of clause 13 or 14, wherein the encoded mutant LbCas12a polypeptide has a polypeptide sequence selected from the even numbered sequences of SEQ ID NO: 4-4022.

Clause 16. The isolated polynucleotide sequence of any one of clauses 13-15, wherein the mutant LbCas12a polynucleotide sequence has 95% to 99% identity to a nucleotide sequence selected from the odd numbered sequences of SEQ ID NO: 3-4021.

Clause 17. The isolated polynucleotide sequence of any one of clauses 13-16, wherein the mutant LbCas12a polynucleotide has a nucleotide sequence selected from the odd numbered sequences of SEQ ID NO: 3-4021.

Clause 18. The isolated polynucleotide sequence of any one of clauses 13-17, wherein the encoded mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 19. The isolated polynucleotide sequence of any one of clauses 13-18, wherein the encoded mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D as compared to the wild-type LbCas12a polypeptide sequence of SEQ ID NO: 2.

Clause 20. The isolated mutant LbCas12a polynucleotide of any one of clauses 13-19, wherein the mutant LbCas12a polynucleotide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 21. The isolated mutant LbCas12a polynucleotide of any one of clauses 13-20, wherein the encoded mutant LbCas12a polypeptide comprises a substitution mutation selected from:
(a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or
(b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121.

Clause 22. The isolated mutant LbCas12a polynucleotide of any one of clauses 13-21, wherein the multiple substitution mutations comprise: E88A/E795Q, E125K/E795Q, G146R/E795Q, R182V/E795Q, V491D/E795Q, Q529I/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, G146R/R182V/E795Q/P799V/T814K, or E125K/G146R/R182V/E795Q/D665N/E981V.

Clause 23. The isolated mutant LbCas12a polynucleotide of any one of clauses 13-22, wherein the multiple substitution mutations comprise: E88A/E795Q, E125K/E795Q, G146R/E795Q, R182V/E795Q, V491D/E795Q, Q529I/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K, and provide an improvement in CRISPR/LbCas12a-associated nuclease activity at non-canonical TTTT PAM sites as compared to the wild-type LbCas12a polypeptide sequence.

Clause 24. The isolated mutant LbCas12a polynucleotide of any one of clauses 13-23, wherein the encoded mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q529I/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 25. The isolated mutant LbCas12a polynucleotide of any one of clauses 13-24, wherein the encoded mutant LbCas12a polypeptide is G146R/R182V/E795Q (SEQ ID NO: 3984).

Clause 26. The isolated mutant LbCas12a polynucleotide of any one of clauses 13-25, wherein the mutant LbCas12a polynucleotide is selected from SEQ ID NO: 801, 427, 2901, 155, 693, 97, 953, 133, 1729, 641, 719, 1013, 929, 705, 833, 987, 113, 249, 3957, 47, 69, 1959, 879, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, 4019, or 4021.

Clause 27. The isolated mutant LbCas12a polynucleotide of any one of clauses 13-26, wherein the mutant LbCas12a polynucleotide is selected from SEQ ID NO: 801, 427, 2901, 155, 693, 97, 953, 133, 1729, 1013, 929, 705, 113, 249, 531, 597, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, or 4019, and encodes a mutant LbCas12a polypeptide that provides an improvement in CRISPR/LbCas12a-associated nuclease activity at non-canonical TTTT PAM sites as compared to the wild-type LbCas12a polypeptide sequence.

Clause 28. The isolated mutant LbCas12a polynucleotide of any one of clauses 13-27, wherein the mutant LbCas12a polynucleotide is SEQ ID NO: 3983.

Clause 29. A vector or plasmid comprising the polynucleotide sequence of any one of clauses 13-28.

Clause 30. A cell comprising the polynucleotide sequence of any one of clauses 13-28 or the vector or plasmid of clause 29.

Clause 31. An isolated ribonucleoprotein complex comprising a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 32. The isolated ribonucleoprotein complex of clause 31, wherein the mutant LbCas12a polypeptide has a polypeptide sequence selected from the even numbered sequences of SEQ ID NO: 4-4022.

Clause 33. The isolated ribonucleoprotein complex of clause 31 or 32, wherein the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 34. The isolated ribonucleoprotein complex of any one of clauses 31-33, wherein the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2.

Clause 35. The isolated ribonucleoprotein complex of any one of clauses 31-34, wherein the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 36. The isolated ribonucleoprotein complex of any one of clauses 31-35, wherein the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 37. The isolated ribonucleoprotein complex of any one of clauses 31-36, wherein the mutant LbCas12a polypeptide is G146R/R182V/E795Q (SEQ ID NO: 3984).

Clause 38. A method for increasing efficiency of gene editing at non-canonical TTTT PAM sites in a cell with a CRISPR ribonucleoprotein complex, the method comprising: contacting a cell with the CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 39. The method of clause 38, wherein the mutant LbCas12a polypeptide has a polypeptide sequence selected from the even numbered sequences of SEQ ID NO: 4-4022.

Clause 40. The method of clause 38 or 39, wherein the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 41. The method of any one of clauses 38-40, wherein the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2.

Clause 42. The method of any one of clauses 38-41, wherein the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO:

70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 43. The method of any one of clauses 38-42, wherein the mutant LbCas12a polypeptide comprises a substitution mutation selected from:
(a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or
(b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121.

Clause 44. The method of any one of clauses 38-43, wherein the multiple substitution mutations comprise: E88A/E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K.

Clause 45. The method of any one of clauses 38-44, wherein the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 46. The method of any one of clauses 38-45, wherein the mutant LbCas12a polypeptide is G146R/R182V/E795Q (SEQ ID NO: 3984).

Clause 47. A kit for increasing efficiency of gene editing at non-canonical TTTT PAM sites in a cell, the kit comprising:
a CRISPR ribonucleoprotein complex that includes a guide RNA and a mutant LbCas12a polypeptide comprising at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 48. The kit of clause 47, wherein the mutant LbCas12a polypeptide has a polypeptide sequence selected from the even numbered sequences of SEQ ID NO: 4-4022.

Clause 49. The kit of clause 47 or 48, wherein the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 50. The kit of any one of clauses 47-49, wherein the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2.

Clause 51. The kit of any one of clauses 47-50, wherein the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 52. The kit of any one of clauses 47-51, wherein the mutant LbCas12a polypeptide comprises a substitution mutation selected from:
(a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121.

Clause 53. The kit of any one of clauses 47-52, wherein the multiple substitution mutations comprise: E88A/E795Q, E125K/E795Q, G146R/E795Q, R182V/E795Q, V491D/E795Q, Q529I/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K.

Clause 54. The kit of any one of clauses 47-53, wherein the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q529I/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 55. The kit of any one of clauses 47-54, wherein the mutant LbCas12a polypeptide is G146R/R182V/E795Q (SEQ ID NO: 3984).

Clause 56. Use of a mutant LbCas12a polypeptide for improving CRISPR/LbCas12a-associated nuclease activity at non-canonical TTTT PAM sites, wherein the mutant LbCas12a polypeptide comprises at least one amino acid substitution introduced into a wild-type LbCas12a polypeptide sequence of SEQ ID NO: 2, provided that the mutant LbCas12a polypeptide provides an improvement in CRISPR/LbCas12a-associated nuclease activity at non-canonical TTTT PAM sites as compared to the wild-type LbCas12a polypeptide sequence.

Clause 57. The use of clause 56, wherein the mutant LbCas12a polypeptide has a polypeptide sequence selected from the even numbered sequences of SEQ ID NO: 4-4022.

Clause 58. The use of clause 56 or 57, wherein the mutant LbCas12a polypeptide comprises at least one amino acid substitution at positions 81, 125, 145, 146, 152, 182, 396, 478, 491, 582, 595, 606, 646, 665, 795, 799, 814, 839, 841, 858, 860, 890, 898, 909, 913, 981, 1020, 1083, or 1121 of the wild-type LbCas12a polypeptide sequence of SEQ ID NO: 2.

Clause 59. The use of any one of clauses 56-58, wherein the mutant LbCas12a polypeptide comprises at least one amino acid substitution selected from F81E, E125K, N145R, G146R, T152K, R182V, S396D, K478R, V491D, N582R, K595R, Y606F, Y646H, D665N, E795Q, P799V, T814G, L839F, I841A, E858V, I860R, W890A, E898N, H909K, E913R, E981V, S1020E, V1083W, or K1121D of the wild-type LbCas12a polypeptide sequence of SEQ ID NO: 2.

Clause 60. The use of any one of clauses 56-59, wherein the mutant LbCas12a polypeptide is selected from: F81E, SEQ ID NO: 802; E125K, SEQ ID NO: 428; N145R, SEQ ID NO: 2902; G146R, SEQ ID NO: 156; T152K, SEQ ID NO: 694; R182V, SEQ ID NO: 98; S396D, SEQ ID NO: 108; K478R, SEQ ID NO: 134; V491D, SEQ ID NO: 954; N582R, SEQ ID NO: 1730; K595R, SEQ ID NO: 184; Y606F, SEQ ID NO: 642; Y646H, SEQ ID NO: 720; D665N, SEQ ID NO: 1014; E795Q, SEQ ID NO: 930; P799V, SEQ ID NO: 706; T814G, SEQ ID NO: 162; L839F, SEQ ID NO: 834; I841A, SEQ ID NO: 988; E858V, SEQ ID NO: 114; I860R, SEQ ID NO: 250; W890A, SEQ ID NO: 3958; E898N, SEQ ID NO: 48; H909K, SEQ ID NO: 70; E913R, SEQ ID NO: 1960; E981V, SEQ ID NO: 880; S1020E, SEQ ID NO: 532; V1083W, SEQ ID NO: 132; or K1121D, SEQ ID NO: 598.

Clause 61. The use of any one of clauses 56-60, wherein the mutant LbCas12a polypeptide comprises a substitution mutation selected from:

(a) a single substitution mutation introduced into the wild-type LbCas12a polypeptide sequence of SEQ ID NO: 2 selected from the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121; or (b) a multiple substitution mutation introduced into the wild-type LbCas12a polypeptide sequence of SEQ ID NO: 2 selected from at least two of the following positions: F81, E125, N145, G146, T152, R182, S396, K478, V491, N582, K595, Y606, Y646, D665, E795, P799, T814, L839, I841, E858, I860, W890, E898, H909, E913, E981, S1020, V1083, or K1121.

Clause 62. The use of any one of clauses 56-61, wherein the multiple substitution mutations comprise: E88A/

E795Q, E125K/E795Q, G146R/E795Q, R182V/E795Q, V491D/E795Q, Q5291/E795Q, Y646H/E795Q, D665N/E795Q, T814K/E795Q, L839F/E795Q, Q906F/E795Q, E795Q/Q1170D, G146R/R182V/E795Q, G146R/E795Q/D665N, G146R/E795Q/E981V, G146R/E795Q/T814K, G146R/R182V/D665N, E125K/R182V/E981V, R182V/P799V/E981V, R182V/T814K/E981V, G146R/P799V/E981V, G146R/R182V/E795Q/F81E, G146R/R182V/E795Q/E125K, G146R/R182V/E795Q/E125A, G146R/R182V/E795Q/P799V, G146R/R182V/E795Q/T814K, G146R/R182V/E795Q/E981V, G146R/R182V/E795Q/D665N, G146R/R182V/P799V/E981V, E125K/G146R/R182V/E795Q/D665N, or G146R/R182V/E795Q/P799V/T814K.

Clause 63. The use of any one of clauses 56-62, wherein the mutant LbCas12a polypeptide is selected from: F81E (SEQ ID NO: 802), E125K (SEQ ID NO: 428), N145R (SEQ ID NO: 2902), G146R (SEQ ID NO: 156), T152K (SEQ ID NO: 694), R182V (SEQ ID NO: 98), V491D (SEQ ID NO: 954), K478R (SEQ ID NO: 134), N582R (SEQ ID NO: 1730), D665N (SEQ ID NO: 1014), E795Q (SEQ ID NO: 930), P799V (SEQ ID NO: 706), E858V (SEQ ID NO: 114), I860R (SEQ ID NO: 250), E913R (SEQ ID NO: 1960), E981V (SEQ ID NO: 880), E88A/E795Q (SEQ ID NO: 3960), E125K/E795Q (SEQ ID NO: 3962), G146R/E795Q (SEQ ID NO: 3964), R182V/E795Q (SEQ ID NO: 3966), V491D/E795Q (SEQ ID NO: 3968), Q5291/E795Q (SEQ ID NO: 3970), Y646H/E795Q (SEQ ID NO: 3972), D665N/E795Q (SEQ ID NO: 3974), T814K/E795Q (SEQ ID NO: 3976), L839F/E795Q (SEQ ID NO: 3978), Q906F/E795Q (SEQ ID NO: 3980), E795Q/Q1170D (SEQ ID NO: 3982), G146R/R182V/E795Q (SEQ ID NO: 3984), G146R/E795Q/D665N (SEQ ID NO: 3986), G146R/E795Q/E981V (SEQ ID NO: 3988), G146R/E795Q/T814K (SEQ ID NO: 3990), G146R/R182V/D665N (SEQ ID NO: 3992), E125K/R182V/E981V (SEQ ID NO: 3994), R182V/P799V/E981V (SEQ ID NO: 3996), R182V/T814K/E981V (SEQ ID NO: 3998), G146R/P799V/E981V (SEQ ID NO: 4000), G146R/R182V/E795Q/F81E (SEQ ID NO: 4002), G146R/R182V/E795Q/E125K (SEQ ID NO: 4004), G146R/R182V/E795Q/E125A (SEQ ID NO: 4006), G146R/R182V/E795Q/P799V (SEQ ID NO: 4008), G146R/R182V/E795Q/T814K (SEQ ID NO: 4010), G146R/R182V/E795Q/E981V (SEQ ID NO: 4012), G146R/R182V/E795Q/D665N (SEQ ID NO: 4014), G146R/R182V/P799V/E981V (SEQ ID NO: 4016), E125K/G146R/R182V/E795Q/D665N (SEQ ID NO: 4018), or G146R/R182V/E795Q/P799V/T814K (SEQ ID NO: 4020).

Clause 64. The use of any one of clauses 56-63, wherein the mutant LbCas12a polypeptide is G146R/R182V/E795Q (SEQ ID NO: 3984).

Clause 65. A method for expressing and purifying a mutant LbCas13a protein, the method comprising:
(a) inserting a nucleotide sequence encoding a mutant LbCas12a polypeptide comprising at least one amino acid substitution compared to a wild-type LbCas12a polypeptide sequence and having 95-99% identity to any one of the even numbered polypeptide sequences of SEQ ID NO: 4-4022 into an expression plasmid;
(b) transforming one or more cells with the expression plasmid;
(c) inducing expression of the transformed plasmid;
(d) isolating the cells;
(e) extracting the mutant LbCas13a protein; and
(f) purifying the mutant LbCas13a protein;
wherein the mutant LbCas12a polypeptide provides an improvement in CRISPR/LbCas12a-associated nuclease activity at non-canonical TTTT PAM sites as compared to a wild-type LbCas12a polypeptide sequence.

Clause 66. The mutant LbCas12a polypeptide produced by the method of clause 65.

REFERENCES

Zetsche et al. "Cpf1 Is a Single RNA-Guided Endonuclease of a Class 2 CRISPR-Cas System," *Cell* 163: 759-771 (2015).

Jinek et al., "A programmable dual-RNA-guided DNA endonuclease in adaptive bacterial immunity," *Science* 337: 816-821 (2012).

Schindele and Puchta, "Engineering CRISPR/LbCas12a for highly efficient, temperature-tolerant plant gene editing," *Plant Biotechnol. J.* 18(5):1118-1120 (2020).

Wrenbeck et al., "Plasmid-based one-pot saturation mutagenesis," *Nat. Methods* 13: 928-930 (2016).

EXAMPLES

Example 1

High-Throughput Measurement of the DNA Cleavage Activity of LbCas12a Variants at TTTT PAM Site in *E. coli*.

A bacterial-based directed evolution of LbCas12a was performed to identify mutations with enhanced cleavage activity. A deep-scanning mutagenesis library was created containing all possible point mutations on the amino acid level over the entire coding sequence of LbCas12a, with most clones contain only one mutation. Wrenbeck et al. *Nat. Methods* 13: 928-930 (2016), which is incorporated by reference herein. This type of library permitted direct evaluation of the phenotype of each point mutation, by measuring their relative survival rates over the LbCas12a wild-type (WT) protein in the bacterial screen.

The screening strain harboring the toxin plasmid was transformed with LbCas12a library and crRNA targeting the HPRT38346 site on the toxin plasmid. After recovery and IPTG induction, cells were plated on LB-chloramphenicol media with arabinose and incubated at 37° C. overnight. LbCas12a expression plasmids carried by the survived *E. coli* cells were extracted and purified. Both input and selected plasmid libraries were PCR amplified, randomly fragmented by Nextera library prep kit, and sequenced on Illumina NextSeq™ with ~40 million reads per library. The frequencies of mutations at each position of LbCas12a in both libraries were measured and normalized to the total coverage of each codon. The relative survival rate of each point mutation was calculated as the ratio of normalized frequency between selected and input library. The phenotype score (or activity score) is calculated as the natural logarithm of the ratio of normalized frequency between selected (Round 4) and Input Library (Round 3), where the normalized frequency of each mutant at each position is calculated as the ratio of specific mutant and synonyms change at each position. Since the degree of cell survival under the arabinose selection is indicative of the cleavage activity of LbCas12a variant at HPRT38346 protospacer, any variants that enriched during the selection over WT would be those with enhanced activity at TTTT PAM.

Figure 1B:
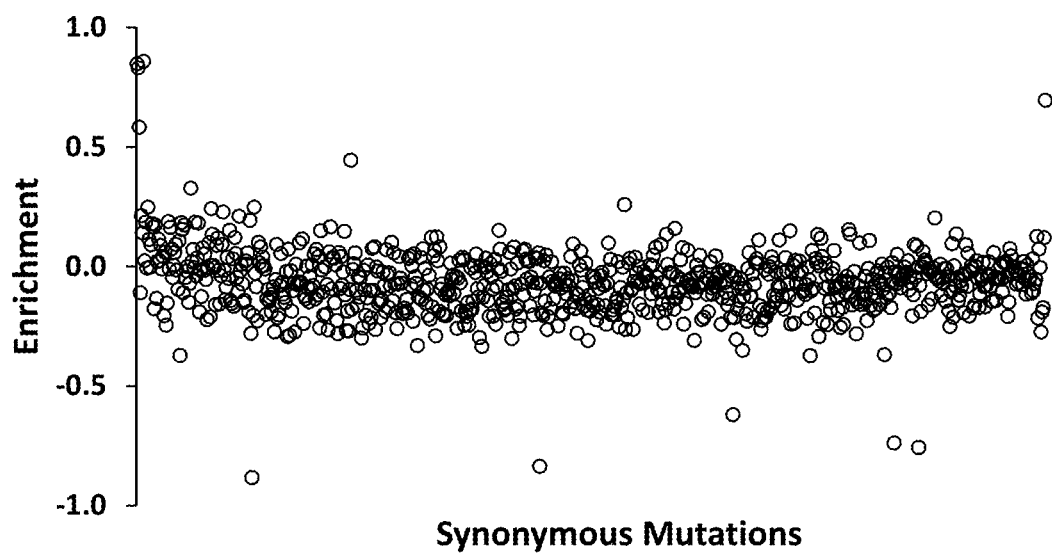
FIG. 1B shows the distribution and enrichment of synonymous mutations.
Figure 1C:
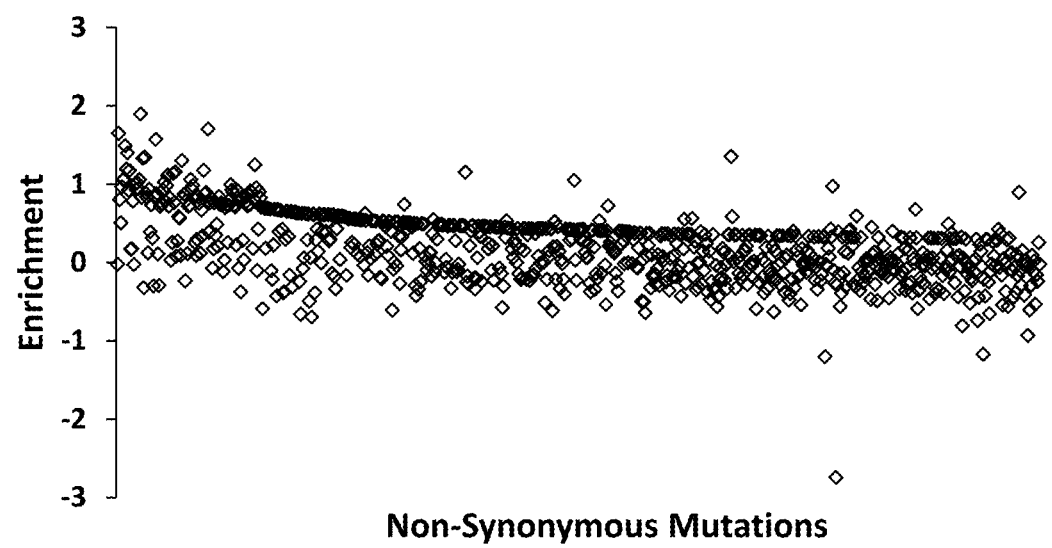
FIG. 1C shows the distribution and enrichment of non-synonymous mutations.

The phenotype scores (or activity score) of 17,278 LbCas12a variants with single point mutation are listed in Table 2. Scores for synonymous changes (n=849, 69% of all positions) tightly clustered around 0, and thus serving as the baseline activity of wild-type LbCas12a (FIG. 1A-C). Overall, 1,977 of 17,278 (~11.4%) point mutations exhibited some benefits with score greater than the 99th percentile (0.248) of all synonymous changes (FIG. 2; Table 2).

Table 2 shows point mutations enriched over the WT protein. The phenotype score is the natural logarithm of relative enrichment of point mutations over two biological replicates with beneficial phenotypes. The primers used for generating saturation mutagenesis library are shown in Table 3.

TABLE 2

| Lachnospiraceae bacterium ND2006 Cas12a Wild-type and Mutants | | | | | | | |
|---|---|---|---|---|---|---|---|
| Mutation | Position | WT residue | Mutant residue | Average score | Standard deviation | NT SEQ ID | AA SEQ ID |
| WT | | Wild-type LbCas12a | | | | 1 | 2 |
| K278D | 278 | K | D | 3.8 | 0.32 | 3 | 4 |
| E433P | 433 | E | P | 3.37 | 2.93 | 5 | 6 |
| V1209R | 1209 | V | R | 3.05 | 2.28 | 7 | 8 |
| K878A | 878 | K | A | 3.02 | 2.73 | 9 | 10 |
| A920P | 920 | A | P | 2.92 | 0.37 | 11 | 12 |
| G715R | 715 | G | R | 2.92 | 3.25 | 13 | 14 |
| N732L | 732 | N | L | 2.75 | 2.81 | 15 | 16 |
| I922R | 922 | I | R | 2.75 | 0.12 | 17 | 18 |
| S431T | 431 | S | T | 2.69 | 2.93 | 19 | 20 |
| F745T | 745 | F | T | 2.46 | 3.01 | 21 | 22 |
| N1081E | 1081 | N | E | 2.44 | 2.97 | 23 | 24 |
| V851F | 851 | V | F | 2.37 | 0.05 | 25 | 26 |
| F1052P | 1052 | F | P | 2.31 | 2.27 | 27 | 28 |
| S431G | 431 | S | G | 2.31 | 2.5 | 29 | 30 |
| D832R | 832 | D | R | 2.27 | 3.46 | 31 | 32 |
| N718Q | 718 | N | Q | 2.27 | 2.61 | 33 | 34 |
| A1222R | 1222 | A | R | 2.26 | 3.34 | 35 | 36 |
| V280R | 280 | V | R | 2.25 | 2.23 | 37 | 38 |
| K804I | 804 | K | I | 2.16 | 0.77 | 39 | 40 |
| R833V | 833 | R | V | 2.09 | 3.19 | 41 | 42 |
| M531S | 531 | M | S | 2.08 | 0.01 | 43 | 44 |
| A966P | 966 | A | P | 2.03 | 0.54 | 45 | 46 |
| E898N | 898 | E | N | 2.03 | 0.02 | 47 | 48 |
| L838D | 838 | L | D | 1.96 | 2.02 | 49 | 50 |
| S185Y | 185 | S | Y | 1.95 | 0.13 | 51 | 52 |
| G477T | 477 | G | T | 1.95 | 0.06 | 53 | 54 |
| D1023S | 1023 | D | S | 1.95 | 0.63 | 55 | 56 |
| H909M | 909 | H | M | 1.94 | 0.52 | 57 | 58 |
| A1169T | 1169 | A | T | 1.92 | 1.36 | 59 | 60 |
| N803F | 803 | N | F | 1.91 | 0.5 | 61 | 62 |
| Q906F | 906 | Q | F | 1.9 | 0.04 | 63 | 64 |
| E217Q | 217 | E | Q | 1.88 | 0.61 | 65 | 66 |
| L128E | 128 | L | E | 1.86 | 3.33 | 67 | 68 |
| H909K | 909 | H | K | 1.86 | 0.18 | 69 | 70 |
| G1009Q | 1009 | G | Q | 1.86 | 1.76 | 71 | 72 |
| L287A | 287 | L | A | 1.86 | 0.63 | 73 | 74 |
| I259S | 259 | I | S | 1.86 | 0.34 | 75 | 76 |
| E939A | 939 | E | A | 1.84 | 1.26 | 77 | 78 |
| K595P | 595 | K | P | 1.84 | 2.71 | 79 | 80 |
| K427Y | 427 | K | Y | 1.83 | 1.75 | 81 | 82 |
| G734L | 734 | G | L | 1.83 | 3.68 | 83 | 84 |
| G430L | 430 | G | L | 1.83 | 3.68 | 85 | 86 |
| K804F | 804 | K | F | 1.8 | 0.83 | 87 | 88 |
| K1227C | 1227 | K | C | 1.76 | 0.7 | 89 | 90 |
| K634T | 634 | K | T | 1.75 | 1.72 | 91 | 92 |
| H633P | 633 | H | P | 1.75 | 1.72 | 93 | 94 |
| Y57E | 57 | Y | E | 1.74 | 0.76 | 95 | 96 |
| R182V | 182 | R | V | 1.7 | 0.11 | 97 | 98 |
| A923R | 923 | A | R | 1.69 | 0.06 | 99 | 100 |
| R836A | 836 | R | A | 1.67 | 2.12 | 101 | 102 |
| N1082E | 1082 | N | E | 1.67 | 2.02 | 103 | 104 |
| A1194D | 1194 | A | D | 1.67 | 0.05 | 105 | 106 |
| S396D | 396 | S | D | 1.67 | 0.19 | 107 | 108 |
| K617S | 617 | K | S | 1.66 | 0.06 | 109 | 110 |
| Q613V | 613 | Q | V | 1.66 | 0.18 | 111 | 112 |
| E858V | 858 | E | V | 1.65 | 0 | 113 | 114 |
| N256R | 256 | N | R | 1.65 | 0.18 | 115 | 116 |
| K42E | 42 | K | E | 1.64 | 2.34 | 117 | 118 |
| I503E | 503 | I | E | 1.64 | 0.07 | 119 | 120 |
| G741L | 741 | G | L | 1.62 | 0.24 | 121 | 122 |
| I102E | 1021 | I | E | 1.6 | 1.19 | 123 | 124 |
| G1103T | 1103 | G | T | 1.59 | 0.18 | 125 | 126 |
| T778P | 778 | T | P | 1.58 | 1.44 | 127 | 128 |
| R1138D | 1138 | R | D | 1.58 | 1.71 | 129 | 130 |
| V1083W | 1083 | V | W | 1.57 | 0.18 | 131 | 132 |
| K478R | 478 | K | R | 1.57 | 0.05 | 133 | 134 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| P806D | 806 | P | D | 1.56 | 0.57 | 135 | 136 |
| K116I | 116 | K | I | 1.55 | 0.44 | 137 | 138 |
| L442F | 442 | L | F | 1.55 | 0.34 | 139 | 140 |
| L301F | 301 | L | F | 1.54 | 1.32 | 141 | 142 |
| A1046C | 1046 | A | C | 1.54 | 3.27 | 143 | 144 |
| F789N | 789 | F | N | 1.54 | 0.83 | 145 | 146 |
| D283M | 283 | D | M | 1.53 | 0.18 | 147 | 148 |
| F289D | 289 | F | D | 1.53 | 0.4 | 149 | 150 |
| F1084C | 1084 | F | C | 1.52 | 0.83 | 151 | 152 |
| N1178E | 1178 | N | E | 1.5 | 0.05 | 153 | 154 |
| G146R | 146 | G | R | 1.49 | 0.02 | 155 | 156 |
| R1165E | 1165 | R | E | 1.49 | 0.05 | 157 | 158 |
| A966N | 966 | A | N | 1.48 | 0.64 | 159 | 160 |
| T814G | 814 | T | G | 1.48 | 0.05 | 161 | 162 |
| L738Y | 738 | L | Y | 1.47 | 0.47 | 163 | 164 |
| G576R | 576 | G | R | 1.47 | 0.08 | 165 | 166 |
| A375W | 375 | A | W | 1.47 | 0.35 | 167 | 168 |
| R737V | 737 | R | V | 1.47 | 0.47 | 169 | 170 |
| N238F | 238 | N | F | 1.47 | 0.23 | 171 | 172 |
| V228T | 228 | V | T | 1.46 | 0.23 | 173 | 174 |
| V24H | 24 | V | H | 1.44 | 0.25 | 175 | 176 |
| S739K | 739 | S | K | 1.43 | 0.31 | 177 | 178 |
| Y11E | 11 | Y | E | 1.42 | 0.66 | 179 | 180 |
| S445N | 445 | S | N | 1.41 | 0.33 | 181 | 182 |
| K595R | 595 | K | R | 1.4 | 0.08 | 183 | 184 |
| T307W | 307 | T | W | 1.39 | 0.22 | 185 | 186 |
| W649A | 649 | W | A | 1.39 | 1.07 | 187 | 188 |
| N772R | 772 | N | R | 1.38 | 0.44 | 189 | 190 |
| V303W | 303 | V | W | 1.38 | 0.1 | 191 | 192 |
| K725H | 725 | K | H | 1.38 | 0.21 | 193 | 194 |
| S710I | 710 | S | I | 1.38 | 1.08 | 195 | 196 |
| Y583L | 583 | Y | L | 1.38 | 0.54 | 197 | 198 |
| S465D | 465 | S | D | 1.37 | 0.11 | 199 | 200 |
| I850S | 850 | I | S | 1.37 | 0.11 | 201 | 202 |
| E743T | 743 | E | T | 1.37 | 0 | 203 | 204 |
| N575P | 575 | N | P | 1.37 | 0.09 | 205 | 206 |
| A685D | 685 | A | D | 1.37 | 0.1 | 207 | 208 |
| S763H | 763 | S | H | 1.37 | 0.14 | 209 | 210 |
| E661W | 661 | E | W | 1.37 | 0.54 | 211 | 212 |
| A1022S | 1022 | A | S | 1.37 | 0.48 | 213 | 214 |
| S388G | 388 | S | G | 1.35 | 0.15 | 215 | 216 |
| Y290M | 290 | Y | M | 1.35 | 1.03 | 217 | 218 |
| E125R | 125 | E | R | 1.34 | 0.08 | 219 | 220 |
| Q1136A | 1136 | Q | A | 1.34 | 1.93 | 221 | 222 |
| T620M | 620 | T | M | 1.34 | 0.55 | 223 | 224 |
| E1202W | 1202 | E | W | 1.33 | 0.02 | 225 | 226 |
| R305T | 305 | R | T | 1.33 | 1.2 | 227 | 228 |
| K634I | 634 | K | I | 1.33 | 1.12 | 229 | 230 |
| V938G | 938 | V | G | 1.33 | 0.44 | 231 | 232 |
| N861I | 861 | N | I | 1.32 | 0.03 | 233 | 234 |
| C175D | 175 | C | D | 1.32 | 0.44 | 235 | 236 |
| K265V | 265 | K | V | 1.32 | 0.54 | 237 | 238 |
| A1022I | 1022 | A | I | 1.32 | 0.43 | 239 | 240 |
| K464L | 464 | K | L | 1.32 | 0.55 | 241 | 242 |
| S1024E | 1024 | S | E | 1.31 | 0.31 | 243 | 244 |
| N861V | 861 | N | V | 1.31 | 0.16 | 245 | 246 |
| P799S | 799 | P | S | 1.3 | 0.05 | 247 | 248 |
| I860R | 860 | I | R | 1.29 | 0.28 | 249 | 250 |
| S750V | 750 | S | V | 1.29 | 0.05 | 251 | 252 |
| F983W | 938 | F | W | 1.27 | 1.03 | 253 | 254 |
| D384W | 384 | D | W | 1.27 | 0.06 | 255 | 256 |
| C805F | 805 | C | F | 1.27 | 0.52 | 257 | 258 |
| S282W | 282 | S | W | 1.27 | 1.52 | 259 | 260 |
| V844N | 844 | V | N | 1.27 | 0.93 | 261 | 262 |
| N864S | 864 | N | S | 1.27 | 0.05 | 263 | 264 |
| E835A | 835 | E | A | 1.26 | 0.05 | 265 | 266 |
| A920T | 920 | A | T | 1.25 | 1.43 | 267 | 268 |
| F639C | 639 | F | C | 1.25 | 0.06 | 269 | 270 |
| K953S | 953 | K | S | 1.25 | 0.41 | 271 | 272 |
| D641I | 641 | D | I | 1.25 | 0.05 | 273 | 274 |
| A1122Q | 1122 | A | Q | 1.25 | 0.31 | 275 | 276 |
| L547H | 547 | L | H | 1.25 | 0.07 | 277 | 278 |
| P342L | 342 | P | L | 1.25 | 0.09 | 279 | 280 |
| F709K | 709 | F | K | 1.25 | 0.92 | 281 | 282 |
| K584E | 584 | K | E | 1.25 | 0.42 | 283 | 284 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| Y262L | 262 | Y | L | 1.24 | 0.12 | 285 | 286 |
| D1207F | 1207 | D | F | 1.24 | 0.11 | 287 | 288 |
| M1134G | 1134 | M | G | 1.23 | 1.73 | 289 | 290 |
| V596K | 596 | V | K | 1.23 | 0.43 | 291 | 292 |
| G576M | 576 | G | M | 1.22 | 0.43 | 293 | 294 |
| L1133T | 1133 | L | T | 1.22 | 0.16 | 295 | 296 |
| K945L | 945 | K | L | 1.22 | 0.17 | 297 | 298 |
| M603Y | 603 | M | Y | 1.22 | 0.21 | 299 | 300 |
| I1211D | 1211 | I | D | 1.21 | 1.39 | 301 | 302 |
| S394Q | 394 | S | Q | 1.21 | 0.14 | 303 | 304 |
| E201I | 201 | E | I | 1.21 | 0.05 | 305 | 306 |
| S642M | 642 | S | M | 1.2 | 0.88 | 307 | 308 |
| M1137Q | 1137 | M | Q | 1.2 | 0.05 | 309 | 310 |
| Q888S | 888 | Q | S | 1.2 | 0.83 | 311 | 312 |
| R56V | 56 | R | V | 1.2 | 0.4 | 313 | 314 |
| L80D | 80 | L | D | 1.2 | 0.84 | 315 | 316 |
| S650A | 650 | S | A | 1.2 | 1.36 | 317 | 318 |
| L13C | 13 | L | C | 1.2 | 0.33 | 319 | 320 |
| Q1170D | 1170 | Q | D | 1.19 | 0.15 | 321 | 322 |
| F1198Q | 1198 | F | Q | 1.19 | 0.93 | 323 | 324 |
| F1198G | 1198 | F | G | 1.19 | 0.93 | 325 | 326 |
| F225R | 225 | F | R | 1.19 | 0.24 | 327 | 328 |
| K478W | 478 | K | W | 1.18 | 0.08 | 329 | 330 |
| I860S | 860 | I | S | 1.17 | 0.09 | 331 | 332 |
| E5Y | 5 | E | Y | 1.17 | 0.22 | 333 | 334 |
| A544T | 544 | A | T | 1.17 | 0.22 | 335 | 336 |
| N933E | 933 | N | E | 1.16 | 0.31 | 337 | 338 |
| A1129G | 1129 | A | G | 1.16 | 0.05 | 339 | 340 |
| H733K | 733 | H | K | 1.16 | 0.31 | 341 | 342 |
| D283R | 283 | D | R | 1.16 | 1.18 | 343 | 344 |
| E125S | 125 | E | S | 1.16 | 0.13 | 345 | 346 |
| N731H | 731 | N | H | 1.15 | 1.06 | 347 | 348 |
| A1129R | 1129 | A | R | 1.15 | 1.81 | 349 | 350 |
| R305D | 305 | R | D | 1.14 | 0.53 | 351 | 352 |
| K478F | 478 | K | F | 1.14 | 0.07 | 353 | 354 |
| D926Q | 926 | D | Q | 1.14 | 0.02 | 355 | 356 |
| Q231S | 231 | Q | S | 1.13 | 0.53 | 357 | 358 |
| L442C | 442 | L | C | 1.13 | 0.21 | 359 | 360 |
| L210Y | 210 | L | Y | 1.13 | 0.83 | 361 | 362 |
| S317M | 317 | S | M | 1.13 | 0.84 | 363 | 364 |
| F289Q | 289 | F | Q | 1.13 | 0.67 | 365 | 366 |
| R867Q | 867 | R | Q | 1.13 | 0.05 | 367 | 368 |
| E223L | 223 | E | L | 1.13 | 0.25 | 369 | 370 |
| E93S | 93 | E | S | 1.13 | 0.15 | 371 | 372 |
| V453R | 453 | V | R | 1.12 | 0.15 | 373 | 374 |
| L1091A | 1091 | L | A | 1.12 | 0.73 | 375 | 376 |
| L408D | 408 | L | D | 1.12 | 1.69 | 377 | 378 |
| A451K | 451 | A | K | 1.12 | 0.15 | 379 | 380 |
| G1196I | 1196 | G | I | 1.12 | 0.83 | 381 | 382 |
| K707Y | 707 | K | Y | 1.12 | 0.26 | 383 | 384 |
| F162H | 162 | F | H | 1.12 | 0.15 | 385 | 386 |
| H67G | 67 | H | G | 1.12 | 0.73 | 387 | 388 |
| E443N | 443 | E | N | 1.11 | 0.72 | 389 | 390 |
| K879D | 879 | K | D | 1.11 | 0.72 | 391 | 392 |
| Q529I | 529 | Q | I | 1.11 | 0.06 | 393 | 394 |
| H370G | 370 | H | G | 1.11 | 0.09 | 395 | 396 |
| K622P | 622 | K | P | 1.11 | 0.83 | 397 | 398 |
| D64Q | 64 | D | Q | 1.1 | 0.16 | 399 | 400 |
| F173T | 173 | F | T | 1.1 | 0.12 | 401 | 402 |
| C1090K | 1090 | C | K | 1.1 | 0.17 | 403 | 404 |
| I951S | 951 | I | S | 1.09 | 0.05 | 405 | 406 |
| V1147Y | 1147 | V | Y | 1.09 | 0.18 | 407 | 408 |
| T246V | 246 | T | V | 1.08 | 0.22 | 409 | 410 |
| D198Q | 198 | D | Q | 1.08 | 0.67 | 411 | 412 |
| K774P | 774 | K | P | 1.08 | 1.21 | 413 | 414 |
| Y11Q | 11 | Y | Q | 1.08 | 0.17 | 415 | 416 |
| T778G | 778 | T | G | 1.07 | 2.27 | 417 | 418 |
| G111Y | 111 | G | Y | 1.07 | 0.06 | 419 | 420 |
| K1210Y | 1210 | K | Y | 1.07 | 0.16 | 421 | 422 |
| E683I | 683 | E | I | 1.07 | 0.32 | 423 | 424 |
| R82E | 82 | R | E | 1.06 | 0.41 | 425 | 426 |
| E125K | 125 | E | N | 1.06 | 0.04 | 427 | 428 |
| S713E | 713 | S | E | 1.06 | 0.08 | 429 | 430 |
| H759G | 759 | H | G | 1.06 | 0.6 | 431 | 432 |
| E90F | 90 | E | F | 1.06 | 0.06 | 433 | 434 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K478L | 478 | K | L | 1.06 | 0.1 | 435 | 436 |
| K478Y | 478 | K | Y | 1.06 | 0.07 | 437 | 438 |
| A766Y | 766 | A | Y | 1.06 | 0.6 | 439 | 440 |
| E125N | 125 | E | N | 1.05 | 0.04 | 441 | 442 |
| A1194V | 1194 | A | V | 1.05 | 0.06 | 443 | 444 |
| K391F | 391 | K | F | 1.05 | 0.27 | 445 | 446 |
| K464A | 464 | K | A | 1.05 | 0.05 | 447 | 448 |
| A923G | 923 | A | G | 1.05 | 0.24 | 449 | 450 |
| Q399V | 399 | Q | V | 1.04 | 0.7 | 451 | 452 |
| R1144H | 1144 | R | H | 1.04 | 0.29 | 453 | 454 |
| N1100M | 1100 | N | M | 1.04 | 0.7 | 455 | 456 |
| F789T | 789 | F | T | 1.04 | 0.39 | 457 | 458 |
| R35G | 35 | R | G | 1.04 | 0.28 | 459 | 460 |
| W890Q | 890 | W | Q | 1.04 | 0.7 | 461 | 462 |
| A21N | 21 | A | N | 1.04 | 0.03 | 463 | 464 |
| K448Y | 448 | K | Y | 1.03 | 0.7 | 465 | 466 |
| D461L | 461 | D | L | 1.03 | 0.59 | 467 | 468 |
| T87P | 87 | T | P | 1.03 | 0.02 | 469 | 470 |
| E433H | 433 | E | H | 1.03 | 0.7 | 471 | 472 |
| K457S | 457 | K | S | 1.03 | 1.68 | 473 | 474 |
| W602Q | 602 | W | Q | 1.03 | 0.4 | 475 | 476 |
| S394C | 394 | S | C | 1.03 | 0.15 | 477 | 478 |
| S485D | 485 | S | D | 1.02 | 0.29 | 479 | 480 |
| K804Y | 804 | K | Y | 1.02 | 0.89 | 481 | 482 |
| I196K | 196 | I | K | 1.02 | 0.05 | 483 | 484 |
| K1079H | 1079 | K | H | 1.02 | 0.7 | 485 | 486 |
| L876S | 876 | L | S | 1.02 | 1.24 | 487 | 488 |
| E755S | 755 | E | S | 1.02 | 0.05 | 489 | 490 |
| I259W | 259 | I | W | 1.02 | 0.7 | 491 | 492 |
| Y1059E | 1059 | Y | E | 1.01 | 0.39 | 493 | 494 |
| T660C | 660 | T | C | 1.01 | 0.17 | 495 | 496 |
| G1196C | 1196 | G | C | 1.01 | 1.41 | 497 | 498 |
| I860E | 860 | I | E | 1.01 | 0.31 | 499 | 500 |
| A239T | 239 | A | T | 1.01 | 0.18 | 501 | 502 |
| E125A | 125 | E | A | 1 | 0.06 | 503 | 504 |
| N861T | 861 | N | T | 0.99 | 0.12 | 505 | 506 |
| I976A | 976 | I | A | 0.99 | 0.52 | 507 | 508 |
| R1073H | 1073 | R | H | 0.99 | 0.1 | 509 | 510 |
| D329F | 329 | D | F | 0.99 | 0.54 | 511 | 512 |
| K568F | 568 | K | F | 0.99 | 0.16 | 513 | 514 |
| T1142Y | 1142 | T | Y | 0.99 | 0.05 | 515 | 516 |
| R482T | 482 | R | T | 0.98 | 0.43 | 517 | 518 |
| A21F | 21 | A | F | 0.98 | 0.62 | 519 | 520 |
| K897H | 897 | K | H | 0.98 | 0.05 | 521 | 522 |
| S1020D | 1020 | S | D | 0.98 | 0.01 | 523 | 524 |
| D437I | 437 | D | I | 0.98 | 1.5 | 525 | 526 |
| K945V | 945 | K | V | 0.98 | 0.12 | 527 | 528 |
| F1099S | 1099 | F | S | 0.98 | 0.15 | 529 | 530 |
| S1020E | 1020 | S | E | 0.98 | 0.12 | 531 | 532 |
| E433Q | 433 | E | Q | 0.98 | 0.52 | 533 | 534 |
| I138Q | 138 | I | Q | 0.98 | 0.21 | 535 | 536 |
| E313C | 313 | E | C | 0.98 | 0.63 | 537 | 538 |
| N1051G | 1051 | N | G | 0.97 | 0.05 | 539 | 540 |
| W1086A | 1086 | W | A | 0.97 | 0.05 | 541 | 542 |
| M626D | 626 | M | D | 0.97 | 0.06 | 543 | 544 |
| N327E | 327 | N | E | 0.97 | 0.18 | 545 | 546 |
| C1090M | 1090 | C | M | 0.97 | 0.05 | 547 | 548 |
| I893Q | 893 | I | Q | 0.97 | 0.05 | 549 | 550 |
| S462E | 462 | S | E | 0.97 | 1.02 | 551 | 552 |
| K374P | 374 | K | P | 0.97 | 0.22 | 553 | 554 |
| G291T | 291 | G | T | 0.97 | 0.12 | 555 | 556 |
| I850Q | 850 | I | Q | 0.97 | 0.19 | 557 | 558 |
| R508G | 508 | R | G | 0.97 | 0.07 | 559 | 560 |
| H733T | 733 | H | T | 0.97 | 1.24 | 561 | 562 |
| Q1197R | 1197 | Q | R | 0.96 | 0.09 | 563 | 564 |
| E95K | 95 | E | K | 0.96 | 0.02 | 565 | 566 |
| S296L | 296 | S | L | 0.96 | 0.3 | 567 | 568 |
| A801L | 801 | A | L | 0.96 | 0.18 | 569 | 570 |
| F466A | 466 | F | A | 0.96 | 1.48 | 571 | 572 |
| K269Y | 269 | K | Y | 0.96 | 0.19 | 573 | 574 |
| G576K | 576 | G | K | 0.95 | 0.3 | 575 | 576 |
| E880T | 880 | E | T | 0.95 | 0.6 | 577 | 578 |
| Q1223S | 1223 | Q | S | 0.95 | 0.1 | 579 | 580 |
| E247P | 247 | E | P | 0.95 | 0.29 | 581 | 582 |
| K774E | 774 | K | E | 0.95 | 0.86 | 583 | 584 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| R1054F | 1054 | R | F | 0.95 | 0.38 | 585 | 586 |
| S1157M | 1157 | S | M | 0.95 | 0.01 | 587 | 588 |
| K568W | 568 | K | W | 0.95 | 0.06 | 589 | 590 |
| K1025G | 1025 | K | G | 0.94 | 0.14 | 591 | 592 |
| K478C | 478 | K | C | 0.94 | 0.1 | 593 | 594 |
| V410P | 410 | V | P | 0.94 | 0.3 | 595 | 596 |
| K1121D | 1121 | K | D | 0.94 | 0.1 | 597 | 598 |
| E285Y | 285 | E | Y | 0.94 | 0.17 | 599 | 600 |
| V428H | 428 | V | H | 0.94 | 1.52 | 601 | 602 |
| K478M | 478 | K | M | 0.93 | 0.11 | 603 | 604 |
| D1148M | 1148 | D | M | 0.93 | 0.44 | 605 | 606 |
| L914K | 914 | L | K | 0.93 | 0.18 | 607 | 608 |
| Y995L | 995 | Y | L | 0.93 | 0.05 | 609 | 610 |
| K881T | 881 | K | T | 0.93 | 3.38 | 611 | 612 |
| K120C | 120 | K | C | 0.93 | 0.54 | 613 | 614 |
| A1173D | 1173 | A | D | 0.93 | 0.11 | 615 | 616 |
| K1121E | 1121 | K | E | 0.92 | 0.08 | 617 | 618 |
| G846L | 846 | G | L | 0.92 | 0.44 | 619 | 620 |
| K478A | 478 | K | A | 0.92 | 0.08 | 621 | 622 |
| G968W | 968 | G | W | 0.92 | 0.54 | 623 | 624 |
| K1121C | 1121 | K | C | 0.92 | 0.27 | 625 | 626 |
| L140A | 140 | L | A | 0.92 | 0.44 | 627 | 628 |
| E947N | 947 | E | N | 0.92 | 0.54 | 629 | 630 |
| S934Q | 934 | S | Q | 0.92 | 0.44 | 631 | 632 |
| D771P | 771 | D | P | 0.92 | 1.06 | 633 | 634 |
| R935M | 935 | R | M | 0.92 | 0.44 | 635 | 636 |
| G624R | 624 | G | R | 0.92 | 0.55 | 637 | 638 |
| E939R | 939 | E | R | 0.92 | 0.54 | 639 | 640 |
| Y606F | 606 | Y | F | 0.92 | 0.07 | 641 | 642 |
| E88S | 88 | E | S | 0.92 | 0.04 | 643 | 644 |
| S599V | 599 | S | V | 0.92 | 0.43 | 645 | 646 |
| V441Q | 441 | V | Q | 0.92 | 1.42 | 647 | 648 |
| E1039T | 1039 | E | T | 0.92 | 0.14 | 649 | 650 |
| F473V | 473 | F | V | 0.92 | 0.06 | 651 | 652 |
| A604H | 604 | A | H | 0.92 | 0.43 | 653 | 654 |
| K326Y | 326 | K | Y | 0.92 | 0.55 | 655 | 656 |
| S855P | 855 | S | P | 0.92 | 0.54 | 657 | 658 |
| C632T | 632 | C | T | 0.92 | 0.55 | 659 | 660 |
| S686F | 686 | S | F | 0.91 | 1.41 | 661 | 662 |
| K478P | 478 | K | P | 0.91 | 0.04 | 663 | 664 |
| F597K | 597 | F | K | 0.91 | 0.56 | 665 | 666 |
| D156K | 156 | D | K | 0.91 | 0.01 | 667 | 668 |
| E852N | 852 | E | N | 0.91 | 0.67 | 669 | 670 |
| R82N | 82 | R | N | 0.91 | 0.1 | 671 | 672 |
| Q1170T | 1170 | Q | T | 0.91 | 1.25 | 673 | 674 |
| S68K | 68 | S | K | 0.91 | 0.04 | 675 | 676 |
| G740P | 740 | G | P | 0.91 | 1.52 | 677 | 678 |
| S642G | 642 | S | G | 0.91 | 0.24 | 679 | 680 |
| K1080T | 1080 | K | T | 0.91 | 3.08 | 681 | 682 |
| E683C | 683 | E | C | 0.91 | 0.43 | 683 | 684 |
| Y262P | 262 | Y | P | 0.91 | 0.44 | 685 | 686 |
| A556V | 556 | A | V | 0.9 | 1.13 | 687 | 688 |
| P1153I | 1153 | P | I | 0.9 | 0.05 | 689 | 690 |
| D495G | 495 | D | G | 0.9 | 0.05 | 691 | 692 |
| T152K | 152 | T | K | 0.9 | 0.03 | 693 | 694 |
| K269F | 269 | K | F | 0.9 | 0.1 | 695 | 696 |
| L1047K | 1047 | L | K | 0.89 | 0.1 | 697 | 698 |
| K1025P | 1025 | K | P | 0.89 | 0.06 | 699 | 700 |
| F474P | 474 | F | P | 0.89 | 0.19 | 701 | 702 |
| K561C | 561 | K | C | 0.89 | 0.55 | 703 | 704 |
| P799V | 799 | P | V | 0.89 | 0.02 | 705 | 706 |
| K326G | 326 | K | G | 0.89 | 0.11 | 707 | 708 |
| A1194C | 1194 | A | C | 0.89 | 0.9 | 709 | 710 |
| N731G | 731 | N | G | 0.88 | 0.08 | 711 | 712 |
| I841G | 841 | I | G | 0.88 | 0.13 | 713 | 714 |
| P342F | 342 | P | F | 0.88 | 0.2 | 715 | 716 |
| I860T | 860 | I | T | 0.88 | 0.1 | 717 | 718 |
| Y646H | 646 | Y | H | 0.87 | 0.01 | 719 | 720 |
| P799Y | 799 | P | Y | 0.87 | 0.18 | 721 | 722 |
| S1024D | 1024 | S | D | 0.87 | 0.08 | 723 | 724 |
| K135P | 135 | K | P | 0.87 | 0.08 | 725 | 726 |
| T480D | 480 | T | D | 0.87 | 1.04 | 727 | 728 |
| L414G | 414 | L | G | 0.87 | 0.23 | 729 | 730 |
| A1057M | 1057 | A | M | 0.87 | 0.03 | 731 | 732 |
| I392D | 392 | I | D | 0.87 | 0.45 | 733 | 734 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K478D | 478 | K | D | 0.86 | 0.01 | 735 | 736 |
| F109R | 109 | F | R | 0.86 | 0.31 | 737 | 738 |
| P271S | 271 | P | S | 0.86 | 0.02 | 739 | 740 |
| N706F | 706 | N | F | 0.86 | 1.32 | 741 | 742 |
| A1169E | 1169 | A | E | 0.86 | 0.13 | 743 | 744 |
| D384L | 384 | D | L | 0.86 | 0.23 | 745 | 746 |
| D729C | 729 | D | C | 0.86 | 1.32 | 747 | 748 |
| S1152E | 1152 | S | E | 0.85 | 1.33 | 749 | 750 |
| F931A | 931 | F | A | 0.85 | 0.45 | 751 | 752 |
| K208S | 208 | K | S | 0.85 | 0.16 | 753 | 754 |
| D1203W | 1203 | D | W | 0.85 | 0.35 | 755 | 756 |
| K1015Y | 1015 | K | Y | 0.84 | 0.14 | 757 | 758 |
| H873W | 873 | H | W | 0.84 | 0.21 | 759 | 760 |
| R182D | 182 | R | D | 0.84 | 0.12 | 761 | 762 |
| P608N | 608 | P | N | 0.84 | 0.84 | 763 | 764 |
| E285W | 285 | E | W | 0.84 | 0.45 | 765 | 766 |
| F19D | 19 | F | D | 0.83 | 0.82 | 767 | 768 |
| K206A | 206 | K | A | 0.83 | 0.31 | 769 | 770 |
| K478Q | 478 | K | Q | 0.83 | 0.1 | 771 | 772 |
| E1202V | 1202 | E | V | 0.83 | 0.1 | 773 | 774 |
| G488T | 488 | G | T | 0.83 | 0.16 | 775 | 776 |
| S1024Y | 1024 | S | Y | 0.83 | 0.26 | 777 | 778 |
| I809C | 809 | I | C | 0.83 | 0.72 | 779 | 780 |
| D64T | 64 | D | T | 0.83 | 0.44 | 781 | 782 |
| N356W | 356 | N | W | 0.83 | 0.02 | 783 | 784 |
| D156Q | 156 | D | Q | 0.83 | 0.08 | 785 | 786 |
| I860Q | 860 | I | Q | 0.83 | 0.13 | 787 | 788 |
| L94Q | 94 | L | Q | 0.83 | 0.12 | 789 | 790 |
| K932Q | 932 | K | Q | 0.82 | 0.31 | 791 | 792 |
| N861M | 861 | N | M | 0.82 | 0.15 | 793 | 794 |
| E484L | 484 | E | L | 0.82 | 0.07 | 795 | 796 |
| E125V | 125 | E | V | 0.82 | 0.2 | 797 | 798 |
| G1069E | 1069 | G | E | 0.82 | 0.31 | 799 | 800 |
| F81E | 81 | F | E | 0.82 | 0.08 | 801 | 802 |
| K478S | 478 | K | S | 0.82 | 0.12 | 803 | 804 |
| I976Q | 976 | I | Q | 0.82 | 0.29 | 805 | 806 |
| S394L | 394 | S | L | 0.82 | 0.02 | 807 | 808 |
| E1220K | 1220 | E | K | 0.82 | 0.25 | 809 | 810 |
| G1143W | 1143 | G | W | 0.82 | 0.7 | 811 | 812 |
| A966C | 966 | A | C | 0.82 | 0.33 | 813 | 814 |
| A406R | 406 | A | R | 0.82 | 0.69 | 815 | 816 |
| K1079P | 1079 | K | P | 0.81 | 2.78 | 817 | 818 |
| K910C | 910 | K | C | 0.81 | 3.35 | 819 | 820 |
| I612R | 612 | I | R | 0.81 | 0.17 | 821 | 822 |
| N179F | 179 | N | F | 0.81 | 0.23 | 823 | 824 |
| E125C | 125 | E | C | 0.81 | 0.07 | 825 | 826 |
| G111Q | 111 | G | Q | 0.81 | 0.17 | 827 | 828 |
| L779W | 779 | L | W | 0.81 | 0.06 | 829 | 830 |
| D501V | 501 | D | V | 0.8 | 0.67 | 831 | 832 |
| L839F | 839 | L | F | 0.8 | 0.18 | 833 | 834 |
| F1198A | 1198 | F | A | 0.8 | 0.32 | 835 | 836 |
| L255W | 255 | L | W | 0.8 | 0.18 | 837 | 838 |
| E204S | 204 | E | S | 0.8 | 0.05 | 839 | 840 |
| F81T | 81 | F | T | 0.8 | 0.24 | 841 | 842 |
| E125T | 125 | E | T | 0.8 | 0.07 | 843 | 844 |
| S684L | 684 | S | L | 0.8 | 0.22 | 845 | 846 |
| K253H | 253 | K | H | 0.8 | 0.06 | 847 | 848 |
| R867H | 867 | R | H | 0.79 | 0.05 | 849 | 850 |
| E433W | 433 | E | W | 0.79 | 0.05 | 851 | 852 |
| S790F | 790 | S | F | 0.79 | 0.55 | 853 | 854 |
| G114Y | 114 | G | Y | 0.79 | 0.23 | 855 | 856 |
| P806M | 806 | P | M | 0.79 | 0.06 | 857 | 858 |
| A404N | 404 | A | N | 0.79 | 0.24 | 859 | 860 |
| Y294E | 294 | Y | E | 0.79 | 0.05 | 861 | 862 |
| Q264S | 264 | Q | S | 0.79 | 0.05 | 863 | 864 |
| S185L | 185 | S | L | 0.79 | 0.06 | 865 | 866 |
| N306C | 306 | N | C | 0.79 | 0.35 | 867 | 868 |
| Q399D | 399 | Q | D | 0.79 | 0.24 | 869 | 870 |
| Y426Q | 426 | Y | Q | 0.79 | 0.08 | 871 | 872 |
| L435I | 435 | L | I | 0.79 | 0.27 | 873 | 874 |
| N861L | 861 | N | L | 0.79 | 0.02 | 875 | 876 |
| V942I | 942 | V | I | 0.79 | 0.34 | 877 | 878 |
| E981V | 981 | E | V | 0.79 | 0.03 | 879 | 880 |
| K698C | 698 | K | C | 0.79 | 0.23 | 881 | 882 |
| R1138T | 1138 | R | T | 0.78 | 0.24 | 883 | 884 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| L301C | 301 | L | C | 0.78 | 0.61 | 885 | 886 |
| N327Y | 327 | N | Y | 0.78 | 0.23 | 887 | 888 |
| L899K | 899 | L | K | 0.78 | 0.23 | 889 | 890 |
| G991T | 991 | G | T | 0.78 | 0.23 | 891 | 892 |
| V851H | 851 | V | H | 0.78 | 0.34 | 893 | 894 |
| G1103K | 1103 | G | K | 0.78 | 0.34 | 895 | 896 |
| G1009L | 1009 | G | L | 0.78 | 0.23 | 897 | 898 |
| S317P | 317 | S | P | 0.78 | 0.23 | 899 | 900 |
| S934A | 934 | S | A | 0.78 | 0.34 | 901 | 902 |
| E852K | 852 | E | K | 0.78 | 0.23 | 903 | 904 |
| A108Y | 108 | A | Y | 0.78 | 0.34 | 905 | 906 |
| I860K | 860 | I | K | 0.78 | 0.15 | 907 | 908 |
| E939V | 939 | E | V | 0.78 | 0.24 | 909 | 910 |
| W999T | 999 | W | T | 0.78 | 1.32 | 911 | 912 |
| D188M | 188 | D | M | 0.78 | 0.24 | 913 | 914 |
| S1152D | 1152 | S | D | 0.78 | 1.22 | 915 | 916 |
| G335N | 335 | G | N | 0.78 | 0.23 | 917 | 918 |
| R158A | 158 | R | A | 0.78 | 0.23 | 919 | 920 |
| S905Q | 905 | S | Q | 0.77 | 0.23 | 921 | 922 |
| N1186E | 1186 | N | E | 0.77 | 0.33 | 923 | 924 |
| K979I | 979 | K | I | 0.77 | 0.34 | 925 | 926 |
| H633I | 633 | H | I | 0.77 | 0.34 | 927 | 928 |
| E795Q | 795 | E | Q | 0.77 | 0.09 | 929 | 930 |
| V38E | 38 | V | E | 0.77 | 0.09 | 931 | 932 |
| Y616V | 616 | Y | V | 0.77 | 0.34 | 933 | 934 |
| I809N | 809 | I | N | 0.77 | 0.23 | 935 | 936 |
| G488K | 488 | G | K | 0.77 | 0.23 | 937 | 938 |
| A1194R | 1194 | A | R | 0.77 | 1.31 | 939 | 940 |
| A364W | 364 | A | W | 0.77 | 0.23 | 941 | 942 |
| K1199F | 1199 | K | F | 0.77 | 0.74 | 943 | 944 |
| F227N | 227 | F | N | 0.77 | 0.66 | 945 | 946 |
| N1166E | 1166 | N | E | 0.77 | 0.15 | 947 | 948 |
| V511H | 511 | V | H | 0.77 | 0.22 | 949 | 950 |
| E292N | 292 | E | N | 0.77 | 0.34 | 951 | 952 |
| V491D | 491 | V | D | 0.77 | 0.1 | 953 | 954 |
| R1071V | 1071 | R | V | 0.77 | 0.34 | 955 | 956 |
| G477P | 477 | G | P | 0.76 | 0.02 | 957 | 958 |
| K688D | 688 | K | D | 0.76 | 0.1 | 959 | 960 |
| A506L | 506 | A | L | 0.76 | 1.33 | 961 | 962 |
| K310I | 310 | K | I | 0.76 | 0.34 | 963 | 964 |
| S288Q | 288 | S | Q | 0.76 | 2.07 | 965 | 966 |
| S394V | 394 | S | V | 0.76 | 0.08 | 967 | 968 |
| V673W | 673 | V | W | 0.76 | 0.23 | 969 | 970 |
| D641Q | 641 | D | Q | 0.76 | 0.23 | 971 | 972 |
| F227A | 227 | F | A | 0.76 | 0.33 | 973 | 974 |
| Y646W | 646 | Y | W | 0.76 | 0.12 | 975 | 976 |
| T977I | 977 | T | I | 0.76 | 0.21 | 977 | 978 |
| D156M | 156 | D | M | 0.76 | 0.2 | 979 | 980 |
| A1022R | 1022 | A | R | 0.76 | 0.98 | 981 | 982 |
| D1207S | 1207 | D | S | 0.76 | 0.01 | 983 | 984 |
| E947R | 947 | E | R | 0.76 | 0.07 | 985 | 986 |
| I841A | 841 | I | A | 0.76 | 0.03 | 987 | 988 |
| F466R | 466 | F | R | 0.76 | 0.14 | 989 | 990 |
| K20R | 20 | K | R | 0.75 | 0.12 | 991 | 992 |
| Y1106Q | 1106 | Y | Q | 0.75 | 1.22 | 993 | 994 |
| N1100D | 1100 | N | D | 0.75 | 0.22 | 995 | 996 |
| T814K | 814 | T | K | 0.75 | 0.1 | 997 | 998 |
| S286Q | 286 | S | Q | 0.75 | 1.19 | 999 | 1000 |
| T8A | 8 | T | A | 0.75 | 0.26 | 1001 | 1002 |
| E939K | 939 | E | K | 0.75 | 0.29 | 1003 | 1004 |
| A761Y | 761 | A | Y | 0.75 | 0.02 | 1005 | 1006 |
| Q1170F | 1170 | Q | F | 0.75 | 0.02 | 1007 | 1008 |
| Y974G | 974 | Y | G | 0.75 | 0.14 | 1009 | 1010 |
| A1129Q | 1129 | A | Q | 0.75 | 0.25 | 1011 | 1012 |
| D665N | 665 | D | N | 0.74 | 0.09 | 1013 | 1014 |
| D559A | 559 | D | A | 0.74 | 0.22 | 1015 | 1016 |
| K1025C | 1025 | K | C | 0.74 | 0.04 | 1017 | 1018 |
| K561I | 561 | K | I | 0.74 | 0.22 | 1019 | 1020 |
| E1044L | 1044 | E | L | 0.74 | 0.13 | 1021 | 1022 |
| M1128S | 1128 | M | S | 0.74 | 0.06 | 1023 | 1024 |
| I62A | 62 | I | A | 0.74 | 0.33 | 1025 | 1026 |
| R482D | 482 | R | D | 0.74 | 0.05 | 1027 | 1028 |
| K687G | 687 | K | G | 0.74 | 0.23 | 1029 | 1030 |
| K879L | 879 | K | L | 0.74 | 0.14 | 1031 | 1032 |
| L4N | 4 | L | N | 0.74 | 0.31 | 1033 | 1034 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K478G | 478 | K | G | 0.74 | 0.07 | 1035 | 1036 |
| E88A | 88 | E | A | 0.74 | 0.18 | 1037 | 1038 |
| R182L | 182 | R | L | 0.74 | 0.04 | 1039 | 1040 |
| R1165L | 1165 | R | L | 0.74 | 1.26 | 1041 | 1042 |
| V1154P | 1154 | V | P | 0.74 | 0.05 | 1043 | 1044 |
| A685M | 685 | A | M | 0.74 | 0.03 | 1045 | 1046 |
| L875H | 875 | L | H | 0.73 | 1.26 | 1047 | 1048 |
| G475I | 475 | G | I | 0.73 | 0.08 | 1049 | 1050 |
| N1081Q | 1081 | N | Q | 0.73 | 0.17 | 1051 | 1052 |
| F655D | 655 | F | D | 0.73 | 1.32 | 1053 | 1054 |
| K1015F | 1015 | K | F | 0.73 | 0.06 | 1055 | 1056 |
| E125M | 125 | E | M | 0.73 | 0.2 | 1057 | 1058 |
| F337T | 337 | F | T | 0.73 | 0.1 | 1059 | 1060 |
| Y549G | 549 | Y | G | 0.73 | 0.09 | 1061 | 1062 |
| R182P | 182 | R | P | 0.73 | 0.07 | 1063 | 1064 |
| S409N | 409 | S | N | 0.73 | 0.26 | 1065 | 1066 |
| K937V | 937 | K | V | 0.73 | 0.25 | 1067 | 1068 |
| I344G | 344 | I | G | 0.73 | 0.09 | 1069 | 1070 |
| K1015D | 1015 | K | D | 0.72 | 0.08 | 1071 | 1072 |
| T778R | 778 | T | R | 0.72 | 0.34 | 1073 | 1074 |
| F19E | 19 | F | E | 0.72 | 0.32 | 1075 | 1076 |
| N577E | 577 | N | E | 0.72 | 0.16 | 1077 | 1078 |
| K478V | 478 | K | V | 0.72 | 0.06 | 1079 | 1080 |
| T378G | 378 | T | G | 0.72 | 0.66 | 1081 | 1082 |
| K478T | 478 | K | T | 0.72 | 0.12 | 1083 | 1084 |
| D654M | 654 | D | M | 0.72 | 1.15 | 1085 | 1086 |
| R1033G | 1033 | R | G | 0.72 | 0.26 | 1087 | 1088 |
| E858Y | 858 | E | Y | 0.72 | 0.08 | 1089 | 1090 |
| I866R | 866 | I | R | 0.72 | 0.65 | 1091 | 1092 |
| E95S | 95 | E | S | 0.72 | 0.03 | 1093 | 1094 |
| K434T | 434 | K | T | 0.71 | 2.2 | 1095 | 1096 |
| F81D | 81 | F | D | 0.71 | 0.06 | 1097 | 1098 |
| M456L | 456 | M | L | 0.71 | 0.09 | 1099 | 1100 |
| S780V | 780 | S | V | 0.71 | 0.32 | 1101 | 1102 |
| I369D | 369 | I | D | 0.71 | 0.24 | 1103 | 1104 |
| V1083S | 1083 | V | S | 0.71 | 0.19 | 1105 | 1106 |
| L555I | 555 | L | I | 0.71 | 0.06 | 1107 | 1108 |
| K1096Q | 1096 | K | Q | 0.7 | 0.65 | 1109 | 1110 |
| R482Q | 482 | R | Q | 0.7 | 0.01 | 1111 | 1112 |
| A742W | 742 | A | W | 0.7 | 0.55 | 1113 | 1114 |
| K1121I | 1121 | K | I | 0.7 | 0.08 | 1115 | 1116 |
| S644R | 644 | S | R | 0.7 | 0.7 | 1117 | 1118 |
| K1096F | 1096 | K | F | 0.7 | 0.36 | 1119 | 1120 |
| N306E | 306 | N | E | 0.7 | 0.36 | 1121 | 1122 |
| N306G | 306 | N | G | 0.7 | 1.2 | 1123 | 1124 |
| Q401V | 401 | Q | V | 0.7 | 0.13 | 1125 | 1126 |
| G393P | 393 | G | P | 0.7 | 0.21 | 1127 | 1128 |
| F197H | 197 | F | H | 0.7 | 0.1 | 1129 | 1130 |
| K948E | 948 | K | E | 0.7 | 0.12 | 1131 | 1132 |
| T346Q | 346 | T | Q | 0.69 | 1.2 | 1133 | 1134 |
| N263W | 263 | N | W | 0.69 | 0.05 | 1135 | 1136 |
| D156T | 156 | D | T | 0.69 | 0.05 | 1137 | 1138 |
| G293P | 293 | G | P | 0.69 | 0.1 | 1139 | 1140 |
| D782M | 782 | D | M | 0.69 | 0.06 | 1141 | 1142 |
| F119K | 119 | F | K | 0.69 | 1.18 | 1143 | 1144 |
| K415A | 415 | K | A | 0.69 | 1.19 | 1145 | 1146 |
| R1138Q | 1138 | R | Q | 0.69 | 0.21 | 1147 | 1148 |
| K1101E | 1101 | K | E | 0.69 | 1.09 | 1149 | 1150 |
| Y1018R | 1018 | Y | R | 0.69 | 1.24 | 1151 | 1152 |
| N1105S | 1105 | N | S | 0.69 | 0.2 | 1153 | 1154 |
| A375Y | 375 | A | Y | 0.69 | 0.1 | 1155 | 1156 |
| S312Y | 312 | S | Y | 0.69 | 1.2 | 1157 | 1158 |
| R182Q | 182 | R | Q | 0.69 | 0.05 | 1159 | 1160 |
| L446K | 446 | L | K | 0.69 | 0.21 | 1161 | 1162 |
| I205E | 205 | I | E | 0.69 | 1.09 | 1163 | 1164 |
| V300K | 300 | V | K | 0.69 | 0.21 | 1165 | 1166 |
| G1103A | 1103 | G | A | 0.69 | 0.11 | 1167 | 1168 |
| V921M | 921 | V | M | 0.69 | 1.19 | 1169 | 1170 |
| K208A | 208 | K | A | 0.69 | 0.21 | 1171 | 1172 |
| K274G | 274 | K | G | 0.69 | 0.09 | 1173 | 1174 |
| W1063N | 1063 | W | N | 0.69 | 0.06 | 1175 | 1176 |
| E852T | 852 | E | T | 0.68 | 0.17 | 1177 | 1178 |
| S609D | 609 | S | D | 0.68 | 0.09 | 1179 | 1180 |
| T295V | 295 | T | V | 0.68 | 0.22 | 1181 | 1182 |
| T1019E | 1019 | T | E | 0.68 | 0.07 | 1183 | 1184 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| L586T | 586 | L | T | 0.68 | 0.22 | 1185 | 1186 |
| M187D | 187 | M | D | 0.68 | 0.04 | 1187 | 1188 |
| Q567C | 567 | Q | C | 0.68 | 0.03 | 1189 | 1190 |
| E298A | 298 | E | A | 0.68 | 1.19 | 1191 | 1192 |
| E925R | 925 | E | R | 0.68 | 0.4 | 1193 | 1194 |
| P342E | 342 | P | E | 0.68 | 0.12 | 1195 | 1196 |
| Y1049I | 1049 | Y | I | 0.68 | 0.1 | 1197 | 1198 |
| G1183P | 1183 | G | P | 0.68 | 1.18 | 1199 | 1200 |
| I798C | 798 | I | C | 0.68 | 0.36 | 1201 | 1202 |
| L738R | 738 | L | R | 0.68 | 0.39 | 1203 | 1204 |
| K478I | 478 | K | I | 0.68 | 0.09 | 1205 | 1206 |
| F682A | 682 | F | A | 0.68 | 0.62 | 1207 | 1208 |
| S1024P | 1024 | S | P | 0.68 | 0.14 | 1209 | 1210 |
| D832S | 832 | D | S | 0.68 | 0.43 | 1211 | 1212 |
| K390S | 390 | K | S | 0.68 | 0.06 | 1213 | 1214 |
| F655N | 655 | F | N | 0.67 | 0.26 | 1215 | 1216 |
| P647Y | 647 | P | Y | 0.67 | 1.19 | 1217 | 1218 |
| L914T | 914 | L | T | 0.67 | 0.66 | 1219 | 1220 |
| S1157Q | 1157 | S | Q | 0.67 | 0.41 | 1221 | 1222 |
| N928V | 928 | N | V | 0.67 | 0.09 | 1223 | 1224 |
| F525N | 525 | F | N | 0.67 | 0.09 | 1225 | 1226 |
| E858L | 858 | E | L | 0.67 | 0.15 | 1227 | 1228 |
| N656F | 656 | N | F | 0.67 | 0.21 | 1229 | 1230 |
| K272W | 272 | K | W | 0.67 | 0.11 | 1231 | 1232 |
| K444G | 444 | K | G | 0.67 | 0.08 | 1233 | 1234 |
| G902M | 902 | G | M | 0.67 | 0.17 | 1235 | 1236 |
| I1195K | 1195 | I | K | 0.67 | 0.09 | 1237 | 1238 |
| S1029K | 1029 | S | K | 0.67 | 0.37 | 1239 | 1240 |
| D156S | 156 | D | S | 0.66 | 0.09 | 1241 | 1242 |
| L727S | 727 | L | S | 0.66 | 0.49 | 1243 | 1244 |
| Y562E | 562 | Y | E | 0.66 | 0.24 | 1245 | 1246 |
| F884T | 884 | F | T | 0.66 | 0.72 | 1247 | 1248 |
| T967C | 967 | T | C | 0.66 | 2.42 | 1249 | 1250 |
| V280T | 280 | V | T | 0.66 | 2.72 | 1251 | 1252 |
| N861F | 861 | N | F | 0.66 | 0.16 | 1253 | 1254 |
| S143L | 143 | S | L | 0.65 | 0.25 | 1255 | 1256 |
| S1020C | 1020 | S | C | 0.65 | 0.94 | 1257 | 1258 |
| S394W | 394 | S | W | 0.65 | 0.08 | 1259 | 1260 |
| D537C | 537 | D | C | 0.65 | 1.19 | 1261 | 1262 |
| G624C | 624 | G | C | 0.65 | 0.38 | 1263 | 1264 |
| F289A | 289 | F | A | 0.65 | 0.06 | 1265 | 1266 |
| K92R | 92 | K | R | 0.65 | 0.16 | 1267 | 1268 |
| V24Q | 24 | V | Q | 0.65 | 0.12 | 1269 | 1270 |
| I798S | 798 | I | S | 0.65 | 0.06 | 1271 | 1272 |
| N179Q | 179 | N | Q | 0.65 | 0.03 | 1273 | 1274 |
| I241D | 241 | I | D | 0.65 | 1.08 | 1275 | 1276 |
| E217G | 217 | E | G | 0.65 | 0.21 | 1277 | 1278 |
| R182C | 182 | R | C | 0.65 | 0.13 | 1279 | 1280 |
| N849R | 849 | N | R | 0.65 | 0.44 | 1281 | 1282 |
| R1138M | 1138 | R | M | 0.65 | 0.15 | 1283 | 1284 |
| N577W | 577 | N | W | 0.65 | 0.05 | 1285 | 1286 |
| K1025Y | 1025 | K | Y | 0.65 | 0.64 | 1287 | 1288 |
| T480V | 480 | T | V | 0.65 | 0.07 | 1289 | 1290 |
| I1195G | 1195 | I | G | 0.65 | 0.16 | 1291 | 1292 |
| M986C | 986 | M | C | 0.65 | 0.54 | 1293 | 1294 |
| V411Q | 411 | V | Q | 0.64 | 0.54 | 1295 | 1296 |
| L914G | 914 | L | G | 0.64 | 0.23 | 1297 | 1298 |
| K274T | 274 | K | T | 0.64 | 0.04 | 1299 | 1300 |
| V758W | 758 | V | W | 0.64 | 0.08 | 1301 | 1302 |
| F745N | 745 | F | N | 0.64 | 1.12 | 1303 | 1304 |
| L94H | 94 | L | H | 0.64 | 0.54 | 1305 | 1306 |
| S905C | 905 | S | C | 0.64 | 0.03 | 1307 | 1308 |
| K310D | 310 | K | D | 0.64 | 0.72 | 1309 | 1310 |
| S465Q | 465 | S | Q | 0.64 | 0.1 | 1311 | 1312 |
| F931V | 931 | F | V | 0.64 | 0.17 | 1313 | 1314 |
| P342W | 342 | P | W | 0.64 | 0.02 | 1315 | 1316 |
| P589Y | 589 | P | Y | 0.64 | 0.64 | 1317 | 1318 |
| K1155V | 1155 | K | V | 0.64 | 0.06 | 1319 | 1320 |
| P806H | 806 | P | H | 0.64 | 0.41 | 1321 | 1322 |
| K269S | 269 | K | S | 0.64 | 0.07 | 1323 | 1324 |
| I124N | 124 | I | N | 0.64 | 0.44 | 1325 | 1326 |
| E416P | 416 | E | P | 0.64 | 0.7 | 1327 | 1328 |
| P799C | 799 | P | C | 0.63 | 0.04 | 1329 | 1330 |
| V958M | 958 | V | M | 0.63 | 0.25 | 1331 | 1332 |
| N263L | 263 | N | L | 0.63 | 0.55 | 1333 | 1334 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| F1045N | 1045 | F | N | 0.63 | 0.03 | 1335 | 1336 |
| K1015M | 1015 | K | M | 0.63 | 0.06 | 1337 | 1338 |
| N30Y | 30 | N | Y | 0.63 | 0.04 | 1339 | 1340 |
| L593T | 593 | L | T | 0.63 | 0.64 | 1341 | 1342 |
| E412C | 412 | E | C | 0.63 | 0.12 | 1343 | 1344 |
| E852W | 852 | E | W | 0.63 | 0.39 | 1345 | 1346 |
| P515C | 515 | P | C | 0.63 | 0.28 | 1347 | 1348 |
| K26C | 26 | K | C | 0.63 | 1.1 | 1349 | 1350 |
| A1201G | 1201 | A | G | 0.63 | 0.54 | 1351 | 1352 |
| S14V | 14 | S | V | 0.63 | 0.06 | 1353 | 1354 |
| V428Y | 428 | V | Y | 0.63 | 0.27 | 1355 | 1356 |
| K269A | 269 | K | A | 0.63 | 0.16 | 1357 | 1358 |
| E98H | 98 | E | H | 0.63 | 0.05 | 1359 | 1360 |
| N226T | 226 | N | T | 0.63 | 0.35 | 1361 | 1362 |
| I868L | 868 | I | L | 0.63 | 0.03 | 1363 | 1364 |
| N864L | 864 | N | L | 0.63 | 0.54 | 1365 | 1366 |
| E39I | 39 | E | I | 0.63 | 0.09 | 1367 | 1368 |
| G1159I | 1159 | G | I | 0.63 | 0.38 | 1369 | 1370 |
| M1134S | 1134 | M | S | 0.63 | 1.32 | 1371 | 1372 |
| Y616E | 616 | Y | E | 0.63 | 0.03 | 1373 | 1374 |
| V491N | 491 | V | N | 0.63 | 0.16 | 1375 | 1376 |
| E178I | 178 | E | I | 0.63 | 0.44 | 1377 | 1378 |
| I1034E | 1034 | I | E | 0.63 | 0.08 | 1379 | 1380 |
| T777L | 777 | T | L | 0.63 | 0.34 | 1381 | 1382 |
| L180E | 180 | L | E | 0.63 | 0.24 | 1383 | 1384 |
| T814L | 814 | T | L | 0.63 | 0.05 | 1385 | 1386 |
| V511S | 511 | V | S | 0.62 | 0.42 | 1387 | 1388 |
| L210K | 210 | L | K | 0.62 | 0.2 | 1389 | 1390 |
| Y469A | 469 | Y | A | 0.62 | 0.08 | 1391 | 1392 |
| F273P | 273 | F | P | 0.62 | 0.23 | 1393 | 1394 |
| S163D | 163 | S | D | 0.62 | 0.59 | 1395 | 1396 |
| G1196S | 1196 | G | S | 0.62 | 0.38 | 1397 | 1398 |
| N33W | 33 | N | W | 0.62 | 0.06 | 1399 | 1400 |
| K591H | 591 | K | H | 0.62 | 0.64 | 1401 | 1402 |
| K688S | 688 | K | S | 0.62 | 0.08 | 1403 | 1404 |
| I996M | 996 | I | M | 0.62 | 0.01 | 1405 | 1406 |
| V851R | 851 | V | R | 0.62 | 0.1 | 1407 | 1408 |
| E913Y | 913 | E | Y | 0.62 | 0.74 | 1409 | 1410 |
| K478N | 478 | K | N | 0.62 | 0.05 | 1411 | 1412 |
| D156C | 156 | D | C | 0.62 | 0.17 | 1413 | 1414 |
| K536R | 536 | K | R | 0.62 | 0.01 | 1415 | 1416 |
| K688P | 688 | K | P | 0.62 | 0.08 | 1417 | 1418 |
| V758Q | 758 | V | Q | 0.62 | 0.05 | 1419 | 1420 |
| E125Q | 125 | E | Q | 0.61 | 0.03 | 1421 | 1422 |
| S739I | 739 | S | I | 0.61 | 0.44 | 1423 | 1424 |
| R35A | 35 | R | A | 0.61 | 0.28 | 1425 | 1426 |
| D823M | 823 | D | M | 0.61 | 0.45 | 1427 | 1428 |
| T1019D | 1019 | T | D | 0.61 | 0.03 | 1429 | 1430 |
| P1153L | 1153 | P | L | 0.61 | 0.05 | 1431 | 1432 |
| K1025A | 1025 | K | A | 0.61 | 0.15 | 1433 | 1434 |
| E795L | 795 | E | L | 0.61 | 0.05 | 1435 | 1436 |
| F1043C | 1043 | F | C | 0.61 | 0.01 | 1437 | 1438 |
| V491H | 491 | V | H | 0.61 | 0.17 | 1439 | 1440 |
| E165N | 165 | E | N | 0.61 | 0.28 | 1441 | 1442 |
| P799K | 799 | P | K | 0.61 | 0.09 | 1443 | 1444 |
| D46R | 46 | D | R | 0.61 | 0.01 | 1445 | 1446 |
| A685Q | 685 | A | Q | 0.61 | 0.03 | 1447 | 1448 |
| Y781E | 781 | Y | E | 0.6 | 0.26 | 1449 | 1450 |
| N30F | 30 | N | F | 0.6 | 0.02 | 1451 | 1452 |
| N1070R | 1070 | N | R | 0.6 | 0.01 | 1453 | 1454 |
| P806E | 806 | P | E | 0.6 | 0.5 | 1455 | 1456 |
| E913N | 913 | E | N | 0.6 | 0.05 | 1457 | 1458 |
| Y1018Q | 1018 | Y | Q | 0.6 | 0.54 | 1459 | 1460 |
| L751C | 751 | L | C | 0.6 | 0.57 | 1461 | 1462 |
| G588Y | 588 | G | Y | 0.6 | 0.36 | 1463 | 1464 |
| L927D | 927 | L | D | 0.6 | 0.16 | 1465 | 1466 |
| K984A | 984 | K | A | 0.6 | 0.22 | 1467 | 1468 |
| I1141R | 1141 | I | R | 0.6 | 0.11 | 1469 | 1470 |
| R86F | 86 | R | F | 0.6 | 0.11 | 1471 | 1472 |
| G49C | 49 | G | C | 0.6 | 0.19 | 1473 | 1474 |
| E207P | 207 | E | P | 0.59 | 0.34 | 1475 | 1476 |
| K1121P | 1121 | K | P | 0.59 | 0.15 | 1477 | 1478 |
| A1212G | 1212 | A | G | 0.59 | 0.09 | 1479 | 1480 |
| E479C | 479 | E | C | 0.59 | 0 | 1481 | 1482 |
| G49T | 49 | G | T | 0.59 | 0.45 | 1483 | 1484 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| Y381M | 381 | Y | M | 0.59 | 0.07 | 1485 | 1486 |
| D156I | 156 | D | I | 0.59 | 0.11 | 1487 | 1488 |
| K421S | 421 | K | S | 0.59 | 0.18 | 1489 | 1490 |
| L308C | 308 | L | C | 0.59 | 0.03 | 1491 | 1492 |
| K1177Q | 1177 | K | Q | 0.59 | 0.1 | 1493 | 1494 |
| Y854R | 854 | Y | R | 0.59 | 0.12 | 1495 | 1496 |
| S394F | 394 | S | F | 0.59 | 0.93 | 1497 | 1498 |
| K272G | 272 | K | G | 0.59 | 0.08 | 1499 | 1500 |
| V357E | 357 | V | E | 0.59 | 0.15 | 1501 | 1502 |
| E39Q | 39 | E | Q | 0.59 | 0.15 | 1503 | 1504 |
| D654K | 654 | D | K | 0.59 | 0.33 | 1505 | 1506 |
| K1121V | 1121 | K | V | 0.59 | 0.02 | 1507 | 1508 |
| H759F | 759 | H | F | 0.59 | 0.29 | 1509 | 1510 |
| Y516G | 516 | Y | G | 0.59 | 0.41 | 1511 | 1512 |
| S117T | 117 | S | T | 0.59 | 0.05 | 1513 | 1514 |
| L756K | 756 | L | K | 0.59 | 0.05 | 1515 | 1516 |
| A685L | 685 | A | L | 0.58 | 0.2 | 1517 | 1518 |
| A652V | 652 | A | V | 0.58 | 0.69 | 1519 | 1520 |
| K568P | 568 | K | P | 0.58 | 0.11 | 1521 | 1522 |
| F474T | 474 | F | T | 0.58 | 0.07 | 1523 | 1524 |
| D729Y | 729 | D | Y | 0.58 | 0.52 | 1525 | 1526 |
| I860G | 860 | I | G | 0.58 | 0.16 | 1527 | 1528 |
| L400D | 400 | L | D | 0.58 | 0.05 | 1529 | 1530 |
| G1143I | 1143 | G | I | 0.58 | 0.05 | 1531 | 1532 |
| E898A | 898 | E | A | 0.58 | 0.05 | 1533 | 1534 |
| D194H | 194 | D | H | 0.58 | 0.93 | 1535 | 1536 |
| G1143R | 1143 | G | R | 0.58 | 0.02 | 1537 | 1538 |
| K1205Y | 1205 | K | Y | 0.58 | 0.05 | 1539 | 1540 |
| T307G | 307 | T | G | 0.58 | 0.06 | 1541 | 1542 |
| A970K | 970 | A | K | 0.58 | 0.93 | 1543 | 1544 |
| V1089Q | 1089 | V | Q | 0.58 | 0.05 | 1545 | 1546 |
| F273A | 273 | F | A | 0.58 | 0.07 | 1547 | 1548 |
| V842T | 842 | V | T | 0.58 | 0.4 | 1549 | 1550 |
| F702K | 702 | F | K | 0.58 | 0.06 | 1551 | 1552 |
| A406K | 406 | A | K | 0.58 | 0.25 | 1553 | 1554 |
| S212K | 212 | S | K | 0.58 | 0.05 | 1555 | 1556 |
| S143A | 143 | S | A | 0.58 | 0 | 1557 | 1558 |
| K514H | 514 | K | H | 0.58 | 0.07 | 1559 | 1560 |
| H759W | 759 | H | W | 0.58 | 0.26 | 1561 | 1562 |
| A1046R | 1046 | A | R | 0.58 | 0.06 | 1563 | 1564 |
| S431W | 431 | S | W | 0.58 | 0.05 | 1565 | 1566 |
| R174F | 174 | R | F | 0.58 | 0.93 | 1567 | 1568 |
| K116E | 116 | K | E | 0.58 | 0.05 | 1569 | 1570 |
| E223R | 223 | E | R | 0.58 | 0.93 | 1571 | 1572 |
| F1043G | 1043 | F | G | 0.58 | 0.06 | 1573 | 1574 |
| L856Y | 856 | L | Y | 0.58 | 0.05 | 1575 | 1576 |
| K267S | 267 | K | S | 0.58 | 0.05 | 1577 | 1578 |
| K522L | 522 | K | L | 0.58 | 0.91 | 1579 | 1580 |
| A172H | 172 | A | H | 0.58 | 0.05 | 1581 | 1582 |
| N263E | 263 | N | E | 0.57 | 0.05 | 1583 | 1584 |
| F931R | 931 | F | R | 0.57 | 0.05 | 1585 | 1586 |
| K910E | 910 | K | E | 0.57 | 0.33 | 1587 | 1588 |
| D708L | 708 | D | L | 0.57 | 0.06 | 1589 | 1590 |
| E674M | 674 | E | M | 0.57 | 0.19 | 1591 | 1592 |
| I860H | 860 | I | H | 0.57 | 0.05 | 1593 | 1594 |
| K107D | 107 | K | D | 0.57 | 0.19 | 1595 | 1596 |
| L1091Y | 1091 | L | Y | 0.57 | 1.03 | 1597 | 1598 |
| E1044Y | 1044 | E | Y | 0.57 | 0.06 | 1599 | 1600 |
| E137L | 137 | E | L | 0.57 | 0.62 | 1601 | 1602 |
| F131P | 131 | F | P | 0.57 | 0.93 | 1603 | 1604 |
| L914H | 914 | L | H | 0.57 | 0.93 | 1605 | 1606 |
| L839T | 839 | L | T | 0.57 | 0.08 | 1607 | 1608 |
| T1019K | 1019 | T | K | 0.57 | 1.03 | 1609 | 1610 |
| T1019R | 1019 | T | R | 0.57 | 1.03 | 1611 | 1612 |
| L459D | 459 | L | D | 0.57 | 0.93 | 1613 | 1614 |
| F304N | 304 | F | N | 0.57 | 0.06 | 1615 | 1616 |
| N238L | 238 | N | L | 0.57 | 0.05 | 1617 | 1618 |
| Q1136M | 1136 | Q | M | 0.57 | 0.29 | 1619 | 1620 |
| I1021R | 1021 | I | R | 0.57 | 1.39 | 1621 | 1622 |
| K167T | 167 | K | T | 0.57 | 0.05 | 1623 | 1624 |
| T181H | 181 | T | H | 0.57 | 0.05 | 1625 | 1626 |
| K972R | 972 | K | R | 0.57 | 0.08 | 1627 | 1628 |
| N1186M | 1186 | N | M | 0.57 | 1.03 | 1629 | 1630 |
| K457I | 457 | K | I | 0.57 | 0.05 | 1631 | 1632 |
| K457M | 457 | K | M | 0.57 | 0.93 | 1633 | 1634 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| S445E | 445 | S | E | 0.57 | 0.19 | 1635 | 1636 |
| L324I | 324 | L | I | 0.57 | 0.16 | 1637 | 1638 |
| D871A | 871 | D | A | 0.57 | 0.05 | 1639 | 1640 |
| D450C | 450 | D | C | 0.57 | 1.03 | 1641 | 1642 |
| Q231P | 231 | Q | P | 0.57 | 0.05 | 1643 | 1644 |
| I904C | 904 | I | C | 0.57 | 0.22 | 1645 | 1646 |
| K595Q | 595 | K | Q | 0.57 | 0.06 | 1647 | 1648 |
| A406C | 406 | A | C | 0.57 | 0.29 | 1649 | 1650 |
| W362Y | 362 | W | Y | 0.57 | 0.92 | 1651 | 1652 |
| H909P | 909 | H | P | 0.57 | 0.61 | 1653 | 1654 |
| D625M | 625 | D | M | 0.57 | 0.06 | 1655 | 1656 |
| P1176N | 1176 | P | N | 0.56 | 0.05 | 1657 | 1658 |
| A1173K | 1173 | A | K | 0.56 | 0.05 | 1659 | 1660 |
| L66C | 66 | L | C | 0.56 | 1.02 | 1661 | 1662 |
| Q529G | 529 | Q | G | 0.56 | 0.07 | 1663 | 1664 |
| K1121F | 1121 | K | F | 0.56 | 0.12 | 1665 | 1666 |
| G532P | 532 | G | P | 0.56 | 0.07 | 1667 | 1668 |
| R182T | 182 | R | T | 0.56 | 0.13 | 1669 | 1670 |
| F490Q | 490 | F | Q | 0.56 | 1.04 | 1671 | 1672 |
| K1121G | 1121 | K | G | 0.56 | 0.1 | 1673 | 1674 |
| K614P | 614 | K | P | 0.56 | 0.64 | 1675 | 1676 |
| E858T | 858 | E | T | 0.56 | 0.93 | 1677 | 1678 |
| K811F | 811 | K | F | 0.56 | 0.05 | 1679 | 1680 |
| D505T | 505 | D | T | 0.56 | 0.07 | 1681 | 1682 |
| S1132V | 1132 | S | V | 0.56 | 0.84 | 1683 | 1684 |
| K522I | 522 | K | I | 0.56 | 0.31 | 1685 | 1686 |
| N309G | 309 | N | G | 0.56 | 0.06 | 1687 | 1688 |
| V1083T | 1083 | V | T | 0.56 | 2.08 | 1689 | 1690 |
| S780Q | 780 | S | Q | 0.56 | 0.08 | 1691 | 1692 |
| K427D | 427 | K | D | 0.56 | 0.05 | 1693 | 1694 |
| F474N | 474 | F | N | 0.56 | 0.06 | 1695 | 1696 |
| H1228C | 1228 | H | C | 0.56 | 0.05 | 1697 | 1698 |
| F289M | 289 | F | M | 0.56 | 1.16 | 1699 | 1700 |
| Y606L | 606 | Y | L | 0.55 | 0.06 | 1701 | 1702 |
| I111A | 1111 | I | A | 0.55 | 0.26 | 1703 | 1704 |
| K274R | 274 | K | R | 0.55 | 0.18 | 1705 | 1706 |
| T230H | 230 | T | H | 0.55 | 0.06 | 1707 | 1708 |
| E579F | 579 | E | F | 0.55 | 0.06 | 1709 | 1710 |
| T16G | 16 | T | G | 0.55 | 0.95 | 1711 | 1712 |
| K269G | 269 | K | G | 0.55 | 0.07 | 1713 | 1714 |
| G353K | 353 | G | K | 0.55 | 0.3 | 1715 | 1716 |
| I417H | 417 | I | H | 0.55 | 0.47 | 1717 | 1718 |
| Y781S | 781 | Y | S | 0.55 | 0.13 | 1719 | 1720 |
| I860N | 860 | I | N | 0.55 | 0.04 | 1721 | 1722 |
| R737D | 737 | R | D | 0.55 | 0.19 | 1723 | 1724 |
| K1015W | 1015 | K | W | 0.55 | 0.07 | 1725 | 1726 |
| K361Y | 361 | K | Y | 0.55 | 0.06 | 1727 | 1728 |
| N582R | 582 | N | R | 0.55 | 0.06 | 1729 | 1730 |
| F884R | 884 | F | R | 0.55 | 0.39 | 1731 | 1732 |
| L210T | 210 | L | T | 0.55 | 0.31 | 1733 | 1734 |
| K110F | 110 | K | F | 0.55 | 0.11 | 1735 | 1736 |
| K1121S | 1121 | K | S | 0.55 | 0.11 | 1737 | 1738 |
| K917V | 917 | K | V | 0.55 | 0.31 | 1739 | 1740 |
| 685Y | 685 | A | Y | 0.55 | 0.23 | 1741 | 1742 |
| A364C | 364 | A | C | 0.55 | 0.03 | 1743 | 1744 |
| M949Q | 949 | M | Q | 0.54 | 0.24 | 1745 | 1746 |
| D1207C | 1207 | D | C | 0.54 | 0.13 | 1747 | 1748 |
| I1111C | 1111 | I | C | 0.54 | 0.31 | 1749 | 1750 |
| K444Y | 444 | K | Y | 0.54 | 0.41 | 1751 | 1752 |
| M1128E | 1128 | M | E | 0.54 | 0.05 | 1753 | 1754 |
| L301Y | 301 | L | Y | 0.54 | 0.22 | 1755 | 1756 |
| N1081P | 1081 | N | P | 0.54 | 0.31 | 1757 | 1758 |
| Y549W | 549 | Y | W | 0.54 | 0.23 | 1759 | 1760 |
| V280M | 280 | V | M | 0.54 | 0.26 | 1761 | 1762 |
| G222L | 222 | G | L | 0.54 | 0.31 | 1763 | 1764 |
| S1119M | 1119 | S | M | 0.54 | 0.01 | 1765 | 1766 |
| A166T | 166 | A | T | 0.54 | 0.31 | 1767 | 1768 |
| A166K | 166 | A | K | 0.54 | 0.23 | 1769 | 1770 |
| T1019I | 1019 | T | I | 0.54 | 0.42 | 1771 | 1772 |
| K1121W | 1121 | K | W | 0.54 | 0.04 | 1773 | 1774 |
| R747W | 747 | R | W | 0.54 | 0.54 | 1775 | 1776 |
| K787F | 787 | K | F | 0.54 | 0.83 | 1777 | 1778 |
| D122A | 122 | D | A | 0.54 | 0.03 | 1779 | 1780 |
| K361L | 361 | K | L | 0.54 | 0.68 | 1781 | 1782 |
| T181E | 181 | T | E | 0.54 | 0.05 | 1783 | 1784 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K269H | 269 | K | H | 0.53 | 0.12 | 1785 | 1786 |
| A966E | 966 | A | E | 0.53 | 0.12 | 1787 | 1788 |
| T27P | 27 | T | P | 0.53 | 0.04 | 1789 | 1790 |
| D1207G | 1207 | D | G | 0.53 | 0.07 | 1791 | 1792 |
| H502V | 502 | H | V | 0.53 | 0.48 | 1793 | 1794 |
| N306Q | 306 | N | Q | 0.53 | 0.04 | 1795 | 1796 |
| V757R | 757 | V | R | 0.53 | 0.15 | 1797 | 1798 |
| R482Y | 482 | R | Y | 0.53 | 0.05 | 1799 | 1800 |
| Y918M | 918 | Y | M | 0.53 | 0.16 | 1801 | 1802 |
| L1098M | 1098 | L | M | 0.53 | 0.01 | 1803 | 1804 |
| Y605M | 605 | Y | M | 0.53 | 0.05 | 1805 | 1806 |
| L914E | 914 | L | E | 0.53 | 0.03 | 1807 | 1808 |
| G475D | 475 | G | D | 0.53 | 0.08 | 1809 | 1810 |
| R747D | 747 | R | D | 0.53 | 0.04 | 1811 | 1812 |
| K591L | 591 | K | L | 0.53 | 0.36 | 1813 | 1814 |
| M722S | 722 | M | S | 0.53 | 0.18 | 1815 | 1816 |
| D133C | 133 | D | C | 0.53 | 0.12 | 1817 | 1818 |
| V758T | 758 | V | T | 0.53 | 0.19 | 1819 | 1820 |
| E285C | 285 | E | C | 0.53 | 0.41 | 1821 | 1822 |
| N933R | 933 | N | R | 0.52 | 0.39 | 1823 | 1824 |
| S763V | 763 | S | V | 0.52 | 0.11 | 1825 | 1826 |
| D1207N | 1207 | D | N | 0.52 | 0.15 | 1827 | 1828 |
| N590H | 590 | N | H | 0.52 | 0.24 | 1829 | 1830 |
| S394E | 394 | S | E | 0.52 | 0.03 | 1831 | 1832 |
| K272C | 272 | K | C | 0.52 | 0.03 | 1833 | 1834 |
| E683L | 683 | E | L | 0.52 | 0.11 | 1835 | 1836 |
| G341L | 341 | G | L | 0.52 | 0.28 | 1837 | 1838 |
| P271G | 271 | P | G | 0.52 | 0.11 | 1839 | 1840 |
| L1192C | 1192 | L | C | 0.52 | 0.01 | 1841 | 1842 |
| S1093I | 1093 | S | I | 0.52 | 0.18 | 1843 | 1844 |
| M722C | 722 | M | C | 0.52 | 0.32 | 1845 | 1846 |
| T1019N | 1019 | T | N | 0.52 | 0.13 | 1847 | 1848 |
| E885T | 885 | E | T | 0.52 | 0.27 | 1849 | 1850 |
| K415P | 415 | K | P | 0.52 | 0.32 | 1851 | 1852 |
| G475M | 475 | G | M | 0.52 | 0.06 | 1853 | 1854 |
| Y583T | 583 | Y | T | 0.52 | 0.43 | 1855 | 1856 |
| D729G | 729 | D | G | 0.52 | 0.54 | 1857 | 1858 |
| E1044A | 1044 | E | A | 0.52 | 0.09 | 1859 | 1860 |
| E221N | 221 | E | N | 0.52 | 0.44 | 1861 | 1862 |
| I850H | 850 | I | H | 0.51 | 0.1 | 1863 | 1864 |
| K568S | 568 | K | S | 0.51 | 0.23 | 1865 | 1866 |
| K269T | 269 | K | T | 0.51 | 0.17 | 1867 | 1868 |
| E1044T | 1044 | E | T | 0.51 | 0.38 | 1869 | 1870 |
| K269C | 269 | K | C | 0.51 | 0.03 | 1871 | 1872 |
| K514S | 514 | K | S | 0.51 | 0.03 | 1873 | 1874 |
| D1207A | 1207 | D | A | 0.51 | 0.02 | 1875 | 1876 |
| D559C | 559 | D | C | 0.51 | 0.43 | 1877 | 1878 |
| S14Q | 14 | S | Q | 0.51 | 0.05 | 1879 | 1880 |
| D792R | 792 | D | R | 0.51 | 0.04 | 1881 | 1882 |
| K387V | 387 | K | V | 0.51 | 0.07 | 1883 | 1884 |
| Y854G | 854 | Y | G | 0.51 | 0.12 | 1885 | 1886 |
| K499A | 499 | K | A | 0.51 | 0.14 | 1887 | 1888 |
| R482W | 482 | R | W | 0.51 | 0.15 | 1889 | 1890 |
| D919I | 919 | D | I | 0.51 | 0.83 | 1891 | 1892 |
| R1165Q | 1165 | R | Q | 0.5 | 0.27 | 1893 | 1894 |
| A1194W | 1194 | A | W | 0.5 | 0.93 | 1895 | 1896 |
| Y1066O | 1066 | Y | C | 0.5 | 0.15 | 1897 | 1898 |
| S763K | 763 | S | K | 0.5 | 0.02 | 1899 | 1900 |
| K1121T | 1121 | K | T | 0.5 | 0.14 | 1901 | 1902 |
| I859P | 859 | I | P | 0.5 | 0.94 | 1903 | 1904 |
| G576N | 576 | G | N | 0.5 | 0.43 | 1905 | 1906 |
| K72G | 72 | K | G | 0.5 | 0.14 | 1907 | 1908 |
| V228C | 228 | V | C | 0.5 | 0.22 | 1909 | 1910 |
| T1016F | 1016 | T | F | 0.5 | 0.15 | 1911 | 1912 |
| Y781R | 781 | Y | R | 0.5 | 0.1 | 1913 | 1914 |
| E285P | 285 | E | P | 0.5 | 0.03 | 1915 | 1916 |
| S1024F | 1024 | S | F | 0.5 | 0.12 | 1917 | 1918 |
| S1053V | 1053 | S | V | 0.5 | 0.15 | 1919 | 1920 |
| I22R | 22 | I | R | 0.5 | 0.53 | 1921 | 1922 |
| I184E | 184 | I | E | 0.5 | 0.36 | 1923 | 1924 |
| N179L | 179 | N | L | 0.5 | 0.07 | 1925 | 1926 |
| S1024V | 1024 | S | V | 0.5 | 0.05 | 1927 | 1928 |
| E416Q | 416 | E | Q | 0.5 | 0.11 | 1929 | 1930 |
| R182M | 182 | R | M | 0.5 | 0.27 | 1931 | 1932 |
| R645T | 645 | R | T | 0.49 | 0.61 | 1933 | 1934 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| R182A | 182 | R | A | 0.49 | 0.07 | 1935 | 1936 |
| E674L | 674 | E | L | 0.49 | 0.02 | 1937 | 1938 |
| D283I | 283 | D | I | 0.49 | 0.06 | 1939 | 1940 |
| S394T | 394 | S | T | 0.49 | 0 | 1941 | 1942 |
| N889T | 889 | N | T | 0.49 | 0.08 | 1943 | 1944 |
| K1155S | 1155 | K | S | 0.49 | 0.42 | 1945 | 1946 |
| S248E | 248 | S | E | 0.49 | 0.05 | 1947 | 1948 |
| A970G | 970 | A | G | 0.49 | 0.16 | 1949 | 1950 |
| K1015G | 1015 | K | G | 0.49 | 0.04 | 1951 | 1952 |
| F197R | 197 | F | R | 0.49 | 0.07 | 1953 | 1954 |
| K116Y | 116 | K | Y | 0.49 | 0.06 | 1955 | 1956 |
| E88P | 88 | E | P | 0.49 | 0.33 | 1957 | 1958 |
| E913R | 913 | E | R | 0.49 | 0.03 | 1959 | 1960 |
| V783I | 783 | V | I | 0.49 | 0.5 | 1961 | 1962 |
| A685F | 685 | A | F | 0.49 | 0.26 | 1963 | 1964 |
| V428Q | 428 | V | Q | 0.49 | 0.05 | 1965 | 1966 |
| D213K | 213 | D | K | 0.49 | 0.18 | 1967 | 1968 |
| E88R | 88 | E | R | 0.49 | 0.21 | 1969 | 1970 |
| G353V | 353 | G | V | 0.49 | 0.13 | 1971 | 1972 |
| D871C | 871 | D | C | 0.49 | 0.57 | 1973 | 1974 |
| E835Q | 835 | E | Q | 0.48 | 0.19 | 1975 | 1976 |
| L629N | 629 | L | N | 0.48 | 0.32 | 1977 | 1978 |
| K84A | 84 | K | A | 0.48 | 0.88 | 1979 | 1980 |
| T266Q | 266 | T | Q | 0.48 | 0.68 | 1981 | 1982 |
| F1045T | 1045 | F | T | 0.48 | 0.18 | 1983 | 1984 |
| K272S | 272 | K | S | 0.48 | 0.11 | 1985 | 1986 |
| N656W | 656 | N | W | 0.48 | 0.16 | 1987 | 1988 |
| I922L | 922 | I | L | 0.48 | 0.07 | 1989 | 1990 |
| K568A | 568 | K | A | 0.48 | 0.16 | 1991 | 1992 |
| K167M | 167 | K | M | 0.48 | 0.41 | 1993 | 1994 |
| A1022D | 1022 | A | D | 0.48 | 0.22 | 1995 | 1996 |
| F709N | 709 | F | N | 0.48 | 0.5 | 1997 | 1998 |
| Y854E | 854 | Y | E | 0.48 | 0.11 | 1999 | 2000 |
| R737M | 737 | R | M | 0.48 | 0.03 | 2001 | 2002 |
| F131N | 131 | F | N | 0.48 | 1.69 | 2003 | 2004 |
| I417L | 417 | I | L | 0.48 | 0.27 | 2005 | 2006 |
| K478H | 478 | K | H | 0.48 | 0.05 | 2007 | 2008 |
| V690R | 690 | V | R | 0.48 | 0.12 | 2009 | 2010 |
| K1025V | 1025 | K | V | 0.48 | 0.02 | 2011 | 2012 |
| E981R | 981 | E | R | 0.47 | 0.5 | 2013 | 2014 |
| S681F | 681 | S | F | 0.47 | 0.1 | 2015 | 2016 |
| K807L | 807 | K | L | 0.47 | 0.13 | 2017 | 2018 |
| K110V | 110 | K | V | 0.47 | 0.11 | 2019 | 2020 |
| E683V | 683 | E | V | 0.47 | 0.01 | 2021 | 2022 |
| T1142W | 1142 | T | W | 0.47 | 0.13 | 2023 | 2024 |
| S143C | 143 | S | C | 0.47 | 0.09 | 2025 | 2026 |
| K1050R | 1050 | K | R | 0.47 | 0.02 | 2027 | 2028 |
| D156R | 156 | D | R | 0.47 | 0.04 | 2029 | 2030 |
| K1015L | 1015 | K | L | 0.47 | 0.08 | 2031 | 2032 |
| E835R | 835 | E | R | 0.47 | 0.19 | 2033 | 2034 |
| N577G | 577 | N | G | 0.47 | 0.08 | 2035 | 2036 |
| T776I | 776 | T | I | 0.47 | 1.44 | 2037 | 2038 |
| T776R | 776 | T | R | 0.47 | 1.43 | 2039 | 2040 |
| I850M | 850 | I | M | 0.47 | 0.16 | 2041 | 2042 |
| R836Q | 836 | R | Q | 0.47 | 0.19 | 2043 | 2044 |
| S394M | 394 | S | M | 0.47 | 0.14 | 2045 | 2046 |
| E217W | 217 | E | W | 0.47 | 0.11 | 2047 | 2048 |
| V441P | 441 | V | P | 0.47 | 0.05 | 2049 | 2050 |
| K1121Q | 1121 | K | Q | 0.47 | 0.08 | 2051 | 2052 |
| D156P | 156 | D | P | 0.47 | 0.07 | 2053 | 2054 |
| G477E | 477 | G | E | 0.47 | 0.07 | 2055 | 2056 |
| E398K | 398 | E | K | 0.46 | 0.45 | 2057 | 2058 |
| N590M | 590 | N | M | 0.46 | 0.33 | 2059 | 2060 |
| K536M | 536 | K | M | 0.46 | 1.29 | 2061 | 2062 |
| P997K | 997 | P | K | 0.46 | 0.25 | 2063 | 2064 |
| Y781D | 781 | Y | D | 0.46 | 0 | 2065 | 2066 |
| F1127A | 1127 | F | A | 0.46 | 0.6 | 2067 | 2068 |
| K1096M | 1096 | K | M | 0.46 | 0.05 | 2069 | 2070 |
| S929K | 929 | S | K | 0.46 | 0.12 | 2071 | 2072 |
| K662C | 662 | K | C | 0.46 | 0.03 | 2073 | 2074 |
| S1225A | 1225 | S | A | 0.46 | 0.01 | 2075 | 2076 |
| K937H | 937 | K | H | 0.46 | 0.31 | 2077 | 2078 |
| K1061F | 1061 | K | F | 0.46 | 0.07 | 2079 | 2080 |
| N630W | 630 | N | W | 0.46 | 0.11 | 2081 | 2082 |
| V816K | 816 | V | K | 0.46 | 0.1 | 2083 | 2084 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| T1145H | 1145 | T | H | 0.46 | 0.82 | 2085 | 2086 |
| E412Y | 412 | E | Y | 0.46 | 0.07 | 2087 | 2088 |
| L585R | 585 | L | R | 0.46 | 0.21 | 2089 | 2090 |
| K520T | 520 | K | T | 0.46 | 0.08 | 2091 | 2092 |
| V491Q | 491 | V | Q | 0.46 | 0.14 | 2093 | 2094 |
| A1129C | 1129 | A | C | 0.46 | 0.15 | 2095 | 2096 |
| D1207P | 1207 | D | P | 0.46 | 0.03 | 2097 | 2098 |
| K269Q | 269 | K | Q | 0.46 | 0 | 2099 | 2100 |
| K984F | 984 | K | F | 0.46 | 0.28 | 2101 | 2102 |
| L839V | 839 | L | V | 0.46 | 0.1 | 2103 | 2104 |
| H759E | 759 | H | E | 0.46 | 0.73 | 2105 | 2106 |
| E885Y | 885 | E | Y | 0.46 | 0.29 | 2107 | 2108 |
| K1061A | 1061 | K | A | 0.46 | 0.09 | 2109 | 2110 |
| G973K | 973 | G | K | 0.45 | 0.24 | 2111 | 2112 |
| S1140F | 1140 | S | F | 0.45 | 0.08 | 2113 | 2114 |
| K272A | 272 | K | A | 0.45 | 0.02 | 2115 | 2116 |
| D1207R | 1207 | D | R | 0.45 | 0.11 | 2117 | 2118 |
| E125L | 125 | E | L | 0.45 | 0.09 | 2119 | 2120 |
| D283S | 283 | D | S | 0.45 | 0.02 | 2121 | 2122 |
| N481W | 481 | N | W | 0.45 | 0.21 | 2123 | 2124 |
| D1207M | 1207 | D | M | 0.45 | 0.07 | 2125 | 2126 |
| P799T | 799 | P | T | 0.45 | 0.07 | 2127 | 2128 |
| Y781G | 781 | Y | G | 0.45 | 0.05 | 2129 | 2130 |
| S763N | 763 | S | N | 0.45 | 0.03 | 2131 | 2132 |
| A1046Y | 1046 | A | Y | 0.45 | 0.34 | 2133 | 2134 |
| I860C | 860 | I | C | 0.45 | 0.54 | 2135 | 2136 |
| S445Q | 445 | S | Q | 0.45 | 0.05 | 2137 | 2138 |
| E95L | 95 | E | L | 0.45 | 0.16 | 2139 | 2140 |
| F597T | 597 | F | T | 0.45 | 0.99 | 2141 | 2142 |
| F224A | 224 | F | A | 0.45 | 0.34 | 2143 | 2144 |
| R867S | 867 | R | S | 0.45 | 0.6 | 2145 | 2146 |
| E1039S | 1039 | E | S | 0.45 | 0.15 | 2147 | 2148 |
| A749E | 749 | A | E | 0.45 | 0.73 | 2149 | 2150 |
| I765R | 765 | I | R | 0.45 | 0.26 | 2151 | 2152 |
| M746R | 746 | M | R | 0.45 | 0.34 | 2153 | 2154 |
| K1177L | 1177 | K | L | 0.44 | 0.1 | 2155 | 2156 |
| F197A | 197 | F | A | 0.44 | 0.07 | 2157 | 2158 |
| I425G | 425 | I | G | 0.44 | 0.73 | 2159 | 2160 |
| M1128D | 1128 | M | D | 0.44 | 0.06 | 2161 | 2162 |
| V216C | 216 | V | C | 0.44 | 0.05 | 2163 | 2164 |
| K614Y | 614 | K | Y | 0.44 | 0.26 | 2165 | 2166 |
| H200F | 200 | H | F | 0.44 | 0.16 | 2167 | 2168 |
| G991C | 991 | G | C | 0.44 | 0.72 | 2169 | 2170 |
| K413Y | 413 | K | Y | 0.44 | 0.05 | 2171 | 2172 |
| K269E | 269 | K | E | 0.44 | 0.04 | 2173 | 2174 |
| N311G | 311 | N | G | 0.44 | 0.84 | 2175 | 2176 |
| T307M | 307 | T | M | 0.44 | 0.84 | 2177 | 2178 |
| I138A | 138 | I | A | 0.44 | 0.15 | 2179 | 2180 |
| F728C | 728 | F | C | 0.44 | 0.72 | 2181 | 2182 |
| L779A | 779 | L | A | 0.44 | 0.01 | 2183 | 2184 |
| A493N | 493 | A | N | 0.44 | 0.06 | 2185 | 2186 |
| N327H | 327 | N | H | 0.44 | 0.26 | 2187 | 2188 |
| S644K | 644 | S | K | 0.44 | 0.12 | 2189 | 2190 |
| S212T | 212 | S | T | 0.44 | 0.83 | 2191 | 2192 |
| E313T | 313 | E | T | 0.44 | 1.14 | 2193 | 2194 |
| K272Y | 272 | K | Y | 0.44 | 0.02 | 2195 | 2196 |
| E330K | 330 | E | K | 0.44 | 0.1 | 2197 | 2198 |
| I138G | 138 | I | G | 0.44 | 0.83 | 2199 | 2200 |
| G1009H | 1009 | G | H | 0.44 | 0.72 | 2201 | 2202 |
| T1092G | 1092 | T | G | 0.44 | 0.03 | 2203 | 2204 |
| E852Q | 852 | E | Q | 0.44 | 0.42 | 2205 | 2206 |
| E1097Q | 1097 | E | Q | 0.43 | 0.83 | 2207 | 2208 |
| F810R | 810 | F | R | 0.43 | 0.45 | 2209 | 2210 |
| N861H | 861 | N | H | 0.43 | 0.73 | 2211 | 2212 |
| E913I | 913 | E | I | 0.43 | 0.08 | 2213 | 2214 |
| F109K | 109 | F | K | 0.43 | 0.73 | 2215 | 2216 |
| K89M | 89 | K | M | 0.43 | 0.05 | 2217 | 2218 |
| K1015Q | 1015 | K | Q | 0.43 | 0.02 | 2219 | 2220 |
| R102E | 102 | R | E | 0.43 | 0.83 | 2221 | 2222 |
| T1142A | 1142 | T | A | 0.43 | 0.13 | 2223 | 2224 |
| S710W | 710 | S | W | 0.43 | 0.72 | 2225 | 2226 |
| D122R | 122 | D | R | 0.43 | 0.09 | 2227 | 2228 |
| K269V | 269 | K | V | 0.43 | 0.03 | 2229 | 2230 |
| D611Q | 611 | D | Q | 0.43 | 0.03 | 2231 | 2232 |
| S609F | 609 | S | F | 0.43 | 0.84 | 2233 | 2234 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| T152G | 152 | T | G | 0.43 | 0.05 | 2235 | 2236 |
| Y605I | 605 | Y | I | 0.43 | 0.08 | 2237 | 2238 |
| I951Q | 951 | I | Q | 0.43 | 0.73 | 2239 | 2240 |
| M626P | 626 | M | P | 0.43 | 0.02 | 2241 | 2242 |
| N76L | 76 | N | L | 0.43 | 0.73 | 2243 | 2244 |
| F1010P | 1010 | F | P | 0.43 | 0.72 | 2245 | 2246 |
| D136L | 136 | D | L | 0.43 | 0.83 | 2247 | 2248 |
| S394K | 394 | S | K | 0.43 | 0.08 | 2249 | 2250 |
| N837V | 837 | N | V | 0.43 | 0.25 | 2251 | 2252 |
| K278C | 278 | K | C | 0.43 | 0.26 | 2253 | 2254 |
| N862C | 862 | N | C | 0.43 | 0.26 | 2255 | 2256 |
| A172E | 172 | A | E | 0.43 | 0.83 | 2257 | 2258 |
| G291K | 291 | G | K | 0.43 | 0.23 | 2259 | 2260 |
| F81N | 81 | F | N | 0.43 | 0.14 | 2261 | 2262 |
| I259G | 259 | I | G | 0.43 | 0.03 | 2263 | 2264 |
| A901K | 901 | A | K | 0.43 | 0.83 | 2265 | 2266 |
| V216A | 216 | V | A | 0.43 | 0 | 2267 | 2268 |
| A1201I | 1201 | A | I | 0.43 | 0.25 | 2269 | 2270 |
| F436R | 436 | F | R | 0.43 | 0.58 | 2271 | 2272 |
| F109C | 109 | F | C | 0.43 | 0.17 | 2273 | 2274 |
| A923E | 923 | A | E | 0.43 | 0.83 | 2275 | 2276 |
| N75P | 75 | N | P | 0.43 | 0.16 | 2277 | 2278 |
| I911G | 911 | I | G | 0.43 | 0.83 | 2279 | 2280 |
| G477S | 477 | G | S | 0.43 | 0.08 | 2281 | 2282 |
| D156Y | 156 | D | Y | 0.43 | 0.12 | 2283 | 2284 |
| K269W | 269 | K | W | 0.43 | 0.16 | 2285 | 2286 |
| Y956Q | 956 | Y | Q | 0.43 | 0.73 | 2287 | 2288 |
| V236H | 236 | V | H | 0.43 | 0.83 | 2289 | 2290 |
| L1115Y | 1115 | L | Y | 0.43 | 0.83 | 2291 | 2292 |
| V816H | 816 | V | H | 0.43 | 0.83 | 2293 | 2294 |
| K272F | 272 | K | F | 0.43 | 0.07 | 2295 | 2296 |
| D461W | 461 | D | W | 0.43 | 0.26 | 2297 | 2298 |
| N1186Y | 1186 | N | Y | 0.43 | 0.82 | 2299 | 2300 |
| K265H | 265 | K | H | 0.43 | 0.83 | 2301 | 2302 |
| K707H | 707 | K | H | 0.43 | 0.72 | 2303 | 2304 |
| G335T | 335 | G | T | 0.43 | 0.14 | 2305 | 2306 |
| L738K | 738 | L | K | 0.43 | 0.83 | 2307 | 2308 |
| D122G | 122 | D | G | 0.43 | 0.26 | 2309 | 2310 |
| I581V | 581 | I | V | 0.43 | 0.14 | 2311 | 2312 |
| K1121H | 1121 | K | H | 0.43 | 0.16 | 2313 | 2314 |
| I78S | 78 | I | S | 0.43 | 0.82 | 2315 | 2316 |
| I1021S | 1021 | I | S | 0.43 | 0.26 | 2317 | 2318 |
| Y705C | 705 | Y | C | 0.43 | 0.02 | 2319 | 2320 |
| F473R | 473 | F | R | 0.42 | 0.14 | 2321 | 2322 |
| A451E | 451 | A | E | 0.42 | 0.22 | 2323 | 2324 |
| L927K | 927 | L | K | 0.42 | 0.25 | 2325 | 2326 |
| V216H | 216 | V | H | 0.42 | 0.51 | 2327 | 2328 |
| S163I | 163 | S | I | 0.42 | 0.72 | 2329 | 2330 |
| S332L | 332 | S | L | 0.42 | 0.72 | 2331 | 2332 |
| Y1102N | 1102 | Y | N | 0.42 | 0.26 | 2333 | 2334 |
| M1035F | 1035 | M | F | 0.42 | 0.06 | 2335 | 2336 |
| I612E | 612 | I | E | 0.42 | 0.72 | 2337 | 2338 |
| A1184W | 1184 | A | W | 0.42 | 0.82 | 2339 | 2340 |
| E98W | 98 | E | W | 0.42 | 0.06 | 2341 | 2342 |
| D1041V | 1041 | D | V | 0.42 | 0.4 | 2343 | 2344 |
| S1024W | 1024 | S | W | 0.42 | 0.24 | 2345 | 2346 |
| I369H | 369 | I | H | 0.42 | 0.06 | 2347 | 2348 |
| N157P | 157 | N | P | 0.42 | 0.72 | 2349 | 2350 |
| K752H | 752 | K | H | 0.42 | 0.73 | 2351 | 2352 |
| A1057D | 1057 | A | D | 0.42 | 0.26 | 2353 | 2354 |
| I841C | 841 | I | C | 0.42 | 0.13 | 2355 | 2356 |
| R359K | 359 | R | K | 0.42 | 0.72 | 2357 | 2358 |
| K1017F | 1017 | K | F | 0.42 | 0.83 | 2359 | 2360 |
| F530R | 530 | F | R | 0.42 | 0.85 | 2361 | 2362 |
| T777P | 777 | T | P | 0.42 | 0.24 | 2363 | 2364 |
| G242I | 242 | G | I | 0.42 | 0.26 | 2365 | 2366 |
| N889M | 889 | N | M | 0.42 | 0.06 | 2367 | 2368 |
| K1121L | 1121 | K | L | 0.42 | 0 | 2369 | 2370 |
| K1015S | 1015 | K | S | 0.42 | 0.05 | 2371 | 2372 |
| I736H | 736 | I | H | 0.42 | 0.83 | 2373 | 2374 |
| Y700G | 700 | Y | G | 0.42 | 0.72 | 2375 | 2376 |
| D665H | 665 | D | H | 0.42 | 0.04 | 2377 | 2378 |
| Q203D | 203 | Q | D | 0.42 | 0.17 | 2379 | 2380 |
| G477V | 477 | G | V | 0.42 | 0.08 | 2381 | 2382 |
| E479W | 479 | E | W | 0.42 | 0.07 | 2383 | 2384 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| T246C | 246 | T | C | 0.42 | 0.15 | 2385 | 2386 |
| I470L | 470 | I | L | 0.42 | 0.26 | 2387 | 2388 |
| S282N | 282 | S | N | 0.42 | 0.72 | 2389 | 2390 |
| K391Y | 391 | K | Y | 0.42 | 0.26 | 2391 | 2392 |
| K897A | 897 | K | A | 0.42 | 0.02 | 2393 | 2394 |
| Y1221M | 1221 | Y | M | 0.42 | 0.02 | 2395 | 2396 |
| Y903P | 903 | Y | P | 0.42 | 0.83 | 2397 | 2398 |
| V828Y | 828 | V | Y | 0.42 | 0.72 | 2399 | 2400 |
| Y903G | 903 | Y | G | 0.42 | 0.72 | 2401 | 2402 |
| Y554M | 554 | Y | M | 0.42 | 0.14 | 2403 | 2404 |
| K1015C | 1015 | K | C | 0.42 | 0.13 | 2405 | 2406 |
| L497D | 497 | L | D | 0.42 | 0.71 | 2407 | 2408 |
| I860F | 860 | I | F | 0.42 | 0.05 | 2409 | 2410 |
| I569D | 569 | I | D | 0.42 | 0.27 | 2411 | 2412 |
| L101C | 101 | L | C | 0.42 | 0.18 | 2413 | 2414 |
| F227H | 227 | F | H | 0.42 | 0.83 | 2415 | 2416 |
| I234D | 234 | I | D | 0.42 | 0.83 | 2417 | 2418 |
| F1027M | 1027 | F | M | 0.42 | 0.19 | 2419 | 2420 |
| K107M | 107 | K | M | 0.41 | 0.08 | 2421 | 2422 |
| Y781W | 781 | Y | W | 0.41 | 0.18 | 2423 | 2424 |
| E98M | 98 | E | M | 0.41 | 0.96 | 2425 | 2426 |
| D384T | 384 | D | T | 0.41 | 0.03 | 2427 | 2428 |
| L693D | 693 | L | D | 0.41 | 0.48 | 2429 | 2430 |
| K349G | 349 | K | G | 0.41 | 0.26 | 2431 | 2432 |
| L281Y | 281 | L | Y | 0.41 | 0.36 | 2433 | 2434 |
| D572W | 572 | D | W | 0.41 | 0.12 | 2435 | 2436 |
| L566H | 566 | L | H | 0.41 | 0.84 | 2437 | 2438 |
| E913K | 913 | E | K | 0.41 | 0.02 | 2439 | 2440 |
| I557V | 557 | I | V | 0.41 | 0.27 | 2441 | 2442 |
| N731E | 731 | N | E | 0.41 | 0.17 | 2443 | 2444 |
| T716Q | 716 | T | Q | 0.41 | 1.78 | 2445 | 2446 |
| I831L | 831 | I | L | 0.41 | 0.1 | 2447 | 2448 |
| Y1018E | 1018 | Y | E | 0.41 | 0 | 2449 | 2450 |
| L1065R | 1065 | L | R | 0.41 | 0.16 | 2451 | 2452 |
| I419R | 419 | I | R | 0.41 | 0.09 | 2453 | 2454 |
| I314Q | 314 | I | Q | 0.41 | 0.14 | 2455 | 2456 |
| M1134R | 1134 | M | R | 0.41 | 0.02 | 2457 | 2458 |
| A1188L | 1188 | A | L | 0.41 | 0.79 | 2459 | 2460 |
| S168V | 168 | S | V | 0.41 | 0.14 | 2461 | 2462 |
| P799R | 799 | P | R | 0.41 | 0.03 | 2463 | 2464 |
| C805L | 805 | C | L | 0.41 | 0.17 | 2465 | 2466 |
| T16A | 16 | T | A | 0.41 | 0.74 | 2467 | 2468 |
| D782Q | 782 | D | Q | 0.41 | 0.08 | 2469 | 2470 |
| D122M | 122 | D | M | 0.41 | 0.25 | 2471 | 2472 |
| Y1162A | 1162 | Y | A | 0.41 | 0.73 | 2473 | 2474 |
| S143G | 143 | S | G | 0.41 | 0.05 | 2475 | 2476 |
| S1020L | 1020 | S | L | 0.41 | 0.01 | 2477 | 2478 |
| K1205P | 1205 | K | P | 0.41 | 0.46 | 2479 | 2480 |
| G254D | 254 | G | D | 0.4 | 0.43 | 2481 | 2482 |
| R182G | 182 | R | G | 0.4 | 0 | 2483 | 2484 |
| R1112W | 1112 | R | W | 0.4 | 0.31 | 2485 | 2486 |
| T480I | 480 | T | I | 0.4 | 0.35 | 2487 | 2488 |
| L492H | 492 | L | H | 0.4 | 0.06 | 2489 | 2490 |
| K52P | 52 | K | P | 0.4 | 0.74 | 2491 | 2492 |
| L744M | 744 | L | M | 0.4 | 0.17 | 2493 | 2494 |
| L210N | 210 | L | N | 0.4 | 0.07 | 2495 | 2496 |
| I1072S | 1072 | I | S | 0.4 | 0.21 | 2497 | 2498 |
| G734Q | 734 | G | Q | 0.4 | 0.05 | 2499 | 2500 |
| I205C | 205 | I | C | 0.4 | 0.07 | 2501 | 2502 |
| Y115P | 115 | Y | P | 0.4 | 0.29 | 2503 | 2504 |
| T1224D | 1224 | T | D | 0.4 | 0.69 | 2505 | 2506 |
| L699D | 699 | L | D | 0.4 | 0.09 | 2507 | 2508 |
| G1196E | 1196 | G | E | 0.4 | 0.11 | 2509 | 2510 |
| K3M | 3 | K | M | 0.4 | 0.75 | 2511 | 2512 |
| K272V | 272 | K | V | 0.4 | 0.09 | 2513 | 2514 |
| L876A | 876 | L | A | 0.4 | 0.1 | 2515 | 2516 |
| R482H | 482 | R | H | 0.4 | 0.11 | 2517 | 2518 |
| Y678E | 678 | Y | E | 0.4 | 0.72 | 2519 | 2520 |
| E292M | 292 | E | M | 0.4 | 0.03 | 2521 | 2522 |
| Y77W | 77 | Y | W | 0.4 | 0.25 | 2523 | 2524 |
| S1024G | 1024 | S | G | 0.4 | 0.04 | 2525 | 2526 |
| E95A | 95 | E | A | 0.4 | 0.02 | 2527 | 2528 |
| E981F | 981 | E | F | 0.4 | 0.11 | 2529 | 2530 |
| A1173N | 1173 | A | N | 0.4 | 0.13 | 2531 | 2532 |
| D495E | 495 | D | E | 0.4 | 0.08 | 2533 | 2534 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K272P | 272 | K | P | 0.4 | 0.14 | 2535 | 2536 |
| A404R | 404 | A | R | 0.4 | 0.21 | 2537 | 2538 |
| V921G | 921 | V | G | 0.4 | 0.04 | 2539 | 2540 |
| Y1221K | 1221 | Y | K | 0.4 | 0.12 | 2541 | 2542 |
| K373F | 373 | K | F | 0.4 | 0.2 | 2543 | 2544 |
| F728S | 728 | F | S | 0.4 | 0.45 | 2545 | 2546 |
| I418K | 418 | I | K | 0.4 | 0.02 | 2547 | 2548 |
| E1217F | 1217 | E | F | 0.4 | 0.83 | 2549 | 2550 |
| F224G | 224 | F | G | 0.4 | 0.23 | 2551 | 2552 |
| S143M | 143 | S | M | 0.4 | 0.05 | 2553 | 2554 |
| D156G | 156 | D | G | 0.4 | 0 | 2555 | 2556 |
| A1022E | 1022 | A | E | 0.4 | 0.17 | 2557 | 2558 |
| N481F | 481 | N | F | 0.4 | 0.13 | 2559 | 2560 |
| I69P | 69 | I | P | 0.4 | 0.09 | 2561 | 2562 |
| K361V | 361 | K | V | 0.4 | 0.06 | 2563 | 2564 |
| T776E | 776 | T | E | 0.4 | 1.72 | 2565 | 2566 |
| K1064 | 1064 | K | M | 0.39 | 0.59 | 2567 | 2568 |
| G475K | 475 | G | K | 0.39 | 0.11 | 2569 | 2570 |
| K1026P | 1026 | K | P | 0.39 | 0.11 | 2571 | 2572 |
| S409D | 409 | S | D | 0.39 | 0.21 | 2573 | 2574 |
| N577A | 577 | N | A | 0.39 | 0.18 | 2575 | 2576 |
| Y646S | 646 | Y | S | 0.39 | 0.21 | 2577 | 2578 |
| I951L | 951 | I | L | 0.39 | 0.14 | 2579 | 2580 |
| D1163C | 1163 | D | C | 0.39 | 0.11 | 2581 | 2582 |
| G114Q | 114 | G | Q | 0.39 | 0.24 | 2583 | 2584 |
| N862L | 862 | N | L | 0.39 | 0.25 | 2585 | 2586 |
| N656I | 656 | N | I | 0.39 | 0.37 | 2587 | 2588 |
| K1177E | 1177 | K | E | 0.39 | 0.22 | 2589 | 2590 |
| L94D | 94 | L | D | 0.39 | 0.08 | 2591 | 2592 |
| S2H | 2 | S | H | 0.39 | 0.75 | 2593 | 2594 |
| K478E | 478 | K | E | 0.39 | 0.11 | 2595 | 2596 |
| L324E | 324 | L | E | 0.39 | 0.06 | 2597 | 2598 |
| L779V | 779 | L | V | 0.39 | 0.25 | 2599 | 2600 |
| I419Q | 419 | I | Q | 0.39 | 0.02 | 2601 | 2602 |
| A563G | 563 | A | G | 0.39 | 0.13 | 2603 | 2604 |
| T1019W | 1019 | T | W | 0.39 | 0.03 | 2605 | 2606 |
| F1052I | 1052 | F | I | 0.39 | 0.14 | 2607 | 2608 |
| K932F | 932 | K | F | 0.39 | 0.05 | 2609 | 2610 |
| K910I | 910 | K | I | 0.39 | 0.05 | 2611 | 2612 |
| Q567P | 567 | Q | P | 0.39 | 0.04 | 2613 | 2614 |
| V38D | 38 | V | D | 0.39 | 0.09 | 2615 | 2616 |
| A801D | 801 | A | D | 0.39 | 0.05 | 2617 | 2618 |
| G49I | 49 | G | I | 0.39 | 0.04 | 2619 | 2620 |
| V411D | 411 | V | D | 0.39 | 0.02 | 2621 | 2622 |
| F440E | 440 | F | E | 0.39 | 0.05 | 2623 | 2624 |
| Y827R | 827 | Y | R | 0.38 | 0.14 | 2625 | 2626 |
| E443Y | 443 | E | Y | 0.38 | 0.34 | 2627 | 2628 |
| Y57M | 57 | Y | M | 0.38 | 0.03 | 2629 | 2630 |
| Y700V | 700 | Y | V | 0.38 | 0.09 | 2631 | 2632 |
| N468E | 468 | N | E | 0.38 | 0.2 | 2633 | 2634 |
| M187R | 187 | M | R | 0.38 | 0.03 | 2635 | 2636 |
| G968P | 968 | G | P | 0.38 | 0.34 | 2637 | 2638 |
| M603S | 603 | M | S | 0.38 | 0.01 | 2639 | 2640 |
| N311E | 311 | N | E | 0.38 | 0.09 | 2641 | 2642 |
| N91G | 91 | N | G | 0.38 | 0.48 | 2643 | 2644 |
| K274Q | 274 | K | Q | 0.38 | 0.07 | 2645 | 2646 |
| T181D | 181 | T | D | 0.38 | 0.12 | 2647 | 2648 |
| R305V | 305 | R | V | 0.38 | 0.05 | 2649 | 2650 |
| E1204R | 1204 | E | R | 0.38 | 0.17 | 2651 | 2652 |
| K448C | 448 | K | C | 0.38 | 0.01 | 2653 | 2654 |
| L446W | 446 | L | W | 0.38 | 0.09 | 2655 | 2656 |
| A1122K | 1122 | A | K | 0.38 | 0.16 | 2657 | 2658 |
| R35N | 35 | R | N | 0.38 | 0.74 | 2659 | 2660 |
| L727I | 727 | L | I | 0.38 | 0.34 | 2661 | 2662 |
| I196W | 196 | I | W | 0.38 | 0.31 | 2663 | 2664 |
| N732I | 732 | N | I | 0.38 | 0.75 | 2665 | 2666 |
| Y58S | 58 | Y | S | 0.38 | 0.08 | 2667 | 2668 |
| I78V | 78 | I | V | 0.38 | 0.32 | 2669 | 2670 |
| K413V | 413 | K | V | 0.38 | 0.21 | 2671 | 2672 |
| K26V | 26 | K | V | 0.38 | 0.74 | 2673 | 2674 |
| K878T | 878 | K | T | 0.38 | 0.04 | 2675 | 2676 |
| E913L | 913 | E | L | 0.37 | 0.06 | 2677 | 2678 |
| A667R | 667 | A | R | 0.37 | 0.18 | 2679 | 2680 |
| N857S | 857 | N | S | 0.37 | 0.34 | 2681 | 2682 |
| S763T | 763 | S | T | 0.37 | 0.04 | 2683 | 2684 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K1017A | 1017 | K | A | 0.37 | 0.08 | 2685 | 2686 |
| F530G | 530 | F | G | 0.37 | 0.56 | 2687 | 2688 |
| V491E | 491 | V | E | 0.37 | 0.05 | 2689 | 2690 |
| G846W | 846 | G | W | 0.37 | 0 | 2691 | 2692 |
| K1210L | 1210 | K | L | 0.37 | 0.82 | 2693 | 2694 |
| D665R | 665 | D | R | 0.37 | 0.06 | 2695 | 2696 |
| I1072Y | 1072 | I | Y | 0.37 | 0.33 | 2697 | 2698 |
| S296V | 296 | S | V | 0.37 | 0.01 | 2699 | 2700 |
| N955L | 955 | N | L | 0.37 | 0.06 | 2701 | 2702 |
| I911Q | 911 | I | Q | 0.37 | 0.64 | 2703 | 2704 |
| I189E | 189 | I | E | 0.37 | 0.17 | 2705 | 2706 |
| D156V | 156 | D | V | 0.37 | 0.05 | 2707 | 2708 |
| T1016E | 1016 | T | E | 0.37 | 0.18 | 2709 | 2710 |
| Y646R | 646 | Y | R | 0.37 | 0.61 | 2711 | 2712 |
| N179A | 179 | N | A | 0.37 | 0.36 | 2713 | 2714 |
| F436M | 436 | F | M | 0.37 | 0.03 | 2715 | 2716 |
| T814A | 814 | T | A | 0.37 | 0.16 | 2717 | 2718 |
| V783R | 783 | V | R | 0.37 | 0.08 | 2719 | 2720 |
| E285T | 285 | E | T | 0.37 | 0.24 | 2721 | 2722 |
| E791T | 791 | E | T | 0.37 | 0.05 | 2723 | 2724 |
| G848R | 848 | G | R | 0.37 | 0.08 | 2725 | 2726 |
| T891Y | 891 | T | Y | 0.37 | 0.04 | 2727 | 2728 |
| E479L | 479 | E | L | 0.37 | 0.11 | 2729 | 2730 |
| D877T | 877 | D | T | 0.37 | 0.73 | 2731 | 2732 |
| Q975Y | 975 | Q | Y | 0.36 | 0.13 | 2733 | 2734 |
| T152R | 152 | T | R | 0.36 | 0.04 | 2735 | 2736 |
| Y294K | 294 | Y | K | 0.36 | 0.34 | 2737 | 2738 |
| E88I | 88 | E | I | 0.36 | 0 | 2739 | 2740 |
| V24M | 24 | V | M | 0.36 | 0.29 | 2741 | 2742 |
| P589V | 589 | P | V | 0.36 | 0.1 | 2743 | 2744 |
| A685N | 685 | A | N | 0.36 | 0.35 | 2745 | 2746 |
| S710K | 710 | S | K | 0.36 | 0.31 | 2747 | 2748 |
| K421I | 421 | K | I | 0.36 | 0.26 | 2749 | 2750 |
| N582W | 582 | N | W | 0.36 | 0.2 | 2751 | 2752 |
| D1005S | 1005 | D | S | 0.36 | 1.11 | 2753 | 2754 |
| M1131P | 1131 | M | P | 0.36 | 0.28 | 2755 | 2756 |
| K1025F | 1025 | K | F | 0.36 | 0.05 | 2757 | 2758 |
| Y872D | 872 | Y | D | 0.36 | 0.02 | 2759 | 2760 |
| K940R | 940 | K | R | 0.36 | 0.48 | 2761 | 2762 |
| E913G | 913 | E | G | 0.36 | 0.11 | 2763 | 2764 |
| S143R | 143 | S | R | 0.36 | 0.08 | 2765 | 2766 |
| M558Y | 558 | M | Y | 0.36 | 0.1 | 2767 | 2768 |
| N889D | 889 | N | D | 0.36 | 0.04 | 2769 | 2770 |
| D1056E | 1056 | D | E | 0.36 | 0.15 | 2771 | 2772 |
| V422Y | 422 | V | Y | 0.36 | 0.28 | 2773 | 2774 |
| A1046H | 1046 | A | H | 0.36 | 0.62 | 2775 | 2776 |
| V441N | 441 | V | N | 0.36 | 0.02 | 2777 | 2778 |
| I636L | 636 | I | L | 0.36 | 1.32 | 2779 | 2780 |
| R887A | 887 | R | A | 0.36 | 0.04 | 2781 | 2782 |
| E88T | 88 | E | T | 0.36 | 0.12 | 2783 | 2784 |
| F1123Q | 1123 | F | Q | 0.36 | 0.38 | 2785 | 2786 |
| I22A | 22 | I | A | 0.36 | 0.2 | 2787 | 2788 |
| I557S | 557 | I | S | 0.36 | 0.08 | 2789 | 2790 |
| G740E | 740 | G | E | 0.36 | 0.64 | 2791 | 2792 |
| H733Q | 733 | H | Q | 0.36 | 0.08 | 2793 | 2794 |
| G624L | 624 | G | L | 0.36 | 0.22 | 2795 | 2796 |
| E104K | 104 | E | K | 0.36 | 0.12 | 2797 | 2798 |
| I829S | 829 | I | S | 0.36 | 0.23 | 2799 | 2800 |
| F669C | 669 | F | C | 0.36 | 0.07 | 2801 | 2802 |
| W890V | 890 | W | V | 0.36 | 0.04 | 2803 | 2804 |
| L13I | 13 | L | I | 0.36 | 0.12 | 2805 | 2806 |
| K937F | 937 | K | F | 0.36 | 0 | 2807 | 2808 |
| A761P | 761 | A | P | 0.36 | 0.13 | 2809 | 2810 |
| K1015E | 1015 | K | E | 0.36 | 0.09 | 2811 | 2812 |
| K499Y | 499 | K | Y | 0.36 | 0.22 | 2813 | 2814 |
| Y903D | 903 | Y | D | 0.36 | 0.11 | 2815 | 2816 |
| A1181G | 1181 | A | G | 0.36 | 0.01 | 2817 | 2818 |
| Y606M | 606 | Y | M | 0.36 | 0.09 | 2819 | 2820 |
| N145S | 145 | N | S | 0.36 | 0.02 | 2821 | 2822 |
| V38Q | 38 | V | Q | 0.36 | 0 | 2823 | 2824 |
| Y705V | 705 | Y | V | 0.36 | 0.01 | 2825 | 2826 |
| S987M | 987 | S | M | 0.35 | 0.31 | 2827 | 2828 |
| A1046V | 1046 | A | V | 0.35 | 0.26 | 2829 | 2830 |
| E913M | 913 | E | M | 0.35 | 0.02 | 2831 | 2832 |
| D156N | 156 | D | N | 0.35 | 0.09 | 2833 | 2834 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K1015P | 1015 | K | P | 0.35 | 0.05 | 2835 | 2836 |
| S985Q | 985 | S | Q | 0.35 | 0.08 | 2837 | 2838 |
| F884V | 884 | F | V | 0.35 | 0.16 | 2839 | 2840 |
| E292V | 292 | E | V | 0.35 | 0.05 | 2841 | 2842 |
| N1070L | 1070 | N | L | 0.35 | 0.76 | 2843 | 2844 |
| S658F | 658 | S | F | 0.35 | 0.34 | 2845 | 2846 |
| A920M | 920 | A | M | 0.35 | 0.1 | 2847 | 2848 |
| S317F | 317 | S | F | 0.35 | 0.11 | 2849 | 2850 |
| Y974V | 974 | Y | V | 0.35 | 0.1 | 2851 | 2852 |
| Y487W | 487 | Y | W | 0.35 | 0.02 | 2853 | 2854 |
| Y918L | 918 | Y | L | 0.35 | 0.31 | 2855 | 2856 |
| I418N | 418 | I | N | 0.35 | 0.7 | 2857 | 2858 |
| K72V | 72 | K | V | 0.35 | 0.1 | 2859 | 2860 |
| D350M | 350 | D | M | 0.35 | 0.06 | 2861 | 2862 |
| D188C | 188 | D | C | 0.35 | 0.01 | 2863 | 2864 |
| V236C | 236 | V | C | 0.35 | 0.05 | 2865 | 2866 |
| N509L | 509 | N | L | 0.35 | 0.02 | 2867 | 2868 |
| Q613T | 613 | Q | T | 0.35 | 0.13 | 2869 | 2870 |
| Q279D | 279 | Q | D | 0.35 | 0.44 | 2871 | 2872 |
| S1140W | 1140 | S | W | 0.35 | 0.13 | 2873 | 2874 |
| K272M | 272 | K | M | 0.35 | 0.06 | 2875 | 2876 |
| G848T | 848 | G | T | 0.35 | 0.49 | 2877 | 2878 |
| E90K | 90 | E | K | 0.35 | 0.08 | 2879 | 2880 |
| N1082T | 1082 | N | T | 0.35 | 0.09 | 2881 | 2882 |
| E88W | 88 | E | W | 0.35 | 0 | 2883 | 2884 |
| N481V | 481 | N | V | 0.35 | 0.02 | 2885 | 2886 |
| D329E | 329 | D | E | 0.35 | 0.06 | 2887 | 2888 |
| I318Q | 318 | I | Q | 0.35 | 0.13 | 2889 | 2890 |
| L94K | 94 | L | K | 0.35 | 0.38 | 2891 | 2892 |
| Y469K | 469 | Y | K | 0.35 | 0.06 | 2893 | 2894 |
| N706Y | 706 | N | Y | 0.35 | 0.01 | 2895 | 2896 |
| F992G | 992 | F | G | 0.35 | 0.13 | 2897 | 2898 |
| M592R | 592 | M | R | 0.35 | 0.03 | 2899 | 2900 |
| N145R | 145 | N | R | 0.35 | 0.01 | 2901 | 2902 |
| A685R | 685 | A | R | 0.35 | 0.45 | 2903 | 2904 |
| V1089H | 1089 | V | H | 0.35 | 0.06 | 2905 | 2906 |
| D823A | 823 | D | A | 0.35 | 0.05 | 2907 | 2908 |
| Y827P | 827 | Y | P | 0.35 | 0.64 | 2909 | 2910 |
| N718R | 718 | N | R | 0.35 | 0.2 | 2911 | 2912 |
| V783Q | 783 | V | Q | 0.35 | 0.04 | 2913 | 2914 |
| K698D | 698 | K | D | 0.35 | 0.02 | 2915 | 2916 |
| Y1018D | 1018 | Y | D | 0.34 | 0.05 | 2917 | 2918 |
| K415E | 415 | K | E | 0.34 | 0.7 | 2919 | 2920 |
| K1015V | 1015 | K | V | 0.34 | 0.06 | 2921 | 2922 |
| V303Y | 303 | V | Y | 0.34 | 0.59 | 2923 | 2924 |
| D405F | 405 | D | F | 0.34 | 0.38 | 2925 | 2926 |
| K267V | 267 | K | V | 0.34 | 0.12 | 2927 | 2928 |
| Y469C | 469 | Y | C | 0.34 | 0.29 | 2929 | 2930 |
| N732M | 732 | N | M | 0.34 | 0.39 | 2931 | 2932 |
| Y670L | 670 | Y | L | 0.34 | 0.13 | 2933 | 2934 |
| H909C | 909 | H | C | 0.34 | 0.13 | 2935 | 2936 |
| W1086I | 1086 | W | I | 0.34 | 0.05 | 2937 | 2938 |
| K107A | 107 | K | A | 0.34 | 0.06 | 2939 | 2940 |
| F197N | 197 | F | N | 0.34 | 0.03 | 2941 | 2942 |
| E178R | 178 | E | R | 0.34 | 0.05 | 2943 | 2944 |
| P964N | 964 | P | N | 0.34 | 0.27 | 2945 | 2946 |
| W355E | 355 | W | E | 0.34 | 0.04 | 2947 | 2948 |
| F219H | 219 | F | H | 0.34 | 0.13 | 2949 | 2950 |
| K274S | 274 | K | S | 0.34 | 0.05 | 2951 | 2952 |
| R1033D | 1033 | R | D | 0.34 | 0.12 | 2953 | 2954 |
| Q613M | 613 | Q | M | 0.34 | 0.7 | 2955 | 2956 |
| E201Y | 201 | E | Y | 0.34 | 0.02 | 2957 | 2958 |
| R482V | 482 | R | V | 0.34 | 0.1 | 2959 | 2960 |
| D729W | 729 | D | W | 0.34 | 0.59 | 2961 | 2962 |
| E285L | 285 | E | L | 0.34 | 0.47 | 2963 | 2964 |
| F810C | 810 | F | C | 0.34 | 0.13 | 2965 | 2966 |
| S14I | 14 | S | I | 0.34 | 0 | 2967 | 2968 |
| K807N | 807 | K | N | 0.34 | 0.29 | 2969 | 2970 |
| S333M | 333 | S | M | 0.34 | 0.19 | 2971 | 2972 |
| K272L | 272 | K | L | 0.34 | 0.05 | 2973 | 2974 |
| Y974D | 974 | Y | D | 0.34 | 0.14 | 2975 | 2976 |
| H909Q | 909 | H | Q | 0.34 | 0.05 | 2977 | 2978 |
| S485P | 485 | S | P | 0.34 | 0.01 | 2979 | 2980 |
| E913P | 913 | E | P | 0.34 | 0.7 | 2981 | 2982 |
| D1207I | 1207 | D | I | 0.34 | 0.21 | 2983 | 2984 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| M1035N | 1035 | M | N | 0.34 | 0.38 | 2985 | 2986 |
| Q613C | 613 | Q | C | 0.34 | 0.01 | 2987 | 2988 |
| F490A | 490 | F | A | 0.34 | 0.02 | 2989 | 2990 |
| G114M | 114 | G | M | 0.34 | 0.09 | 2991 | 2992 |
| I841P | 841 | I | P | 0.34 | 0.01 | 2993 | 2994 |
| E39Y | 39 | E | Y | 0.34 | 0.14 | 2995 | 2996 |
| F655M | 655 | F | M | 0.34 | 0.27 | 2997 | 2998 |
| N263S | 263 | N | S | 0.34 | 0.15 | 2999 | 3000 |
| K945I | 945 | K | I | 0.34 | 0.39 | 3001 | 3002 |
| E247V | 247 | E | V | 0.34 | 0.15 | 3003 | 3004 |
| R82Q | 82 | R | Q | 0.34 | 0.04 | 3005 | 3006 |
| K253A | 253 | K | A | 0.34 | 0.59 | 3007 | 3008 |
| Y290A | 290 | Y | A | 0.34 | 0.05 | 3009 | 3010 |
| L1115N | 1115 | L | N | 0.34 | 0.59 | 3011 | 3012 |
| D501K | 501 | D | K | 0.34 | 0.58 | 3013 | 3014 |
| S79P | 79 | S | P | 0.34 | 0.21 | 3015 | 3016 |
| E815P | 815 | E | P | 0.34 | 0.26 | 3017 | 3018 |
| R482N | 482 | R | N | 0.34 | 0.59 | 3019 | 3020 |
| F162C | 162 | F | C | 0.33 | 0.6 | 3021 | 3022 |
| L1047N | 1047 | L | N | 0.33 | 0.02 | 3023 | 3024 |
| F597I | 597 | F | I | 0.33 | 0.07 | 3025 | 3026 |
| I841S | 841 | I | S | 0.33 | 0.14 | 3027 | 3028 |
| N732R | 732 | N | R | 0.33 | 0.18 | 3029 | 3030 |
| K1015T | 1015 | K | T | 0.33 | 0.05 | 3031 | 3032 |
| K413D | 413 | K | D | 0.33 | 0.15 | 3033 | 3034 |
| V376Y | 376 | V | Y | 0.33 | 0.17 | 3035 | 3036 |
| N656E | 656 | N | E | 0.33 | 0.25 | 3037 | 3038 |
| V303S | 303 | V | S | 0.33 | 0.22 | 3039 | 3040 |
| S982V | 982 | S | V | 0.33 | 0.41 | 3041 | 3042 |
| K1017L | 1017 | K | L | 0.33 | 0 | 3043 | 3044 |
| K83R | 83 | K | R | 0.33 | 0.02 | 3045 | 3046 |
| K1101Y | 1101 | K | Y | 0.33 | 0.5 | 3047 | 3048 |
| I209T | 209 | I | T | 0.33 | 0.57 | 3049 | 3050 |
| G973M | 973 | G | M | 0.33 | 0.25 | 3051 | 3052 |
| E247L | 247 | E | L | 0.33 | 0.38 | 3053 | 3054 |
| T776F | 776 | T | F | 0.33 | 0.13 | 3055 | 3056 |
| N861S | 861 | N | S | 0.33 | 0.47 | 3057 | 3058 |
| L492N | 492 | L | N | 0.33 | 0.11 | 3059 | 3060 |
| K448A | 448 | K | A | 0.33 | 0.18 | 3061 | 3062 |
| E90W | 90 | E | W | 0.33 | 0.18 | 3063 | 3064 |
| E98T | 98 | E | T | 0.33 | 0.18 | 3065 | 3066 |
| T988K | 988 | T | K | 0.33 | 0.06 | 3067 | 3068 |
| K499R | 499 | K | R | 0.33 | 0.11 | 3069 | 3070 |
| E743K | 743 | E | K | 0.33 | 0.23 | 3071 | 3072 |
| I503S | 503 | I | S | 0.33 | 0.02 | 3073 | 3074 |
| H714R | 714 | H | R | 0.33 | 0.02 | 3075 | 3076 |
| Y1018S | 1018 | Y | S | 0.33 | 0.19 | 3077 | 3078 |
| L261A | 261 | L | A | 0.33 | 0.7 | 3079 | 3080 |
| T776W | 776 | T | W | 0.33 | 0.26 | 3081 | 3082 |
| Y1068P | 1068 | Y | P | 0.33 | 0.59 | 3083 | 3084 |
| P342H | 342 | P | H | 0.33 | 0.18 | 3085 | 3086 |
| S780W | 780 | S | W | 0.33 | 0.13 | 3087 | 3088 |
| F1099K | 1099 | F | K | 0.33 | 0.6 | 3089 | 3090 |
| V758Y | 758 | V | Y | 0.33 | 0.11 | 3091 | 3092 |
| V280C | 280 | V | C | 0.33 | 0.1 | 3093 | 3094 |
| F1198R | 1198 | F | R | 0.33 | 0.6 | 3095 | 3096 |
| D489E | 489 | D | E | 0.33 | 0.21 | 3097 | 3098 |
| A334F | 334 | A | F | 0.33 | 0.41 | 3099 | 3100 |
| A970C | 970 | A | C | 0.33 | 0.02 | 3101 | 3102 |
| D1180T | 1180 | D | T | 0.33 | 0.69 | 3103 | 3104 |
| K1017E | 1017 | K | E | 0.33 | 0.28 | 3105 | 3106 |
| N718H | 718 | N | H | 0.33 | 0.15 | 3107 | 3108 |
| L914Y | 914 | L | Y | 0.32 | 0.08 | 3109 | 3110 |
| I557Y | 557 | I | Y | 0.32 | 0.5 | 3111 | 3112 |
| M592T | 592 | M | T | 0.32 | 0.29 | 3113 | 3114 |
| K274A | 274 | K | A | 0.32 | 0.01 | 3115 | 3116 |
| L954R | 954 | L | R | 0.32 | 0.06 | 3117 | 3118 |
| M603W | 603 | M | W | 0.32 | 0.1 | 3119 | 3120 |
| D631N | 631 | D | N | 0.32 | 0.14 | 3121 | 3122 |
| Y678A | 678 | Y | A | 0.32 | 0.73 | 3123 | 3124 |
| K1121N | 1121 | K | N | 0.32 | 0.15 | 3125 | 3126 |
| E88V | 88 | E | V | 0.32 | 0.19 | 3127 | 3128 |
| K648P | 648 | K | P | 0.32 | 0.7 | 3129 | 3130 |
| T776Y | 776 | T | Y | 0.32 | 0.03 | 3131 | 3132 |
| K1026G | 1026 | K | G | 0.32 | 0.09 | 3133 | 3134 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| R284V | 284 | R | V | 0.32 | 1.2 | 3135 | 3136 |
| Y827D | 827 | Y | D | 0.32 | 0.07 | 3137 | 3138 |
| D877G | 877 | D | G | 0.32 | 0.12 | 3139 | 3140 |
| E674C | 674 | E | C | 0.32 | 0.15 | 3141 | 3142 |
| S431L | 431 | S | L | 0.32 | 0.88 | 3143 | 3144 |
| S394H | 394 | S | H | 0.32 | 0.01 | 3145 | 3146 |
| Y781Q | 781 | Y | Q | 0.32 | 0.01 | 3147 | 3148 |
| K1121Y | 1121 | K | Y | 0.32 | 0.15 | 3149 | 3150 |
| I205V | 205 | I | V | 0.32 | 0.26 | 3151 | 3152 |
| R86A | 86 | R | A | 0.32 | 0.06 | 3153 | 3154 |
| L914A | 914 | L | A | 0.32 | 0.05 | 3155 | 3156 |
| L779S | 779 | L | S | 0.32 | 0.09 | 3157 | 3158 |
| Y872Q | 872 | Y | Q | 0.32 | 0.03 | 3159 | 3160 |
| T480E | 480 | T | E | 0.32 | 0.43 | 3161 | 3162 |
| K135V | 135 | K | V | 0.32 | 0.02 | 3163 | 3164 |
| A1113M | 1113 | A | M | 0.32 | 0.09 | 3165 | 3166 |
| R482A | 482 | R | A | 0.32 | 0.04 | 3167 | 3168 |
| D450A | 450 | D | A | 0.32 | 0.1 | 3169 | 3170 |
| Q703P | 703 | Q | P | 0.32 | 0.06 | 3171 | 3172 |
| A1181Q | 1181 | A | Q | 0.32 | 0.7 | 3173 | 3174 |
| V907A | 907 | V | A | 0.32 | 0.03 | 3175 | 3176 |
| D535E | 535 | D | E | 0.32 | 0.35 | 3177 | 3178 |
| E858M | 858 | E | M | 0.32 | 0.23 | 3179 | 3180 |
| S929Q | 929 | S | Q | 0.32 | 0.01 | 3181 | 3182 |
| G697R | 697 | G | R | 0.32 | 0.14 | 3183 | 3184 |
| N449C | 449 | N | C | 0.32 | 0.57 | 3185 | 3186 |
| M558H | 558 | M | H | 0.32 | 0.04 | 3187 | 3188 |
| Y294S | 294 | Y | S | 0.32 | 0.06 | 3189 | 3190 |
| E539L | 539 | E | L | 0.32 | 0.06 | 3191 | 3192 |
| Y294D | 294 | Y | D | 0.31 | 0.09 | 3193 | 3194 |
| Q941T | 941 | Q | T | 0.31 | 0.23 | 3195 | 3196 |
| F151L | 151 | F | L | 0.31 | 0.03 | 3197 | 3198 |
| N186Y | 186 | N | Y | 0.31 | 0.32 | 3199 | 3200 |
| P587S | 587 | P | S | 0.31 | 0.23 | 3201 | 3202 |
| D46F | 46 | D | F | 0.31 | 0.15 | 3203 | 3204 |
| E221W | 221 | E | W | 0.31 | 0.01 | 3205 | 3206 |
| I841Y | 841 | I | Y | 0.31 | 0.02 | 3207 | 3208 |
| S286K | 286 | S | K | 0.31 | 0.13 | 3209 | 3210 |
| D1207Y | 1207 | D | Y | 0.31 | 0.03 | 3211 | 3212 |
| K278Y | 278 | K | Y | 0.31 | 0.08 | 3213 | 3214 |
| L321K | 321 | L | K | 0.31 | 0.1 | 3215 | 3216 |
| F474V | 474 | F | V | 0.31 | 0.02 | 3217 | 3218 |
| N1077H | 1077 | N | H | 0.31 | 0.13 | 3219 | 3220 |
| E178L | 178 | E | L | 0.31 | 0.2 | 3221 | 3222 |
| L1065E | 1065 | L | E | 0.31 | 0.08 | 3223 | 3224 |
| Y77S | 77 | Y | S | 0.31 | 0.16 | 3225 | 3226 |
| D1207T | 1207 | D | T | 0.31 | 0.07 | 3227 | 3228 |
| N1166K | 1166 | N | K | 0.31 | 0.03 | 3229 | 3230 |
| Y670D | 670 | Y | D | 0.31 | 0.03 | 3231 | 3232 |
| N861Y | 861 | N | Y | 0.31 | 0.21 | 3233 | 3234 |
| E412P | 412 | E | P | 0.31 | 1.32 | 3235 | 3236 |
| E95W | 95 | E | W | 0.31 | 0.41 | 3237 | 3238 |
| D708A | 708 | D | A | 0.31 | 0.19 | 3239 | 3240 |
| S60T | 60 | S | T | 0.31 | 0.29 | 3241 | 3242 |
| K787Y | 787 | K | Y | 0.31 | 0.21 | 3243 | 3244 |
| Y700D | 700 | Y | D | 0.31 | 0.06 | 3245 | 3246 |
| A1201R | 1201 | A | R | 0.31 | 0.08 | 3247 | 3248 |
| A766V | 766 | A | V | 0.31 | 0.01 | 3249 | 3250 |
| D559Y | 559 | D | Y | 0.31 | 0.01 | 3251 | 3252 |
| E95T | 95 | E | T | 0.31 | 0.11 | 3253 | 3254 |
| A139R | 139 | A | R | 0.31 | 0.33 | 3255 | 3256 |
| D458T | 458 | D | T | 0.31 | 0.04 | 3257 | 3258 |
| K804L | 804 | K | L | 0.31 | 0.11 | 3259 | 3260 |
| Q941D | 941 | Q | D | 0.31 | 0.34 | 3261 | 3262 |
| A920G | 920 | A | G | 0.31 | 0.18 | 3263 | 3264 |
| Y381T | 381 | Y | T | 0.31 | 0.16 | 3265 | 3266 |
| K692Y | 692 | K | Y | 0.31 | 0.01 | 3267 | 3268 |
| D832E | 832 | D | E | 0.31 | 0.16 | 3269 | 3270 |
| T246A | 246 | T | A | 0.31 | 0.11 | 3271 | 3272 |
| Y237F | 237 | Y | F | 0.3 | 0.02 | 3273 | 3274 |
| V842W | 842 | V | W | 0.3 | 0.32 | 3275 | 3276 |
| G668L | 668 | G | L | 0.3 | 0.17 | 3277 | 3278 |
| E695L | 695 | E | L | 0.3 | 0.11 | 3279 | 3280 |
| L132R | 132 | L | R | 0.3 | 0.12 | 3281 | 3282 |
| K775M | 775 | K | M | 0.3 | 0.24 | 3283 | 3284 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| R158K | 158 | R | K | 0.3 | 0.65 | 3285 | 3286 |
| Y840L | 840 | Y | L | 0.3 | 0.3 | 3287 | 3288 |
| W890G | 890 | W | G | 0.3 | 0.05 | 3289 | 3290 |
| D437S | 437 | D | S | 0.3 | 0.47 | 3291 | 3292 |
| E858N | 858 | E | N | 0.3 | 0.19 | 3293 | 3294 |
| A1201S | 1201 | A | S | 0.3 | 0.64 | 3295 | 3296 |
| L1192G | 1192 | L | G | 0.3 | 0.25 | 3297 | 3298 |
| G576C | 576 | G | C | 0.3 | 0.2 | 3299 | 3300 |
| D877A | 877 | D | A | 0.3 | 0.04 | 3301 | 3302 |
| K1121M | 1121 | K | M | 0.3 | 0.1 | 3303 | 3304 |
| K1079Q | 1079 | K | Q | 0.3 | 0.13 | 3305 | 3306 |
| N157C | 157 | N | C | 0.3 | 0.34 | 3307 | 3308 |
| K979M | 979 | K | M | 0.3 | 0.65 | 3309 | 3310 |
| K199P | 199 | K | P | 0.3 | 0.14 | 3311 | 3312 |
| L414K | 414 | L | K | 0.3 | 0.01 | 3313 | 3314 |
| D297A | 297 | D | A | 0.3 | 0.07 | 3315 | 3316 |
| L738C | 738 | L | C | 0.3 | 0.26 | 3317 | 3318 |
| G475L | 475 | G | L | 0.3 | 0.21 | 3319 | 3320 |
| V411S | 411 | V | S | 0.3 | 0.02 | 3321 | 3322 |
| I318A | 318 | I | A | 0.3 | 1.18 | 3323 | 3324 |
| G335L | 335 | G | L | 0.3 | 0.08 | 3325 | 3326 |
| Y903S | 903 | Y | S | 0.3 | 0.2 | 3327 | 3328 |
| K1026H | 1026 | K | H | 0.3 | 0.01 | 3329 | 3330 |
| L914I | 914 | L | I | 0.3 | 0.01 | 3331 | 3332 |
| N955C | 955 | N | C | 0.3 | 1.51 | 3333 | 3334 |
| L1091R | 1091 | L | R | 0.3 | 0.07 | 3335 | 3336 |
| N63Q | 63 | N | Q | 0.3 | 0.15 | 3337 | 3338 |
| K1026D | 1026 | K | D | 0.3 | 0.19 | 3339 | 3340 |
| S1020P | 1020 | S | P | 0.3 | 0.08 | 3341 | 3342 |
| S1225W | 1225 | S | W | 0.3 | 0.05 | 3343 | 3344 |
| M949R | 949 | M | R | 0.3 | 0.1 | 3345 | 3346 |
| Y700R | 700 | Y | R | 0.3 | 0.54 | 3347 | 3348 |
| N327L | 327 | N | L | 0.3 | 0.12 | 3349 | 3350 |
| S982M | 982 | S | M | 0.3 | 0.09 | 3351 | 3352 |
| F19C | 19 | F | C | 0.3 | 0 | 3353 | 3354 |
| S780A | 780 | S | A | 0.3 | 0.01 | 3355 | 3356 |
| L839A | 839 | L | A | 0.29 | 0.01 | 3357 | 3358 |
| E981T | 981 | E | T | 0.29 | 0.21 | 3359 | 3360 |
| D283L | 283 | D | L | 0.29 | 0.05 | 3361 | 3362 |
| K269P | 269 | K | P | 0.29 | 0.46 | 3363 | 3364 |
| E981S | 981 | E | S | 0.29 | 0.02 | 3365 | 3366 |
| E88K | 88 | E | K | 0.29 | 0.02 | 3367 | 3368 |
| R86V | 86 | R | V | 0.29 | 0.14 | 3369 | 3370 |
| F81P | 81 | F | P | 0.29 | 0.17 | 3371 | 3372 |
| V193Q | 193 | V | Q | 0.29 | 0.05 | 3373 | 3374 |
| S1132C | 1132 | S | C | 0.29 | 0.7 | 3375 | 3376 |
| K1003D | 1003 | K | D | 0.29 | 0.18 | 3377 | 3378 |
| T480Y | 480 | T | Y | 0.29 | 0.06 | 3379 | 3380 |
| T1016Y | 1016 | T | Y | 0.29 | 0.12 | 3381 | 3382 |
| D283Q | 283 | D | Q | 0.29 | 0.34 | 3383 | 3384 |
| N356F | 356 | N | F | 0.29 | 0.09 | 3385 | 3386 |
| K372R | 372 | K | R | 0.29 | 0.44 | 3387 | 3388 |
| T778I | 778 | T | I | 0.29 | 0.3 | 3389 | 3390 |
| R82Y | 82 | R | Y | 0.29 | 0.05 | 3391 | 3392 |
| F328A | 328 | F | A | 0.29 | 0.26 | 3393 | 3394 |
| Y606E | 606 | Y | E | 0.29 | 0.09 | 3395 | 3396 |
| L97A | 97 | L | A | 0.29 | 0.03 | 3397 | 3398 |
| A1181R | 1181 | A | R | 0.29 | 0.32 | 3399 | 3400 |
| K265Y | 265 | K | Y | 0.29 | 0 | 3401 | 3402 |
| V574S | 574 | V | S | 0.29 | 0.54 | 3403 | 3404 |
| R102N | 102 | R | N | 0.29 | 0.05 | 3405 | 3406 |
| K536D | 536 | K | D | 0.29 | 0.39 | 3407 | 3408 |
| D926A | 926 | D | A | 0.29 | 0.21 | 3409 | 3410 |
| M1134Y | 1134 | M | Y | 0.29 | 0.11 | 3411 | 3412 |
| L927R | 927 | L | R | 0.29 | 0.12 | 3413 | 3414 |
| N1156T | 1156 | N | T | 0.29 | 0.24 | 3415 | 3416 |
| L94Y | 94 | L | Y | 0.29 | 0.21 | 3417 | 3418 |
| T480M | 480 | T | M | 0.29 | 0.18 | 3419 | 3420 |
| F702R | 702 | F | R | 0.29 | 0.18 | 3421 | 3422 |
| Y57D | 57 | Y | D | 0.29 | 0.14 | 3423 | 3424 |
| L586I | 586 | L | I | 0.29 | 0.08 | 3425 | 3426 |
| K120Q | 120 | K | Q | 0.29 | 0.06 | 3427 | 3428 |
| Y183S | 183 | Y | S | 0.29 | 0.11 | 3429 | 3430 |
| G697A | 697 | G | A | 0.29 | 0.14 | 3431 | 3432 |
| N849H | 849 | N | H | 0.29 | 0.83 | 3433 | 3434 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| K120T | 120 | K | T | 0.29 | 0.09 | 3435 | 3436 |
| K320Q | 320 | K | Q | 0.29 | 0.1 | 3437 | 3438 |
| G588L | 588 | G | L | 0.29 | 0.01 | 3439 | 3440 |
| L498K | 498 | L | K | 0.29 | 0.09 | 3441 | 3442 |
| N772P | 772 | N | P | 0.29 | 0.54 | 3443 | 3444 |
| Y1221L | 1221 | Y | L | 0.29 | 0.12 | 3445 | 3446 |
| R1144P | 1144 | R | P | 0.29 | 0.11 | 3447 | 3448 |
| I859L | 859 | I | L | 0.29 | 0.18 | 3449 | 3450 |
| F227Q | 227 | F | Q | 0.29 | 0.01 | 3451 | 3452 |
| L97H | 97 | L | H | 0.29 | 0.21 | 3453 | 3454 |
| V491R | 491 | V | R | 0.29 | 0.07 | 3455 | 3456 |
| Y1167L | 1167 | Y | L | 0.29 | 1.5 | 3457 | 3458 |
| N582Q | 582 | N | Q | 0.29 | 0.03 | 3459 | 3460 |
| Y956F | 956 | Y | F | 0.29 | 0.53 | 3461 | 3462 |
| T891R | 891 | T | R | 0.29 | 0.18 | 3463 | 3464 |
| N772C | 772 | N | C | 0.29 | 0.44 | 3465 | 3466 |
| S432G | 432 | S | G | 0.29 | 0.04 | 3467 | 3468 |
| F789V | 789 | F | V | 0.29 | 0.07 | 3469 | 3470 |
| K272R | 272 | K | R | 0.29 | 0.06 | 3471 | 3472 |
| E695Y | 695 | E | Y | 0.29 | 0.06 | 3473 | 3474 |
| F473C | 473 | F | C | 0.29 | 0.03 | 3475 | 3476 |
| K1050Y | 1050 | K | Y | 0.28 | 0.03 | 3477 | 3478 |
| N582H | 582 | N | H | 0.28 | 0.11 | 3479 | 3480 |
| G488A | 488 | G | A | 0.28 | 0.11 | 3481 | 3482 |
| G291W | 291 | G | W | 0.28 | 0.11 | 3483 | 3484 |
| D156A | 156 | D | A | 0.28 | 0.11 | 3485 | 3486 |
| F131D | 131 | F | D | 0.28 | 0.05 | 3487 | 3488 |
| K1015N | 1015 | K | N | 0.28 | 0.1 | 3489 | 3490 |
| I911C | 911 | I | C | 0.28 | 0.05 | 3491 | 3492 |
| F1198M | 1198 | F | M | 0.28 | 0.15 | 3493 | 3494 |
| S929I | 929 | S | I | 0.28 | 0.14 | 3495 | 3496 |
| N1081C | 1081 | N | C | 0.28 | 0.07 | 3497 | 3498 |
| F144R | 144 | F | R | 0.28 | 0.04 | 3499 | 3500 |
| K265E | 265 | K | E | 0.28 | 0.06 | 3501 | 3502 |
| K265F | 265 | K | F | 0.28 | 0.05 | 3503 | 3504 |
| E330H | 330 | E | H | 0.28 | 0.02 | 3505 | 3506 |
| E217V | 217 | E | V | 0.28 | 0.19 | 3507 | 3508 |
| I1111P | 1111 | I | P | 0.28 | 0.11 | 3509 | 3510 |
| A998R | 998 | A | R | 0.28 | 1.08 | 3511 | 3512 |
| N772T | 772 | N | T | 0.28 | 0.15 | 3513 | 3514 |
| F151N | 151 | F | N | 0.28 | 0.06 | 3515 | 3516 |
| N590K | 590 | N | K | 0.28 | 0.2 | 3517 | 3518 |
| S185G | 185 | S | G | 0.28 | 0.21 | 3519 | 3520 |
| T1019F | 1019 | T | F | 0.28 | 0.08 | 3521 | 3522 |
| E815W | 815 | E | W | 0.28 | 0.25 | 3523 | 3524 |
| F474D | 474 | F | D | 0.28 | 0.13 | 3525 | 3526 |
| W1218F | 1218 | W | F | 0.28 | 0.65 | 3527 | 3528 |
| N1081F | 1081 | N | F | 0.28 | 0.11 | 3529 | 3530 |
| D1146E | 1146 | D | E | 0.28 | 0.2 | 3531 | 3532 |
| Y294M | 294 | Y | M | 0.28 | 0.06 | 3533 | 3534 |
| N1182Q | 1182 | N | Q | 0.28 | 0.28 | 3535 | 3536 |
| I496M | 496 | I | M | 0.28 | 0.04 | 3537 | 3538 |
| Y562H | 562 | Y | H | 0.28 | 0.11 | 3539 | 3540 |
| Y616C | 616 | Y | C | 0.28 | 0.15 | 3541 | 3542 |
| Y1124E | 1124 | Y | E | 0.28 | 0.12 | 3543 | 3544 |
| S296D | 296 | S | D | 0.28 | 0.02 | 3545 | 3546 |
| G830I | 830 | G | I | 0.28 | 1.5 | 3547 | 3548 |
| S1132G | 1132 | S | G | 0.28 | 0.47 | 3549 | 3550 |
| E130W | 130 | E | W | 0.28 | 0.14 | 3551 | 3552 |
| T814H | 814 | T | H | 0.28 | 0.08 | 3553 | 3554 |
| N1178S | 1178 | N | S | 0.28 | 0.1 | 3555 | 3556 |
| D541E | 541 | D | E | 0.28 | 0.12 | 3557 | 3558 |
| T85L | 85 | T | L | 0.28 | 0.05 | 3559 | 3560 |
| G902L | 902 | G | L | 0.28 | 0.18 | 3561 | 3562 |
| R182S | 182 | R | S | 0.28 | 0.08 | 3563 | 3564 |
| D919A | 919 | D | A | 0.28 | 0.12 | 3565 | 3566 |
| D1032E | 1032 | D | E | 0.28 | 0.06 | 3567 | 3568 |
| Y494K | 494 | Y | K | 0.28 | 0.02 | 3569 | 3570 |
| S14M | 14 | S | M | 0.28 | 0.11 | 3571 | 3572 |
| E379Y | 379 | E | Y | 0.28 | 0.21 | 3573 | 3574 |
| E302P | 302 | E | P | 0.28 | 0.21 | 3575 | 3576 |
| N651D | 651 | N | D | 0.28 | 0.19 | 3577 | 3578 |
| N577L | 577 | N | L | 0.28 | 0.01 | 3579 | 3580 |
| D407P | 407 | D | P | 0.28 | 0.26 | 3581 | 3582 |
| N481Q | 481 | N | Q | 0.28 | 0.22 | 3583 | 3584 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| E90R | 90 | E | R | 0.28 | 0.09 | 3585 | 3586 |
| I643S | 643 | I | S | 0.28 | 0.09 | 3587 | 3588 |
| I736K | 736 | I | K | 0.28 | 1.5 | 3589 | 3590 |
| E207A | 207 | E | A | 0.28 | 0.07 | 3591 | 3592 |
| I831M | 831 | I | M | 0.28 | 0.2 | 3593 | 3594 |
| Y524G | 524 | Y | G | 0.28 | 0.4 | 3595 | 3596 |
| K1017V | 1017 | K | V | 0.28 | 0.1 | 3597 | 3598 |
| A150I | 150 | A | I | 0.28 | 0.29 | 3599 | 3600 |
| K110R | 110 | K | R | 0.28 | 0.09 | 3601 | 3602 |
| R867T | 867 | R | T | 0.28 | 1.19 | 3603 | 3604 |
| I189Q | 189 | I | Q | 0.28 | 0.03 | 3605 | 3606 |
| L1192N | 1192 | L | N | 0.28 | 0.05 | 3607 | 3608 |
| I196G | 196 | I | G | 0.28 | 0.11 | 3609 | 3610 |
| K1017P | 1017 | K | P | 0.28 | 0.33 | 3611 | 3612 |
| I831R | 831 | I | R | 0.28 | 1.19 | 3613 | 3614 |
| T1019L | 1019 | T | L | 0.28 | 0.1 | 3615 | 3616 |
| S212R | 212 | S | R | 0.28 | 0.2 | 3617 | 3618 |
| K538Y | 538 | K | Y | 0.28 | 0.41 | 3619 | 3620 |
| A556S | 556 | A | S | 0.28 | 0.1 | 3621 | 3622 |
| P528N | 528 | P | N | 0.28 | 0.07 | 3623 | 3624 |
| G254K | 254 | G | K | 0.28 | 0.21 | 3625 | 3626 |
| T230Y | 230 | T | Y | 0.28 | 0.18 | 3627 | 3628 |
| K1015A | 1015 | K | A | 0.28 | 0.03 | 3629 | 3630 |
| G475P | 475 | G | P | 0.28 | 0.06 | 3631 | 3632 |
| S987Q | 987 | S | Q | 0.27 | 0.5 | 3633 | 3634 |
| E467I | 467 | E | I | 0.27 | 0.52 | 3635 | 3636 |
| A108C | 108 | A | C | 0.27 | 0.3 | 3637 | 3638 |
| I184K | 184 | I | K | 0.27 | 0.13 | 3639 | 3640 |
| E579G | 579 | E | G | 0.27 | 0 | 3641 | 3642 |
| W1063Y | 1063 | W | Y | 0.27 | 0.21 | 3643 | 3644 |
| L140R | 140 | L | R | 0.27 | 0.03 | 3645 | 3646 |
| K595I | 595 | K | I | 0.27 | 0.22 | 3647 | 3648 |
| F81K | 81 | F | K | 0.27 | 0.14 | 3649 | 3650 |
| E299M | 299 | E | M | 0.27 | 0.21 | 3651 | 3652 |
| D1023R | 1023 | D | R | 0.27 | 0.21 | 3653 | 3654 |
| P997I | 997 | P | I | 0.27 | 0.21 | 3655 | 3656 |
| F669V | 669 | F | V | 0.27 | 0.11 | 3657 | 3658 |
| L744D | 744 | L | D | 0.27 | 0.21 | 3659 | 3660 |
| L498F | 498 | L | F | 0.27 | 0.09 | 3661 | 3662 |
| K1079I | 1079 | K | I | 0.27 | 0.05 | 3663 | 3664 |
| E539K | 539 | E | K | 0.27 | 0.38 | 3665 | 3666 |
| F328V | 328 | F | V | 0.27 | 0.05 | 3667 | 3668 |
| I557H | 557 | I | H | 0.27 | 0.05 | 3669 | 3670 |
| L261D | 261 | L | D | 0.27 | 0.06 | 3671 | 3672 |
| I62S | 62 | I | S | 0.27 | 0.01 | 3673 | 3674 |
| N837Q | 837 | N | Q | 0.27 | 0.19 | 3675 | 3676 |
| T778A | 778 | T | A | 0.27 | 0.08 | 3677 | 3678 |
| E479V | 479 | E | V | 0.27 | 0.02 | 3679 | 3680 |
| K1025H | 1025 | K | H | 0.27 | 0.05 | 3681 | 3682 |
| I234R | 234 | I | R | 0.27 | 0.04 | 3683 | 3684 |
| S609T | 609 | S | T | 0.27 | 0.23 | 3685 | 3686 |
| M1035H | 1035 | M | H | 0.27 | 0.05 | 3687 | 3688 |
| Y494R | 494 | Y | R | 0.27 | 0.07 | 3689 | 3690 |
| D122P | 122 | D | P | 0.27 | 0.05 | 3691 | 3692 |
| F530C | 530 | F | C | 0.27 | 0.19 | 3693 | 3694 |
| F627H | 627 | F | H | 0.27 | 0.21 | 3695 | 3696 |
| Y262V | 262 | Y | V | 0.27 | 0.07 | 3697 | 3698 |
| I392R | 392 | I | R | 0.27 | 0.29 | 3699 | 3700 |
| V1037M | 1037 | V | M | 0.27 | 0.34 | 3701 | 3702 |
| C805N | 805 | C | N | 0.27 | 0.01 | 3703 | 3704 |
| Y214T | 214 | Y | T | 0.27 | 0 | 3705 | 3706 |
| E683Y | 683 | E | Y | 0.27 | 0.01 | 3707 | 3708 |
| I736T | 736 | I | T | 0.27 | 0.65 | 3709 | 3710 |
| D297E | 297 | D | E | 0.27 | 0.1 | 3711 | 3712 |
| I418T | 418 | I | T | 0.27 | 0.2 | 3713 | 3714 |
| T814R | 814 | T | R | 0.27 | 0.13 | 3715 | 3716 |
| L856S | 856 | L | S | 0.27 | 0.19 | 3717 | 3718 |
| K427C | 427 | K | C | 0.27 | 0.09 | 3719 | 3720 |
| A901D | 901 | A | D | 0.27 | 0.49 | 3721 | 3722 |
| K391Q | 391 | K | Q | 0.27 | 0.26 | 3723 | 3724 |
| V783F | 783 | V | F | 0.27 | 0.18 | 3725 | 3726 |
| G335E | 335 | G | E | 0.27 | 0.25 | 3727 | 3728 |
| K917Q | 917 | K | Q | 0.27 | 0.11 | 3729 | 3730 |
| E795C | 795 | E | C | 0.27 | 0.17 | 3731 | 3732 |
| F197E | 197 | F | E | 0.27 | 0.27 | 3733 | 3734 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| F1027D | 1027 | F | D | 0.27 | 0.16 | 3735 | 3736 |
| L1150F | 1150 | L | F | 0.27 | 0.27 | 3737 | 3738 |
| S686Q | 686 | S | Q | 0.26 | 0.44 | 3739 | 3740 |
| L37D | 37 | L | D | 0.26 | 0.32 | 3741 | 3742 |
| T480H | 480 | T | H | 0.26 | 0.14 | 3743 | 3744 |
| E743Q | 743 | E | Q | 0.26 | 0.14 | 3745 | 3746 |
| K107L | 107 | K | L | 0.26 | 0.01 | 3747 | 3748 |
| N808P | 808 | N | P | 0.26 | 0 | 3749 | 3750 |
| K564S | 564 | K | S | 0.26 | 0.09 | 3751 | 3752 |
| N803H | 803 | N | H | 0.26 | 0.11 | 3753 | 3754 |
| S1020F | 1020 | S | F | 0.26 | 0.01 | 3755 | 3756 |
| I1104T | 1104 | I | T | 0.26 | 0.49 | 3757 | 3758 |
| N306W | 306 | N | W | 0.26 | 0.05 | 3759 | 3760 |
| D1120E | 1120 | D | E | 0.26 | 0.03 | 3761 | 3762 |
| D1146Q | 1146 | D | Q | 0.26 | 0.08 | 3763 | 3764 |
| R1073Y | 1073 | R | Y | 0.26 | 0.34 | 3765 | 3766 |
| Y872S | 872 | Y | S | 0.26 | 0.01 | 3767 | 3768 |
| Y429H | 429 | Y | H | 0.26 | 0.33 | 3769 | 3770 |
| D423R | 423 | D | R | 0.26 | 0.2 | 3771 | 3772 |
| K785I | 785 | K | I | 0.26 | 0.54 | 3773 | 3774 |
| E299A | 299 | E | A | 0.26 | 0.14 | 3775 | 3776 |
| W1218Q | 1218 | W | Q | 0.26 | 0.13 | 3777 | 3778 |
| G846Y | 846 | G | Y | 0.26 | 0.39 | 3779 | 3780 |
| A761R | 761 | A | R | 0.26 | 0.88 | 3781 | 3782 |
| K940S | 940 | K | S | 0.26 | 0.01 | 3783 | 3784 |
| N1081L | 1081 | N | L | 0.26 | 0.28 | 3785 | 3786 |
| S1225F | 1225 | S | F | 0.26 | 0.06 | 3787 | 3788 |
| I318L | 318 | I | L | 0.26 | 0.1 | 3789 | 3790 |
| F980V | 980 | F | V | 0.26 | 0.11 | 3791 | 3792 |
| P826D | 826 | P | D | 0.26 | 0.15 | 3793 | 3794 |
| E981L | 981 | E | L | 0.26 | 0.27 | 3795 | 3796 |
| S1132L | 1132 | S | L | 0.26 | 0.01 | 3797 | 3798 |
| T777W | 777 | T | W | 0.26 | 0.1 | 3799 | 3800 |
| A604Q | 604 | A | Q | 0.26 | 0.13 | 3801 | 3802 |
| D283K | 283 | D | K | 0.26 | 0.54 | 3803 | 3804 |
| D637K | 637 | D | K | 0.26 | 0.1 | 3805 | 3806 |
| K72Y | 72 | K | Y | 0.26 | 0.02 | 3807 | 3808 |
| E130A | 130 | E | A | 0.26 | 1 | 3809 | 3810 |
| T1145E | 1145 | T | E | 0.26 | 0.44 | 3811 | 3812 |
| N803T | 803 | N | T | 0.26 | 0.01 | 3813 | 3814 |
| F225C | 225 | F | C | 0.26 | 0.19 | 3815 | 3816 |
| E925S | 925 | E | S | 0.26 | 0.14 | 3817 | 3818 |
| N356H | 356 | N | H | 0.26 | 0.11 | 3819 | 3820 |
| S79F | 79 | S | F | 0.26 | 0.39 | 3821 | 3822 |
| N1156H | 1156 | N | H | 0.26 | 0 | 3823 | 3824 |
| I831S | 831 | I | S | 0.26 | 0.19 | 3825 | 3826 |
| Q853M | 853 | Q | M | 0.26 | 0.26 | 3827 | 3828 |
| T540Q | 540 | T | Q | 0.26 | 0 | 3829 | 3830 |
| A1094D | 1094 | A | D | 0.26 | 0.27 | 3831 | 3832 |
| E232R | 232 | E | R | 0.26 | 0.16 | 3833 | 3834 |
| G242L | 242 | G | L | 0.26 | 0.34 | 3835 | 3836 |
| K1079L | 1079 | K | L | 0.26 | 0.29 | 3837 | 3838 |
| M1137R | 1137 | M | R | 0.26 | 0.09 | 3839 | 3840 |
| I996G | 996 | I | G | 0.26 | 0.11 | 3841 | 3842 |
| M603A | 603 | M | A | 0.26 | 0.02 | 3843 | 3844 |
| S1132F | 1132 | S | F | 0.26 | 0.57 | 3845 | 3846 |
| V38L | 38 | V | L | 0.26 | 0.24 | 3847 | 3848 |
| V908M | 908 | V | M | 0.26 | 0.16 | 3849 | 3850 |
| D122V | 122 | D | V | 0.26 | 0.13 | 3851 | 3852 |
| L856V | 856 | L | V | 0.26 | 0.07 | 3853 | 3854 |
| I904L | 904 | I | L | 0.26 | 0.04 | 3855 | 3856 |
| W1063D | 1063 | W | D | 0.26 | 0.16 | 3857 | 3858 |
| F1149I | 1149 | F | I | 0.26 | 0.1 | 3859 | 3860 |
| R883T | 883 | R | T | 0.26 | 0 | 3861 | 3862 |
| C1116E | 1116 | C | E | 0.26 | 0.07 | 3863 | 3864 |
| Y494M | 494 | Y | M | 0.26 | 0 | 3865 | 3866 |
| D407R | 407 | D | R | 0.26 | 0.07 | 3867 | 3868 |
| K89V | 89 | K | V | 0.26 | 0.02 | 3869 | 3870 |
| Q735P | 735 | Q | P | 0.26 | 0.69 | 3871 | 3872 |
| K1017M | 1017 | K | M | 0.26 | 0.06 | 3873 | 3874 |
| A1022H | 1022 | A | H | 0.26 | 0.26 | 3875 | 3876 |
| S739C | 739 | S | C | 0.26 | 0.04 | 3877 | 3878 |
| H759K | 759 | H | K | 0.26 | 0.54 | 3879 | 3880 |
| Y11D | 11 | Y | D | 0.26 | 0.06 | 3881 | 3882 |
| I138K | 138 | I | K | 0.25 | 0.11 | 3883 | 3884 |

TABLE 2-continued

Lachnospiraceae bacterium ND2006 Cas12a Wild-type and Mutants

| Mutation | Position | WT residue | Mutant residue | Average score | Standard deviation | NT SEQ ID | AA SEQ ID |
|---|---|---|---|---|---|---|---|
| I1111Q | 1111 | I | Q | 0.25 | 0.12 | 3885 | 3886 |
| R1144G | 1144 | R | G | 0.25 | 0.18 | 3887 | 3888 |
| I800L | 800 | I | L | 0.25 | 0.15 | 3889 | 3890 |
| D1148E | 1148 | D | E | 0.25 | 0.17 | 3891 | 3892 |
| D40N | 40 | D | N | 0.25 | 0.06 | 3893 | 3894 |
| G1196F | 1196 | G | F | 0.25 | 0.01 | 3895 | 3896 |
| V844R | 844 | V | R | 0.25 | 0.32 | 3897 | 3898 |
| L459Q | 459 | L | Q | 0.25 | 0.01 | 3899 | 3900 |
| D32E | 32 | D | E | 0.25 | 0.02 | 3901 | 3902 |
| E382F | 382 | E | F | 0.25 | 0.16 | 3903 | 3904 |
| S394P | 394 | S | P | 0.25 | 0.08 | 3905 | 3906 |
| N928C | 928 | N | C | 0.25 | 0.24 | 3907 | 3908 |
| H759P | 759 | H | P | 0.25 | 0.14 | 3909 | 3910 |
| Y854D | 854 | Y | D | 0.25 | 0.03 | 3911 | 3912 |
| D423Q | 423 | D | Q | 0.25 | 0.25 | 3913 | 3914 |
| N356T | 356 | N | T | 0.25 | 0.1 | 3915 | 3916 |
| D708E | 708 | D | E | 0.25 | 0.12 | 3917 | 3918 |
| N864F | 864 | N | F | 0.25 | 0.1 | 3919 | 3920 |
| T1019Y | 1019 | T | Y | 0.25 | 0.09 | 3921 | 3922 |
| R86M | 86 | R | M | 0.25 | 0.04 | 3923 | 3924 |
| F131C | 131 | F | C | 0.25 | 0.15 | 3925 | 3926 |
| N1082H | 1082 | N | H | 0.25 | 0.09 | 3927 | 3928 |
| D40S | 40 | D | S | 0.25 | 2.12 | 3929 | 3930 |
| D461A | 461 | D | A | 0.25 | 0.22 | 3931 | 3932 |
| E88H | 88 | E | H | 0.25 | 0.11 | 3933 | 3934 |
| A766N | 766 | A | N | 0.25 | 0.44 | 3935 | 3936 |
| V491S | 491 | V | S | 0.25 | 0.07 | 3937 | 3938 |
| E330R | 330 | E | R | 0.25 | 0.16 | 3939 | 3940 |
| F173V | 173 | F | V | 0.25 | 0.11 | 3941 | 3942 |
| Q567S | 567 | Q | S | 0.25 | 0.49 | 3943 | 3944 |
| V574P | 574 | V | P | 0.25 | 0 | 3945 | 3946 |
| K413C | 413 | K | C | 0.25 | 0.54 | 3947 | 3948 |
| D535A | 535 | D | A | 0.25 | 0.11 | 3949 | 3950 |
| P964Q | 964 | P | Q | 0.25 | 0.05 | 3951 | 3952 |
| S143K | 143 | S | K | 0.25 | 0.01 | 3953 | 3954 |
| L751H | 751 | L | H | 0.25 | 0.44 | 3955 | 3956 |

TABLE 3

Primers for creating LbCas12a Saturation Mutagenesis Library

| Name | Sequence (5'→3') | SEQ ID NO |
|---|---|---|
| LbCas12a_NNK_1 | tataagaaggagatatacatNNKAGCAAACTGGAAAAGTTCAC | 4023 |
| LbCas12a_NNK_2 | aagaaggagatatacatatgNNKAAACTGGAAAAGTTCACCAA | 4024 |
| LbCas12a_NNK_3 | aaggagatatacatatgAGCNNKCTGGAAAAGTTCACCAACTG | 4025 |
| LbCas12a_NNK_4 | gagatatacatatgAGCAAANNKGAAAAGTTCACCAACTGTTA | 4026 |
| LbCas12a_NNK_5 | atatacatatgAGCAAACTGNNKAAGTTCACCAACTGTTATAG | 4027 |
| LbCas12a_NNK_6 | tacatatgAGCAAACTGGAANNKTTCACCAACTGTTATAGCCT | 4028 |
| LbCas12a_NNK_7 | atatgAGCAAACTGGAAAAGNNKACCAACTGTTATAGCCTGAG | 4029 |
| LbCas12a_NNK_8 | tgAGCAAACTGGAAAAGTTCNNKAACTGTTATAGCCTGAGCAA | 4030 |
| LbCas12a_NNK_9 | GCAAACTGGAAAAGTTCACCNNKTGTTATAGCCTGAGCAAAAC | 4031 |
| LbCas12a_NNK_10 | AACTGGAAAAGTTCACCAACNNKTATAGCCTGAGCAAAACCCT | 4032 |
| LbCas12a_NNK_11 | TGGAAAAGTTCACCAACTGTNNKAGCCTGAGCAAAACCCTGCG | 4033 |
| LbCas12a_NNK_12 | AAAAGTTCACCAACTGTTATNNKCTGAGCAAAACCCTGCGTTT | 4034 |
| LbCas12a_NNK_13 | AGTTCACCAACTGTTATAGCNNKAGCAAAACCCTGCGTTTTAA | 4035 |
| LbCas12a_NNK_14 | TCACCAACTGTTATAGCCTGNNKAAAACCCTGCGTTTTAAAGC | 4036 |

TABLE 3-continued

Primers for creating LbCas12a Saturation Mutagenesis Library

| Name | Sequence (5'→3') | SEQ ID NO |
|---|---|---|
| LbCas12a_NNK_15 | CCAACTGTTATAGCCTGAGCNNKACCCTGCGTTTTAAAGCAAT | 4037 |
| LbCas12a_NNK_16 | ACTGTTATAGCCTGAGCAAANNKCTGCGTTTTAAAGCAATTCC | 4038 |
| LbCas12a_NNK_17 | GTTATAGCCTGAGCAAAACCNNKCGTTTTAAAGCAATTCCGGT | 4039 |
| LbCas12a_NNK_18 | ATAGCCTGAGCAAAACCCTGNNKTTTAAAGCAATTCCGGTTGG | 4040 |
| LbCas12a_NNK_19 | GCCTGAGCAAAACCCTGCGTNNKAAAGCAATTCCGGTTGGTAA | 4041 |
| LbCas12a_NNK_20 | TGAGCAAAACCCTGCGTTTTNNKGCAATTCCGGTTGGTAAAAC | 4042 |
| LbCas12a_NNK_21 | GCAAAACCCTGCGTTTTAAANNKATTCCGGTTGGTAAAACCCA | 4043 |
| LbCas12a_NNK_22 | AAACCCTGCGTTTTAAAGCANNKCCGGTTGGTAAAACCCAAGA | 4044 |
| LbCas12a_NNK_23 | CCCTGCGTTTTAAAGCAATTNNKGTTGGTAAAACCCAAGAGAA | 4045 |
| LbCas12a_NNK_24 | TGCGTTTTAAAGCAATTCCGNNKGGTAAAACCCAAGAGAACAT | 4046 |
| LbCas12a_NNK_25 | GTTTTAAAGCAATTCCGGTTNNKAAAACCCAAGAGAACATTGA | 4047 |
| LbCas12a_NNK_26 | TTAAAGCAATTCCGGTTGGTNNKACCCAAGAGAACATTGATAA | 4048 |
| LbCas12a_NNK_27 | AAGCAATTCCGGTTGGTAAANNKCAAGAGAACATTGATAATAA | 4049 |
| LbCas12a_NNK_28 | CAATTCCGGTTGGTAAAACCNNKGAGAACATTGATAATAAACG | 4050 |
| LbCas12a_NNK_29 | TTCCGGTTGGTAAAACCCAANNKAACATTGATAATAAACGCCT | 4051 |
| LbCas12a_NNK_30 | CGGTTGGTAAAACCCAAGAGNNKATTGATAATAAACGCCTGCT | 4052 |
| LbCas12a_NNK_31 | TTGGTAAAACCCAAGAGAACNNKGATAATAAACGCCTGCTGGT | 4053 |
| LbCas12a_NNK_32 | GTAAAACCCAAGAGAACATTNNKAATAAACGCCTGCTGGTCGA | 4054 |
| LbCas12a_NNK_33 | AAACCCAAGAGAACATTGATNNKAAACGCCTGCTGGTCGAAGA | 4055 |
| LbCas12a_NNK_34 | CCCAAGAGAACATTGATAATNNKCGCCTGCTGGTCGAAGATGA | 4056 |
| LbCas12a_NNK_35 | AAGAGAACATTGATAATAAANNKCTGCTGGTCGAAGATGAAAA | 4057 |
| LbCas12a_NNK_36 | AGAACATTGATAATAAACGCNNKCTGGTCGAAGATGAAAAACG | 4058 |
| LbCas12a_NNK_37 | ACATTGATAATAAACGCCTGNNKGTCGAAGATGAAAAACGCGC | 4059 |
| LbCas12a_NNK_38 | TTGATAATAAACGCCTGCTGNNKGAAGATGAAAAACGCGCTGA | 4060 |
| LbCas12a_NNK_39 | ATAATAAACGCCTGCTGGTCNNKGATGAAAAACGCGCTGAAGA | 4061 |
| LbCas12a_NNK_40 | ATAAACGCCTGCTGGTCGAANNKGAAAAACGCGCTGAAGATTA | 4062 |
| LbCas12a_NNK_41 | AACGCCTGCTGGTCGAAGATNNKAAACGCGCTGAAGATTATAA | 4063 |
| LbCas12a_NNK_42 | GCCTGCTGGTCGAAGATGAANNKCGCGCTGAAGATTATAAAGG | 4064 |
| LbCas12a_NNK_43 | TGCTGGTCGAAGATGAAAAANNKGCTGAAGATTATAAAGGCGT | 4065 |
| LbCas12a_NNK_44 | TGGTCGAAGATGAAAAACGCNNKGAAGATTATAAAGGCGTGAA | 4066 |
| LbCas12a_NNK_45 | TCGAAGATGAAAAACGCGCTNNKGATTATAAAGGCGTGAAAAA | 4067 |
| LbCas12a_NNK_46 | AAGATGAAAAACGCGCTGAANNKTATAAAGGCGTGAAAAAACT | 4068 |
| LbCas12a_NNK_47 | ATGAAAAACGCGCTGAAGATNNKAAAGGCGTGAAAAAACTGCT | 4069 |
| LbCas12a_NNK_48 | AAAAACGCGCTGAAGATTATNNKGGCGTGAAAAAACTGCTGGA | 4070 |
| LbCas12a_NNK_49 | AACGCGCTGAAGATTATAAANNKGTGAAAAAACTGCTGGATCG | 4071 |
| LbCas12a_NNK_50 | GCGCTGAAGATTATAAAGGCNNKAAAAAACTGCTGGATCGCTA | 4072 |
| LbCas12a_NNK_51 | CTGAAGATTATAAAGGCGTGNNKAAACTGCTGGATCGCTATTA | 4073 |
| LbCas12a_NNK_52 | AAGATTATAAAGGCGTGAAANNKCTGCTGGATCGCTATTATCT | 4074 |

TABLE 3-continued

Primers for creating LbCas12a Saturation Mutagenesis Library

| Name | Sequence (5'→3') | SEQ ID NO |
|---|---|---|
| LbCas12a_NNK_53 | ATTATAAAGGCGTGAAAAAANNKCTGGATCGCTATTATCTGAG | 4075 |
| LbCas12a_NNK_54 | ATAAAGGCGTGAAAAAACTGNNKGATCGCTATTATCTGAGCTT | 4076 |
| LbCas12a_NNK_55 | AAGGCGTGAAAAAACTGCTGNNKCGCTATTATCTGAGCTTCAT | 4077 |
| LbCas12a_NNK_56 | GCGTGAAAAAACTGCTGGATNNKTATTATCTGAGCTTCATTAA | 4078 |
| LbCas12a_NNK_57 | TGAAAAAACTGCTGGATCGCNNKTATCTGAGCTTCATTAACGA | 4079 |
| LbCas12a_NNK_58 | AAAAACTGCTGGATCGCTATNNKCTGAGCTTCATTAACGATGT | 4080 |
| LbCas12a_NNK_59 | AACTGCTGGATCGCTATTATNNKAGCTTCATTAACGATGTGCT | 4081 |
| LbCas12a_NNK_60 | TGCTGGATCGCTATTATCTGNNKTTCATTAACGATGTGCTGCA | 4082 |
| LbCas12a_NNK_61 | TGGATCGCTATTATCTGAGCNNKATTAACGATGTGCTGCACAG | 4083 |
| LbCas12a_NNK_62 | ATCGCTATTATCTGAGCTTCNNKAACGATGTGCTGCACAGCAT | 4084 |
| LbCas12a_NNK_63 | GCTATTATCTGAGCTTCATTNNKGATGTGCTGCACAGCATTAA | 4085 |
| LbCas12a_NNK_64 | ATTATCTGAGCTTCATTAACNNKGTGCTGCACAGCATTAAACT | 4086 |
| LbCas12a_NNK_65 | ATCTGAGCTTCATTAACGATNNKCTGCACAGCATTAAACTGAA | 4087 |
| LbCas12a_NNK_66 | TGAGCTTCATTAACGATGTGNNKCACAGCATTAAACTGAAGAA | 4088 |
| LbCas12a_NNK_67 | GCTTCATTAACGATGTGCTGNNKAGCATTAAACTGAAGAACCT | 4089 |
| LbCas12a_NNK_68 | TCATTAACGATGTGCTGCACNNKATTAAACTGAAGAACCTGAA | 4090 |
| LbCas12a_NNK_69 | TTAACGATGTGCTGCACAGCNNKAAACTGAAGAACCTGAACAA | 4091 |
| LbCas12a_NNK_70 | ACGATGTGCTGCACAGCATTNNKCTGAAGAACCTGAACAACTA | 4092 |
| LbCas12a_NNK_71 | ATGTGCTGCACAGCATTAAANNKAAGAACCTGAACAACTATAT | 4093 |
| LbCas12a_NNK_72 | TGCTGCACAGCATTAAACTGNNKAACCTGAACAACTATATCAG | 4094 |
| LbCas12a_NNK_73 | TGCACAGCATTAAACTGAAGNNKCTGAACAACTATATCAGCCT | 4095 |
| LbCas12a_NNK_74 | ACAGCATTAAACTGAAGAACNNKAACAACTATATCAGCCTGTT | 4096 |
| LbCas12a_NNK_75 | GCATTAAACTGAAGAACCTGNNKAACTATATCAGCCTGTTTCG | 4097 |
| LbCas12a_NNK_76 | TTAAACTGAAGAACCTGAACNNKTATATCAGCCTGTTTCGTAA | 4098 |
| LbCas12a_NNK_77 | AACTGAAGAACCTGAACAACNNKATCAGCCTGTTTCGTAAAAA | 4099 |
| LbCas12a_NNK_78 | TGAAGAACCTGAACAACTATNNKAGCCTGTTTCGTAAAAAAAC | 4100 |
| LbCas12a_NNK_79 | AGAACCTGAACAACTATATCNNKCTGTTTCGTAAAAAAACCCG | 4101 |
| LbCas12a_NNK_80 | ACCTGAACAACTATATCAGCNNKTTTCGTAAAAAAACCCGCAC | 4102 |
| LbCas12a_NNK_81 | TGAACAACTATATCAGCCTGNNKCGTAAAAAAACCCGCACCGA | 4103 |
| LbCas12a_NNK_82 | ACAACTATATCAGCCTGTTTNNKAAAAAAACCCGCACCGAAAA | 4104 |
| LbCas12a_NNK_83 | ACTATATCAGCCTGTTTCGTNNKAAAACCCGCACCGAAAAAGA | 4105 |
| LbCas12a_NNK_84 | ATATCAGCCTGTTTCGTAAANNKACCCGCACCGAAAAAGAAAA | 4106 |
| LbCas12a_NNK_85 | TCAGCCTGTTTCGTAAAAAANNKCGCACCGAAAAGAAAACAA | 4107 |
| LbCas12a_NNK_86 | GCCTGTTTCGTAAAAAAACNNKACCGAAAAAGAAAACAAAGA | 4108 |
| LbCas12a_NNK_87 | TGTTTCGTAAAAAAACCCGCNNKGAAAAAGAAAACAAAGAGCT | 4109 |
| LbCas12a_NNK_88 | TTCGTAAAAAAACCCGCACCNNKAAAGAAAACAAAGAGCTGGA | 4110 |
| LbCas12a_NNK_89 | GTAAAAAAACCCGCACCGAANNKGAAAACAAAGAGCTGGAAAA | 4111 |

TABLE 3-continued

Primers for creating LbCas12a Saturation Mutagenesis Library

| Name | Sequence (5'→3') | SEQ ID NO |
|---|---|---|
| LbCas12a_NNK_90 | AAAAAACCCGCACCGAAAAANNKAACAAAGAGCTGGAAAACCT | 4112 |
| LbCas12a_NNK_91 | AAACCCGCACCGAAAAAGAANNKAAAGAGCTGGAAAACCTGGA | 4113 |
| LbCas12a_NNK_92 | CCCGCACCGAAAAAGAAAACNNKGAGCTGGAAAACCTGGAAAT | 4114 |
| LbCas12a_NNK_93 | GCACCGAAAAGAAAACAAANNKCTGGAAAACCTGGAAATCAA | 4115 |
| LbCas12a_NNK_94 | cCGAAAAGAAAACAAAGAGNNKGAAAACCTGGAAATCAATCT | 4116 |
| LbCas12a_NNK_95 | AAAAAGAAACAAAGAGCTGNNKAACCTGGAAATCAATCTGCG | 4117 |
| LbCas12a_NNK_96 | AAGAAAACAAAGAGCTGGAANNKCTGGAAATCAATCTGCGTAA | 4118 |
| LbCas12a_NNK_97 | AAAACAAAGAGCTGGAAAACNNKGAAATCAATCTGCGTAAAGA | 4119 |
| LbCas12a_NNK_98 | ACAAAGAGCTGGAAAACCTGNNKATCAATCTGCGTAAAGAAAT | 4120 |
| LbCas12a_NNK_99 | AAGAGCTGGAAAACCTGGAANNKAATCTGCGTAAAGAAATCGC | 4121 |
| LbCas12a_NNK_100 | AGCTGGAAAACCTGGAAATCNNKCTGCGTAAAGAAATCGCCAA | 4122 |
| LbCas12a_NNK_101 | TGGAAAACCTGGAAATCAATNNKCGTAAAGAAATCGCCAAAGC | 4123 |
| LbCas12a_NNK_102 | AAAACCTGGAAATCAATCTGNNKAAAGAAATCGCCAAAGCGTT | 4124 |
| LbCas12a_NNK_103 | ACCTGGAAATCAATCTGCGTNNKGAAATCGCCAAAGCGTTTAA | 4125 |
| LbCas12a_NNK_104 | TGGAAATCAATCTGCGTAAANNKATCGCCAAAGCGTTTAAAGG | 4126 |
| LbCas12a_NNK_105 | AAATCAATCTGCGTAAAGAANNKGCCAAAGCGTTTAAAGGTAA | 4127 |
| LbCas12a_NNK_106 | TCAATCTGCGTAAAGAAATCNNKAAAGCGTTTAAAGGTAACGA | 4128 |
| LbCas12a_NNK_107 | ATCTGCGTAAAGAAATCGCCNNKGCGTTTAAAGGTAACGAGGG | 4129 |
| LbCas12a_NNK_108 | TGCGTAAAGAAATCGCCAAANNKTTTAAAGGTAACGAGGGTTA | 4130 |
| LbCas12a_NNK_109 | GTAAAGAAATCGCCAAAGCGNNKAAAGGTAACGAGGGTTATAA | 4131 |
| LbCas12a_NNK_110 | AAGAAATCGCCAAAGCGTTTNNKGGTAACGAGGGTTATAAAAG | 4132 |
| LbCas12a_NNK_111 | AAATCGCCAAAGCGTTTAAANNKAACGAGGGTTATAAAAGCCT | 4133 |
| LbCas12a_NNK_112 | TCGCCAAAGCGTTTAAAGGTNNKGAGGGTTATAAAAGCCTGTT | 4134 |
| LbCas12a_NNK_113 | CCAAAGCGTTTAAAGGTAACNNKGGTTATAAAAGCCTGTTCAA | 4135 |
| LbCas12a_NNK_114 | AAGCGTTTAAAGGTAACGAGNNKTATAAAAGCCTGTTCAAGAA | 4136 |
| LbCas12a_NNK_115 | CGTTTAAAGGTAACGAGGGTNNKAAAAGCCTGTTCAAGAAAGA | 4137 |
| LbCas12a_NNK_116 | TTAAAGGTAACGAGGGTTATNNKAGCCTGTTCAAGAAAGACAT | 4138 |
| LbCas12a_NNK_117 | AAGGTAACGAGGGTTATAAANNKCTGTTCAAGAAAGACATCAT | 4139 |
| LbCas12a_NNK_118 | GTAACGAGGGTTATAAAAGCNNKTTCAAGAAAGACATCATCGA | 4140 |
| LbCas12a_NNK_119 | ACGAGGGTTATAAAAGCCTGNNKAAGAAAGACATCATCGAAAC | 4141 |
| LbCas12a_NNK_120 | AGGGTTATAAAAGCCTGTTCNNKAAAGACATCATCGAAACCAT | 4142 |
| LbCas12a_NNK_121 | GTTATAAAAGCCTGTTCAAGNNKGACATCATCGAAACCATTCT | 4143 |
| LbCas12a_NNK_122 | ATAAAAGCCTGTTCAAGAAANNKATCATCGAAACCATTCTGCC | 4144 |
| LbCas12a_NNK_123 | AAAGCCTGTTCAAGAAAGACNNKATCGAAACCATTCTGCCGGA | 4145 |
| LbCas12a_NNK_124 | GCCTGTTCAAGAAAGACATCNNKGAAACCATTCTGCCGGAATT | 4146 |
| LbCas12a_NNK_125 | TGTTCAAGAAAGACATCATCNNKACCATTCTGCCGGAATTTCT | 4147 |
| LbCas12a_NNK_126 | TCAAGAAAGACATCATCGAANNKATTCTGCCGGAATTTCTGGA | 4148 |
| LbCas12a_NNK_127 | AGAAAGACATCATCGAAACCNNKCTGCCGGAATTTCTGGATGA | 4149 |

TABLE 3-continued

Primers for creating LbCas12a Saturation Mutagenesis Library

| Name | Sequence (5'→3') | SEQ ID NO |
|---|---|---|
| LbCas12a_NNK_128 | AAGACATCATCGAAACCATTNNKCCGGAATTTCTGGATGATAA | 4150 |
| LbCas12a_NNK_129 | ACATCATCGAAACCATTCTGNNKGAATTTCTGGATGATAAAGA | 4151 |
| LbCas12a_NNK_130 | TCATCGAAACCATTCTGCCGNNKTTTCTGGATGATAAAGATGA | 4152 |
| LbCas12a_NNK_131 | TCGAAACCATTCTGCCGGAANNKCTGGATGATAAAGATGAAAT | 4153 |
| LbCas12a_NNK_132 | AAACCATTCTGCCGGAATTTNNKGATGATAAAGATGAAATTGC | 4154 |
| LbCas12a_NNK_133 | CCATTCTGCCGGAATTTCTGNNKGATAAAGATGAAATTGCCCT | 4155 |
| LbCas12a_NNK_134 | TTCTGCCGGAATTTCTGGATNNKAAAGATGAAATTGCCCTGGT | 4156 |
| LbCas12a_NNK_135 | TGCCGGAATTTCTGGATGATNNKGATGAAATTGCCCTGGTGAA | 4157 |
| LbCas12a_NNK_136 | CGGAATTTCTGGATGATAAANNKGAAATTGCCCTGGTGAATAG | 4158 |
| LbCas12a_NNK_137 | AATTTCTGGATGATAAAGATNNKATTGCCCTGGTGAATAGCTT | 4159 |
| LbCas12a_NNK_138 | TTCTGGATGATAAAGATGAANNKGCCCTGGTGAATAGCTTTAA | 4160 |
| LbCas12a_NNK_139 | TGGATGATAAAGATGAAATTNNKCTGGTGAATAGCTTTAATGG | 4161 |
| LbCas12a_NNK_140 | ATGATAAAGATGAAATTGCCNNKGTGAATAGCTTTAATGGCTT | 4162 |
| LbCas12a_NNK_141 | ATAAAGATGAAATTGCCCTGNNKAATAGCTTTAATGGCTTTAC | 4163 |
| LbCas12a_NNK_142 | AAGATGAAATTGCCCTGGTGNNKAGCTTTAATGGCTTTACCAC | 4164 |
| LbCas12a_NNK_143 | ATGAAATTGCCCTGGTGAATNNKTTTAATGGCTTTACCACCGC | 4165 |
| LbCas12a_NNK_144 | AAATTGCCCTGGTGAATAGCNNKAATGGCTTTACCACCGCATT | 4166 |
| LbCas12a_NNK_145 | TTGCCCTGGTGAATAGCTTTNNKGGCTTTACCACCGCATTTAC | 4167 |
| LbCas12a_NNK_146 | CCCTGGTGAATAGCTTTAATNNKTTTACCACCGCATTTACCGG | 4168 |
| LbCas12a_NNK_147 | TGGTGAATAGCTTTAATGGCNNKACCACCGCATTTACCGGCTT | 4169 |
| LbCas12a_NNK_148 | TGAATAGCTTTAATGGCTTTNNKACCGCATTTACCGGCTTTTT | 4170 |
| LbCas12a_NNK_149 | ATAGCTTTAATGGCTTTACCNNKGCATTTACCGGCTTTTTTGA | 4171 |
| LbCas12a_NNK_150 | GCTTTAATGGCTTTACCACCNNKTTTACCGGCTTTTTTGATAA | 4172 |
| LbCas12a_NNK_151 | TTAATGGCTTTACCACCGCANNKACCGGCTTTTTTGATAATCG | 4173 |
| LbCas12a_NNK_152 | ATGGCTTTACCACCGCATTTNNKGGCTTTTTTGATAATCGCGA | 4174 |
| LbCas12a_NNK_153 | GCTTTACCACCGCATTTACCNNKTTTTTTGATAATCGCGAAAA | 4175 |
| LbCas12a_NNK_154 | TTACCACCGCATTTACCGGCNNKTTTGATAATCGCGAAAACAT | 4176 |
| LbCas12a_NNK_155 | CCACCGCATTTACCGGCTTTNNKGATAATCGCGAAAACATGTT | 4177 |
| LbCas12a_NNK_156 | CCGCATTTACCGGCTTTTTTNNKAATCGCGAAAACATGTTCAG | 4178 |
| LbCas12a_NNK_157 | CATTTACCGGCTTTTTTGATNNKCGCGAAAACATGTTCAGCGA | 4179 |
| LbCas12a_NNK_158 | TTACCGGCTTTTTTGATAATNNKGAAAACATGTTCAGCGAAGA | 4180 |
| LbCas12a_NNK_159 | CCGGCTTTTTTGATAATCGCNNKAACATGTTCAGCGAAGAAGC | 4181 |
| LbCas12a_NNK_160 | GCTTTTTTGATAATCGCGAANNKATGTTCAGCGAAGAAGCAAA | 4182 |
| LbCas12a_NNK_161 | TTTTTGATAATCGCGAAAACNNKTTCAGCGAAGAAGCAAAAAG | 4183 |
| LbCas12a_NNK_162 | TTGATAATCGCGAAAACATGNNKAGCGAAGAAGCAAAAAGCAC | 4184 |
| LbCas12a_NNK_163 | ATAATCGCGAAAACATGTTCNNKGAAGAAGCAAAAAGCACCAG | 4185 |
| LbCas12a_NNK_164 | ATCGCGAAAACATGTTCAGCNNKGAAGCAAAAAGCACCAGCAT | 4186 |

TABLE 3-continued

Primers for creating LbCas12a Saturation Mutagenesis Library

| Name | Sequence (5'→3') | SEQ ID NO |
|---|---|---|
| LbCas12a_NNK_165 | GCGAAAACATGTTCAGCGAANNKGCAAAAAGCACCAGCATTGC | 4187 |
| LbCas12a_NNK_166 | AAAACATGTTCAGCGAAGAANNKAAAAGCACCAGCATTGCATT | 4188 |
| LbCas12a_NNK_167 | ACATGTTCAGCGAAGAAGCANNKAGCACCAGCATTGCATTTCG | 4189 |
| LbCas12a_NNK_168 | TGTTCAGCGAAGAAGCAAAANNKACCAGCATTGCATTTCGCTG | 4190 |
| LbCas12a_NNK_169 | TCAGCGAAGAAGCAAAAAGCNNKAGCATTGCATTTCGCTGCAT | 4191 |
| LbCas12a_NNK_170 | GCGAAGAAGCAAAAAGCACCNNKATTGCATTTCGCTGCATTAA | 4192 |
| LbCas12a_NNK_171 | AAGAAGCAAAAAGCACCAGCNNKGCATTTCGCTGCATTAATGA | 4193 |
| LbCas12a_NNK_172 | AAGCAAAAAGCACCAGCATTNNKTTTCGCTGCATTAATGAAAA | 4194 |
| LbCas12a_NNK_173 | CAAAAAGCACCAGCATTGCANNKCGCTGCATTAATGAAAATCT | 4195 |
| LbCas12a_NNK_174 | AAAGCACCAGCATTGCATTTNNKTGCATTAATGAAAATCTGAC | 4196 |
| LbCas12a_NNK_175 | GCACCAGCATTGCATTTCGCNNKATTAATGAAAATCTGACCCG | 4197 |
| LbCas12a_NNK_176 | CCAGCATTGCATTTCGCTGCNNKAATGAAAATCTGACCCGCTA | 4198 |
| LbCas12a_NNK_177 | GCATTGCATTTCGCTGCATTNNKGAAAATCTGACCCGCTACAT | 4199 |
| LbCas12a_NNK_178 | TTGCATTTCGCTGCATTAATNNKAATCTGACCCGCTACATTAG | 4200 |
| LbCas12a_NNK_179 | CATTTCGCTGCATTAATGAANNKCTGACCCGCTACATTAGCAA | 4201 |
| LbCas12a_NNK_180 | TTCGCTGCATTAATGAAAATNNKACCCGCTACATTAGCAACAT | 4202 |
| LbCas12a_NNK_181 | GCTGCATTAATGAAAATCTGNNKCGCTACATTAGCAACATGGA | 4203 |
| LbCas12a_NNK_182 | GCATTAATGAAAATCTGACCNNKTACATTAGCAACATGGATAT | 4204 |
| LbCas12a_NNK_183 | TTAATGAAAATCTGACCCGCNNKATTAGCAACATGGATATCTT | 4205 |
| LbCas12a_NNK_184 | ATGAAAATCTGACCCGCTACNNKAGCAACATGGATATCTTTGA | 4206 |
| LbCas12a_NNK_185 | AAAATCTGACCCGCTACATTNNKAACATGGATATCTTTGAAAA | 4207 |
| LbCas12a_NNK_186 | ATCTGACCCGCTACATTAGCNNKATGGATATCTTTGAAAAAGT | 4208 |
| LbCas12a_NNK_187 | TGACCCGCTACATTAGCAACNNKGATATCTTTGAAAAAGTGGA | 4209 |
| LbCas12a_NNK_188 | ccCGCTACATTAGCAACATGNNKATCTTTGAAAAAGTGGACGC | 4210 |
| LbCas12a_NNK_189 | GCTACATTAGCAACATGGATNNKTTTGAAAAAGTGGACGCGAT | 4211 |
| LbCas12a_NNK_190 | ACATTAGCAACATGGATATCNNKGAAAAAGTGGACGCGATCTT | 4212 |
| LbCas12a_NNK_191 | TTAGCAACATGGATATCTTTNNKAAAGTGGACGCGATCTTCGA | 4213 |
| LbCas12a_NNK_192 | GCAACATGGATATCTTTGAANNKGTGGACGCGATCTTCGATAA | 4214 |
| LbCas12a_NNK_193 | ACATGGATATCTTTGAAAAANNKGACGCGATCTTCGATAAACA | 4215 |
| LbCas12a_NNK_194 | TGGATATCTTTGAAAAAGTGNNKGCGATCTTCGATAAACACGA | 4216 |
| LbCas12a_NNK_195 | ATATCTTTGAAAAAGTGGACNNKATCTTCGATAAACACGAAGT | 4217 |
| LbCas12a_NNK_196 | TCTTTGAAAAAGTGGACGCGNNKTTCGATAAACACGAAGTGCA | 4218 |
| LbCas12a_NNK_197 | TTGAAAAAGTGGACGCGATCNNKGATAAACACGAAGTGCAAGA | 4219 |
| LbCas12a_NNK_198 | AAAAGTGGACGCGATCTTCNNKAAACACGAAGTGCAAGAGAT | 4220 |
| LbCas12a_NNK_199 | AAGTGGACGCGATCTTCGATNNKCACGAAGTGCAAGAGATCAA | 4221 |
| LbCas12a_NNK_200 | TGGACGCGATCTTCGATAAANNKGAAGTGCAAGAGATCAAAGA | 4222 |
| LbCas12a_NNK_201 | ACGCGATCTTCGATAAACACNNKGTGCAAGAGATCAAAGAGAA | 4223 |
| LbCas12a_NNK_202 | CGATCTTCGATAAACACGAANNKCAAGAGATCAAAGAGAAAAT | 4224 |

TABLE 3-continued

Primers for creating LbCas12a Saturation Mutagenesis Library

| Name | Sequence (5'→3') | SEQ ID NO |
|---|---|---|
| LbCas12a_NNK_203 | TCTTCGATAAACACGAAGTGNNKGAGATCAAAGAGAAAATCCT | 4225 |
| LbCas12a_NNK_204 | TCGATAAACACGAAGTGCAANNKATCAAAGAGAAAATCCTGAA | 4226 |
| LbCas12a_NNK_205 | ATAAACACGAAGTGCAAGAGNNKAAAGAGAAAATCCTGAACAG | 4227 |
| LbCas12a_NNK_206 | AACACGAAGTGCAAGAGATCNNKGAGAAAATCCTGAACAGCGA | 4228 |
| LbCas12a_NNK_207 | ACGAAGTGCAAGAGATCAAANNKAAAATCCTGAACAGCGATTA | 4229 |
| LbCas12a_NNK_208 | AAGTGCAAGAGATCAAAGAGNNKATCCTGAACAGCGATTATGA | 4230 |
| LbCas12a_NNK_209 | TGCAAGAGATCAAAGAGAAANNKCTGAACAGCGATTATGACGT | 4231 |
| LbCas12a_NNK_210 | AAGAGATCAAAGAGAAAATCNNKAACAGCGATTATGACGTCGA | 4232 |
| LbCas12a_NNK_211 | AGATCAAAGAGAAAATCCTGNNKAGCGATTATGACGTCGAAGA | 4233 |
| LbCas12a_NNK_212 | TCAAAGAGAAAATCCTGAACNNKGATTATGACGTCGAAGATTT | 4234 |
| LbCas12a_NNK_213 | AAGAGAAAATCCTGAACAGCNNKTATGACGTCGAAGATTTTTT | 4235 |
| LbCas12a_NNK_214 | AGAAAATCCTGAACAGCGATNNKGACGTCGAAGATTTTTTGA | 4236 |
| LbCas12a_NNK_215 | AAATCCTGAACAGCGATTATNNKGTCGAAGATTTTTTGAAGG | 4237 |
| LbCas12a_NNK_216 | TCCTGAACAGCGATTATGACNNKGAAGATTTTTTGAAGGCGA | 4238 |
| LbCas12a_NNK_217 | TGAACAGCGATTATGACGTCNNKGATTTTTTGAAGGCGAGTT | 4239 |
| LbCas12a_NNK_218 | ACAGCGATTATGACGTCGAANNKTTTTTGAAGGCGAGTTCTT | 4240 |
| LbCas12a_NNK_219 | GCGATTATGACGTCGAAGATNNKTTTGAAGGCGAGTTCTTTAA | 4241 |
| LbCas12a_NNK_220 | ATTATGACGTCGAAGATTTTNNKGAAGGCGAGTTCTTTAACTT | 4242 |
| LbCas12a_NNK_221 | ATGACGTCGAAGATTTTTTNNKGGCGAGTTCTTTAACTTCGT | 4243 |
| LbCas12a_NNK_222 | ACGTCGAAGATTTTTTGAANNKGAGTTCTTTAACTTCGTTCT | 4244 |
| LbCas12a_NNK_223 | TCGAAGATTTTTTGAAGGCNNKTTCTTTAACTTCGTTCTGAC | 4245 |
| LbCas12a_NNK_224 | AAGATTTTTTGAAGGCGAGNNKTTTAACTTCGTTCTGACCCA | 4246 |
| LbCas12a_NNK_225 | ATTTTTTGAAGGCGAGTTCNNKAACTTCGTTCTGACCCAAGA | 4247 |
| LbCas12a_NNK_226 | TTTTTGAAGGCGAGTTCTTTNNKTTCGTTCTGACCCAAGAAGG | 4248 |
| LbCas12a_NNK_227 | TTGAAGGCGAGTTCTTTAACNNKGTTCTGACCCAAGAAGGTAT | 4249 |
| LbCas12a_NNK_228 | AAGGCGAGTTCTTTAACTTCNNKCTGACCCAAGAAGGTATCGA | 4250 |
| LbCas12a_NNK_229 | GCGAGTTCTTTAACTTCGTTNNKACCCAAGAAGGTATCGACGT | 4251 |
| LbCas12a_NNK_230 | AGTTCTTTAACTTCGTTCTGNNKCAAGAAGGTATCGACGTTTA | 4252 |
| LbCas12a_NNK_231 | TCTTTAACTTCGTTCTGACCNNKGAAGGTATCGACGTTTATAA | 4253 |
| LbCas12a_NNK_232 | TTAACTTCGTTCTGACCCAANNKGGTATCGACGTTTATAACGC | 4254 |
| LbCas12a_NNK_233 | ACTTCGTTCTGACCCAAGAANNKATCGACGTTTATAACGCAAT | 4255 |
| LbCas12a_NNK_234 | TCGTTCTGACCCAAGAAGGTNNKGACGTTTATAACGCAATTAT | 4256 |
| LbCas12a_NNK_235 | TTCTGACCCAAGAAGGTATCNNKGTTTATAACGCAATTATTGG | 4257 |
| LbCas12a_NNK_236 | TGACCCAAGAAGGTATCGACNNKTATAACGCAATTATTGGTGG | 4258 |
| LbCas12a_NNK_237 | CCCAAGAAGGTATCGACGTTNNKAACGCAATTATTGGTGGTTT | 4259 |
| LbCas12a_NNK_238 | AAGAAGGTATCGACGTTTATNNKGCAATTATTGGTGGTTTTGT | 4260 |
| LbCas12a_NNK_239 | AAGGTATCGACGTTTATAACNNKATTATTGGTGGTTTTGTTAC | 4261 |

TABLE 3-continued

Primers for creating LbCas12a Saturation Mutagenesis Library

| Name | Sequence (5'→3') | SEQ ID NO |
|---|---|---|
| LbCas12a_NNK_240 | GTATCGACGTTTATAACGCANNKATTGGTGGTTTTGTTACCGA | 4262 |
| LbCas12a_NNK_241 | TCGACGTTTATAACGCAATTNNKGGTGGTTTTGTTACCGAAAG | 4263 |
| LbCas12a_NNK_242 | ACGTTTATAACGCAATTATTNNKGGTTTTGTTACCGAAAGCGG | 4264 |
| LbCas12a_NNK_243 | TTTATAACGCAATTATTGGTNNKTTTGTTACCGAAAGCGGTGA | 4265 |
| LbCas12a_NNK_244 | ATAACGCAATTATTGGTGGTNNKGTTACCGAAAGCGGTGAGAA | 4266 |
| LbCas12a_NNK_245 | ACGCAATTATTGGTGGTTTTNNKACCGAAAGCGGTGAGAAAAT | 4267 |
| LbCas12a_NNK_246 | CAATTATTGGTGGTTTTGTTNNKGAAAGCGGTGAGAAAATCAA | 4268 |
| LbCas12a_NNK_247 | TTATTGGTGGTTTTGTTACCNNKAGCGGTGAGAAAATCAAAGG | 4269 |
| LbCas12a_NNK_248 | TTGGTGGTTTTGTTACCGAANNKGGTGAGAAAATCAAAGGCCT | 4270 |
| LbCas12a_NNK_249 | GTGGTTTTGTTACCGAAAGCNNKGAGAAAATCAAAGGCCTGAA | 4271 |
| LbCas12a_NNK_250 | GTTTTGTTACCGAAAGCGGTNNKAAAATCAAAGGCCTGAATGA | 4272 |
| LbCas12a_NNK_251 | TTGTTACCGAAAGCGGTGAGNNKATCAAAGGCCTGAATGAATA | 4273 |
| LbCas12a_NNK_252 | TTACCGAAAGCGGTGAGAAANNKAAAGGCCTGAATGAATATAT | 4274 |
| LbCas12a_NNK_253 | CCGAAAGCGGTGAGAAAATCNNKGGCCTGAATGAATATATCAA | 4275 |
| LbCas12a_NNK_254 | AAAGCGGTGAGAAAATCAAANNKCTGAATGAATATATCAACCT | 4276 |
| LbCas12a_NNK_255 | GCGGTGAGAAAATCAAAGGCNNKAATGAATATATCAACCTGTA | 4277 |
| LbCas12a_NNK_256 | GTGAGAAAATCAAAGGCCTGNNKGAATATATCAACCTGTATAA | 4278 |
| LbCas12a_NNK_257 | AGAAAATCAAAGGCCTGAATNNKTATATCAACCTGTATAACCA | 4279 |
| LbCas12a_NNK_258 | AAATCAAAGGCCTGAATGAANNKATCAACCTGTATAACCAGAA | 4280 |
| LbCas12a_NNK_259 | TCAAAGGCCTGAATGAATATNNKAACCTGTATAACCAGAAAAC | 4281 |
| LbCas12a_NNK_260 | AAGGCCTGAATGAATATATCNNKCTGTATAACCAGAAAACCAA | 4282 |
| LbCas12a_NNK_261 | GCCTGAATGAATATATCAACNNKTATAACCAGAAAACCAAACA | 4283 |
| LbCas12a_NNK_262 | TGAATGAATATATCAACCTGNNKAACCAGAAAACCAAACAGAA | 4284 |
| LbCas12a_NNK_263 | ATGAATATATCAACCTGTATNNKCAGAAAACCAAACAGAAACT | 4285 |
| LbCas12a_NNK_264 | AATATATCAACCTGTATAACNNKAAAACCAAACAGAAACTGCC | 4286 |
| LbCas12a_NNK_265 | ATATCAACCTGTATAACCAGNNKACCAAACAGAAACTGCCGAA | 4287 |
| LbCas12a_NNK_266 | TCAACCTGTATAACCAGAAANNKAAACAGAAACTGCCGAAATT | 4288 |
| LbCas12a_NNK_267 | ACCTGTATAACCAGAAAACCNNKCAGAAACTGCCGAAATTCAA | 4289 |
| LbCas12a_NNK_268 | TGTATAACCAGAAAACCAAANNKAAACTGCCGAAATTCAAACC | 4290 |
| LbCas12a_NNK_269 | ATAACCAGAAAACCAAACAGNNKCTGCCGAAATTCAAACCGCT | 4291 |
| LbCas12a_NNK_270 | ACCAGAAAACCAAACAGAAANNKCCGAAATTCAAACCGCTGTA | 4292 |
| LbCas12a_NNK_271 | AGAAAACCAAACAGAAACTGNNKAAATTCAAACCGCTGTATAA | 4293 |
| LbCas12a_NNK_272 | AAACCAAACAGAAACTGCCGNNKTTCAAACCGCTGTATAAACA | 4294 |
| LbCas12a_NNK_273 | CCAAACAGAAACTGCCGAAANNKAAACCGCTGTATAAACAGGT | 4295 |
| LbCas12a_NNK_274 | AACAGAAACTGCCGAAATTCNNKCCGCTGTATAAACAGGTTCT | 4296 |
| LbCas12a_NNK_275 | AGAAACTGCCGAAATTCAAANNKCTGTATAAACAGGTTCTGAG | 4297 |
| LbCas12a_NNK_276 | AACTGCCGAAATTCAAACCGNNKTATAAACAGGTTCTGAGCGA | 4298 |
| LbCas12a_NNK_277 | TGCCGAAATTCAAACCGCTGNNKAAACAGGTTCTGAGCGATCG | 4299 |

TABLE 3-continued

Primers for creating LbCas12a Saturation Mutagenesis Library

| Name | Sequence (5'→3') | SEQ ID NO |
|---|---|---|
| LbCas12a_NNK_278 | CGAAATTCAAACCGCTGTATNNKCAGGTTCTGAGCGATCGTGA | 4300 |
| LbCas12a_NNK_279 | AATTCAAACCGCTGTATAAANNKGTTCTGAGCGATCGTGAAAG | 4301 |
| LbCas12a_NNK_280 | TCAAACCGCTGTATAAACAGNNKCTGAGCGATCGTGAAAGCCT | 4302 |
| LbCas12a_NNK_281 | AACCGCTGTATAAACAGGTTNNKAGCGATCGTGAAAGCCTGAG | 4303 |
| LbCas12a_NNK_282 | CGCTGTATAAACAGGTTCTGNNKGATCGTGAAAGCCTGAGCTT | 4304 |
| LbCas12a_NNK_283 | TGTATAAACAGGTTCTGAGCNNKCGTGAAAGCCTGAGCTTTTA | 4305 |
| LbCas12a_NNK_284 | ATAAACAGGTTCTGAGCGATNNKGAAAGCCTGAGCTTTTATGG | 4306 |
| LbCas12a_NNK_285 | AACAGGTTCTGAGCGATCGTNNKAGCCTGAGCTTTTATGGTGA | 4307 |
| LbCas12a_NNK_286 | AGGTTCTGAGCGATCGTGAANNKCTGAGCTTTTATGGTGAAGG | 4308 |
| LbCas12a_NNK_287 | TTCTGAGCGATCGTGAAAGCNNKAGCTTTTATGGTGAAGGTTA | 4309 |
| LbCas12a_NNK_288 | TGAGCGATCGTGAAAGCCTGNNKTTTTATGGTGAAGGTTATAC | 4310 |
| LbCas12a_NNK_289 | GCGATCGTGAAAGCCTGAGCNNKTATGGTGAAGGTTATACCAG | 4311 |
| LbCas12a_NNK_290 | ATCGTGAAAGCCTGAGCTTTNNKGGTGAAGGTTATACCAGTGA | 4312 |
| LbCas12a_NNK_291 | GTGAAAGCCTGAGCTTTTATNNKGAAGGTTATACCAGTGATGA | 4313 |
| LbCas12a_NNK_292 | AAAGCCTGAGCTTTTATGGTNNKGGTTATACCAGTGATGAAGA | 4314 |
| LbCas12a_NNK_293 | GCCTGAGCTTTTATGGTGAANNKTATACCAGTGATGAAGAGGT | 4315 |
| LbCas12a_NNK_294 | TGAGCTTTTATGGTGAAGGTNNKACCAGTGATGAAGAGGTTCT | 4316 |
| LbCas12a_NNK_295 | GCTTTTATGGTGAAGGTTATNNKAGTGATGAAGAGGTTCTGGA | 4317 |
| LbCas12a_NNK_296 | TTTATGGTGAAGGTTATACCNNKGATGAAGAGGTTCTGGAAGT | 4318 |
| LbCas12a_NNK_297 | ATGGTGAAGGTTATACCAGTNNKGAAGAGGTTCTGGAAGTTTT | 4319 |
| LbCas12a_NNK_298 | GTGAAGGTTATACCAGTGATNNKGAGGTTCTGGAAGTTTTTCG | 4320 |
| LbCas12a_NNK_299 | AAGGTTATACCAGTGATGAANNKGTTCTGGAAGTTTTTCGTAA | 4321 |
| LbCas12a_NNK_300 | GTTATACCAGTGATGAAGAGNNKCTGGAAGTTTTTCGTAACAC | 4322 |
| LbCas12a_NNK_301 | ATACCAGTGATGAAGAGGTTNNKGAAGTTTTTCGTAACACCCT | 4323 |
| LbCas12a_NNK_302 | CCAGTGATGAAGAGGTTCTGNNKGTTTTTCGTAACACCCTGAA | 4324 |
| LbCas12a_NNK_303 | GTGATGAAGAGGTTCTGGAANNKTTTCGTAACACCCTGAATAA | 4325 |
| LbCas12a_NNK_304 | ATGAAGAGGTTCTGGAAGTTNNKCGTAACACCCTGAATAAAAA | 4326 |
| LbCas12a_NNK_305 | AAGAGGTTCTGGAAGTTTTTNNKAACACCCTGAATAAAAACAG | 4327 |
| LbCas12a_NNK_306 | AGGTTCTGGAAGTTTTTCGTNNKACCCTGAATAAAAACAGCGA | 4328 |
| LbCas12a_NNK_307 | TTCTGGAAGTTTTTCGTAACNNKCTGAATAAAAACAGCGAGAT | 4329 |
| LbCas12a_NNK_308 | TGGAAGTTTTTCGTAACACCNNKAATAAAAACAGCGAGATCTT | 4330 |
| LbCas12a_NNK_309 | AAGTTTTTCGTAACACCCTGNNKAAAAACAGCGAGATCTTTAG | 4331 |
| LbCas12a_NNK_310 | TTTTTCGTAACACCCTGAATNNKAACAGCGAGATCTTTAGCAG | 4332 |
| LbCas12a_NNK_311 | TTCGTAACACCCTGAATAAANNKAGCGAGATCTTTAGCAGCAT | 4333 |
| LbCas12a_NNK_312 | GTAACACCCTGAATAAAAACNNKGAGATCTTTAGCAGCATCAA | 4334 |
| LbCas12a_NNK_313 | ACACCCTGAATAAAAACAGCNNKATCTTTAGCAGCATCAAAAA | 4335 |
| LbCas12a_NNK_314 | CCCTGAATAAAAACAGCGAGNNKTTTAGCAGCATCAAAAAGCT | 4336 |

TABLE 3-continued

Primers for creating LbCas12a Saturation Mutagenesis Library

| Name | Sequence (5'→3') | SEQ ID NO |
|---|---|---|
| LbCas12a_NNK_315 | TGAATAAAAACAGCGAGATCNNKAGCAGCATCAAAAAGCTTGA | 4337 |
| LbCas12a_NNK_316 | ATAAAAACAGCGAGATCTTTNNKAGCATCAAAAAGCTTGAGAA | 4338 |
| LbCas12a_NNK_317 | AAAACAGCGAGATCTTTAGCNNKATCAAAAAGCTTGAGAAACT | 4339 |
| LbCas12a_NNK_318 | ACAGCGAGATCTTTAGCAGCNNKAAAAAGCTTGAGAAACTGTT | 4340 |
| LbCas12a_NNK_319 | GCGAGATCTTTAGCAGCATCNNKAAGCTTGAGAAACTGTTCAA | 4341 |
| LbCas12a_NNK_320 | AGATCTTTAGCAGCATCAAANNKCTTGAGAAACTGTTCAAAAA | 4342 |
| LbCas12a_NNK_321 | TCTTTAGCAGCATCAAAAAGNNKGAGAAACTGTTCAAAAACTT | 4343 |
| LbCas12a_NNK_322 | TTAGCAGCATCAAAAAGCTTNNKAAACTGTTCAAAAACTTTGA | 4344 |
| LbCas12a_NNK_323 | GCAGCATCAAAAAGCTTGAGNNKCTGTTCAAAAACTTTGATGA | 4345 |
| LbCas12a_NNK_324 | GCATCAAAAAGCTTGAGAAANNKTTCAAAAACTTTGATGAGTA | 4346 |
| LbCas12a_NNK_325 | TCAAAAAGCTTGAGAAACTGNNKAAAAACTTTGATGAGTATAG | 4347 |
| LbCas12a_NNK_326 | AAAAGCTTGAGAAACTGTTCNNKAACTTTGATGAGTATAGCAG | 4348 |
| LbCas12a_NNK_327 | AGCTTGAGAAACTGTTCAAANNKTTTGATGAGTATAGCAGCGC | 4349 |
| LbCas12a_NNK_328 | TTGAGAAACTGTTCAAAAACNNKGATGAGTATAGCAGCGCAGG | 4350 |
| LbCas12a_NNK_329 | AGAAACTGTTCAAAAACTTTNNKGAGTATAGCAGCGCAGGCAT | 4351 |
| LbCas12a_NNK_330 | AACTGTTCAAAAACTTTGATNNKTATAGCAGCGCAGGCATCTT | 4352 |
| LbCas12a_NNK_331 | TGTTCAAAAACTTTGATGAGNNKAGCAGCGCAGGCATCTTTGT | 4353 |
| LbCas12a_NNK_332 | TCAAAAACTTTGATGAGTATNNKAGCGCAGGCATCTTTGTTAA | 4354 |
| LbCas12a_NNK_333 | AAAACTTTGATGAGTATAGCNNKGCAGGCATCTTTGTTAAAAA | 4355 |
| LbCas12a_NNK_334 | ACTTTGATGAGTATAGCAGCNNKGGCATCTTTGTTAAAAATGG | 4356 |
| LbCas12a_NNK_335 | TTGATGAGTATAGCAGCGCANNKATCTTTGTTAAAAATGGTCC | 4357 |
| LbCas12a_NNK_336 | ATGAGTATAGCAGCGCAGGCNNKTTTGTTAAAAATGGTCCGGC | 4358 |
| LbCas12a_NNK_337 | AGTATAGCAGCGCAGGCATCNNKGTTAAAAATGGTCCGGCAAT | 4359 |
| LbCas12a_NNK_338 | ATAGCAGCGCAGGCATCTTTNNKAAAAATGGTCCGGCAATTAG | 4360 |
| LbCas12a_NNK_339 | GCAGCGCAGGCATCTTTGTTNNKAATGGTCCGGCAATTAGCAC | 4361 |
| LbCas12a_NNK_340 | GCGCAGGCATCTTTGTTAAANNKGGTCCGGCAATTAGCACCAT | 4362 |
| LbCas12a_NNK_341 | CAGGCATCTTTGTTAAAAATNNKCCGGCAATTAGCACCATCAG | 4363 |
| LbCas12a_NNK_342 | GCATCTTTGTTAAAAATGGTNNKGCAATTAGCACCATCAGCAA | 4364 |
| LbCas12a_NNK_343 | TCTTTGTTAAAAATGGTCCGNNKATTAGCACCATCAGCAAAGA | 4365 |
| LbCas12a_NNK_344 | TTGTTAAAAATGGTCCGGCANNKAGCACCATCAGCAAAGATAT | 4366 |
| LbCas12a_NNK_345 | TTAAAAATGGTCCGGCAATTNNKACCATCAGCAAAGATATTTT | 4367 |
| LbCas12a_NNK_346 | AAAATGGTCCGGCAATTAGCNNKATCAGCAAAGATATTTTTGG | 4368 |
| LbCas12a_NNK_347 | ATGGTCCGGCAATTAGCACCNNKAGCAAAGATATTTTTGGCGA | 4369 |
| LbCas12a_NNK_348 | GTCCGGCAATTAGCACCATCNNKAAAGATATTTTTGGCGAATG | 4370 |
| LbCas12a_NNK_349 | CGGCAATTAGCACCATCAGCNNKGATATTTTTGGCGAATGGAA | 4371 |
| LbCas12a_NNK_350 | CAATTAGCACCATCAGCAAANNKATTTTTGGCGAATGGAATGT | 4372 |
| LbCas12a_NNK_351 | TTAGCACCATCAGCAAAGATNNKTTTGGCGAATGGAATGTGAT | 4373 |
| LbCas12a_NNK_352 | GCACCATCAGCAAAGATATTNNKGGCGAATGGAATGTGATCCG | 4374 |

TABLE 3-continued

Primers for creating LbCas12a Saturation Mutagenesis Library

| Name | Sequence (5'→3') | SEQ ID NO |
|---|---|---|
| LbCas12a_NNK_353 | CCATCAGCAAAGATATTTTTNNKGAATGGAATGTGATCCGCGA | 4375 |
| LbCas12a_NNK_354 | TCAGCAAAGATATTTTTGGCNNKTGGAATGTGATCCGCGATAA | 4376 |
| LbCas12a_NNK_355 | GCAAAGATATTTTTGGCGAANNKAATGTGATCCGCGATAAATG | 4377 |
| LbCas12a_NNK_356 | AAGATATTTTTGGCGAATGGNNKGTGATCCGCGATAAATGGAA | 4378 |
| LbCas12a_NNK_357 | ATATTTTTGGCGAATGGAATNNKATCCGCGATAAATGGAATGC | 4379 |
| LbCas12a_NNK_358 | TTTTTGGCGAATGGAATGTGNNKCGCGATAAATGGAATGCCGA | 4380 |
| LbCas12a_NNK_359 | TTGGCGAATGGAATGTGATCNNKGATAAATGGAATGCCGAATA | 4381 |
| LbCas12a_NNK_360 | GCGAATGGAATGTGATCCGCNNKAAATGGAATGCCGAATATGA | 4382 |
| LbCas12a_NNK_361 | AATGGAATGTGATCCGCGATNNKTGGAATGCCGAATATGATGA | 4383 |
| LbCas12a_NNK_362 | GGAATGTGATCCGCGATAAANNKAATGCCGAATATGATGATAT | 4384 |
| LbCas12a_NNK_363 | ATGTGATCCGCGATAAATGGNNKGCCGAATATGATGATATCCA | 4385 |
| LbCas12a_NNK_364 | TGATCCGCGATAAATGGAATNNKGAATATGATGATATCCACCT | 4386 |
| LbCas12a_NNK_365 | TCCGCGATAAATGGAATGCCNNKTATGATGATATCCACCTGAA | 4387 |
| LbCas12a_NNK_366 | GCGATAAATGGAATGCCGAANNKGATGATATCCACCTGAAAAA | 4388 |
| LbCas12a_NNK_367 | ATAAATGGAATGCCGAATATNNKGATATCCACCTGAAAAAAAA | 4389 |
| LbCas12a_NNK_368 | AATGGAATGCCGAATATGATNNKATCCACCTGAAAAAAAAGGC | 4390 |
| LbCas12a_NNK_369 | GGAATGCCGAATATGATGATNNKCACCTGAAAAAAAAGGCCGT | 4391 |
| LbCas12a_NNK_370 | ATGCCGAATATGATGATATCNNKCTGAAAAAAAAGGCCGTGGT | 4392 |
| LbCas12a_NNK_371 | CCGAATATGATGATATCCACNNKAAAAAAAAGGCCGTGGTGAC | 4393 |
| LbCas12a_NNK_372 | AATATGATGATATCCACCTGNNKAAAAAGGCCGTGGTGACCGA | 4394 |
| LbCas12a_NNK_373 | ATGATGATATCCACCTGAAANNKAAGGCCGTGGTGACCGAGAA | 4395 |
| LbCas12a_NNK_374 | ATGATATCCACCTGAAAAAANNKGCCGTGGTGACCGAGAAATA | 4396 |
| LbCas12a_NNK_375 | ATATCCACCTGAAAAAAAAGNNKGTGGTGACCGAGAAATATGA | 4397 |
| LbCas12a_NNK_376 | TCCACCTGAAAAAAAAGGCCNNKGTGACCGAGAAATATGAAGA | 4398 |
| LbCas12a_NNK_377 | ACCTGAAAAAAAAGGCCGTGNNKACCGAGAAATATGAAGATGA | 4399 |
| LbCas12a_NNK_378 | TGAAAAAAAAGGCCGTGGTGNNKGAGAAATATGAAGATGATCG | 4400 |
| LbCas12a_NNK_379 | AAAAAAAGGCCGTGGTGACCNNKAAATATGAAGATGATCGTCG | 4401 |
| LbCas12a_NNK_380 | AAAAGGCCGTGGTGACCGAGNNKTATGAAGATGATCGTCGTAA | 4402 |
| LbCas12a_NNK_381 | AGGCCGTGGTGACCGAGAAANNKGAAGATGATCGTCGTAAAAG | 4403 |
| LbCas12a_NNK_382 | CCGTGGTGACCGAGAAATATNNKGATGATCGTCGTAAAAGCTT | 4404 |
| LbCas12a_NNK_383 | TGGTGACCGAGAAATATGAANNKGATCGTCGTAAAAGCTTCAA | 4405 |
| LbCas12a_NNK_384 | TGACCGAGAAATATGAAGATNNKCGTCGTAAAAGCTTCAAGAA | 4406 |
| LbCas12a_NNK_385 | CCGAGAAATATGAAGATGATNNKCGTAAAAGCTTCAAGAAAAT | 4407 |
| LbCas12a_NNK_386 | AGAAATATGAAGATGATCGTNNKAAAAGCTTCAAGAAAATTGG | 4408 |
| LbCas12a_NNK_387 | AATATGAAGATGATCGTCGTNNKAGCTTCAAGAAAATTGGTAG | 4409 |
| LbCas12a_NNK_388 | ATGAAGATGATCGTCGTAAANNKTTCAAGAAAATTGGTAGCTT | 4410 |
| LbCas12a_NNK_389 | AAGATGATCGTCGTAAAAGCNNKAAGAAAATTGGTAGCTTTAG | 4411 |

TABLE 3-continued

Primers for creating LbCas12a Saturation Mutagenesis Library

| Name | Sequence (5'→3') | SEQ ID NO |
|---|---|---|
| LbCas12a_NNK_390 | ATGATCGTCGTAAAAGCTTCNNKAAAATTGGTAGCTTTAGCCT | 4412 |
| LbCas12a_NNK_391 | ATCGTCGTAAAAGCTTCAAGNNKATTGGTAGCTTTAGCCTGGA | 4413 |
| LbCas12a_NNK_392 | GTCGTAAAAGCTTCAAGAAANNKGGTAGCTTTAGCCTGGAACA | 4414 |
| LbCas12a_NNK_393 | GTAAAAGCTTCAAGAAAATTNNKAGCTTTAGCCTGGAACAGCT | 4415 |
| LbCas12a_NNK_394 | AAAGCTTCAAGAAAATTGGTNNKTTTAGCCTGGAACAGCTGCA | 4416 |
| LbCas12a_NNK_395 | GCTTCAAGAAAATTGGTAGCNNKAGCCTGGAACAGCTGCAAGA | 4417 |
| LbCas12a_NNK_396 | TCAAGAAAATTGGTAGCTTTNNKCTGGAACAGCTGCAAGAATA | 4418 |
| LbCas12a_NNK_397 | AGAAAATTGGTAGCTTTAGCNNKGAACAGCTGCAAGAATATGC | 4419 |
| LbCas12a_NNK_398 | AAATTGGTAGCTTTAGCCTGNNKCAGCTGCAAGAATATGCAGA | 4420 |
| LbCas12a_NNK_399 | TTGGTAGCTTTAGCCTGGAANNKCTGCAAGAATATGCAGATGC | 4421 |
| LbCas12a_NNK_400 | GTAGCTTTAGCCTGGAACAGNNKCAAGAATATGCAGATGCAGA | 4422 |
| LbCas12a_NNK_401 | GCTTTAGCCTGGAACAGCTGNNKGAATATGCAGATGCAGATCT | 4423 |
| LbCas12a_NNK_402 | TTAGCCTGGAACAGCTGCAANNKTATGCAGATGCAGATCTGAG | 4424 |
| LbCas12a_NNK_403 | GCCTGGAACAGCTGCAAGAANNKGCAGATGCAGATCTGAGCGT | 4425 |
| LbCas12a_NNK_404 | TGGAACAGCTGCAAGAATATNNKGATGCAGATCTGAGCGTTGT | 4426 |
| LbCas12a_NNK_405 | AACAGCTGCAAGAATATGCANNKGCAGATCTGAGCGTTGTGGA | 4427 |
| LbCas12a_NNK_406 | AGCTGCAAGAATATGCAGATNNKGATCTGAGCGTTGTGGAAAA | 4428 |
| LbCas12a_NNK_407 | TGCAAGAATATGCAGATGCANNKCTGAGCGTTGTGGAAAAACT | 4429 |
| LbCas12a_NNK_408 | AAGAATATGCAGATGCAGATNNKAGCGTTGTGGAAAAACTGAA | 4430 |
| LbCas12a_NNK_409 | AATATGCAGATGCAGATCTGNNKGTTGTGGAAAAACTGAAAGA | 4431 |
| LbCas12a_NNK_410 | ATGCAGATGCAGATCTGAGCNNKGTGGAAAAACTGAAAGAAAT | 4432 |
| LbCas12a_NNK_411 | CAGATGCAGATCTGAGCGTTNNKGAAAAACTGAAAGAAATCAT | 4433 |
| LbCas12a_NNK_412 | ATGCAGATCTGAGCGTTGTGNNKAAACTGAAAGAAATCATCAT | 4434 |
| LbCas12a_NNK_413 | CAGATCTGAGCGTTGTGGAANNKCTGAAAGAAATCATCATTCA | 4435 |
| LbCas12a_NNK_414 | ATCTGAGCGTTGTGGAAAAANNKAAAGAAATCATCATTCAGAA | 4436 |
| LbCas12a_NNK_415 | TGAGCGTTGTGGAAAAACTGNNKGAAATCATCATTCAGAAGGT | 4437 |
| LbCas12a_NNK_416 | GCGTTGTGGAAAAACTGAAANNKATCATCATTCAGAAGGTGGA | 4438 |
| LbCas12a_NNK_417 | TTGTGGAAAAACTGAAAGAANNKATCATTCAGAAGGTGGACGA | 4439 |
| LbCas12a_NNK_418 | TGGAAAAACTGAAAGAAATCNNKATTCAGAAGGTGGACGAGAT | 4440 |
| LbCas12a_NNK_419 | AAAAACTGAAAGAAATCATCNNKCAGAAGGTGGACGAGATCTA | 4441 |
| LbCas12a_NNK_420 | AACTGAAAGAAATCATCATTNNKAAGGTGGACGAGATCTATAA | 4442 |
| LbCas12a_NNK_421 | TGAAAGAAATCATCATTCAGNNKGTGGACGAGATCTATAAAGT | 4443 |
| LbCas12a_NNK_422 | AAGAAATCATCATTCAGAAGNNKGACGAGATCTATAAAGTTTA | 4444 |
| LbCas12a_NNK_423 | AAATCATCATTCAGAAGGTGNNKGAGATCTATAAAGTTTATGG | 4445 |
| LbCas12a_NNK_424 | TCATCATTCAGAAGGTGGACNNKATCTATAAAGTTTATGGTAG | 4446 |
| LbCas12a_NNK_425 | TCATTCAGAAGGTGGACGAGNNKTATAAAGTTTATGGTAGCAG | 4447 |
| LbCas12a_NNK_426 | TTCAGAAGGTGGACGAGATCNNKAAAGTTTATGGTAGCAGCGA | 4448 |
| LbCas12a_NNK_427 | AGAAGGTGGACGAGATCTATNNKGTTTATGGTAGCAGCGAAAA | 4449 |

TABLE 3-continued

Primers for creating LbCas12a Saturation Mutagenesis Library

| Name | Sequence (5'→3') | SEQ ID NO |
|---|---|---|
| LbCas12a_NNK_428 | AGGTGGACGAGATCTATAAANNKTATGGTAGCAGCGAAAAACT | 4450 |
| LbCas12a_NNK_429 | TGGACGAGATCTATAAAGTTNNKGGTAGCAGCGAAAAACTGTT | 4451 |
| LbCas12a_NNK_430 | ACGAGATCTATAAAGTTTATNNKAGCAGCGAAAAACTGTTCGA | 4452 |
| LbCas12a_NNK_431 | AGATCTATAAAGTTTATGGTNNKAGCGAAAAACTGTTCGATGC | 4453 |
| LbCas12a_NNK_432 | TCTATAAAGTTTATGGTAGCNNKGAAAAACTGTTCGATGCAGA | 4454 |
| LbCas12a_NNK_433 | ATAAAGTTTATGGTAGCAGCNNKAAACTGTTCGATGCAGATTT | 4455 |
| LbCas12a_NNK_434 | AAGTTTATGGTAGCAGCGAANNKCTGTTCGATGCAGATTTTGT | 4456 |
| LbCas12a_NNK_435 | TTTATGGTAGCAGCGAAAAANNKTTCGATGCAGATTTTGTTCT | 4457 |
| LbCas12a_NNK_436 | ATGGTAGCAGCGAAAAACTGNNKGATGCAGATTTTGTTCTGGA | 4458 |
| LbCas12a_NNK_437 | GTAGCAGCGAAAAACTGTTCNNKGCAGATTTTGTTCTGGAAAA | 4459 |
| LbCas12a_NNK_438 | GCAGCGAAAAACTGTTCGATNNKGATTTTGTTCTGGAAAAAAG | 4460 |
| LbCas12a_NNK_439 | GCGAAAAACTGTTCGATGCANNKTTTGTTCTGGAAAAAAGCCT | 4461 |
| LbCas12a_NNK_440 | AAAAACTGTTCGATGCAGATNNKGTTCTGGAAAAAAGCCTGAA | 4462 |
| LbCas12a_NNK_441 | AACTGTTCGATGCAGATTTTNNKCTGGAAAAAAGCCTGAAAAA | 4463 |
| LbCas12a_NNK_442 | TGTTCGATGCAGATTTTGTTNNKGAAAAAAGCCTGAAAAAGAA | 4464 |
| LbCas12a_NNK_443 | TCGATGCAGATTTTGTTCTGNNKAAAAGCCTGAAAAAGAATGA | 4465 |
| LbCas12a_NNK_444 | ATGCAGATTTTGTTCTGGAANNKAGCCTGAAAAAGAATGATGC | 4466 |
| LbCas12a_NNK_445 | CAGATTTTGTTCTGGAAAAANNKCTGAAAAAGAATGATGCCGT | 4467 |
| LbCas12a_NNK_446 | ATTTTGTTCTGGAAAAAAGCNNKAAAAAGAATGATGCCGTTGT | 4468 |
| LbCas12a_NNK_447 | TTGTTCTGGAAAAAAGCCTGNNKAAGAATGATGCCGTTGTGGC | 4469 |
| LbCas12a_NNK_448 | TTCTGGAAAAAAGCCTGAAANNKAATGATGCCGTTGTGGCCAT | 4470 |
| LbCas12a_NNK_449 | TGGAAAAAAGCCTGAAAAAGNNKGATGCCGTTGTGGCCATTAT | 4471 |
| LbCas12a_NNK_450 | AAAAAGCCTGAAAAGAATNNKGCCGTTGTGGCCATTATGAA | 4472 |
| LbCas12a_NNK_451 | AAAGCCTGAAAAGAATGATNNKGTTGTGGCCATTATGAAAGA | 4473 |
| LbCas12a_NNK_452 | GCCTGAAAAAGAATGATGCCNNKGTGGCCATTATGAAAGATCT | 4474 |
| LbCas12a_NNK_453 | TGAAAAGAATGATGCCGTTNNKGCCATTATGAAAGATCTGCT | 4475 |
| LbCas12a_NNK_454 | AAAAGAATGATGCCGTTGTGNNKATTATGAAAGATCTGCTGGA | 4476 |
| LbCas12a_NNK_455 | AGAATGATGCCGTTGTGGCCNNKATGAAAGATCTGCTGGATAG | 4477 |
| LbCas12a_NNK_456 | ATGATGCCGTTGTGGCCATTNNKAAAGATCTGCTGGATAGCGT | 4478 |
| LbCas12a_NNK_457 | ATGCCGTTGTGGCCATTATGNNKGATCTGCTGGATAGCGTTAA | 4479 |
| LbCas12a_NNK_458 | CCGTTGTGGCCATTATGAAANNKCTGCTGGATAGCGTTAAGAG | 4480 |
| LbCas12a_NNK_459 | TTGTGGCCATTATGAAAGATNNKCTGGATAGCGTTAAGAGCTT | 4481 |
| LbCas12a_NNK_460 | TGGCCATTATGAAAGATCTGNNKGATAGCGTTAAGAGCTTCGA | 4482 |
| LbCas12a_NNK_461 | CCATTATGAAAGATCTGCTGNNKAGCGTTAAGAGCTTCGAGAA | 4483 |
| LbCas12a_NNK_462 | TTATGAAAGATCTGCTGGATNNKGTTAAGAGCTTCGAGAATTA | 4484 |
| LbCas12a_NNK_463 | TGAAAGATCTGCTGGATAGCNNKAAGAGCTTCGAGAATTACAT | 4485 |
| LbCas12a_NNK_464 | AAGATCTGCTGGATAGCGTTNNKAGCTTCGAGAATTACATCAA | 4486 |

TABLE 3-continued

Primers for creating LbCas12a Saturation Mutagenesis Library

| Name | Sequence (5'→3') | SEQ ID NO |
|---|---|---|
| LbCas12a_NNK_465 | ATCTGCTGGATAGCGTTAAGNNKTTCGAGAATTACATCAAAGC | 4487 |
| LbCas12a_NNK_466 | TGCTGGATAGCGTTAAGAGCNNKGAGAATTACATCAAAGCCTT | 4488 |
| LbCas12a_NNK_467 | TGGATAGCGTTAAGAGCTTCNNKAATTACATCAAAGCCTTTTT | 4489 |
| LbCas12a_NNK_468 | ATAGCGTTAAGAGCTTCGAGNNKTACATCAAAGCCTTTTTTGG | 4490 |
| LbCas12a_NNK_469 | GCGTTAAGAGCTTCGAGAATNNKATCAAAGCCTTTTTTGGTGA | 4491 |
| LbCas12a_NNK_470 | TTAAGAGCTTCGAGAATTACNNKAAAGCCTTTTTTGGTGAGGG | 4492 |
| LbCas12a_NNK_471 | AGAGCTTCGAGAATTACATCNNKGCCTTTTTTGGTGAGGGCAA | 4493 |
| LbCas12a_NNK_472 | GCTTCGAGAATTACATCAAANNKTTTTTTGGTGAGGGCAAAGA | 4494 |
| LbCas12a_NNK_473 | TCGAGAATTACATCAAAGCCNNKTTTGGTGAGGGCAAAGAAAC | 4495 |
| LbCas12a_NNK_474 | AGAATTACATCAAAGCCTTTNNKGGTGAGGGCAAAGAAACCAA | 4496 |
| LbCas12a_NNK_475 | ATTACATCAAAGCCTTTTTTNNKGAGGGCAAAGAAACCAATCG | 4497 |
| LbCas12a_NNK_476 | ACATCAAAGCCTTTTTTGGTNNKGGCAAAGAAACCAATCGTGA | 4498 |
| LbCas12a_NNK_477 | TCAAAGCCTTTTTTGGTGAGNNKAAAGAAACCAATCGTGATGA | 4499 |
| LbCas12a_NNK_478 | AAGCCTTTTTTGGTGAGGGCNNKGAAACCAATCGTGATGAAAG | 4500 |
| LbCas12a_NNK_479 | CCTTTTTTGGTGAGGGCAAANNKACCAATCGTGATGAAAGTTT | 4501 |
| LbCas12a_NNK_480 | TTTTTGGTGAGGGCAAAGAANNKAATCGTGATGAAAGTTTCTA | 4502 |
| LbCas12a_NNK_481 | TTGGTGAGGGCAAAGAAACCNNKCGTGATGAAAGTTTCTATGG | 4503 |
| LbCas12a_NNK_482 | GTGAGGGCAAAGAAACCAATNNKGATGAAAGTTTCTATGGCGA | 4504 |
| LbCas12a_NNK_483 | AGGGCAAAGAAACCAATCGTNNKGAAAGTTTCTATGGCGATTT | 4505 |
| LbCas12a_NNK_484 | GCAAAGAAACCAATCGTGATNNKAGTTTCTATGGCGATTTTGT | 4506 |
| LbCas12a_NNK_485 | AAGAAACCAATCGTGATGAANNKTTCTATGGCGATTTTGTGCT | 4507 |
| LbCas12a_NNK_486 | AAACCAATCGTGATGAAAGTNNKTATGGCGATTTTGTGCTGGC | 4508 |
| LbCas12a_NNK_487 | CCAATCGTGATGAAAGTTTCNNKGGCGATTTTGTGCTGGCCTA | 4509 |
| LbCas12a_NNK_488 | ATCGTGATGAAAGTTTCTATNNKGATTTTGTGCTGGCCTATGA | 4510 |
| LbCas12a_NNK_489 | GTGATGAAAGTTTCTATGGCNNKTTTGTGCTGGCCTATGATAT | 4511 |
| LbCas12a_NNK_490 | ATGAAAGTTTCTATGGCGATNNKGTGCTGGCCTATGATATTCT | 4512 |
| LbCas12a_NNK_491 | AAAGTTTCTATGGCGATTTTNNKCTGGCCTATGATATTCTGCT | 4513 |
| LbCas12a_NNK_492 | GTTTCTATGGCGATTTTGTGNNKGCCTATGATATTCTGCTGAA | 4514 |
| LbCas12a_NNK_493 | TCTATGGCGATTTTGTGCTGNNKTATGATATTCTGCTGAAAGT | 4515 |
| LbCas12a_NNK_494 | ATGGCGATTTTGTGCTGGCCNNKGATATTCTGCTGAAAGTGGA | 4516 |
| LbCas12a_NNK_495 | GCGATTTTGTGCTGGCCTATNNKATTCTGCTGAAAGTGGACCA | 4517 |
| LbCas12a_NNK_496 | ATTTTGTGCTGGCCTATGATNNKCTGCTGAAAGTGGACCATAT | 4518 |
| LbCas12a_NNK_497 | TTGTGCTGGCCTATGATATTNNKCTGAAAGTGGACCATATTTA | 4519 |
| LbCas12a_NNK_498 | TGCTGGCCTATGATATTCTGNNKAAAGTGGACCATATTTATGA | 4520 |
| LbCas12a_NNK_499 | TGGCCTATGATATTCTGCTGNNKGTGGACCATATTTATGATGC | 4521 |
| LbCas12a_NNK_500 | CCTATGATATTCTGCTGAAANNKGACCATATTTATGATGCCAT | 4522 |
| LbCas12a_NNK_501 | ATGATATTCTGCTGAAAGTGNNKCATATTTATGATGCCATTCG | 4523 |
| LbCas12a_NNK_502 | ATATTCTGCTGAAAGTGGACNNKATTTATGATGCCATTCGCAA | 4524 |

TABLE 3-continued

Primers for creating LbCas12a Saturation Mutagenesis Library

| Name | Sequence (5'→3') | SEQ ID NO |
|---|---|---|
| LbCas12a_NNK_503 | TTCTGCTGAAAGTGGACCATNNKTATGATGCCATTCGCAATTA | 4525 |
| LbCas12a_NNK_504 | TGCTGAAAGTGGACCATATTNNKGATGCCATTCGCAATTATGT | 4526 |
| LbCas12a_NNK_505 | TGAAAGTGGACCATATTTATNNKGCCATTCGCAATTATGTTAC | 4527 |
| LbCas12a_NNK_506 | AAGTGGACCATATTTATGATNNKATTCGCAATTATGTTACCCA | 4528 |
| LbCas12a_NNK_507 | TGGACCATATTTATGATGCCNNKCGCAATTATGTTACCCAGAA | 4529 |
| LbCas12a_NNK_508 | ACCATATTTATGATGCCATTNNKAATTATGTTACCCAGAAACC | 4530 |
| LbCas12a_NNK_509 | ATATTTATGATGCCATTCGCNNKTATGTTACCCAGAAACCGTA | 4531 |
| LbCas12a_NNK_510 | TTTATGATGCCATTCGCAATNNKGTTACCCAGAAACCGTATAG | 4532 |
| LbCas12a_NNK_511 | ATGATGCCATTCGCAATTATNNKACCCAGAAACCGTATAGCAA | 4533 |
| LbCas12a_NNK_512 | ATGCCATTCGCAATTATGTTNNKCAGAAACCGTATAGCAAAGA | 4534 |
| LbCas12a_NNK_513 | CCATTCGCAATTATGTTACCNNKAAACCGTATAGCAAAGACAA | 4535 |
| LbCas12a_NNK_514 | TTCGCAATTATGTTACCCAGNNKCCGTATAGCAAAGACAAGTT | 4536 |
| LbCas12a_NNK_515 | GCAATTATGTTACCCAGAAANNKTATAGCAAAGACAAGTTCAA | 4537 |
| LbCas12a_NNK_516 | ATTATGTTACCCAGAAACCGNNKAGCAAAGACAAGTTCAAACT | 4538 |
| LbCas12a_NNK_517 | ATGTTACCCAGAAACCGTATNNKAAAGACAAGTTCAAACTGTA | 4539 |
| LbCas12a_NNK_518 | TTACCCAGAAACCGTATAGCNNKGACAAGTTCAAACTGTACTT | 4540 |
| LbCas12a_NNK_519 | CCCAGAAACCGTATAGCAAANNKAAGTTCAAACTGTACTTTCA | 4541 |
| LbCas12a_NNK_520 | AGAAACCGTATAGCAAAGACNNKTTCAAACTGTACTTTCAGAA | 4542 |
| LbCas12a_NNK_521 | AACCGTATAGCAAAGACAAGNNKAAACTGTACTTTCAGAACCC | 4543 |
| LbCas12a_NNK_522 | CGTATAGCAAAGACAAGTTCNNKCTGTACTTTCAGAACCCGCA | 4544 |
| LbCas12a_NNK_523 | ATAGCAAAGACAAGTTCAAANNKTACTTTCAGAACCCGCAGTT | 4545 |
| LbCas12a_NNK_524 | GCAAAGACAAGTTCAAACTGNNKTTTCAGAACCCGCAGTTTAT | 4546 |
| LbCas12a_NNK_525 | AAGACAAGTTCAAACTGTACNNKCAGAACCCGCAGTTTATGGG | 4547 |
| LbCas12a_NNK_526 | ACAAGTTCAAACTGTACTTTNNKAACCCGCAGTTTATGGGTGG | 4548 |
| LbCas12a_NNK_527 | AGTTCAAACTGTACTTTCAGNNKCCGCAGTTTATGGGTGGTTG | 4549 |
| LbCas12a_NNK_528 | TCAAACTGTACTTTCAGAACNNKCAGTTTATGGGTGGTTGGGA | 4550 |
| LbCas12a_NNK_529 | AACTGTACTTTCAGAACCCGNNKTTTATGGGTGGTTGGGATAA | 4551 |
| LbCas12a_NNK_530 | TGTACTTTCAGAACCCGCAGNNKATGGGTGGTTGGGATAAAGA | 4552 |
| LbCas12a_NNK_531 | ACTTTCAGAACCCGCAGTTTNNKGGTGGTTGGGATAAAGATAA | 4553 |
| LbCas12a_NNK_532 | TTCAGAACCCGCAGTTTATGNNKGGTTGGGATAAAGATAAAGA | 4554 |
| LbCas12a_NNK_533 | AGAACCCGCAGTTTATGGGTNNKTGGGATAAAGATAAAGAAAC | 4555 |
| LbCas12a_NNK_534 | ACCCGCAGTTTATGGGTGGTNNKGATAAAGATAAAGAAACCGA | 4556 |
| LbCas12a_NNK_535 | CGCAGTTTATGGGTGGTTGGNNKAAAGATAAAGAAACCGATTA | 4557 |
| LbCas12a_NNK_536 | AGTTTATGGGTGGTTGGGATNNKGATAAAGAAACCGATTATCG | 4558 |
| LbCas12a_NNK_537 | TTATGGGTGGTTGGGATAAANNKAAAGAAACCGATTATCGTGC | 4559 |
| LbCas12a_NNK_538 | TGGGTGGTTGGGATAAAGATNNKGAAACCGATTATCGTGCCAC | 4560 |
| LbCas12a_NNK_539 | GTGGTTGGGATAAAGATAAANNKACCGATTATCGTGCCACCAT | 4561 |

TABLE 3-continued

Primers for creating LbCas12a Saturation Mutagenesis Library

| Name | Sequence (5'→3') | SEQ ID NO |
|---|---|---|
| LbCas12a_NNK_540 | GTTGGGATAAAGATAAAGAANNKGATTATCGTGCCACCATCCT | 4562 |
| LbCas12a_NNK_541 | GGGATAAAGATAAAGAAACCNNKTATCGTGCCACCATCCTGCG | 4563 |
| LbCas12a_NNK_542 | ATAAAGATAAAGAAACCGATNNKCGTGCCACCATCCTGCGTTA | 4564 |
| LbCas12a_NNK_543 | AAGATAAAGAAACCGATTATNNKGCCACCATCCTGCGTTATGG | 4565 |
| LbCas12a_NNK_544 | ATAAAGAAACCGATTATCGTNNKACCATCCTGCGTTATGGTAG | 4566 |
| LbCas12a_NNK_545 | AAGAAACCGATTATCGTGCCNNKATCCTGCGTTATGGTAGTAA | 4567 |
| LbCas12a_NNK_546 | AAACCGATTATCGTGCCACCNNKCTGCGTTATGGTAGTAAATA | 4568 |
| LbCas12a_NNK_547 | CCGATTATCGTGCCACCATCNNKCGTTATGGTAGTAAATACTA | 4569 |
| LbCas12a_NNK_548 | ATTATCGTGCCACCATCCTGNNKTATGGTAGTAAATACTATCT | 4570 |
| LbCas12a_NNK_549 | ATCGTGCCACCATCCTGCGTNNKGGTAGTAAATACTATCTGGC | 4571 |
| LbCas12a_NNK_550 | GTGCCACCATCCTGCGTTATNNKAGTAAATACTATCTGGCCAT | 4572 |
| LbCas12a_NNK_551 | CCACCATCCTGCGTTATGGTNNKAAATACTATCTGGCCATCAT | 4573 |
| LbCas12a_NNK_552 | CCATCCTGCGTTATGGTAGTNNKTACTATCTGGCCATCATGGA | 4574 |
| LbCas12a_NNK_553 | TCCTGCGTTATGGTAGTAAANNKTATCTGGCCATCATGGACAA | 4575 |
| LbCas12a_NNK_554 | TGCGTTATGGTAGTAAATACNNKCTGGCCATCATGGACAAAAA | 4576 |
| LbCas12a_NNK_555 | GTTATGGTAGTAAATACTATNNKGCCATCATGGACAAAAAATA | 4577 |
| LbCas12a_NNK_556 | ATGGTAGTAAATACTATCTGNNKATCATGGACAAAAAATACGC | 4578 |
| LbCas12a_NNK_557 | GTAGTAAATACTATCTGGCCNNKATGGACAAAAAATACGCAAA | 4579 |
| LbCas12a_NNK_558 | GTAAATACTATCTGGCCATCNNKGACAAAAAATACGCAAAATG | 4580 |
| LbCas12a_NNK_559 | AATACTATCTGGCCATCATGNNKAAAAAATACGCAAAATGCCT | 4581 |
| LbCas12a_NNK_560 | ACTATCTGGCCATCATGGACNNKAAATACGCAAAATGCCTGCA | 4582 |
| LbCas12a_NNK_561 | ATCTGGCCATCATGGACAAANNKTACGCAAAATGCCTGCAGAA | 4583 |
| LbCas12a_NNK_562 | TGGCCATCATGGACAAAAAANNKGCAAAATGCCTGCAGAAAAT | 4584 |
| LbCas12a_NNK_563 | CCATCATGGACAAAAAATACNNKAAATGCCTGCAGAAAATCGA | 4585 |
| LbCas12a_NNK_564 | TCATGGACAAAAAATACGCANNKTGCCTGCAGAAAATCGACAA | 4586 |
| LbCas12a_NNK_565 | TGGACAAAAAATACGCAAAANNKCTGCAGAAAATCGACAAAGA | 4587 |
| LbCas12a_NNK_566 | ACAAAAAATACGCAAAATGCNNKCAGAAAATCGACAAAGATGA | 4588 |
| LbCas12a_NNK_567 | AAAAATACGCAAAATGCCTGNNKAAAATCGACAAAGATGATGT | 4589 |
| LbCas12a_NNK_568 | AATACGCAAAATGCCTGCAGNNKATCGACAAAGATGATGTGAA | 4590 |
| LbCas12a_NNK_569 | ACGCAAAATGCCTGCAGAAANNKGACAAAGATGATGTGAATGG | 4591 |
| LbCas12a_NNK_570 | CAAAATGCCTGCAGAAAATCNNKAAAGATGATGTGAATGGCAA | 4592 |
| LbCas12a_NNK_571 | AATGCCTGCAGAAAATCGACNNKGATGATGTGAATGGCAACTA | 4593 |
| LbCas12a_NNK_572 | GCCTGCAGAAAATCGACAAANNKGATGTGAATGGCAACTATGA | 4594 |
| LbCas12a_NNK_573 | TGCAGAAAATCGACAAAGATNNKGTGAATGGCAACTATGAAAA | 4595 |
| LbCas12a_NNK_574 | AGAAAATCGACAAAGATGATNNKAATGGCAACTATGAAAAAAT | 4596 |
| LbCas12a_NNK_575 | AAATCGACAAAGATGATGTGNNKGGCAACTATGAAAAAATCAA | 4597 |
| LbCas12a_NNK_576 | TCGACAAAGATGATGTGAATNNKAACTATGAAAAAATCAACTA | 4598 |
| LbCas12a_NNK_577 | ACAAAGATGATGTGAATGGCNNKTATGAAAAAATCAACTACAA | 4599 |

TABLE 3-continued

Primers for creating LbCas12a Saturation Mutagenesis Library

| Name | Sequence (5'→3') | SEQ ID NO |
|---|---|---|
| LbCas12a_NNK_578 | AAGATGATGTGAATGGCAACNNKGAAAAAATCAACTACAAACT | 4600 |
| LbCas12a_NNK_579 | ATGATGTGAATGGCAACTATNNKAAAATCAACTACAAACTGCT | 4601 |
| LbCas12a_NNK_580 | ATGTGAATGGCAACTATGAANNKATCAACTACAAACTGCTGCC | 4602 |
| LbCas12a_NNK_581 | TGAATGGCAACTATGAAAAANNKAACTACAAACTGCTGCCTGG | 4603 |
| LbCas12a_NNK_582 | ATGGCAACTATGAAAAATCNNKTACAAACTGCTGCCTGGTCC | 4604 |
| LbCas12a_NNK_583 | GCAACTATGAAAAAATCAACNNKAAACTGCTGCCTGGTCCGAA | 4605 |
| LbCas12a_NNK_584 | ACTATGAAAAATCAACTACNNKCTGCTGCCTGGTCCGAATAA | 4606 |
| LbCas12a_NNK_585 | ATGAAAAATCAACTACAAANNKCTGCCTGGTCCGAATAAAAT | 4607 |
| LbCas12a_NNK_586 | AAAAAATCAACTACAAACTGNNKCCTGGTCCGAATAAAATGCT | 4608 |
| LbCas12a_NNK_587 | AAATCAACTACAAACTGCTGNNKGGTCCGAATAAAATGCTGCC | 4609 |
| LbCas12a_NNK_588 | TCAACTACAAACTGCTGCCTNNKCCGAATAAAATGCTGCCGAA | 4610 |
| LbCas12a_NNK_589 | ACTACAAACTGCTGCCTGGTNNKAATAAAATGCTGCCGAAAGT | 4611 |
| LbCas12a_NNK_590 | ACAAACTGCTGCCTGGTCCGNNKAAAATGCTGCCGAAAGTGTT | 4612 |
| LbCas12a_NNK_591 | AACTGCTGCCTGGTCCGAATNNKATGCTGCCGAAAGTGTTCTT | 4613 |
| LbCas12a_NNK_592 | TGCTGCCTGGTCCGAATAAANNKCTGCCGAAAGTGTTCTTTAG | 4614 |
| LbCas12a_NNK_593 | TGCCTGGTCCGAATAAAATGNNKCCGAAAGTGTTCTTTAGCAA | 4615 |
| LbCas12a_NNK_594 | CTGGTCCGAATAAAATGCTGNNKAAAGTGTTCTTTAGCAAGAA | 4616 |
| LbCas12a_NNK_595 | GTCCGAATAAAATGCTGCCGNNKGTGTTCTTTAGCAAGAAATG | 4617 |
| LbCas12a_NNK_596 | CGAATAAAATGCTGCCGAAANNKTTCTTTAGCAAGAAATGGAT | 4618 |
| LbCas12a_NNK_597 | ATAAAATGCTGCCGAAAGTGNNKTTTAGCAAGAAATGGATGGC | 4619 |
| LbCas12a_NNK_598 | AAATGCTGCCGAAAGTGTTCNNKAGCAAGAAATGGATGGCCTA | 4620 |
| LbCas12a_NNK_599 | TGCTGCCGAAAGTGTTCTTTNNKAAGAAATGGATGGCCTATTA | 4621 |
| LbCas12a_NNK_600 | TGCCGAAAGTGTTCTTTAGCNNKAAATGGATGGCCTATTATAA | 4622 |
| LbCas12a_NNK_601 | CGAAAGTGTTCTTTAGCAAGNNKTGGATGGCCTATTATAACCC | 4623 |
| LbCas12a_NNK_602 | AAGTGTTCTTTAGCAAGAAANNKATGGCCTATTATAACCCGAG | 4624 |
| LbCas12a_NNK_603 | TGTTCTTTAGCAAGAAATGGNNKGCCTATTATAACCCGAGCGA | 4625 |
| LbCas12a_NNK_604 | TCTTTAGCAAGAAATGGATGNNKTATTATAACCCGAGCGAGGA | 4626 |
| LbCas12a_NNK_605 | TTAGCAAGAAATGGATGGCCNNKTATAACCCGAGCGAGGATAT | 4627 |
| LbCas12a_NNK_606 | GCAAGAAATGGATGGCCTATNNKAACCCGAGCGAGGATATTCA | 4628 |
| LbCas12a_NNK_607 | AGAAATGGATGGCCTATTATNNKCCGAGCGAGGATATTCAAAA | 4629 |
| LbCas12a_NNK_608 | AATGGATGGCCTATTATAACNNKAGCGAGGATATTCAAAAGAT | 4630 |
| LbCas12a_NNK_609 | GGATGGCCTATTATAACCCGNNKGAGGATATTCAAAAGATCTA | 4631 |
| LbCas12a_NNK_610 | TGGCCTATTATAACCCGAGCNNKGATATTCAAAAGATCTACAA | 4632 |
| LbCas12a_NNK_611 | cCTATTATAACCCGAGCGAGNNKATTCAAAAGATCTACAAAAA | 4633 |
| LbCas12a_NNK_612 | ATTATAACCCGAGCGAGGATNNKCAAAAGATCTACAAAAATGG | 4634 |
| LbCas12a_NNK_613 | ATAACCCGAGCGAGGATATTNNKAAGATCTACAAAAATGGCAC | 4635 |
| LbCas12a_NNK_614 | ACCCGAGCGAGGATATTCAANNKATCTACAAAAATGGCACCTT | 4636 |

TABLE 3-continued

Primers for creating LbCas12a Saturation Mutagenesis Library

| Name | Sequence (5'→3') | SEQ ID NO |
|---|---|---|
| LbCas12a_NNK_615 | CGAGCGAGGATATTCAAAAGNNKTACAAAAATGGCACCTTTAA | 4637 |
| LbCas12a_NNK_616 | GCGAGGATATTCAAAAGATCNNKAAAAATGGCACCTTTAAAAA | 4638 |
| LbCas12a_NNK_617 | AGGATATTCAAAAGATCTACNNKAATGGCACCTTTAAAAAGGG | 4639 |
| LbCas12a_NNK_618 | ATATTCAAAAGATCTACAAANNKGGCACCTTTAAAAAGGGCGA | 4640 |
| LbCas12a_NNK_619 | TTCAAAAGATCTACAAAAATNNKACCTTTAAAAAGGGCGACAT | 4641 |
| LbCas12a_NNK_620 | AAAAGATCTACAAAAATGGCNNKTTTAAAAAGGGCGACATGTT | 4642 |
| LbCas12a_NNK_621 | AGATCTACAAAAATGGCACCNNKAAAAAGGGCGACATGTTCAA | 4643 |
| LbCas12a_NNK_622 | TCTACAAAAATGGCACCTTTNNKAAGGGCGACATGTTCAATCT | 4644 |
| LbCas12a_NNK_623 | ACAAAAATGGCACCTTTAAANNKGGCGACATGTTCAATCTGAA | 4645 |
| LbCas12a_NNK_624 | AAAATGGCACCTTTAAAAAGNNKGACATGTTCAATCTGAACGA | 4646 |
| LbCas12a_NNK_625 | ATGGCACCTTTAAAAAGGGCNNKATGTTCAATCTGAACGATTG | 4647 |
| LbCas12a_NNK_626 | GCACCTTTAAAAAGGGCGACNNKTTCAATCTGAACGATTGCCA | 4648 |
| LbCas12a_NNK_627 | CCTTTAAAAAGGGCGACATGNNKAATCTGAACGATTGCCACAA | 4649 |
| LbCas12a_NNK_628 | TTAAAAAGGGCGACATGTTCNNKCTGAACGATTGCCACAAACT | 4650 |
| LbCas12a_NNK_629 | AAAAGGGCGACATGTTCAATNNKAACGATTGCCACAAACTGAT | 4651 |
| LbCas12a_NNK_630 | AGGGCGACATGTTCAATCTGNNKGATTGCCACAAACTGATCGA | 4652 |
| LbCas12a_NNK_631 | GCGACATGTTCAATCTGAACNNKTGCCACAAACTGATCGATTT | 4653 |
| LbCas12a_NNK_632 | ACATGTTCAATCTGAACGATNNKCACAAACTGATCGATTTCTT | 4654 |
| LbCas12a_NNK_633 | TGTTCAATCTGAACGATTGCNNKAAACTGATCGATTTCTTCAA | 4655 |
| LbCas12a_NNK_634 | TCAATCTGAACGATTGCCACNNKCTGATCGATTTCTTCAAAGA | 4656 |
| LbCas12a_NNK_635 | ATCTGAACGATTGCCACAAANNKATCGATTTCTTCAAAGATTC | 4657 |
| LbCas12a_NNK_636 | TGAACGATTGCCACAAACTGNNKGATTTCTTCAAAGATTCAAT | 4658 |
| LbCas12a_NNK_637 | ACGATTGCCACAAACTGATCNNKTTCTTCAAAGATTCAATTTC | 4659 |
| LbCas12a_NNK_638 | ATTGCCACAAACTGATCGATNNKTTCAAAGATTCAATTTCGCG | 4660 |
| LbCas12a_NNK_639 | GCCACAAACTGATCGATTTCNNKAAAGATTCAATTTCGCGTTA | 4661 |
| LbCas12a_NNK_640 | ACAAACTGATCGATTTCTTCNNKGATTCAATTTCGCGTTATCC | 4662 |
| LbCas12a_NNK_641 | AACTGATCGATTTCTTCAAANNKTCAATTTCGCGTTATCCGAA | 4663 |
| LbCas12a_NNK_642 | TGATCGATTTCTTCAAAGATNNKATTTCGCGTTATCCGAAATG | 4664 |
| LbCas12a_NNK_643 | TCGATTTCTTCAAAGATTCANNKTCGCGTTATCCGAAATGGTC | 4665 |
| LbCas12a_NNK_644 | ATTTCTTCAAAGATTCAATTNNKCGTTATCCGAAATGGTCCAA | 4666 |
| LbCas12a_NNK_645 | TCTTCAAAGATTCAATTTCGNNKTATCCGAAATGGTCCAATGC | 4667 |
| LbCas12a_NNK_646 | TCAAAGATTCAATTTCGCGTNNKCCGAAATGGTCCAATGCCTA | 4668 |
| LbCas12a_NNK_647 | AAGATTCAATTTCGCGTTATNNKAAATGGTCCAATGCCTATGA | 4669 |
| LbCas12a_NNK_648 | ATTCAATTTCGCGTTATCCGNNKTGGTCCAATGCCTATGATTT | 4670 |
| LbCas12a_NNK_649 | CAATTTCGCGTTATCCGAAANNKTCCAATGCCTATGATTTTAA | 4671 |
| LbCas12a_NNK_650 | TTTCGCGTTATCCGAAATGGNNKAATGCCTATGATTTTAACTT | 4672 |
| LbCas12a_NNK_651 | CGCGTTATCCGAAATGGTCCNNKGCCTATGATTTTAACTTTAG | 4673 |
| LbCas12a_NNK_652 | GTTATCCGAAATGGTCCAATNNKTATGATTTTAACTTTAGCGA | 4674 |

TABLE 3-continued

Primers for creating LbCas12a Saturation Mutagenesis Library

| Name | Sequence (5'→3') | SEQ ID NO |
|---|---|---|
| LbCas12a_NNK_653 | ATCCGAAATGGTCCAATGCCNNKGATTTTAACTTTAGCGAAAC | 4675 |
| LbCas12a_NNK_654 | CGAAATGGTCCAATGCCTATNNKTTTAACTTTAGCGAAACCGA | 4676 |
| LbCas12a_NNK_655 | AATGGTCCAATGCCTATGATNNKAACTTTAGCGAAACCGAAAA | 4677 |
| LbCas12a_NNK_656 | GGTCCAATGCCTATGATTTTNNKTTTAGCGAAACCGAAAAATA | 4678 |
| LbCas12a_NNK_657 | CCAATGCCTATGATTTTAACNNKAGCGAAACCGAAAAATACAA | 4679 |
| LbCas12a_NNK_658 | ATGCCTATGATTTTAACTTTNNKGAAACCGAAAAATACAAAGA | 4680 |
| LbCas12a_NNK_659 | CCTATGATTTTAACTTTAGCNNKACCGAAAAATACAAAGACAT | 4681 |
| LbCas12a_NNK_660 | ATGATTTTAACTTTAGCGAANNKGAAAAATACAAAGACATTGC | 4682 |
| LbCas12a_NNK_661 | ATTTTAACTTTAGCGAAACCNNKAAATACAAAGACATTGCCGG | 4683 |
| LbCas12a_NNK_662 | TTAACTTTAGCGAAACCGAANNKTACAAAGACATTGCCGGTTT | 4684 |
| LbCas12a_NNK_663 | ACTTTAGCGAAACCGAAAAANNKAAAGACATTGCCGGTTTTTA | 4685 |
| LbCas12a_NNK_664 | TTAGCGAAACCGAAAAATACNNKGACATTGCCGGTTTTTATCG | 4686 |
| LbCas12a_NNK_665 | GCGAAACCGAAAAATACAAANNKGATTGCCGGTTTTTATCGCGA | 4687 |
| LbCas12a_NNK_666 | AAACCGAAAAATACAAAGACNNKGCCGGTTTTTATCGCGAAGT | 4688 |
| LbCas12a_NNK_667 | CCGAAAAATACAAAGACATTNNKGGTTTTTATCGCGAAGTGGA | 4689 |
| LbCas12a_NNK_668 | AAAAATACAAAGACATTGCCNNKTTTTATCGCGAAGTGGAAGA | 4690 |
| LbCas12a_NNK_669 | AATACAAAGACATTGCCGGTNNKTATCGCGAAGTGGAAGAACA | 4691 |
| LbCas12a_NNK_670 | ACAAAGACATTGCCGGTTTTNNKCGCGAAGTGGAAGAACAGGG | 4692 |
| LbCas12a_NNK_671 | AAGACATTGCCGGTTTTTATNNKGAAGTGGAAGAACAGGGCTA | 4693 |
| LbCas12a_NNK_672 | ACATTGCCGGTTTTTATCGCNNKGTGGAAGAACAGGGCTATAA | 4694 |
| LbCas12a_NNK_673 | TTGCCGGTTTTTATCGCGAANNKGAAGAACAGGGCTATAAAGT | 4695 |
| LbCas12a_NNK_674 | CCGGTTTTTATCGCGAAGTGNNKGAACAGGGCTATAAAGTGAG | 4696 |
| LbCas12a_NNK_675 | GTTTTTATCGCGAAGTGGAANNKCAGGGCTATAAAGTGAGCTT | 4697 |
| LbCas12a_NNK_676 | TTTATCGCGAAGTGGAAGAANNKGGCTATAAAGTGAGCTTTGA | 4698 |
| LbCas12a_NNK_677 | ATCGCGAAGTGGAAGAACAGNNKTATAAAGTGAGCTTTGAAAG | 4699 |
| LbCas12a_NNK_678 | GCGAAGTGGAAGAACAGGGCNNKAAAGTGAGCTTTGAAAGCGC | 4700 |
| LbCas12a_NNK_679 | AAGTGGAAGAACAGGGCTATNNKGTGAGCTTTGAAAGCGCAAG | 4701 |
| LbCas12a_NNK_680 | TGGAAGAACAGGGCTATAAANNKAGCTTTGAAAGCGCAAGCAA | 4702 |
| LbCas12a_NNK_681 | AAGAACAGGGCTATAAAGTGNNKTTTGAAAGCGCAAGCAAAAA | 4703 |
| LbCas12a_NNK_682 | AACAGGGCTATAAAGTGAGCNNKGAAAGCGCAAGCAAAAAGA | 4704 |
| LbCas12a_NNK_683 | AGGGCTATAAAGTGAGCTTTNNKAGCGCAAGCAAAAAGAGGT | 4705 |
| LbCas12a_NNK_684 | GCTATAAAGTGAGCTTTGAANNKGCAAGCAAAAAGAGGTTGA | 4706 |
| LbCas12a_NNK_685 | ATAAAGTGAGCTTTGAAAGCNNKAGCAAAAAGAGGTTGATAA | 4707 |
| LbCas12a_NNK_686 | AAGTGAGCTTTGAAAGCGCANNKAAAAAGAGGTTGATAAGCT | 4708 |
| LbCas12a_NNK_687 | TGAGCTTTGAAAGCGCAAGCNNKAAAGAGGTTGATAAGCTGGT | 4709 |
| LbCas12a_NNK_688 | GCTTTGAAAGCGCAAGCAAANNKGAGGTTGATAAGCTGGTTGA | 4710 |
| LbCas12a_NNK_689 | TTGAAAGCGCAAGCAAAAAANNKGTTGATAAGCTGGTTGAAGA | 4711 |

TABLE 3-continued

Primers for creating LbCas12a Saturation Mutagenesis Library

| Name | Sequence (5'→3') | SEQ ID NO |
|---|---|---|
| LbCas12a_NNK_690 | AAAGCGCAAGCAAAAAGAGNNKGATAAGCTGGTTGAAGAGGG | 4712 |
| LbCas12a_NNK_691 | GCGCAAGCAAAAAGAGGTTNNKAAGCTGGTTGAAGAGGGCAA | 4713 |
| LbCas12a_NNK_692 | CAAGCAAAAAGAGGTTGATNNKCTGGTTGAAGAGGGCAAACT | 4714 |
| LbCas12a_NNK_693 | GCAAAAAGAGGTTGATAAGNNKGTTGAAGAGGGCAAACTGTA | 4715 |
| LbCas12a_NNK_694 | AAAAAGAGGTTGATAAGCTGNNKGAAGAGGGCAAACTGTATAT | 4716 |
| LbCas12a_NNK_695 | AAGAGGTTGATAAGCTGGTTNNKGAGGGCAAACTGTATATGTT | 4717 |
| LbCas12a_NNK_696 | AGGTTGATAAGCTGGTTGAANNKGGCAAACTGTATATGTTCCA | 4718 |
| LbCas12a_NNK_697 | TTGATAAGCTGGTTGAAGAGNNKAAACTGTATATGTTCCAGAT | 4719 |
| LbCas12a_NNK_698 | ATAAGCTGGTTGAAGAGGGCNNKCTGTATATGTTCCAGATTTA | 4720 |
| LbCas12a_NNK_699 | AGCTGGTTGAAGAGGGCAAANNKTATATGTTCCAGATTTACAA | 4721 |
| LbCas12a_NNK_700 | TGGTTGAAGAGGGCAAACTGNNKATGTTCCAGATTTACAACAA | 4722 |
| LbCas12a_NNK_701 | TTGAAGAGGGCAAACTGTATNNKTTCCAGATTTACAACAAAGA | 4723 |
| LbCas12a_NNK_702 | AAGAGGGCAAACTGTATATGNNKCAGATTTACAACAAAGATTT | 4724 |
| LbCas12a_NNK_703 | AGGGCAAACTGTATATGTTCNNKATTTACAACAAAGATTTTAG | 4725 |
| LbCas12a_NNK_704 | GCAAACTGTATATGTTCCAGNNKTACAACAAAGATTTTAGCGA | 4726 |
| LbCas12a_NNK_705 | AACTGTATATGTTCCAGATTNNKAACAAAGATTTTAGCGACAA | 4727 |
| LbCas12a_NNK_706 | TGTATATGTTCCAGATTTACNNKAAAGATTTTAGCGACAAAAG | 4728 |
| LbCas12a_NNK_707 | ATATGTTCCAGATTTACAACNNKGATTTTAGCGACAAAAGCCA | 4729 |
| LbCas12a_NNK_708 | TGTTCCAGATTTACAACAAANNKTTTAGCGACAAAAGCCATGG | 4730 |
| LbCas12a_NNK_709 | TCCAGATTTACAACAAAGATNNKAGCGACAAAAGCCATGGCAC | 4731 |
| LbCas12a_NNK_710 | AGATTTACAACAAAGATTTTNNKGACAAAAGCCATGGCACCCC | 4732 |
| LbCas12a_NNK_711 | TTTACAACAAAGATTTTAGCNNKAAAAGCCATGGCACCCCGAA | 4733 |
| LbCas12a_NNK_712 | ACAACAAAGATTTTAGCGACNNKAGCCATGGCACCCCGAATCT | 4734 |
| LbCas12a_NNK_713 | ACAAAGATTTTAGCGACAAANNKCATGGCACCCCGAATCTGCA | 4735 |
| LbCas12a_NNK_714 | AAGATTTTAGCGACAAAAGCNNKGGCACCCCGAATCTGCATAC | 4736 |
| LbCas12a_NNK_715 | ATTTTAGCGACAAAAGCCATNNKACCCCGAATCTGCATACCAT | 4737 |
| LbCas12a_NNK_716 | TTAGCGACAAAAGCCATGGCNNKCCGAATCTGCATACCATGTA | 4738 |
| LbCas12a_NNK_717 | GCGACAAAAGCCATGGCACCNNKAATCTGCATACCATGTACTT | 4739 |
| LbCas12a_NNK_718 | ACAAAGCCATGGCACCCCGNNKCTGCATACCATGTACTTTAA | 4740 |
| LbCas12a_NNK_719 | AAAGCCATGGCACCCCGAATNNKCATACCATGTACTTTAAACT | 4741 |
| LbCas12a_NNK_720 | GCCATGGCACCCCGAATCTGNNKACCATGTACTTTAAACTGCT | 4742 |
| LbCas12a_NNK_721 | ATGGCACCCCGAATCTGCATNNKATGTACTTTAAACTGCTGTT | 4743 |
| LbCas12a_NNK_722 | GCACCCCGAATCTGCATACCNNKTACTTTAAACTGCTGTTCGA | 4744 |
| LbCas12a_NNK_723 | CCCCGAATCTGCATACCATGNNKTTTAAACTGCTGTTCGACGA | 4745 |
| LbCas12a_NNK_724 | CGAATCTGCATACCATGTACNNKAAACTGCTGTTCGACGAAAA | 4746 |
| LbCas12a_NNK_725 | ATCTGCATACCATGTACTTTNNKCTGCTGTTCGACGAAAATAA | 4747 |
| LbCas12a_NNK_726 | TGCATACCATGTACTTTAAANNKCTGTTCGACGAAAATAACCA | 4748 |
| LbCas12a_NNK_727 | ATACCATGTACTTTAAACTGNNKTTCGACGAAAATAACCATGG | 4749 |

TABLE 3-continued

Primers for creating LbCas12a Saturation Mutagenesis Library

| Name | Sequence (5'→3') | SEQ ID NO |
|---|---|---|
| LbCas12a_NNK_728 | CCATGTACTTTAAACTGCTGNNKGACGAAAATAACCATGGTCA | 4750 |
| LbCas12a_NNK_729 | TGTACTTTAAACTGCTGTTCNNKGAAAATAACCATGGTCAGAT | 4751 |
| LbCas12a_NNK_730 | ACTTTAAACTGCTGTTCGACNNKAATAACCATGGTCAGATTCG | 4752 |
| LbCas12a_NNK_731 | TTAAACTGCTGTTCGACGAANNKAACCATGGTCAGATTCGTCT | 4753 |
| LbCas12a_NNK_732 | AACTGCTGTTCGACGAAAATNNKCATGGTCAGATTCGTCTGAG | 4754 |
| LbCas12a_NNK_733 | TGCTGTTCGACGAAAATAACNNKGGTCAGATTCGTCTGAGCGG | 4755 |
| LbCas12a_NNK_734 | TGTTCGACGAAAATAACCATNNKCAGATTCGTCTGAGCGGTGG | 4756 |
| LbCas12a_NNK_735 | TCGACGAAAATAACCATGGTNNKATTCGTCTGAGCGGTGGTGC | 4757 |
| LbCas12a_NNK_736 | ACGAAAATAACCATGGTCAGNNKCGTCTGAGCGGTGGTGCCGA | 4758 |
| LbCas12a_NNK_737 | AAAATAACCATGGTCAGATTNNKCTGAGCGGTGGTGCCGAACT | 4759 |
| LbCas12a_NNK_738 | ATAACCATGGTCAGATTCGTNNKAGCGGTGGTGCCGAACTGTT | 4760 |
| LbCas12a_NNK_739 | ACCATGGTCAGATTCGTCTGNNKGGTGGTGCCGAACTGTTTAT | 4761 |
| LbCas12a_NNK_740 | ATGGTCAGATTCGTCTGAGCNNKGGTGCCGAACTGTTTATGCG | 4762 |
| LbCas12a_NNK_741 | GTCAGATTCGTCTGAGCGGTNNKGCCGAACTGTTTATGCGTCG | 4763 |
| LbCas12a_NNK_742 | AGATTCGTCTGAGCGGTGGTNNKGAACTGTTTATGCGTCGTGC | 4764 |
| LbCas12a_NNK_743 | TTCGTCTGAGCGGTGGTGCCNNKCTGTTTATGCGTCGTGCAAG | 4765 |
| LbCas12a_NNK_744 | GTCTGAGCGGTGGTGCCGAANNKTTTATGCGTCGTGCAAGTCT | 4766 |
| LbCas12a_NNK_745 | TGAGCGGTGGTGCCGAACTGNNKATGCGTCGTGCAAGTCTGAA | 4767 |
| LbCas12a_NNK_746 | GCGGTGGTGCCGAACTGTTTNNKCGTCGTGCAAGTCTGAAAAA | 4768 |
| LbCas12a_NNK_747 | GTGGTGCCGAACTGTTTATGNNKCGTGCAAGTCTGAAAAAAGA | 4769 |
| LbCas12a_NNK_748 | GTGCCGAACTGTTTATGCGTNNKGCAAGTCTGAAAAAAGAAGA | 4770 |
| LbCas12a_NNK_749 | CCGAACTGTTTATGCGTCGTNNKAGTCTGAAAAAAGAAGAACT | 4771 |
| LbCas12a_NNK_750 | AACTGTTTATGCGTCGTGCANNKCTGAAAAAAGAAGAACTGGT | 4772 |
| LbCas12a_NNK_751 | TGTTTATGCGTCGTGCAAGTNNKAAAAAAGAAGAACTGGTTGT | 4773 |
| LbCas12a_NNK_752 | TTATGCGTCGTGCAAGTCTGNNKAAAGAAGAACTGGTTGTTCA | 4774 |
| LbCas12a_NNK_753 | TGCGTCGTGCAAGTCTGAAANNKGAAGAACTGGTTGTTCATCC | 4775 |
| LbCas12a_NNK_754 | GTCGTGCAAGTCTGAAAAAANNKGAACTGGTTGTTCATCCGGC | 4776 |
| LbCas12a_NNK_755 | GTGCAAGTCTGAAAAAAGAANNKCTGGTTGTTCATCCGGCAAA | 4777 |
| LbCas12a_NNK_756 | CAAGTCTGAAAAAAGAAGAANNKGTTGTTCATCCGGCAAATAG | 4778 |
| LbCas12a_NNK_757 | GTCTGAAAAAAGAAGAACTGNNKGTTCATCCGGCAAATAGCCC | 4779 |
| LbCas12a_NNK_758 | TGAAAAAGAAGAACTGGTTNNKCATCCGGCAAATAGCCCGAT | 4780 |
| LbCas12a_NNK_759 | AAAAAGAAGAACTGGTTGTTNNKCCGGCAAATAGCCCGATTGC | 4781 |
| LbCas12a_NNK_760 | AAGAAGAACTGGTTGTTCATNNKGCAAATAGCCCGATTGCAAA | 4782 |
| LbCas12a_NNK_761 | AAGAACTGGTTGTTCATCCGNNKAATAGCCCGATTGCAAACAA | 4783 |
| LbCas12a_NNK_762 | AACTGGTTGTTCATCCGGCANNKAGCCCGATTGCAAACAAAAA | 4784 |
| LbCas12a_NNK_763 | TGGTTGTTCATCCGGCAAATNNKCCGATTGCAAACAAAAATCC | 4785 |
| LbCas12a_NNK_764 | TTGTTCATCCGGCAAATAGCNNKATTGCAAACAAAAATCCGGA | 4786 |

TABLE 3-continued

Primers for creating LbCas12a Saturation Mutagenesis Library

| Name | Sequence (5'→3') | SEQ ID NO |
|---|---|---|
| LbCas12a_NNK_765 | TTCATCCGGCAAATAGCCCGNNKGCAAACAAAAATCCGGACAA | 4787 |
| LbCas12a_NNK_766 | ATCCGGCAAATAGCCCGATTNNKAACAAAAATCCGGACAATCC | 4788 |
| LbCas12a_NNK_767 | CGGCAAATAGCCCGATTGCANNKAAAAATCCGGACAATCCGAA | 4789 |
| LbCas12a_NNK_768 | CAAATAGCCCGATTGCAAACNNKAATCCGGACAATCCGAAAAA | 4790 |
| LbCas12a_NNK_769 | ATAGCCCGATTGCAAACAAANNKCCGGACAATCCGAAAAAAAC | 4791 |
| LbCas12a_NNK_770 | GCCCGATTGCAAACAAAAATNNKGACAATCCGAAAAAAACCAC | 4792 |
| LbCas12a_NNK_771 | CGATTGCAAACAAAAATCCGNNKAATCCGAAAAAAACCACGAC | 4793 |
| LbCas12a_NNK_772 | TTGCAAACAAAAATCCGGACNNKCCGAAAAAAACCACGACACT | 4794 |
| LbCas12a_NNK_773 | CAAACAAAAATCCGGACAATNNKAAAAAAACCACGACACTGAG | 4795 |
| LbCas12a_NNK_774 | ACAAAAATCCGGACAATCCGNNKAAAACCACGACACTGAGCTA | 4796 |
| LbCas12a_NNK_775 | AAAATCCGGACAATCCGAAANNKACCACGACACTGAGCTATGA | 4797 |
| LbCas12a_NNK_776 | ATCCGGACAATCCGAAAAAANNKACGACACTGAGCTATGATGT | 4798 |
| LbCas12a_NNK_777 | CGGACAATCCGAAAAAAACCNNKACACTGAGCTATGATGTGTA | 4799 |
| LbCas12a_NNK_778 | ACAATCCGAAAAAAACCACGNNKCTGAGCTATGATGTGTATAA | 4800 |
| LbCas12a_NNK_779 | ATCCGAAAAAAACCACGACANNKAGCTATGATGTGTATAAAGA | 4801 |
| LbCas12a_NNK_780 | CGAAAAAAACCACGACACTGNNKTATGATGTGTATAAAGACAA | 4802 |
| LbCas12a_NNK_781 | AAAAAACCACGACACTGAGCNNKGATGTGTATAAAGACAAACG | 4803 |
| LbCas12a_NNK_782 | AAACCACGACACTGAGCTATNNKGTGTATAAAGACAAACGTTT | 4804 |
| LbCas12a_NNK_783 | CCACGACACTGAGCTATGATNNKTATAAAGACAAACGTTTTAG | 4805 |
| LbCas12a_NNK_784 | CGACACTGAGCTATGATGTGNNKAAAGACAAACGTTTTAGCGA | 4806 |
| LbCas12a_NNK_785 | CACTGAGCTATGATGTGTATNNKGACAAACGTTTTAGCGAGGA | 4807 |
| LbCas12a_NNK_786 | TGAGCTATGATGTGTATAAANNKAAACGTTTTAGCGAGGATCA | 4808 |
| LbCas12a_NNK_787 | GCTATGATGTGTATAAAGACNNKCGTTTTAGCGAGGATCAGTA | 4809 |
| LbCas12a_NNK_J88 | ATGATGTGTATAAAGACAAANNKTTTAGCGAGGATCAGTATGA | 4810 |
| LbCas12a_NNK_J89 | ATGTGTATAAAGACAAACGTNNKAGCGAGGATCAGTATGAACT | 4811 |
| LbCas12a_NNK_790 | TGTATAAAGACAAACGTTTTNNKGAGGATCAGTATGAACTGCA | 4812 |
| LbCas12a_NNK_J91 | ATAAAGACAAACGTTTTAGCNNKGATCAGTATGAACTGCATAT | 4813 |
| LbCas12a_NNK_792 | AAGACAAACGTTTTAGCGAGNNKCAGTATGAACTGCATATCCC | 4814 |
| LbCas12a_NNK_793 | ACAAACGTTTTAGCGAGGATNNKTATGAACTGCATATCCCGAT | 4815 |
| LbCas12a_NNK_794 | AACGTTTTAGCGAGGATCAGNNKGAACTGCATATCCCGATTGC | 4816 |
| LbCas12a_NNK_795 | GTTTTAGCGAGGATCAGTATNNKCTGCATATCCCGATTGCCAT | 4817 |
| LbCas12a_NNK_796 | TTAGCGAGGATCAGTATGAANNKCATATCCCGATTGCCATCAA | 4818 |
| LbCas12a_NNK_797 | GCGAGGATCAGTATGAACTGNNKATCCCGATTGCCATCAATAA | 4819 |
| LbCas12a_NNK_798 | AGGATCAGTATGAACTGCATNNKCCGATTGCCATCAATAAATG | 4820 |
| LbCas12a_NNK_J99 | ATCAGTATGAACTGCATATCNNKATTGCCATCAATAAATGCCC | 4821 |
| LbCas12a_NNK_800 | AGTATGAACTGCATATCCCGNNKGCCATCAATAAATGCCCGAA | 4822 |
| LbCas12a_NNK_801 | ATGAACTGCATATCCCGATTNNKATCAATAAATGCCCGAAAAA | 4823 |
| LbCas12a_NNK_802 | AACTGCATATCCCGATTGCCNNKAATAAATGCCCGAAAAACAT | 4824 |

TABLE 3-continued

Primers for creating LbCas12a Saturation Mutagenesis Library

| Name | Sequence (5'→3') | SEQ ID NO |
|---|---|---|
| LbCas12a_NNK_803 | TGCATATCCCGATTGCCATCNNKAAATGCCCGAAAAACATCTT | 4825 |
| LbCas12a_NNK_804 | ATATCCCGATTGCCATCAATNNKTGCCCGAAAAACATCTTTAA | 4826 |
| LbCas12a_NNK_805 | TCCCGATTGCCATCAATAAANNKCCGAAAAACATCTTTAAGAT | 4827 |
| LbCas12a_NNK_806 | CGATTGCCATCAATAAATGCNNKAAAAACATCTTTAAGATCAA | 4828 |
| LbCas12a_NNK_807 | TTGCCATCAATAAATGCCCGNNKAACATCTTTAAGATCAACAC | 4829 |
| LbCas12a_NNK_808 | CCATCAATAAATGCCCGAAANNKATCTTTAAGATCAACACCGA | 4830 |
| LbCas12a_NNK_809 | TCAATAAATGCCCGAAAAACNNKTTTAAGATCAACACCGAAGT | 4831 |
| LbCas12a_NNK_810 | ATAAATGCCCGAAAAACATCNNKAAGATCAACACCGAAGTTCG | 4832 |
| LbCas12a_NNK_811 | AATGCCCGAAAAACATCTTTNNKATCAACACCGAAGTTCGCGT | 4833 |
| LbCas12a_NNK_812 | GCCCGAAAAACATCTTTAAGNNKAACACCGAAGTTCGCGTGCT | 4834 |
| LbCas12a_NNK_813 | CGAAAAACATCTTTAAGATCNNKACCGAAGTTCGCGTGCTGCT | 4835 |
| LbCas12a_NNK_814 | AAAACATCTTTAAGATCAACNNKGAAGTTCGCGTGCTGCTGAA | 4836 |
| LbCas12a_NNK_815 | ACATCTTTAAGATCAACACCNNKGTTCGCGTGCTGCTGAAACA | 4837 |
| LbCas12a_NNK_816 | TCTTTAAGATCAACACCGAANNKCGCGTGCTGCTGAAACATGA | 4838 |
| LbCas12a_NNK_817 | TTAAGATCAACACCGAAGTTNNKGTGCTGCTGAAACATGATGA | 4839 |
| LbCas12a_NNK_818 | AGATCAACACCGAAGTTCGCNNKCTGCTGAAACATGATGATAA | 4840 |
| LbCas12a_NNK_819 | TCAACACCGAAGTTCGCGTGNNKCTGAAACATGATGATAATCC | 4841 |
| LbCas12a_NNK_820 | ACACCGAAGTTCGCGTGCTGNNKAAACATGATGATAATCCGTA | 4842 |
| LbCas12a_NNK_821 | CCGAAGTTCGCGTGCTGCTGNNKCATGATGATAATCCGTATGT | 4843 |
| LbCas12a_NNK_822 | AAGTTCGCGTGCTGCTGAAANNKGATGATAATCCGTATGTGAT | 4844 |
| LbCas12a_NNK_823 | TTCGCGTGCTGCTGAAACATNNKGATAATCCGTATGTGATTGG | 4845 |
| LbCas12a_NNK_824 | GCGTGCTGCTGAAACATGATNNKAATCCGTATGTGATTGGCAT | 4846 |
| LbCas12a_NNK_825 | TGCTGCTGAAACATGATGATNNKCCGTATGTGATTGGCATTGA | 4847 |
| LbCas12a_NNK_826 | TGCTGAAACATGATGATAATNNKTATGTGATTGGCATTGATCG | 4848 |
| LbCas12a_NNK_827 | TGAAACATGATGATAATCCGNNKGTGATTGGCATTGATCGTGG | 4849 |
| LbCas12a_NNK_828 | AACATGATGATAATCCGTATNNKATTGGCATTGATCGTGGTGA | 4850 |
| LbCas12a_NNK_829 | ATGATGATAATCCGTATGTGNNKGGCATTGATCGTGGTGAACG | 4851 |
| LbCas12a_NNK_830 | ATGATAATCCGTATGTGATTNNKATTGATCGTGGTGAACGTAA | 4852 |
| LbCas12a_NNK_831 | ATAATCCGTATGTGATTGGCNNKGATCGTGGTGAACGTAACCT | 4853 |
| LbCas12a_NNK_832 | ATCCGTATGTGATTGGCATTNNKCGTGGTGAACGTAACCTGCT | 4854 |
| LbCas12a_NNK_833 | CGTATGTGATTGGCATTGATNNKGGTGAACGTAACCTGCTGTA | 4855 |
| LbCas12a_NNK_834 | ATGTGATTGGCATTGATCGTNNKGAACGTAACCTGCTGTATAT | 4856 |
| LbCas12a_NNK_835 | TGATTGGCATTGATCGTGGTNNKCGTAACCTGCTGTATATTGT | 4857 |
| LbCas12a_NNK_836 | TTGGCATTGATCGTGGTGAANNKAACCTGCTGTATATTGTTGT | 4858 |
| LbCas12a_NNK_837 | GCATTGATCGTGGTGAACGTNNKCTGCTGTATATTGTTGTTGT | 4859 |
| LbCas12a_NNK_838 | TTGATCGTGGTGAACGTAACNNKCTGTATATTGTTGTTGTTGA | 4860 |
| LbCas12a_NNK_839 | ATCGTGGTGAACGTAACCTGNNKTATATTGTTGTTGTTGATGG | 4861 |

TABLE 3-continued

Primers for creating LbCas12a Saturation Mutagenesis Library

| Name | Sequence (5'→3') | SEQ ID NO |
|---|---|---|
| LbCas12a_NNK_840 | GTGGTGAACGTAACCTGCTGNNKATTGTTGTTGTTGATGGTAA | 4862 |
| LbCas12a_NNK_841 | GTGAACGTAACCTGCTGTATNNKGTTGTTGTTGATGGTAAAGG | 4863 |
| LbCas12a_NNK_842 | AACGTAACCTGCTGTATATTNNKGTTGTTGATGGTAAAGGCAA | 4864 |
| LbCas12a_NNK_843 | GTAACCTGCTGTATATTGTTNNKGTTGATGGTAAAGGCAACAT | 4865 |
| LbCas12a_NNK_844 | ACCTGCTGTATATTGTTGTTNNKGATGGTAAAGGCAACATCGT | 4866 |
| LbCas12a_NNK_845 | TGCTGTATATTGTTGTTGTTNNKGGTAAAGGCAACATCGTGGA | 4867 |
| LbCas12a_NNK_846 | TGTATATTGTTGTTGTTGATNNKAAAGGCAACATCGTGGAACA | 4868 |
| LbCas12a_NNK_847 | ATATTGTTGTTGTTGATGGTNNKGGCAACATCGTGGAACAGTA | 4869 |
| LbCas12a_NNK_848 | TTGTTGTTGTTGATGGTAAANNKAACATCGTGGAACAGTATAG | 4870 |
| LbCas12a_NNK_849 | TTGTTGTTGATGGTAAAGGCNNKATCGTGGAACAGTATAGTCT | 4871 |
| LbCas12a_NNK_850 | TTGTTGATGGTAAAGGCAACNNKGTGGAACAGTATAGTCTGAA | 4872 |
| LbCas12a_NNK_851 | TTGATGGTAAAGGCAACATCNNKGAACAGTATAGTCTGAACGA | 4873 |
| LbCas12a_NNK_852 | ATGGTAAAGGCAACATCGTGNNKCAGTATAGTCTGAACGAAAT | 4874 |
| LbCas12a_NNK_853 | GTAAAGGCAACATCGTGGAANNKTATAGTCTGAACGAAATTAT | 4875 |
| LbCas12a_NNK_854 | AAGGCAACATCGTGGAACAGNNKAGTCTGAACGAAATTATCAA | 4876 |
| LbCas12a_NNK_855 | GCAACATCGTGGAACAGTATNNKCTGAACGAAATTATCAACAA | 4877 |
| LbCas12a_NNK_856 | ACATCGTGGAACAGTATAGTNNKAACGAAATTATCAACAACTT | 4878 |
| LbCas12a_NNK_857 | TCGTGGAACAGTATAGTCTGNNKGAAATTATCAACAACTTTAA | 4879 |
| LbCas12a_NNK_858 | TGGAACAGTATAGTCTGAACNNKATTATCAACAACTTTAACGG | 4880 |
| LbCas12a_NNK_859 | AACAGTATAGTCTGAACGAANNKATCAACAACTTTAACGGCAT | 4881 |
| LbCas12a_NNK_860 | AGTATAGTCTGAACGAAATTNNKAACAACTTTAACGGCATCCG | 4882 |
| LbCas12a_NNK_861 | ATAGTCTGAACGAAATTATCNNKAACTTTAACGGCATCCGCAT | 4883 |
| LbCas12a_NNK_862 | GTCTGAACGAAATTATCAACNNKTTTAACGGCATCCGCATCAA | 4884 |
| LbCas12a_NNK_863 | TGAACGAAATTATCAACAACNNKAACGGCATCCGCATCAAAAC | 4885 |
| LbCas12a_NNK_864 | ACGAAATTATCAACAACTTTNNKGGCATCCGCATCAAAACCGA | 4886 |
| LbCas12a_NNK_865 | AAATTATCAACAACTTTAACNNKATCCGCATCAAAACCGACTA | 4887 |
| LbCas12a_NNK_866 | TTATCAACAACTTTAACGGCNNKCGCATCAAAACCGACTATCA | 4888 |
| LbCas12a_NNK_867 | TCAACAACTTTAACGGCATCNNKATCAAAACCGACTATCATAG | 4889 |
| LbCas12a_NNK_868 | ACAACTTTAACGGCATCCGCNNKAAAACCGACTATCATAGCCT | 4890 |
| LbCas12a_NNK_869 | ACTTTAACGGCATCCGCATCNNKACCGACTATCATAGCCTGCT | 4891 |
| LbCas12a_NNK_870 | TTAACGGCATCCGCATCAAANNKGACTATCATAGCCTGCTGGA | 4892 |
| LbCas12a_NNK_871 | ACGGCATCCGCATCAAAACCNNKTATCATAGCCTGCTGGACAA | 4893 |
| LbCas12a_NNK_872 | GCATCCGCATCAAAACCGACNNKCATAGCCTGCTGGACAAGAA | 4894 |
| LbCas12a_NNK_873 | TCCGCATCAAAACCGACTATNNKAGCCTGCTGGACAAGAAAGA | 4895 |
| LbCas12a_NNK_874 | GCATCAAAACCGACTATCATNNKCTGCTGGACAAGAAAGAAAA | 4896 |
| LbCas12a_NNK_875 | TCAAAACCGACTATCATAGCNNKCTGGACAAGAAAGAAAAAGA | 4897 |
| LbCas12a_NNK_876 | AAACCGACTATCATAGCCTGNNKGACAAGAAAGAAAAAGAACG | 4898 |
| LbCas12a_NNK_877 | CCGACTATCATAGCCTGCTGNNKAAGAAAGAAAAAGAACGTTT | 4899 |

TABLE 3-continued

Primers for creating LbCas12a Saturation Mutagenesis Library

| Name | Sequence (5'→3') | SEQ ID NO |
|---|---|---|
| LbCas12a_NNK_878 | ACTATCATAGCCTGCTGGACNNKAAAGAAAAAGAACGTTTTGA | 4900 |
| LbCas12a_NNK_879 | ATCATAGCCTGCTGGACAAGNNKGAAAAAGAACGTTTTGAAGC | 4901 |
| LbCas12a_NNK_880 | ATAGCCTGCTGGACAAGAAANNKAAAGAACGTTTTGAAGCACG | 4902 |
| LbCas12a_NNK_881 | GCCTGCTGGACAAGAAAGAANNKGAACGTTTTGAAGCACGTCA | 4903 |
| LbCas12a_NNK_882 | TGCTGGACAAGAAAGAAAAANNKCGTTTTGAAGCACGTCAGAA | 4904 |
| LbCas12a_NNK_883 | TGGACAAGAAAGAAAAAGAANNKTTTGAAGCACGTCAGAACTG | 4905 |
| LbCas12a_NNK_884 | ACAAGAAAGAAAAAGAACGTNNKGAAGCACGTCAGAACTGGAC | 4906 |
| LbCas12a_NNK_885 | AGAAAGAAAAAGAACGTTTTNNKGCACGTCAGAACTGGACCAG | 4907 |
| LbCas12a_NNK_886 | AAGAAAAAGAACGTTTTGAANNKCGTCAGAACTGGACCAGTAT | 4908 |
| LbCas12a_NNK_887 | AAAAAGAACGTTTTGAAGCANNKCAGAACTGGACCAGTATTGA | 4909 |
| LbCas12a_NNK_888 | AAGAACGTTTTGAAGCACGTNNKAACTGGACCAGTATTGAAAA | 4910 |
| LbCas12a_NNK_889 | AACGTTTTGAAGCACGTCAGNNKTGGACCAGTATTGAAAACAT | 4911 |
| LbCas12a_NNK_890 | GTTTTGAAGCACGTCAGAACNNKACCAGTATTGAAAACATCAA | 4912 |
| LbCas12a_NNK_891 | TTGAAGCACGTCAGAACTGGNNKAGTATTGAAAACATCAAAGA | 4913 |
| LbCas12a_NNK_892 | AAGCACGTCAGAACTGGACCNNKATTGAAAACATCAAAGAACT | 4914 |
| LbCas12a_NNK_893 | CACGTCAGAACTGGACCAGTNNKGAAAACATCAAAGAACTGAA | 4915 |
| LbCas12a_NNK_894 | GTCAGAACTGGACCAGTATTNNKAACATCAAAGAACTGAAAGC | 4916 |
| LbCas12a_NNK_895 | AGAACTGGACCAGTATTGAANNKATCAAAGAACTGAAAGCCGG | 4917 |
| LbCas12a_NNK_896 | ACTGGACCAGTATTGAAAACNNKAAAGAACTGAAAGCCGGTTA | 4918 |
| LbCas12a_NNK_897 | GGACCAGTATTGAAAACATCNNKGAACTGAAAGCCGGTTATAT | 4919 |
| LbCas12a_NNK_898 | CCAGTATTGAAAACATCAAANNKCTGAAAGCCGGTTATATTAG | 4920 |
| LbCas12a_NNK_899 | GTATTGAAAACATCAAAGAANNKAAAGCCGGTTATATTAGCCA | 4921 |
| LbCas12a_NNK_900 | TTGAAAACATCAAAGAACTGNNKGCCGGTTATATTAGCCAGGT | 4922 |
| LbCas12a_NNK_901 | AAAACATCAAAGAACTGAAANNKGGTTATATTAGCCAGGTGGT | 4923 |
| LbCas12a_NNK_902 | ACATCAAAGAACTGAAAGCCNNKTATATTAGCCAGGTGGTTCA | 4924 |
| LbCas12a_NNK_903 | TCAAAGAACTGAAAGCCGGTNNKATTAGCCAGGTGGTTCATAA | 4925 |
| LbCas12a_NNK_904 | AAGAACTGAAAGCCGGTTATNNKAGCCAGGTGGTTCATAAAAT | 4926 |
| LbCas12a_NNK_905 | AACTGAAAGCCGGTTATATTNNKCAGGTGGTTCATAAAATCTG | 4927 |
| LbCas12a_NNK_906 | TGAAAGCCGGTTATATTAGCNNKGTGGTTCATAAAATCTGTGA | 4928 |
| LbCas12a_NNK_907 | AAGCCGGTTATATTAGCCAGNNKGTTCATAAAATCTGTGAGCT | 4929 |
| LbCas12a_NNK_908 | CCGGTTATATTAGCCAGGTGNNKCATAAAATCTGTGAGCTGGT | 4930 |
| LbCas12a_NNK_909 | GTTATATTAGCCAGGTGGTTNNKAAAATCTGTGAGCTGGTAGA | 4931 |
| LbCas12a_NNK_910 | ATATTAGCCAGGTGGTTCATNNKATCTGTGAGCTGGTAGAAAA | 4932 |
| LbCas12a_NNK_911 | TTAGCCAGGTGGTTCATAAANNKTGTGAGCTGGTAGAAAAATA | 4933 |
| LbCas12a_NNK_912 | GCCAGGTGGTTCATAAAATCNNKGAGCTGGTAGAAAAATACGA | 4934 |
| LbCas12a_NNK_913 | AGGTGGTTCATAAAATCTGTNNKCTGGTAGAAAAATACGATGC | 4935 |
| LbCas12a_NNK_914 | TGGTTCATAAAATCTGTGAGNNKGTAGAAAAATACGATGCAGT | 4936 |

TABLE 3-continued

Primers for creating LbCas12a Saturation Mutagenesis Library

| Name | Sequence (5'→3') | SEQ ID NO |
|---|---|---|
| LbCas12a_NNK_915 | TTCATAAAATCTGTGAGCTGNNKGAAAAATACGATGCAGTTAT | 4937 |
| LbCas12a_NNK_916 | ATAAAATCTGTGAGCTGGTANNKAAATACGATGCAGTTATTGC | 4938 |
| LbCas12a_NNK_917 | AAATCTGTGAGCTGGTAGAANNKTACGATGCAGTTATTGCACT | 4939 |
| LbCas12a_NNK_918 | TCTGTGAGCTGGTAGAAAAANNKGATGCAGTTATTGCACTGGA | 4940 |
| LbCas12a_NNK_919 | GTGAGCTGGTAGAAAAATACNNKGCAGTTATTGCACTGGAAGA | 4941 |
| LbCas12a_NNK_920 | AGCTGGTAGAAAAATACGATNNKGTTATTGCACTGGAAGATCT | 4942 |
| LbCas12a_NNK_921 | TGGTAGAAAAATACGATGCANNKATTGCACTGGAAGATCTGAA | 4943 |
| LbCas12a_NNK_922 | TAGAAAAATACGATGCAGTTNNKGCACTGGAAGATCTGAATAG | 4944 |
| LbCas12a_NNK_923 | AAAAATACGATGCAGTTATTNNKCTGGAAGATCTGAATAGCGG | 4945 |
| LbCas12a_NNK_924 | AATACGATGCAGTTATTGCANNKGAAGATCTGAATAGCGGTTT | 4946 |
| LbCas12a_NNK_925 | ACGATGCAGTTATTGCACTGNNKGATCTGAATAGCGGTTTCAA | 4947 |
| LbCas12a_NNK_926 | ATGCAGTTATTGCACTGGAANNKCTGAATAGCGGTTTCAAAAA | 4948 |
| LbCas12a_NNK_927 | CAGTTATTGCACTGGAAGATNNKAATAGCGGTTTCAAAAATAG | 4949 |
| LbCas12a_NNK_928 | TTATTGCACTGGAAGATCTGNNKAGCGGTTTCAAAAATAGCCG | 4950 |
| LbCas12a_NNK_929 | TTGCACTGGAAGATCTGAATNNKGGTTTCAAAAATAGCCGTGT | 4951 |
| LbCas12a_NNK_930 | CACTGGAAGATCTGAATAGCNNKTTCAAAAATAGCCGTGTGAA | 4952 |
| LbCas12a_NNK_931 | TGGAAGATCTGAATAGCGGTNNKAAAAATAGCCGTGTGAAAGT | 4953 |
| LbCas12a_NNK_932 | AAGATCTGAATAGCGGTTTCNNKAATAGCCGTGTGAAAGTCGA | 4954 |
| LbCas12a_NNK_933 | ATCTGAATAGCGGTTTCAAANNKAGCCGTGTGAAAGTCGAAAA | 4955 |
| LbCas12a_NNK_934 | TGAATAGCGGTTTCAAAAATNNKCGTGTGAAAGTCGAAAAACA | 4956 |
| LbCas12a_NNK_935 | ATAGCGGTTTCAAAAATAGCNNKGTGAAAGTCGAAAAACAGGT | 4957 |
| LbCas12a_NNK_936 | GCGGTTTCAAAAATAGCCGTNNKAAAGTCGAAAAACAGGTGTA | 4958 |
| LbCas12a_NNK_937 | GTTTCAAAAATAGCCGTGTGNNKGTCGAAAAACAGGTGTATCA | 4959 |
| LbCas12a_NNK_938 | TCAAAAATAGCCGTGTGAAANNKGAAAAACAGGTGTATCAGAA | 4960 |
| LbCas12a_NNK_939 | AAAATAGCCGTGTGAAAGTCNNKAAACAGGTGTATCAGAAATT | 4961 |
| LbCas12a_NNK_940 | ATAGCCGTGTGAAAGTCGAANNKCAGGTGTATCAGAAATTCGA | 4962 |
| LbCas12a_NNK_941 | GCCGTGTGAAAGTCGAAAAANNKGTGTATCAGAAATTCGAGAA | 4963 |
| LbCas12a_NNK_942 | GTGTGAAAGTCGAAAAACAGNNKTATCAGAAATTCGAGAAAAT | 4964 |
| LbCas12a_NNK_943 | TGAAAGTCGAAAAACAGGTGNNKCAGAAATTCGAGAAAATGCT | 4965 |
| LbCas12a_NNK_944 | AAGTCGAAAAACAGGTGTATNNKAAATTCGAGAAAATGCTGAT | 4966 |
| LbCas12a_NNK_945 | TCGAAAAACAGGTGTATCAGNNKTTCGAGAAAATGCTGATCGA | 4967 |
| LbCas12a_NNK_946 | AAAAACAGGTGTATCAGAAANNKGAGAAAATGCTGATCGACAA | 4968 |
| LbCas12a_NNK_947 | AACAGGTGTATCAGAAATTCNNKAAAATGCTGATCGACAAACT | 4969 |
| LbCas12a_NNK_948 | AGGTGTATCAGAAATTCGAGNNKATGCTGATCGACAAACTGAA | 4970 |
| LbCas12a_NNK_949 | TGTATCAGAAATTCGAGAAANNKCTGATCGACAAACTGAACTA | 4971 |
| LbCas12a_NNK_950 | ATCAGAAATTCGAGAAAATGNNKATCGACAAACTGAACTACAT | 4972 |
| LbCas12a_NNK_951 | AGAAATTCGAGAAAATGCTGNNKGACAAACTGAACTACATGGT | 4973 |
| LbCas12a_NNK_952 | AATTCGAGAAAATGCTGATCNNKAAACTGAACTACATGGTCGA | 4974 |

TABLE 3-continued

Primers for creating LbCas12a Saturation Mutagenesis Library

| Name | Sequence (5'→3') | SEQ ID NO |
|---|---|---|
| LbCas12a_NNK_953 | TCGAGAAAATGCTGATCGACNNKCTGAACTACATGGTCGACAA | 4975 |
| LbCas12a_NNK_954 | AGAAAATGCTGATCGACAAANNKAACTACATGGTCGACAAAAA | 4976 |
| LbCas12a_NNK_955 | AAATGCTGATCGACAAACTGNNKTACATGGTCGACAAAAAAAG | 4977 |
| LbCas12a_NNK_956 | TGCTGATCGACAAACTGAACNNKATGGTCGACAAAAAAAGCAA | 4978 |
| LbCas12a_NNK_957 | TGATCGACAAACTGAACTACNNKGTCGACAAAAAAAGCAATCC | 4979 |
| LbCas12a_NNK_958 | TCGACAAACTGAACTACATGNNKGACAAAAAAAGCAATCCGTG | 4980 |
| LbCas12a_NNK_959 | ACAAACTGAACTACATGGTCNNKAAAAAAAGCAATCCGTGTGC | 4981 |
| LbCas12a_NNK_960 | AACTGAACTACATGGTCGACNNKAAAAGCAATCCGTGTGCAAC | 4982 |
| LbCas12a_NNK_961 | TGAACTACATGGTCGACAAANNKAGCAATCCGTGTGCAACCGG | 4983 |
| LbCas12a_NNK_962 | ACTACATGGTCGACAAAAAANNKAATCCGTGTGCAACCGGTGG | 4984 |
| LbCas12a_NNK_963 | ACATGGTCGACAAAAAAGCNNKCCGTGTGCAACCGGTGGTGC | 4985 |
| LbCas12a_NNK_964 | TGGTCGACAAAAAAGCAATNNKTGTGCAACCGGTGGTGCACT | 4986 |
| LbCas12a_NNK_965 | TCGACAAAAAAGCAATCCGNNKGCAACCGGTGGTGCACTGAA | 4987 |
| LbCas12a_NNK_966 | ACAAAAAAGCAATCCGTGTNNKACCGGTGGTGCACTGAAAGG | 4988 |
| LbCas12a_NNK_967 | AAAAAAGCAATCCGTGTGCANNKGGTGGTGCACTGAAAGGTTA | 4989 |
| LbCas12a_NNK_968 | AAAGCAATCCGTGTGCAACCNNKGGTGCACTGAAAGGTTATCA | 4990 |
| LbCas12a_NNK_969 | GCAATCCGTGTGCAACCGGTNNKGCACTGAAAGGTTATCAGAT | 4991 |
| LbCas12a_NNK_970 | ATCCGTGTGCAACCGGTGGTNNKCTGAAAGGTTATCAGATTAC | 4992 |
| LbCas12a_NNK_971 | CGTGTGCAACCGGTGGTGCANNKAAAGGTTATCAGATTACCAA | 4993 |
| LbCas12a_NNK_972 | GTGCAACCGGTGGTGCACTGNNKGGTTATCAGATTACCAACAA | 4994 |
| LbCas12a_NNK_973 | CAACCGGTGGTGCACTGAAANNKTATCAGATTACCAACAAATT | 4995 |
| LbCas12a_NNK_974 | CCGGTGGTGCACTGAAAGGTNNKCAGATTACCAACAAATTTGA | 4996 |
| LbCas12a_NNK_975 | GTGGTGCACTGAAAGGTTATNNKATTACCAACAAATTTGAAAG | 4997 |
| LbCas12a_NNK_976 | GTGCACTGAAAGGTTATCAGNNKACCAACAAATTTGAAAGCTT | 4998 |
| LbCas12a_NNK_977 | CACTGAAAGGTTATCAGATTNNKAACAAATTTGAAAGCTTTAA | 4999 |
| LbCas12a_NNK_978 | TGAAAGGTTATCAGATTACCNNKAAATTTGAAAGCTTTAAAAG | 5000 |
| LbCas12a_NNK_979 | AAGGTTATCAGATTACCAACNNKTTTGAAAGCTTTAAAAGCAT | 5001 |
| LbCas12a_NNK_980 | GTTATCAGATTACCAACAAANNKGAAAGCTTTAAAAGCATGAG | 5002 |
| LbCas12a_NNK_981 | ATCAGATTACCAACAAATTTNNKAGCTTTAAAAGCATGAGCAC | 5003 |
| LbCas12a_NNK_982 | AGATTACCAACAAATTTGAANNKTTTAAAAGCATGAGCACCCA | 5004 |
| LbCas12a_NNK_983 | TTACCAACAAATTTGAAAGCNNKAAAAGCATGAGCACCCAGAA | 5005 |
| LbCas12a_NNK_984 | CCAACAAATTTGAAAGCTTTNNKAGCATGAGCACCCAGAACGG | 5006 |
| LbCas12a_NNK_985 | ACAAATTTGAAAGCTTTAAANNKATGAGCACCCAGAACGGCTT | 5007 |
| LbCas12a_NNK_986 | AATTTGAAAGCTTTAAAAGCNNKAGCACCCAGAACGGCTTTAT | 5008 |
| LbCas12a_NNK_987 | TTGAAAGCTTTAAAAGCATGNNKACCCAGAACGGCTTTATCTT | 5009 |
| LbCas12a_NNK_988 | AAAGCTTTAAAAGCATGAGCNNKCAGAACGGCTTTATCTTCTA | 5010 |
| LbCas12a_NNK_989 | GCTTTAAAAGCATGAGCACCNNKAACGGCTTTATCTTCTATAT | 5011 |

TABLE 3-continued

Primers for creating LbCas12a Saturation Mutagenesis Library

| Name | Sequence (5'→3') | SEQ ID NO |
|---|---|---|
| LbCas12a_NNK_990 | TTAAAAGCATGAGCACCCAGNNKGGCTTTATCTTCTATATTCC | 5012 |
| LbCas12a_NNK_991 | AAAGCATGAGCACCCAGAACNNKTTTATCTTCTATATTCCGGC | 5013 |
| LbCas12a_NNK_992 | GCATGAGCACCCAGAACGGCNNKATCTTCTATATTCCGGCATG | 5014 |
| LbCas12a_NNK_993 | TGAGCACCCAGAACGGCTTTNNKTTCTATATTCCGGCATGGCT | 5015 |
| LbCas12a_NNK_994 | GCACCCAGAACGGCTTTATCNNKTATATTCCGGCATGGCTGAC | 5016 |
| LbCas12a_NNK_995 | CCCAGAACGGCTTTATCTTCNNKATTCCGGCATGGCTGACCAG | 5017 |
| LbCas12a_NNK_996 | AGAACGGCTTTATCTTCTATNNKCCGGCATGGCTGACCAGCAA | 5018 |
| LbCas12a_NNK_997 | ACGGCTTTATCTTCTATATTNNKGCATGGCTGACCAGCAAAAT | 5019 |
| LbCas12a_NNK_998 | GCTTTATCTTCTATATTCCGNNKTGGCTGACCAGCAAAATTGA | 5020 |
| LbCas12a_NNK_999 | TTATCTTCTATATTCCGGCANNKCTGACCAGCAAAATTGATCC | 5021 |
| LbCas12a_NNK_1000 | TCTTCTATATTCCGGCATGGNNKACCAGCAAAATTGATCCGAG | 5022 |
| LbCas12a_NNK_1001 | TCTATATTCCGGCATGGCTGNNKAGCAAAATTGATCCGAGCAC | 5023 |
| LbCas12a_NNK_1002 | ATATTCCGGCATGGCTGACCNNKAAAATTGATCCGAGCACCGG | 5024 |
| LbCas12a_NNK_1003 | TTCCGGCATGGCTGACCAGCNNKATTGATCCGAGCACCGGTTT | 5025 |
| LbCas12a_NNK_1004 | CGGCATGGCTGACCAGCAAANNKGATCCGAGCACCGGTTTTGT | 5026 |
| LbCas12a_NNK_1005 | CATGGCTGACCAGCAAAATTNNKCCGAGCACCGGTTTTGTGAA | 5027 |
| LbCas12a_NNK_1006 | GGCTGACCAGCAAAATTGATNNKAGCACCGGTTTTGTGAACCT | 5028 |
| LbCas12a_NNK_1007 | TGACCAGCAAAATTGATCCGNNKACCGGTTTTGTGAACCTGCT | 5029 |
| LbCas12a_NNK_1008 | CCAGCAAAATTGATCCGAGCNNKGGTTTTGTGAACCTGCTGAA | 5030 |
| LbCas12a_NNK_1009 | GCAAAATTGATCCGAGCACCNNKTTTGTGAACCTGCTGAAAAC | 5031 |
| LbCas12a_NNK_1010 | AAATTGATCCGAGCACCGGTNNKGTGAACCTGCTGAAAACAAA | 5032 |
| LbCas12a_NNK_1011 | TTGATCCGAGCACCGGTTTTNNKAACCTGCTGAAAACAAAATA | 5033 |
| LbCas12a_NNK_1012 | ATCCGAGCACCGGTTTTGTGNNKCTGCTGAAAACAAAATATAC | 5034 |
| LbCas12a_NNK_1013 | CGAGCACCGGTTTTGTGAACNNKCTGAAAACAAAATATACCTC | 5035 |
| LbCas12a_NNK_1014 | GCACCGGTTTTGTGAACCTGNNKAAAACAAAATATACCTCCAT | 5036 |
| LbCas12a_NNK_1015 | CCGGTTTTGTGAACCTGCTGNNKACAAAATATACCTCCATTGC | 5037 |
| LbCas12a_NNK_1016 | GTTTTGTGAACCTGCTGAAANNKAAATATACCTCCATTGCCGA | 5038 |
| LbCas12a_NNK_1017 | TTGTGAACCTGCTGAAAACANNKTATACCTCCATTGCCGACAG | 5039 |
| LbCas12a_NNK_1018 | TGAACCTGCTGAAAACAAAANNKACCTCCATTGCCGACAGCAA | 5040 |
| LbCas12a_NNK_1019 | ACCTGCTGAAAACAAAATATNNKTCCATTGCCGACAGCAAGAA | 5041 |
| LbCas12a_NNK_1020 | TGCTGAAAACAAAATATACCNNKATTGCCGACAGCAAGAAGTT | 5042 |
| LbCas12a_NNK_1021 | TGAAAACAAAATATACCTCCNNKGCCGACAGCAAGAAGTTTAT | 5043 |
| LbCas12a_NNK_1022 | AAACAAAATATACCTCCATTNNKGACAGCAAGAAGTTTATTAG | 5044 |
| LbCas12a_NNK_1023 | CAAAATATACCTCCATTGCCNNKAGCAAGAAGTTTATTAGCAG | 5045 |
| LbCas12a_NNK_1024 | AATATACCTCCATTGCCGACNNKAAGAAGTTTATTAGCAGCTT | 5046 |
| LbCas12a_NNK_1025 | ATACCTCCATTGCCGACAGCNNKAAGTTTATTAGCAGCTTTGA | 5047 |
| LbCas12a_NNK_1026 | CCTCCATTGCCGACAGCAAGNNKTTTATTAGCAGCTTTGATCG | 5048 |
| LbCas12a_NNK_1027 | CCATTGCCGACAGCAAGAAGNNKATTAGCAGCTTTGATCGCAT | 5049 |

TABLE 3-continued

Primers for creating LbCas12a Saturation Mutagenesis Library

| Name | Sequence (5'→3') | SEQ ID NO |
|---|---|---|
| LbCas12a_NNK_1028 | TTGCCGACAGCAAGAAGTTTNNKAGCAGCTTTGATCGCATTAT | 5050 |
| LbCas12a_NNK_1029 | CCGACAGCAAGAAGTTTATTNNKAGCTTTGATCGCATTATGTA | 5051 |
| LbCas12a_NNK_1030 | ACAGCAAGAAGTTTATTAGCNNKTTTGATCGCATTATGTATGT | 5052 |
| LbCas12a_NNK_1031 | GCAAGAAGTTTATTAGCAGCNNKGATCGCATTATGTATGTTCC | 5053 |
| LbCas12a_NNK_1032 | AGAAGTTTATTAGCAGCTTTNNKCGCATTATGTATGTTCCGGA | 5054 |
| LbCas12a_NNK_1033 | AGTTTATTAGCAGCTTTGATNNKATTATGTATGTTCCGGAAGA | 5055 |
| LbCas12a_NNK_1034 | TTATTAGCAGCTTTGATCGCNNKATGTATGTTCCGGAAGAGGA | 5056 |
| LbCas12a_NNK_1035 | TTAGCAGCTTTGATCGCATTNNKTATGTTCCGGAAGAGGACCT | 5057 |
| LbCas12a_NNK_1036 | GCAGCTTTGATCGCATTATGNNKGTTCCGGAAGAGGACCTGTT | 5058 |
| LbCas12a_NNK_1037 | GCTTTGATCGCATTATGTATNNKCCGGAAGAGGACCTGTTTGA | 5059 |
| LbCas12a_NNK_1038 | TTGATCGCATTATGTATGTTNNKGAAGAGGACCTGTTTGAATT | 5060 |
| LbCas12a_NNK_1039 | ATCGCATTATGTATGTTCCGNNKGAGGACCTGTTTGAATTCGC | 5061 |
| LbCas12a_NNK_1040 | GCATTATGTATGTTCCGGAANNKGACCTGTTTGAATTCGCACT | 5062 |
| LbCas12a_NNK_1041 | TTATGTATGTTCCGGAAGAGNNKCTGTTTGAATTCGCACTGGA | 5063 |
| LbCas12a_NNK_1042 | TGTATGTTCCGGAAGAGGACNNKTTTGAATTCGCACTGGATTA | 5064 |
| LbCas12a_NNK_1043 | ATGTTCCGGAAGAGGACCTGNNKGAATTCGCACTGGATTACAA | 5065 |
| LbCas12a_NNK_1044 | TTCCGGAAGAGGACCTGTTTNNKTTCGCACTGGATTACAAAAA | 5066 |
| LbCas12a_NNK_1045 | CGGAAGAGGACCTGTTTGAANNKGCACTGGATTACAAAAATTT | 5067 |
| LbCas12a_NNK_1046 | AAGAGGACCTGTTTGAATTCNNKCTGGATTACAAAAATTTCAG | 5068 |
| LbCas12a_NNK_1047 | AGGACCTGTTTGAATTCGCANNKGATTACAAAAATTTCAGCCG | 5069 |
| LbCas12a_NNK_1048 | ACCTGTTTGAATTCGCACTGNNKTACAAAAATTTCAGCCGTAC | 5070 |
| LbCas12a_NNK_1049 | TGTTTGAATTCGCACTGGATNNKAAAAATTTCAGCCGTACCGA | 5071 |
| LbCas12a_NNK_1050 | TTGAATTCGCACTGGATTACNNKAATTTCAGCCGTACCGATGC | 5072 |
| LbCas12a_NNK_1051 | AATTCGCACTGGATTACAAANNKTTCAGCCGTACCGATGCCGA | 5073 |
| LbCas12a_NNK_1052 | TCGCACTGGATTACAAAAATNNKAGCCGTACCGATGCCGACTA | 5074 |
| LbCas12a_NNK_1053 | CACTGGATTACAAAAATTTCNNKCGTACCGATGCCGACTACAT | 5075 |
| LbCas12a_NNK_1054 | TGGATTACAAAAATTTCAGCNNKACCGATGCCGACTACATCAA | 5076 |
| LbCas12a_NNK_1055 | ATTACAAAAATTTCAGCCGTNNKGATGCCGACTACATCAAAAA | 5077 |
| LbCas12a_NNK_1056 | ACAAAAATTTCAGCCGTACCNNKGCCGACTACATCAAAAAATG | 5078 |
| LbCas12a_NNK_1057 | AAATTTCAGCCGTACCGATNNKGACTACATCAAAAAATGGAA | 5079 |
| LbCas12a_NNK_1058 | ATTTCAGCCGTACCGATGCCNNKTACATCAAAAAATGGAAACT | 5080 |
| LbCas12a_NNK_1059 | TCAGCCGTACCGATGCCGACNNKATCAAAAAATGGAAACTGTA | 5081 |
| LbCas12a_NNK_1060 | GCCGTACCGATGCCGACTACNNKAAAAAATGGAAACTGTACAG | 5082 |
| LbCas12a_NNK_1061 | GTACCGATGCCGACTACATCNNKAAATGGAAACTGTACAGCTA | 5083 |
| LbCas12a_NNK_1062 | CCGATGCCGACTACATCAAANNKTGGAAACTGTACAGCTATGG | 5084 |
| LbCas12a_NNK_1063 | ATGCCGACTACATCAAAAAANNKAAACTGTACAGCTATGGTAA | 5085 |
| LbCas12a_NNK_1064 | CCGACTACATCAAAAAATGGNNKCTGTACAGCTATGGTAACCG | 5086 |

TABLE 3-continued

Primers for creating LbCas12a Saturation Mutagenesis Library

| Name | Sequence (5'→3') | SEQ ID NO |
|---|---|---|
| LbCas12a_NNK_1065 | ACTACATCAAAAAATGGAAANNKTACAGCTATGGTAACCGCAT | 5087 |
| LbCas12a_NNK_1066 | ACATCAAAAAATGGAAACTGNNKAGCTATGGTAACCGCATTCG | 5088 |
| LbCas12a_NNK_1067 | TCAAAAAATGGAAACTGTACNNKTATGGTAACCGCATTCGCAT | 5089 |
| LbCas12a_NNK_1068 | AAAAATGGAAACTGTACAGCNNKGGTAACCGCATTCGCATTTT | 5090 |
| LbCas12a_NNK_1069 | AATGGAAACTGTACAGCTATNNKAACCGCATTCGCATTTTTCG | 5091 |
| LbCas12a_NNK_1070 | GGAAACTGTACAGCTATGGTNNKCGCATTCGCATTTTTCGCAA | 5092 |
| LbCas12a_NNK_1071 | AACTGTACAGCTATGGTAACNNKATTCGCATTTTTCGCAACCC | 5093 |
| LbCas12a_NNK_1072 | TGTACAGCTATGGTAACCGCNNKCGCATTTTTCGCAACCCGAA | 5094 |
| LbCas12a_NNK_1073 | ACAGCTATGGTAACCGCATTNNKATTTTTCGCAACCCGAAGAA | 5095 |
| LbCas12a_NNK_1074 | GCTATGGTAACCGCATTCGCNNKTTTCGCAACCCGAAGAAAAA | 5096 |
| LbCas12a_NNK_1075 | ATGGTAACCGCATTCGCATTNNKCGCAACCCGAAGAAAAACAA | 5097 |
| LbCas12a_NNK_1076 | GTAACCGCATTCGCATTTTTNNKAACCCGAAGAAAAACAATGT | 5098 |
| LbCas12a_NNK_1077 | ACCGCATTCGCATTTTTCGCNNKCCGAAGAAAAACAATGTGTT | 5099 |
| LbCas12a_NNK_1078 | GCATTCGCATTTTTCGCAACNNKAAGAAAAACAATGTGTTCGA | 5100 |
| LbCas12a_NNK_1079 | TTCGCATTTTTCGCAACCCGNNKAAAAACAATGTGTTCGATTG | 5101 |
| LbCas12a_NNK_1080 | GCATTTTTCGCAACCCGAAGNNKAACAATGTGTTCGATTGGGA | 5102 |
| LbCas12a_NNK_1081 | TTTTTCGCAACCCGAAGAAANNKAATGTGTTCGATTGGGAAGA | 5103 |
| LbCas12a_NNK_1082 | TTCGCAACCCGAAGAAAAACNNKGTGTTCGATTGGGAAGAAGT | 5104 |
| LbCas12a_NNK_1083 | GCAACCCGAAGAAAAACAATNNKTTCGATTGGGAAGAAGTTTG | 5105 |
| LbCas12a_NNK_1084 | ACCCGAAGAAAAACAATGTGNNKGATTGGGAAGAAGTTTGTCT | 5106 |
| LbCas12a_NNK_1085 | CGAAGAAAAACAATGTGTTCNNKTGGGAAGAAGTTTGTCTGAC | 5107 |
| LbCas12a_NNK_1086 | AGAAAAACAATGTGTTCGATNNKGAAGAAGTTTGTCTGACCAG | 5108 |
| LbCas12a_NNK_1087 | AAAACAATGTGTTCGATTGGNNKGAAGTTTGTCTGACCAGCGC | 5109 |
| LbCas12a_NNK_1088 | ACAATGTGTTCGATTGGGAANNKGTTTGTCTGACCAGCGCATA | 5110 |
| LbCas12a_NNK_1089 | ATGTGTTCGATTGGGAAGAANNKTGTCTGACCAGCGCATATAA | 5111 |
| LbCas12a_NNK_1090 | TGTTCGATTGGGAAGAAGTTNNKCTGACCAGCGCATATAAAGA | 5112 |
| LbCas12a_NNK_1091 | TCGATTGGGAAGAAGTTTGTNNKACCAGCGCATATAAAGAACT | 5113 |
| LbCas12a_NNK_1092 | ATTGGGAAGAAGTTTGTCTGNNKAGCGCATATAAAGAACTTTT | 5114 |
| LbCas12a_NNK_1093 | GGGAAGAAGTTTGTCTGACCNNKGCATATAAAGAACTTTTCAA | 5115 |
| LbCas12a_NNK_1094 | AAGAAGTTTGTCTGACCAGCNNKTATAAAGAACTTTTCAACAA | 5116 |
| LbCas12a_NNK_1095 | AAGTTTGTCTGACCAGCGCANNKAAAGAACTTTTCAACAAATA | 5117 |
| LbCas12a_NNK_1096 | TTTGTCTGACCAGCGCATATNNKGAACTTTTCAACAAATACGG | 5118 |
| LbCas12a_NNK_1097 | GTCTGACCAGCGCATATAAANNKCTTTTCAACAAATACGGCAT | 5119 |
| LbCas12a_NNK_1098 | TGACCAGCGCATATAAAGAANNKTTCAACAAATACGGCATCAA | 5120 |
| LbCas12a_NNK_1099 | CCAGCGCATATAAAGAACTTNNKAACAAATACGGCATCAACTA | 5121 |
| LbCas12a_NNK_1100 | GCGCATATAAAGAACTTTTCNNKAAATACGGCATCAACTATCA | 5122 |
| LbCas12a_NNK_1101 | CATATAAAGAACTTTTCAACNNKTACGGCATCAACTATCAGCA | 5123 |
| LbCas12a_NNK_1102 | ATAAAGAACTTTTCAACAAANNKGGCATCAACTATCAGCAGGG | 5124 |

TABLE 3-continued

Primers for creating LbCas12a Saturation Mutagenesis Library

| Name | Sequence (5'→3') | SEQ ID NO |
|---|---|---|
| LbCas12a_NNK_1103 | AAGAACTTTTCAACAAATACNNKATCAACTATCAGCAGGGTGA | 5125 |
| LbCas12a_NNK_1104 | AACTTTTCAACAAATACGGCNNKAACTATCAGCAGGGTGATAT | 5126 |
| LbCas12a_NNK_1105 | TTTTCAACAAATACGGCATCNNKTATCAGCAGGGTGATATTCG | 5127 |
| LbCas12a_NNK_1106 | TCAACAAATACGGCATCAACNNKCAGCAGGGTGATATTCGTGC | 5128 |
| LbCas12a_NNK_1107 | ACAAATACGGCATCAACTATNNKCAGGGTGATATTCGTGCACT | 5129 |
| LbCas12a_NNK_1108 | AATACGGCATCAACTATCAGNNKGGTGATATTCGTGCACTGCT | 5130 |
| LbCas12a_NNK_1109 | ACGGCATCAACTATCAGCAGNNKGATATTCGTGCACTGCTGTG | 5131 |
| LbCas12a_NNK_1110 | GCATCAACTATCAGCAGGGTNNKATTCGTGCACTGCTGTGTGA | 5132 |
| LbCas12a_NNK_1111 | TCAACTATCAGCAGGGTGATNNKCGTGCACTGCTGTGTGAACA | 5133 |
| LbCas12a_NNK_1112 | ACTATCAGCAGGGTGATATTNNKGCACTGCTGTGTGAACAGAG | 5134 |
| LbCas12a_NNK_1113 | ATCAGCAGGGTGATATTCGTNNKCTGCTGTGTGAACAGAGCGA | 5135 |
| LbCas12a_NNK_1114 | AGCAGGGTGATATTCGTGCANNKCTGTGTGAACAGAGCGATAA | 5136 |
| LbCas12a_NNK_1115 | AGGGTGATATTCGTGCACTGNNKTGTGAACAGAGCGATAAAGC | 5137 |
| LbCas12a_NNK_1116 | GTGATATTCGTGCACTGCTGNNKGAACAGAGCGATAAAGCGTT | 5138 |
| LbCas12a_NNK_1117 | ATATTCGTGCACTGCTGTGTNNKCAGAGCGATAAAGCGTTTTA | 5139 |
| LbCas12a_NNK_1118 | TTCGTGCACTGCTGTGTGAANNKAGCGATAAAGCGTTTTATAG | 5140 |
| LbCas12a_NNK_1119 | GTGCACTGCTGTGTGAACAGNNKGATAAAGCGTTTTATAGCAG | 5141 |
| LbCas12a_NNK_1120 | CACTGCTGTGTGAACAGAGCNNKAAAGCGTTTTATAGCAGTTT | 5142 |
| LbCas12a_NNK_1121 | TGCTGTGTGAACAGAGCGATNNKGCGTTTTATAGCAGTTTTAT | 5143 |
| LbCas12a_NNK_1122 | TGTGTGAACAGAGCGATAAANNKTTTTATAGCAGTTTTATGGC | 5144 |
| LbCas12a_NNK_1123 | GTGAACAGAGCGATAAAGCGNNKTATAGCAGTTTTATGGCACT | 5145 |
| LbCas12a_NNK_1124 | AACAGAGCGATAAAGCGTTTNNKAGCAGTTTTATGGCACTGAT | 5146 |
| LbCas12a_NNK_1125 | AGAGCGATAAAGCGTTTTATNNKAGTTTTATGGCACTGATGAG | 5147 |
| LbCas12a_NNK_1126 | GCGATAAAGCGTTTTATAGCNNKTTTATGGCACTGATGAGCCT | 5148 |
| LbCas12a_NNK_1127 | ATAAAGCGTTTTATAGCAGTNNKATGGCACTGATGAGCCTGAT | 5149 |
| LbCas12a_NNK_1128 | AAGCGTTTTATAGCAGTTTTNNKGCACTGATGAGCCTGATGCT | 5150 |
| LbCas12a_NNK_1129 | CGTTTTATAGCAGTTTTATGNNKCTGATGAGCCTGATGCTGCA | 5151 |
| LbCas12a_NNK_1130 | TTTATAGCAGTTTTATGGCANNKATGAGCCTGATGCTGCAGAT | 5152 |
| LbCas12a_NNK_1131 | ATAGCAGTTTTATGGCACTGNNKAGCCTGATGCTGCAGATGCG | 5153 |
| LbCas12a_NNK_1132 | GCAGTTTTATGGCACTGATGNNKCTGATGCTGCAGATGCGTAA | 5154 |
| LbCas12a_NNK_1133 | GTTTTATGGCACTGATGAGCNNKATGCTGCAGATGCGTAATAG | 5155 |
| LbCas12a_NNK_1134 | TTATGGCACTGATGAGCCTGNNKCTGCAGATGCGTAATAGCAT | 5156 |
| LbCas12a_NNK_1135 | TGGCACTGATGAGCCTGATGNNKCAGATGCGTAATAGCATTAC | 5157 |
| LbCas12a_NNK_1136 | CACTGATGAGCCTGATGCTGNNKATGCGTAATAGCATTACCGG | 5158 |
| LbCas12a_NNK_1137 | TGATGAGCCTGATGCTGCAGNNKCGTAATAGCATTACCGGTCG | 5159 |
| LbCas12a_NNK_1138 | TGAGCCTGATGCTGCAGATGNNKAATAGCATTACCGGTCGCAC | 5160 |
| LbCas12a_NNK_1139 | GCCTGATGCTGCAGATGCGTNNKAGCATTACCGGTCGCACCGA | 5161 |

TABLE 3-continued

Primers for creating LbCas12a Saturation Mutagenesis Library

| Name | Sequence (5'→3') | SEQ ID NO |
|---|---|---|
| LbCas12a_NNK_1140 | TGATGCTGCAGATGCGTAATNNKATTACCGGTCGCACCGATGT | 5162 |
| LbCas12a_NNK_1141 | TGCTGCAGATGCGTAATAGCNNKACCGGTCGCACCGATGTGGA | 5163 |
| LbCas12a_NNK_1142 | TGCAGATGCGTAATAGCATTNNKGGTCGCACCGATGTGGATTT | 5164 |
| LbCas12a_NNK_1143 | AGATGCGTAATAGCATTACCNNKCGCACCGATGTGGATTTTCT | 5165 |
| LbCas12a_NNK_1144 | TGCGTAATAGCATTACCGGTNNKACCGATGTGGATTTTCTGAT | 5166 |
| LbCas12a_NNK_1145 | GTAATAGCATTACCGGTCGCNNKGATGTGGATTTTCTGATTAG | 5167 |
| LbCas12a_NNK_1146 | ATAGCATTACCGGTCGCACCNNKGTGGATTTTCTGATTAGTCC | 5168 |
| LbCas12a_NNK_1147 | GCATTACCGGTCGCACCGATNNKGATTTTCTGATTAGTCCGGT | 5169 |
| LbCas12a_NNK_1148 | TTACCGGTCGCACCGATGTGNNKTTTCTGATTAGTCCGGTGAA | 5170 |
| LbCas12a_NNK_1149 | CCGGTCGCACCGATGTGGATNNKCTGATTAGTCCGGTGAAAAA | 5171 |
| LbCas12a_NNK_1150 | GTCGCACCGATGTGGATTTTNNKATTAGTCCGGTGAAAAATTC | 5172 |
| LbCas12a_NNK_1151 | GCACCGATGTGGATTTTCTGNNKAGTCCGGTGAAAAATTCCGA | 5173 |
| LbCas12a_NNK_1152 | CCGATGTGGATTTTCTGATTNNKCCGGTGAAAAATTCCGATGG | 5174 |
| LbCas12a_NNK_1153 | ATGTGGATTTTCTGATTAGTNNKGTGAAAAATTCCGATGGCAT | 5175 |
| LbCas12a_NNK_1154 | TGGATTTTCTGATTAGTCCGNNKAAAAATTCCGATGGCATCTT | 5176 |
| LbCas12a_NNK_1155 | ATTTTCTGATTAGTCCGGTGNNKAATTCCGATGGCATCTTTTA | 5177 |
| LbCas12a_NNK_1156 | TTCTGATTAGTCCGGTGAAANNKTCCGATGGCATCTTTTATGA | 5178 |
| LbCas12a_NNK_1157 | TGATTAGTCCGGTGAAAAATNNKGATGGCATCTTTTATGATAG | 5179 |
| LbCas12a_NNK_1158 | TTAGTCCGGTGAAAAATTCCNNKGGCATCTTTTATGATAGCCG | 5180 |
| LbCas12a_NNK_1159 | GTCCGGTGAAAAATTCCGATNNKATCTTTTATGATAGCCGCAA | 5181 |
| LbCas12a_NNK_1160 | CGGTGAAAAATTCCGATGGCNNKTTTTATGATAGCCGCAATTA | 5182 |
| LbCas12a_NNK_1161 | TGAAAAATTCCGATGGCATCNNKTATGATAGCCGCAATTACGA | 5183 |
| LbCas12a_NNK_1162 | AAAATTCCGATGGCATCTTTNNKGATAGCCGCAATTACGAAGC | 5184 |
| LbCas12a_NNK_1163 | ATTCCGATGGCATCTTTTATNNKAGCCGCAATTACGAAGCACA | 5185 |
| LbCas12a_NNK_1164 | CCGATGGCATCTTTTATGATNNKCGCAATTACGAAGCACAAGA | 5186 |
| LbCas12a_NNK_1165 | ATGGCATCTTTTATGATAGCNNKAATTACGAAGCACAAGAAAA | 5187 |
| LbCas12a_NNK_1166 | GCATCTTTTATGATAGCCGCNNKTACGAAGCACAAGAAATGC | 5188 |
| LbCas12a_NNK_1167 | TCTTTTATGATAGCCGCAATNNKGAAGCACAAGAAATGCAAT | 5189 |
| LbCas12a_NNK_1168 | TTTATGATAGCCGCAATTACNNKGCACAAGAAATGCAATTCT | 5190 |
| LbCas12a_NNK_1169 | ATGATAGCCGCAATTACGAANNKCAAGAAATGCAATTCTGCC | 5191 |
| LbCas12a_NNK_1170 | ATAGCCGCAATTACGAAGCANNKGAAATGCAATTCTGCCGAA | 5192 |
| LbCas12a_NNK_1171 | GCCGCAATTACGAAGCACAANNKATGCAATTCTGCCGAAAAA | 5193 |
| LbCas12a_NNK_1172 | GCAATTACGAAGCACAAGAANNKCAATTCTGCCGAAAAACGC | 5194 |
| LbCas12a_NNK_1173 | ATTACGAAGCACAAGAAATNNKATTCTGCCGAAAAACGCAGA | 5195 |
| LbCas12a_NNK_1174 | ACGAAGCACAAGAAATGCANNKCTGCCGAAAAACGCAGATGC | 5196 |
| LbCas12a_NNK_1175 | AAGCACAAGAAATGCAATTNNKCCGAAAAACGCAGATGCAAA | 5197 |
| LbCas12a_NNK_1176 | CACAAGAAATGCAATTCTGNNKAAAAACGCAGATGCAAATGG | 5198 |
| LbCas12a_NNK_1177 | AAGAAAATGCAATTCTGCCGNNKAACGCAGATGCAAATGGTGC | 5199 |

TABLE 3-continued

Primers for creating LbCas12a Saturation Mutagenesis Library

| Name | Sequence (5'→3') | SEQ ID NO |
|---|---|---|
| LbCas12a_NNK_1178 | AAAATGCAATTCTGCCGAAANNKGCAGATGCAAATGGTGCATA | 5200 |
| LbCas12a_NNK_1179 | ATGCAATTCTGCCGAAAAACNNKGATGCAAATGGTGCATATAA | 5201 |
| LbCas12a_NNK_1180 | CAATTCTGCCGAAAAACGCANNKGCAAATGGTGCATATAACAT | 5202 |
| LbCas12a_NNK_1181 | TTCTGCCGAAAAACGCAGATNNKAATGGTGCATATAACATTGC | 5203 |
| LbCas12a_NNK_1182 | TGCCGAAAAACGCAGATGCANNKGGTGCATATAACATTGCACG | 5204 |
| LbCas12a_NNK_1183 | CGAAAAACGCAGATGCAAATNNKGCATATAACATTGCACGTAA | 5205 |
| LbCas12a_NNK_1184 | AAAACGCAGATGCAAATGGTNNKTATAACATTGCACGTAAAGT | 5206 |
| LbCas12a_NNK_1185 | ACGCAGATGCAAATGGTGCANNKAACATTGCACGTAAAGTTCT | 5207 |
| LbCas12a_NNK_1186 | CAGATGCAAATGGTGCATATNNKATTGCACGTAAAGTTCTGTG | 5208 |
| LbCas12a_NNK_1187 | ATGCAAATGGTGCATATAACNNKGCACGTAAAGTTCTGTGGGC | 5209 |
| LbCas12a_NNK_1188 | CAAATGGTGCATATAACATTNNKCGTAAAGTTCTGTGGGCAAT | 5210 |
| LbCas12a_NNK_1189 | ATGGTGCATATAACATTGCANNKAAAGTTCTGTGGGCAATTGG | 5211 |
| LbCas12a_NNK_1190 | GTGCATATAACATTGCACGTNNKGTTCTGTGGGCAATTGGCCA | 5212 |
| LbCas12a_NNK_1191 | CATATAACATTGCACGTAAANNKCTGTGGGCAATTGGCCAGTT | 5213 |
| LbCas12a_NNK_1192 | ATAACATTGCACGTAAAGTTNNKTGGGCAATTGGCCAGTTTAA | 5214 |
| LbCas12a_NNK_1193 | ACATTGCACGTAAAGTTCTGNNKGCAATTGGCCAGTTTAAGAA | 5215 |
| LbCas12a_NNK_1194 | TTGCACGTAAAGTTCTGTGGNNKATTGGCCAGTTTAAGAAAGC | 5216 |
| LbCas12a_NNK_1195 | CACGTAAAGTTCTGTGGGCANNKGGCCAGTTTAAGAAAGCAGA | 5217 |
| LbCas12a_NNK_1196 | GTAAAGTTCTGTGGGCAATTNNKCAGTTTAAGAAAGCAGAAGA | 5218 |
| LbCas12a_NNK_1197 | AAGTTCTGTGGGCAATTGGCNNKTTTAAGAAAGCAGAAGATGA | 5219 |
| LbCas12a_NNK_1198 | TTCTGTGGGCAATTGGCCAGNNKAAGAAAGCAGAAGATGAGAA | 5220 |
| LbCas12a_NNK_1199 | TGTGGGCAATTGGCCAGTTTNNKAAAGCAGAAGATGAGAAGCT | 5221 |
| LbCas12a_NNK_1200 | GGGCAATTGGCCAGTTTAAGNNKGCAGAAGATGAGAAGCTGGA | 5222 |
| LbCas12a_NNK_1201 | CAATTGGCCAGTTTAAGAAANNKGAAGATGAGAAGCTGGACAA | 5223 |
| LbCas12a_NNK_1202 | TTGGCCAGTTTAAGAAAGCANNKGATGAGAAGCTGGACAAAGT | 5224 |
| LbCas12a_NNK_1203 | GCCAGTTTAAGAAAGCAGAANNKGAGAAGCTGGACAAAGTGAA | 5225 |
| LbCas12a_NNK_1204 | AGTTTAAGAAAGCAGAAGATNNKAAGCTGGACAAAGTGAAAAT | 5226 |
| LbCas12a_NNK_1205 | TTAAGAAAGCAGAAGATGAGNNKCTGGACAAAGTGAAAATTGC | 5227 |
| LbCas12a_NNK_1206 | AGAAAGCAGAAGATGAGAAGNNKGACAAAGTGAAAATTGCGAT | 5228 |
| LbCas12a_NNK_1207 | AAGCAGAAGATGAGAAGCTGNNKAAAGTGAAAATTGCGATCAG | 5229 |
| LbCas12a_NNK_1208 | CAGAAGATGAGAAGCTGGACNNKGTGAAAATTGCGATCAGCAA | 5230 |
| LbCas12a_NNK_1209 | AAGATGAGAAGCTGGACAAANNKAAAATTGCGATCAGCAATAA | 5231 |
| LbCas12a_NNK_1210 | ATGAGAAGCTGGACAAAGTGNNKATTGCGATCAGCAATAAAGA | 5232 |
| LbCas12a_NNK_1211 | AGAAGCTGGACAAAGTGAAANNKGCGATCAGCAATAAAGAGTG | 5233 |
| LbCas12a_NNK_1212 | AGCTGGACAAAGTGAAAATTNNKATCAGCAATAAAGAGTGGCT | 5234 |
| LbCas12a_NNK_1213 | TGGACAAAGTGAAAATTGCGNNKAGCAATAAAGAGTGGCTGGA | 5235 |
| LbCas12a_NNK_1214 | ACAAAGTGAAAATTGCGATCNNKAATAAAGAGTGGCTGGAATA | 5236 |

TABLE 3-continued

Primers for creating LbCas12a Saturation Mutagenesis Library

| Name | Sequence (5'→3') | SEQ ID NO |
|---|---|---|
| LbCas12a_NNK_1215 | AAGTGAAAATTGCGATCAGCNNKAAAGAGTGGCTGGAATACGC | 5237 |
| LbCas12a_NNK_1216 | TGAAAATTGCGATCAGCAATNNKGAGTGGCTGGAATACGCACA | 5238 |
| LbCas12a_NNK_1217 | AAATTGCGATCAGCAATAAANNKTGGCTGGAATACGCACAGAC | 5239 |
| LbCas12a_NNK_1218 | TTGCGATCAGCAATAAAGAGNNKCTGGAATACGCACAGACCAG | 5240 |
| LbCas12a_NNK_1219 | CGATCAGCAATAAAGAGTGGNNKGAATACGCACAGACCAGCGT | 5241 |
| LbCas12a_NNK_1220 | TCAGCAATAAAGAGTGGCTGNNKTACGCACAGACCAGCGTTAA | 5242 |
| LbCas12a_NNK_1221 | GCAATAAAGAGTGGCTGGAANNKGCACAGACCAGCGTTAAACA | 5243 |
| LbCas12a_NNK_1222 | ATAAAGAGTGGCTGGAATACNNKCAGACCAGCGTTAAACATGG | 5244 |
| LbCas12a_NNK_1223 | AAGAGTGGCTGGAATACGCANNKACCAGCGTTAAACATGGTCG | 5245 |
| LbCas12a_NNK_1224 | AGTGGCTGGAATACGCACAGNNKAGCGTTAAACATGGTCGTAG | 5246 |
| LbCas12a_NNK_1225 | GGCTGGAATACGCACAGACCNNKGTTAAACATGGTCGTAGCAG | 5247 |
| LbCas12a_NNK_1226 | TGGAATACGCACAGACCAGCNNKAAACATGGTCGTAGCAGTGA | 5248 |
| LbCas12a_NNK_1227 | AATACGCACAGACCAGCGTTNNKCATGGTCGTAGCAGTGATGA | 5249 |
| LbCas12a_NNK_1228 | ACGCACAGACCAGCGTTAAANNKGGTCGTAGCAGTGATGATGA | 5250 |

N is randomly A, C, G, or T in nucleotides 21 and 22 in the sequences.

To demonstrate the utility of the results, the phenotype of LbCas12a mutations at those positions with known outcome were evaluated first, including N527, E795, D156, G532, and K538, that correspond to the M537, F870, E174, S542, or K548 mutations in AsCas12a.

In previous studies, M537R and F870L were selected to create AsCas12a-Ultra to enhance cleavage activity. See U.S. Patent App. Publication No. US 2020/0109382 A1, which is incorporated by reference herein. As the secondary choice at each position, M537K and F870l were beneficial but to a lower degree (Table 4). However, only E795L was successfully transferred to LbCas12a, where N527R negatively affected the enzymatic activity. This discrepancy between AsCas12a and LbCas12a was accurately reflected throughout the screen.

TABLE 4

Mutations in *Acidaminococcus* sp. Cas12a (AsCas12a-Ultra)

| AsCas12a-Ultra | Position 1 | Position 2 |
|---|---|---|
| Optimal | M537R | F870L |
| Secondary | M537K | F870L |

Figure 3A:
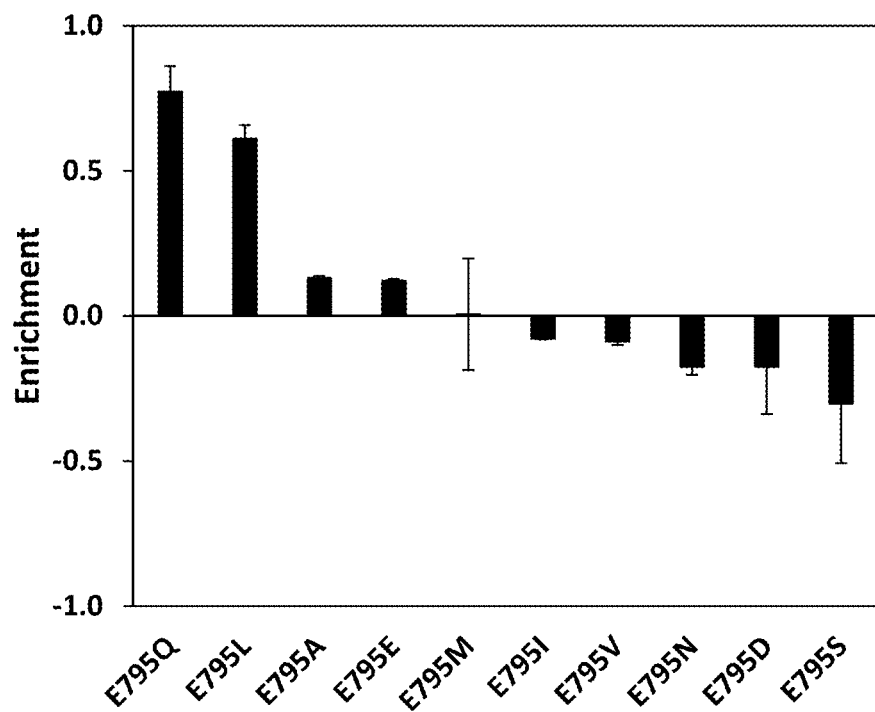
Figure 3B:
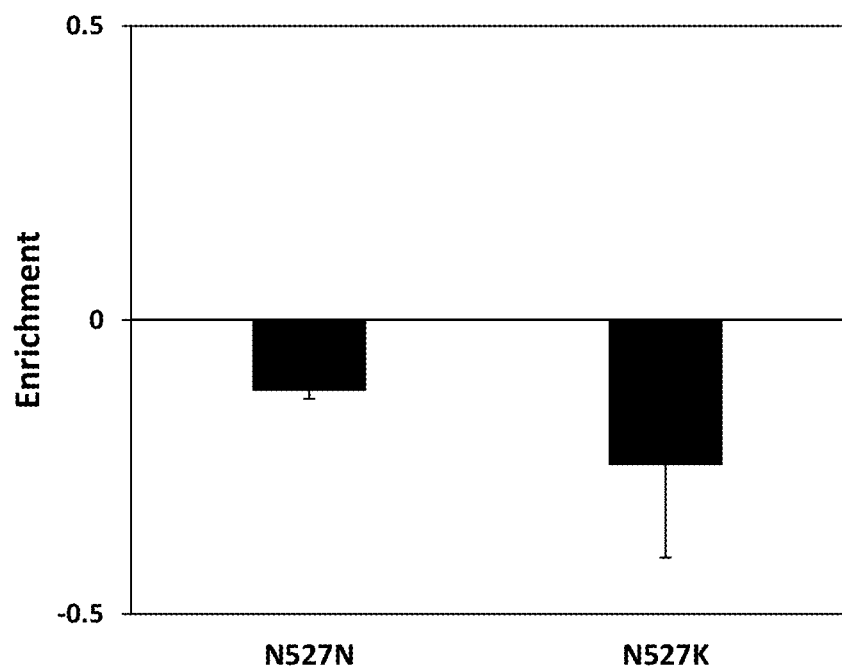
FIG. 3B shows exemplary phenotype scores of N527N and N527K. The other point mutations at this position dropped out of the screen, indicating any change at this position is detrimental.

Examination of the phenotype scores of mutations at E795 revealed a beneficial phenotype of E795L, but not E795I. Moreover, the E795Q outperformed others as the optimal choice of this position (FIG. 3A). In contrast, other than N527N and N527K, most mutations at position N527 dropped out of the screen. Further, compared to the synonymous change (N527N), N527K displayed strong negative phenotype (FIG. 3B). These data indicate mutations at position N527 of LbCas12a is generally detrimental, which is consonant with previous finding on the loss-of-activity of N527R mutant.

Figure 4A:
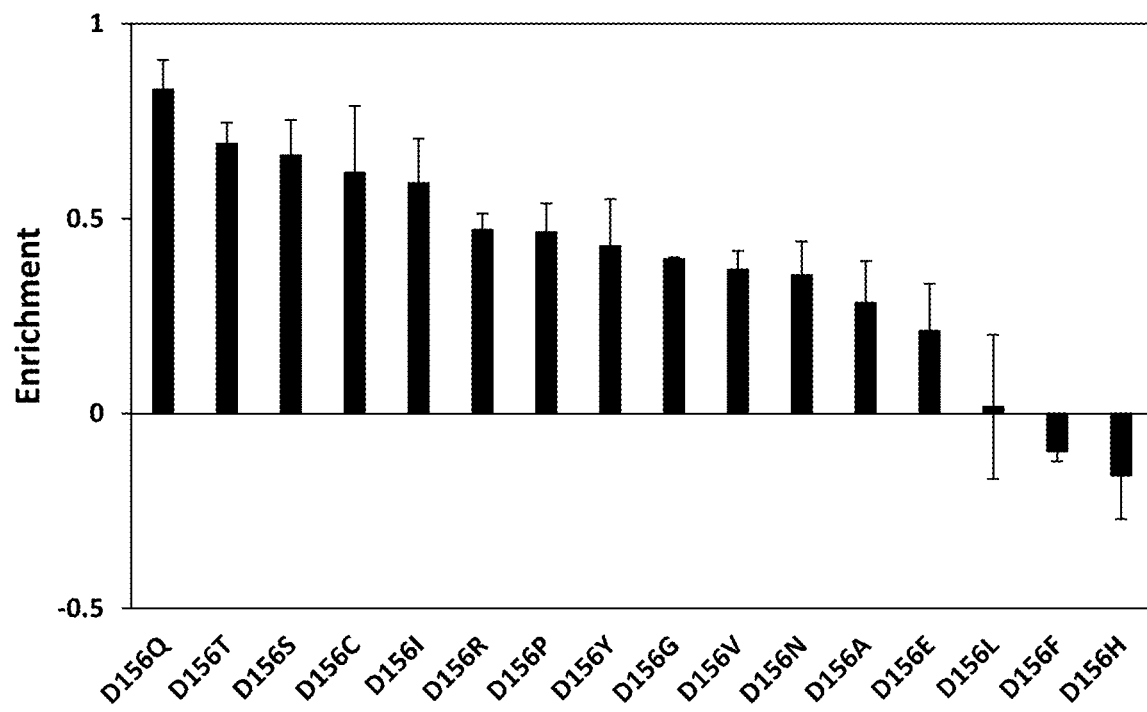
FIG. 4A shows exemplary phenotype scores of point mutations at position D156. A majority of the mutations are tolerated well at this position; leucine appears neutral; and phenylalanine or histidine are detrimental at this position.
Figure 4B:
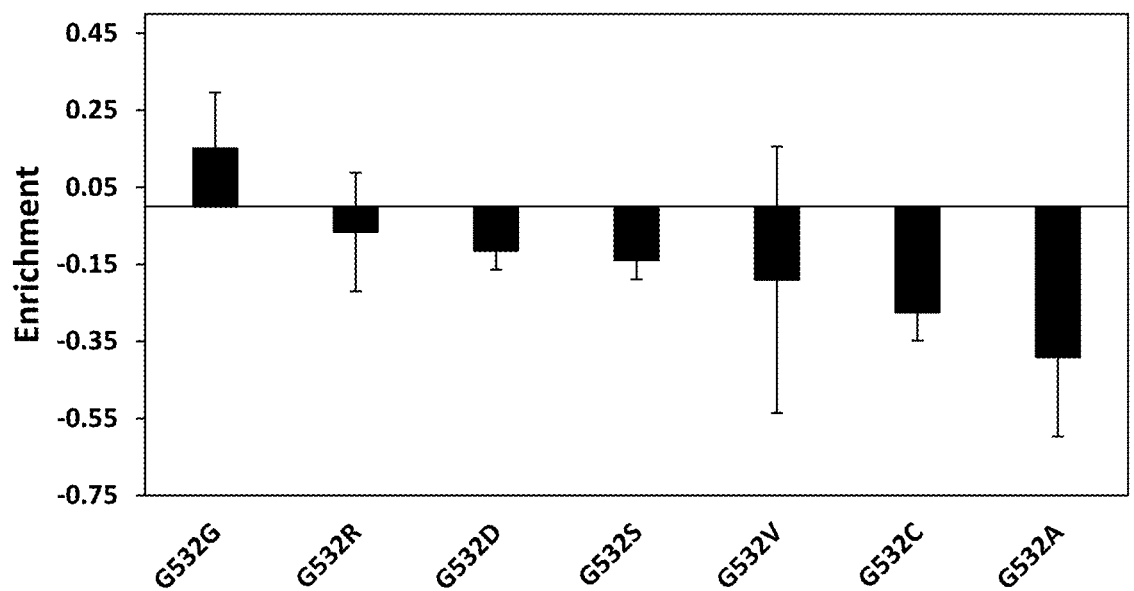
FIG. 4B shows exemplary phenotype scores of point mutations at position G532. Most of the mutations are detrimental at this position.
Figure 5A:
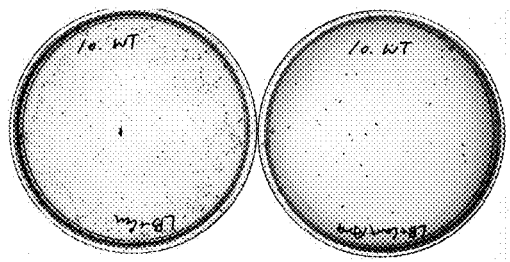
FIG. 5A-J show wild-type LbCas12a (FIG. 5A) and exemplary point mutations (FIG. 5B-J) of with enhanced DNA cleavage activity at TTTT PAM versus a negative control (no HPRT38346 gRNA.
Figure 5B:
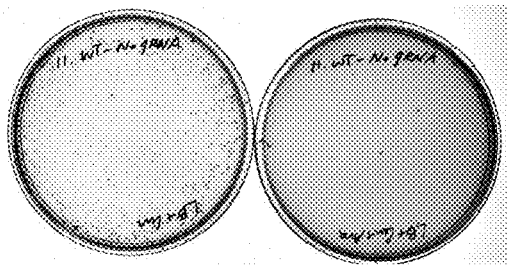
Figure 5C:
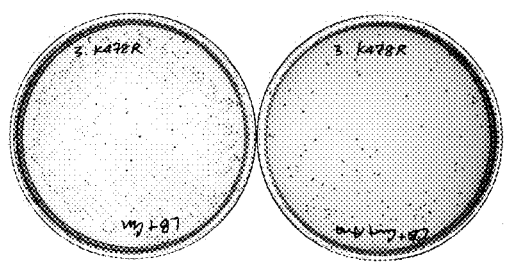
Figure 5D:
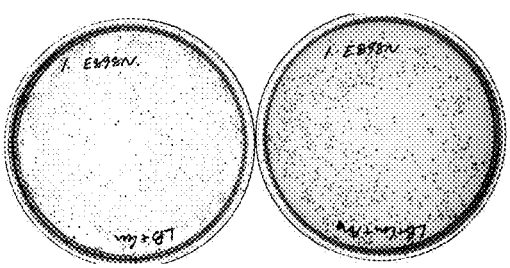
Figure 5E:
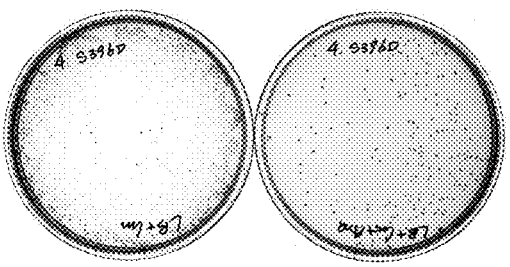
Figure 5F:
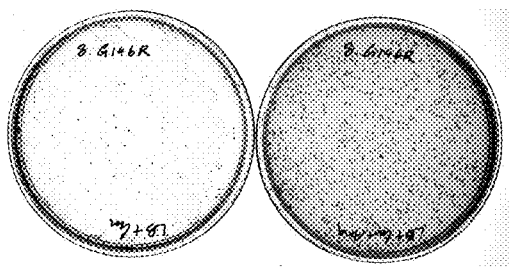
Figure 5G:
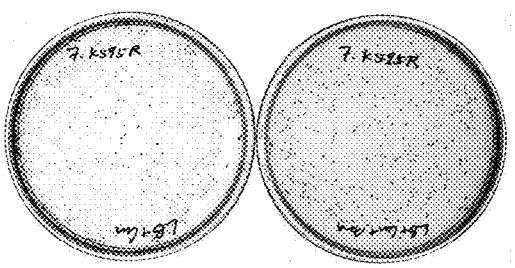
Figure 5H:
Figure 5I:
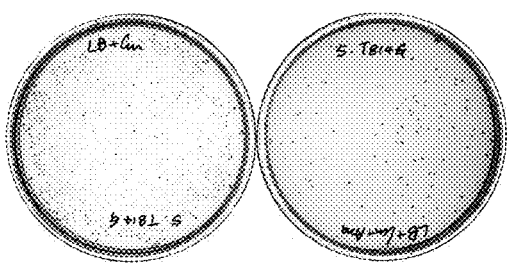
Figure 5J:
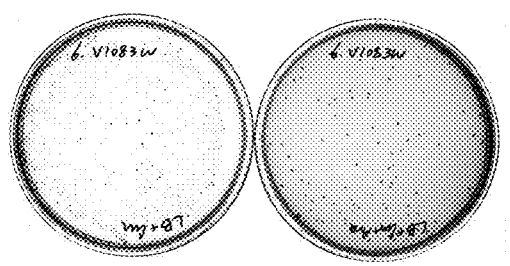

The effect of mutations at D156, G532, and K538 in LbCas12a (Table 5) were evaluated further, since the corresponding mutant (E174R/S542R/K548R) in AsCas12a has previously been shown to improve the activity. First, most mutations at D156, including the D156R, had phenotype scores greater than WT, indicating the analogous mutant discovered in AsCas12a (E174R) can be transferred to LbCas12a with similar outcome (FIG. 4A). The current screen further revealed the D156Q as an optimal mutant. Mutations at G532, including G532R, reduced the activity (FIG. 4B). Nearly all mutants at K538 dropped out of the screen, suggesting mutations at this position are not generally tolerated (data not shown).

TABLE 5

Mutations at D156, G532, and K538 in LbCas12a

| | Mutant 1 | Mutant 2 | Mutant 3 |
|---|---|---|---|
| EnAsCas12a | E184R | S542R | K548R |
| EnLbCas12a | D156R | G523R | K538R |

These results were consistent with previous studies showing D156R is a beneficial mutation for LbCas12a (FIG. 4A). See Schindele and Puchta, *Plant Biotechnol J.* 18(5): 1118-1120 (2010), which is incorporated by reference herein. Taken together, the high-throughput data accurately reproduced and identified mutations with known outcome. In addition, these experiments suggest that point mutations discovered in one Cas12a family member cannot be reliably transferred to others, as most of the activity-enhancing mutants identified in AsCas12a were detrimental in LbCas12a.

Guided by the high-throughput results, a set of LbCas12a variants with novel point mutations (G146R, S396D, K478R, K595R, E795Q, T814G, E898N and V1083W) were cloned and tested for their activity in the context of bacteria selection assay. As shown in FIG. 5C-J, these mutants improved the survival rate of bacteria over WT-LbCas12a upon selection, suggesting they can be added to the WT-LbCas12a, to enhance its intrinsic cleavage activity at TTTT-PAM.

TABLE 6

LbCas12a Single Mutants with Greatest Activity (top-10) and Single Mutants Selected for Further Evaluation

| Mutation | Average Score | Std. Dev. | SEQ ID NO: |
|---|---|---|---|
| K278D | 3.8 | 0.32 | 4 |
| E433P | 3.37 | 2.93 | 6 |
| V1209R | 3.05 | 2.28 | 8 |
| K878A | 3.02 | 2.73 | 10 |
| A920P | 2.92 | 0.37 | 12 |
| G715R | 2.92 | 3.25 | 14 |
| N732L | 2.75 | 2.81 | 16 |
| I922R | 2.75 | 0.12 | 18 |
| S431T | 2.69 | 2.93 | 20 |
| F745T | 2.46 | 3.01 | 22 |
| E898N | 2.03 | 0.02 | 48 |
| H909K | 1.86 | 0.18 | 70 |
| R182V | 1.7 | 0.11 | 98 |
| S396D | 1.67 | 0.19 | 108 |
| E858V | 1.65 | 0 | 114 |
| K478R | 1.57 | 0.05 | 134 |
| V1083W | 1.57 | 0.18 | 132 |
| G146R | 1.49 | 0.02 | 156 |
| T814G | 1.48 | 0.05 | 162 |
| K595R | 1.4 | 0.08 | 184 |
| I860R | 1.29 | 0.28 | 250 |
| E125K | 1.06 | 0.04 | 428 |
| S1020E | 0.98 | 0.12 | 532 |
| K1121D | 0.94 | 0.1 | 598 |
| Y606F | 0.92 | 0.07 | 642 |
| T152K | 0.9 | 0.03 | 694 |
| P799V | 0.89 | 0.02 | 706 |
| Y646H | 0.87 | 0.01 | 720 |
| F81E | 0.82 | 0.08 | 802 |
| L839F | 0.8 | 0.18 | 834 |
| E981V | 0.79 | 0.03 | 880 |
| E795Q | 0.77 | 0.09 | 930 |
| V491D | 0.77 | 0.1 | 954 |
| I841A | 0.76 | 0.03 | 988 |
| D665N | 0.74 | 0.09 | 1014 |

TABLE 6-continued

LbCas12a Single Mutants with Greatest Activity (top-10) and Single Mutants Selected for Further Evaluation

| Mutation | Average Score | Std. Dev. | SEQ ID NO: |
|---|---|---|---|
| N582R | 0.55 | 0.06 | 1730 |
| E913R | 0.49 | 0.03 | 1960 |
| N145R | 0.35 | 0.01 | 2902 |
| W890A | — | — | 3958 |

The ten mutants with top activity in Table 6 are not necessarily the best mutants for enhanced editing at TTTT-PAMs. This is because the phenotype is measured in *E. coli* cells. Other than enhancing DNA cleavage, some mutants were enriched because they reduced toxicity to the host cells or improved solubility or expression level of LbCas12a in *E. coli*. These variants are useful for genome editing of *E. coli* or other bacteria where the toxicity of CRISPR enzymes (Cas12a or Cas9) is a known issue. The WT enzymes are thought to be toxic which cause poor transformation efficiency and editing efficiency. Reducing the toxicity, activity, or expression level of CRISPR enzymes has been shown in the literature to improve editing efficiency. However, this type of toxicity is typically not an issue in mammalian cells. Therefore, to obtain mutants that work better in human cells, further validation of a selected set of mutants was tested in HEK293 cells.

Example 2

LbCas12a Mutants with Enhanced Activity

LbCas12a variants evaluated in this study are listed in Table 7. Site directed mutagenesis was performed to introduce specific point mutations on the expression vector using primers listed in Table 8. The phenotypes of specific single, double, triple, quadruple, quintuple, and sextuple mutations were evaluated in *E. coli* as the colony formation unit (CFU) of each mutant. Those mutants with enhanced CFU upon selection indicated an improved editing efficiency in *E. coli*, regardless of the underlying mechanism.

TABLE 7

LbCas12a variants. Variants with enhanced activity over WT-LbCas12a are indicated with "*".

| No. | Mutation | Nucleotide SEQ ID NO: | Polypeptide SEQ ID NO: |
|---|---|---|---|
| — | Wild-type LbCas12a | 1 | 2 |
| 1 | F81E* | 801 | 802 |
| 2 | E125K* | 427 | 428 |
| 3 | N145R* | 2901 | 2902 |
| 4 | G146R* | 155 | 156 |
| 5 | T152K* | 693 | 694 |
| 6 | R182V* | 97 | 98 |
| 7 | V491D* | 953 | 954 |
| 8 | K478R* | 133 | 134 |
| 9 | N582R* | 1729 | 1730 |
| 10 | Y606F | 641 | 642 |
| 11 | Y646H | 719 | 720 |
| 12 | D665N* | 1013 | 1014 |
| 13 | E795Q* | 929 | 930 |
| 14 | P799V* | 705 | 706 |
| 15 | L839F | 833 | 834 |
| 16 | I841A | 987 | 988 |
| 17 | E858V* | 113 | 114 |
| 18 | I860R* | 249 | 250 |
| 19 | W890A | 3957 | 3958 |
| 20 | E898N | 47 | 48 |
| 21 | H909K | 69 | 70 |
| 22 | E913R* | 1959 | 1960 |

TABLE 7-continued

LbCas12a variants. Variants with enhanced activity
over WT-LbCas12a are indicated with "*".

| No. | Mutation | Nucleotide SEQ ID NO: | Polypeptide SEQ ID NO: |
|---|---|---|---|
| 23 | E981V* | 879 | 880 |
| 24 | S1020E | 531 | 532 |
| 25 | K1121D | 597 | 598 |
| 26 | E88A/E795Q* | 3959 | 3960 |
| 27 | E125K/E795Q* | 3961 | 3962 |
| 28 | G146R/E795Q* | 3963 | 3964 |
| 29 | R182V/E795Q* | 3965 | 3966 |
| 30 | V491D/E795Q* | 3967 | 3968 |
| 31 | Q529I/E795Q* | 3969 | 3970 |
| 32 | Y646H/E795Q* | 3971 | 3972 |
| 33 | D665N/E795Q* | 3973 | 3974 |
| 34 | T814K/E795Q* | 3975 | 3976 |
| 35 | L839F/E795Q* | 3977 | 3978 |
| 36 | Q906F/E795Q* | 3979 | 3980 |
| 37 | E795Q/Q1170D* | 3981 | 3982 |
| 38 | G146R/R182V/E795Q* | 3983 | 3984 |
| 39 | G146R/E795Q/D665N* | 3985 | 3986 |
| 40 | G146R/E795Q/E981V* | 3987 | 3988 |
| 41 | G146R/E795Q/T814K* | 3989 | 3990 |
| 42 | G146R/R182V/D665N* | 3991 | 3992 |
| 43 | E125K/R182V/E981V* | 3993 | 3994 |
| 44 | R182V/P799V/E981V* | 3995 | 3996 |
| 45 | R182V/T814K/E981V* | 3997 | 3998 |
| 46 | G146R/P799V/E981V* | 3999 | 4000 |
| 47 | G146R/R182V/E795Q/F81E* | 4001 | 4002 |
| 48 | G146R/R182V/E795Q/E125K* | 4003 | 4004 |
| 49 | G146R/R182V/E795Q/E125A* | 4005 | 4006 |
| 50 | G146R/R182V/E795Q/P799V* | 4007 | 4008 |
| 51 | G146R/R182V/E795Q/T814K* | 4009 | 4010 |
| 52 | G146R/R182V/E795Q/E981V* | 4011 | 4012 |
| 53 | G146R/R182V/E795Q/D665N* | 4013 | 4014 |
| 54 | G146R/R182V/P799V/E981V* | 4015 | 4016 |
| 55 | E125K/G146R/R182V/E795Q/D665N* | 4017 | 4018 |
| 56 | G146R/R182V/E795Q/P799V/T814K* | 4019 | 4020 |
| 57 | E125K/G146R/R182V/E795Q/D665N/E981V | 4021 | 4022 |

TABLE 8

Primers used for site directed mutagenesis of LbCas12a.

| No | Primer | Sequence (5'→3') | SEQ ID NO |
|---|---|---|---|
| 1 | Lb_F81E_F | CCTGAACAACTATATCAGCCTGGAACGTAAAAAAACCCGCACC | 5251 |
| 2 | Lb_F81E_R | GGTGCGGGTTTTTTTACGTTCCAGGCTGATATAGTTGTTCAGG | 5252 |
| 3 | Lb_E88A_F | GTAAAAAAACCCGCACCGCGAAAGAAAACAAAGAGCTGGAAAA | 5253 |
| 4 | Lb_E88A_R | TTTTCCAGCTCTTTGTTTTCTTTCGCGGTGCGGGTTTTTTTAC | 5254 |
| 5 | Lb_E125K_F | CCTGTTCAAGAAAGACATCATCAAAACCATTCTGCCGGAATTTC | 5255 |
| 6 | Lb_E125K_R | GAAATTCCGGCAGAATGGTTTTGATGATGTCTTTCTTGAACAGG | 5256 |
| 7 | Lb_E125A_F | CCTGTTCAAGAAAGACATCATCGCGACCATTCTGCCGGAATTTC | 5257 |
| 8 | Lb_E125A_R | GAAATTCCGGCAGAATGGTCGCGATGATGTCTTTCTTGAACAGG | 5258 |
| 9 | Lb_N145R_F | GCCCTGGTGAATAGCTTTCGTGGCTTTACCACCGCATTTAC | 5259 |
| 10 | Lb_N145R_R | GTAAATGCGGTGGTAAAGCCACGAAAGCTATTCACCAGGGC | 5260 |
| 11 | Lb_G146R_F | CCCTGGTGAATAGCTTTAATCGTTTTACCACCGCATTTACCG | 5261 |
| 12 | Lb_G146R_R | CGGTAAATGCGGTGGTAAAACGATTAAAGCTATTCACCAGGG | 5262 |
| 13 | Lb_T152K_F | GGCTTTACCACCGCATTTAAAGGCTTTTTGATAATCGCGAA | 5263 |
| 14 | Lb_T152K_R | TTCGCGATTATCAAAAAAGCCTTTAAATGCGGTGGTAAAGCC | 5264 |

TABLE 8-continued

Primers used for site directed mutagenesis of LbCas12a.

| No | Primer | Sequence (5'→3') | SEQ ID NO |
|---|---|---|---|
| 15 | Lb_R182V_F | GCTGCATTAATGAAAATCTGACCGTGTACATTAGCAACATGGATATCTTTGA | 5265 |
| 16 | Lb_R182V_R | TCAAAGATATCCATGTTGCTAATGTACACGGTCAGATTTTCATTAATGCAGC | 5266 |
| 17 | Lb_V491D_F | TGAAAGTTTCTATGGCGATTTTGATCTGGCCTATGATATTCTGCTG | 5267 |
| 18 | Lb_V491D_R | CAGCAGAATATCATAGGCCAGATCAAAATCGCCATAGAAACTTTCA | 5268 |
| 19 | Lb_K478R_F | AAGCCTTTTTTGGTGAGGGCCGTGAAACCAATCGTGATGAAAG | 5269 |
| 20 | Lb_K478R_R | CTTTCATCACGATTGGTTTCACGGCCCTCACCAAAAAAGGCTT | 5270 |
| 21 | Lb_Q529I_F | AACTGTACTTTCAGAACCCGATTTTTATGGGTGGTTGGGATAAAG | 5271 |
| 22 | Lb_Q529I_R | CTTTATCCCAACCACCCATAAAAATCGGGTTCTGAAAGTACAGTT | 5272 |
| 23 | Lb_N582R_F | GTGAATGGCAACTATGAAAAAATCCGTTACAAACTGCTGCCTGGT | 5273 |
| 24 | Lb_N582R_R | ACCAGGCAGCAGTTTGTAACGGATTTTTTCATAGTTGCCATTCAC | 5274 |
| 25 | Lb_Y606F_F | GCAAGAAATGGATGGCCTATTTTAACCCGAGCGAGGATATT | 5275 |
| 26 | Lb_Y606F_R | AATATCCTCGCTCGGGTTAAAATAGGCCATCCATTTCTTGC | 5276 |
| 27 | Lb_Y646H_F | TTCAAAGATTCAATTTCGCGTCATCCGAAATGGTCCAATGC | 5277 |
| 28 | Lb_Y646H_R | GCATTGGACCATTTCGGATGACGCGAAATTGAATCTTTGAA | 5278 |
| 29 | Lb_D665N_F | CTTTAGCGAAACCGAAAATACAAAAACATTGCCGGTTTTTATCG | 5279 |
| 30 | Lb_D665N_R | CGATAAAAACCGGCAATGTTTTTGTATTTTTCGGTTTCGCTAAAG | 5280 |
| 31 | Lb_E795Q_F | GTTTTAGCGAGGATCAGTATCAGCTGCATATCCCGATTGCCAT | 5281 |
| 32 | Lb_E795Q_R | ATGGCAATCGGGATATGCAGCTGATACTGATCCTCGCTAAAAC | 5282 |
| 33 | Lb_P799V_F | AGGATCAGTATGAACTGCATATCGTGATTGCCATCAATAAATGCCC | 5283 |
| 34 | Lb_P799V_R | GGGCATTTATTGATGGCAATCACGATATGCAGTTCATACTGATCCT | 5284 |
| 35 | Lb_T814K_F | CCCGAAAAACATCTTTAAGATCAACAAAGAAGTTCGCGTGCTGC | 5285 |
| 36 | Lb_T814K_R | GCAGCACGCGAACTTCTTTGTTGATCTTAAAGATGTTTTTCGGG | 5286 |
| 37 | Lb_L839F_F | CGTGGTGAACGTAACCTGTTTTATATTGTTGTTGATGGTAAAGG | 5287 |
| 38 | Lb_L839F_R | CCTTTACCATCAACAACAACAATATAAAACAGGTTACGTTCACCACG | 5288 |
| 39 | Lb_I841A_F | GTGAACGTAACCTGCTGTATGCGGTTGTTGATGGTAAAGGC | 5289 |
| 40 | Lb_I841A_R | GCCTTTACCATCAACAACAACCGCATACAGCAGGTTACGTTCAC | 5290 |
| 41 | Lb_E858V_F | GTGGAACAGTATAGTCTGAACGTGATTATCAACAACTTTAACGGCAT | 5291 |
| 42 | Lb_E858V_R | ATGCCGTTAAAGTTGTTGATAATCACGTTCAGACTATACTGTTCCAC | 5292 |
| 43 | Lb_I860R_F | AGTATAGTCTGAACGAAATTCGTAACAACTTTAACGGCATCCG | 5293 |
| 44 | Lb_I860R_R | CGGATGCCGTTAAAGTTGTTACGAATTTCGTTCAGACTATACT | 5294 |
| 45 | Lb_W890A_F | GTTTTGAAGCACGTCAGAACGCGACCAGTATTGAAAACATCAAAGAAC | 5295 |
| 46 | Lb_W890A_R | GTTCTTTGATGTTTTCAATACTGGTCGCGTTCTGACGTGCTTCAAAAC | 5296 |
| 47 | Lb_E898N_F | CCAGTATTGAAAACATCAAAAACCTGAAAGCCGGTTATATTAG | 5297 |
| 48 | Lb_E898N_R | CTAATATAACCGGCTTTCAGGTTTTTGATGTTTTCAATACTGG | 5298 |
| 49 | Lb_Q906F_F | CTGAAAGCCGGTTATATTAGCTTTGTGGTTCATAAAATCTGTGAGCT | 5299 |
| 50 | Lb_Q906F_R | AGCTCACAGATTTTATGAACCACAAAGCTAATATAACCGGCTTTCAG | 5300 |
| 51 | Lb_H909K_F | GTTATATTAGCCAGGTGGTTAAAAAAAATCTGTGAGCTGGTAGA | 5301 |

TABLE 8-continued

Primers used for site directed mutagenesis of LbCas12a.

| No | Primer | Sequence (5'→3') | SEQ ID NO |
|---|---|---|---|
| 52 | Lb_H909K_R | TCTACCAGCTCACAGATTTTTTTAACCACCTGGCTAATATAAC | 5302 |
| 53 | Lb_E913R_F | CCAGGTGGTTCATAAAATCTGTCGTCTGGTAGAAAAATACGATGCAGT | 5303 |
| 54 | Lb_E913R_R | ACTGCATCGTATTTTTCTACCAGACGACAGATTTTATGAACCACCTGG | 5304 |
| 55 | Lb_E981V_F | AAAGGTTATCAGATTACCAACAAATTTGTGAGCTTTAAAAGCATGAGCAC | 5305 |
| 56 | Lb_E981V_R | GTGCTCATGCTTTTAAAGCTCACAAATTTGTTGGTAATCTGATAACCTTT | 5306 |
| 57 | Lb_S1020E_F | AACCTGCTGAAAACAAAATATACCGAAATTGCCGACAGCAAGAAG | 5307 |
| 58 | Lb_S1020E_R | CTTCTTGCTGTCGGCAATTTCGGTATATTTTGTTTTCAGCAGGTT | 5308 |
| 59 | Lb_K1121D_F | CTGTGTGAACAGAGCGATGATGCGTTTTATAGCAGTTTTATGGC | 5309 |
| 60 | Lb_K1121D_R | GCCATAAAACTGCTATAAAACGCATCATCGCTCTGTTCACACAG | 5310 |
| 61 | Lb_Q1170D_F | AGCCGCAATTACGAAGCAGATGAAAATGCAATTCTGCCGAAA | 5311 |
| 62 | Lb_Q1170D_R | TTTCGGCAGAATTGCATTTTCATCTGCTTCGTAATTGCGGCT | 5312 |
| 63 | Lb_E795Q/P799V_F | CGTTTTAGCGAGGATCAGTATCAGCTGCATATCGTGATTGCCATCAATAAATGCCCG | 5313 |
| 64 | Lb_E795Q/P799V_R | CGGGCATTTATTGATGGCAATCACGATATGCAGCTGATACTGATCCTCGCTAAAACG | 5314 |

The LbCas12a mutants were transformed into E. coli BL21(DE3) cells, a colony with the appropriate strain was used to inoculate TB media with kanamycin (0.05 mg/mL) and grown at 37° C. until an OD of approximately 0.9 was reached, then the flask was cooled to 18° C. for 30 minutes. The addition of 500 µL of 1 M IPTG was used to induce protein expression, followed by growth at 18° C. for 19 hours. Cells were harvested and the cell pellet was re-suspended and lysed on an Avestin Emulsiflex C3 pre-chilled to 4° C. at 15-20 kpsi with three passes. The lysate was centrifuged at 16,000×g for 20 minutes at 4° C. to remove cell debris.

The cleared lysate was put over a HisTrap™ HP column (Cytiva). The procedure consisted of equilibrating the resin with His. Bind® buffer (20 mM NaPO4 pH 6.8, 0.5 M NaCl, 10 mM imidazole, 5% glycerol), followed by sample loading. The sample was washed with His-Bind buffer, followed by an additional standard wash and a 10% "B" wash consisting of 10% His-Elution buffer (10 mM NaPO4 pH 6.8, 250 mM NaCl, 150 mM imidazole, 5% glycerol). Finally, the sample was eluted using His-Elution buffer.

The partially purified Cas13a variants were then put over a HiTrap® Heparin HP column. The procedure consisted of equilibrating the resin with the Heparin-Bind buffer (20 mM NaPO4 pH 6.8, 250 mM NaCl, 10% glycerol), followed by sample loading. The sample was then washed with Heparin-Bind buffer, followed by a 5% "B" wash consisting of 5% Heparin Elution buffer (10 mM NaPO4 pH 6.8, 1 M NaCl, 10% glycerol). Finally, the purified protein was eluted using Heparin Elution buffer (10 mM NaPO4, pH 6.8, 1 M NaCl, 10% glycerol). Finally, the purified protein was eluted using Heparin.

The purified LbCas12a mutants were concentrated to approximately 10 mg/mL and stored at −20° C. in storage buffer containing 25 mM Tris-HCl pH 7.4, 0.3 M NaCl, 1 mM EDTA, 1 mM DTT, and 50% glycerol.

Example 3

Editing Efficiency of LbCas12a Variants in Human Cells

To evaluate the genome editing efficiency of each variant, LbCas12a-RNPs (1 µM) were assembled using 4 crRNAs targeting human HPRT gene (Table 9). The assembled RNPs (50 nM) were delivered into HEK293 cells by Lonza nucleofection (SF buffer, CM-130), and the editing efficiency was measured by T7 endonuclease I assay 48-hours post-delivery (Table 10; FIG. 6A).

TABLE 9 crRNAs and primer sequences used in the T7EI assay.

| Name | Sequence (5'→3') | Purpose | SEQ ID NO |
|---|---|---|---|
| crRNA-1* | UAAUUUCUACUAAGUGUAGAUAACACACCCAAGGAAAGACUAUG | HPRT 38116-AS-23 crRNA | 5315 |
| crRNA-2* | UAAUUUCUACUAAGUGUAGAUAUAGUCUUUCCUUGGGUGUGUUA | HPRT 38094-S-23 crRNA | 5316 |
| crRNA-3* | UAAUUUCUACUAAGUGUAGAUAUCCGUGCUGAGUGUACCAUGCA | HPRT 38146-AS-23 crRNA | 5317 |

TABLE 9-continued crRNAs and primer sequences used in the T7EI assay.

| Name | Sequence (5'→3') | Purpose | SEQ ID NO |
|---|---|---|---|
| crRNA-4* | UAAUUUCUACUAAGUGUAGAUUUGUAGGAUAUG CCCUUGACUAU | HPRT 38486-S-23 crRNA | 5318 |
| HPRT7 FWD | AAGAATGTTGTGATAAAAGGTGATGCT | Primer for T7EI | 5319 |
| HPRT7 RWD | ACACATCCATGGGACTTCTGCCTC | Primer for T7EI | 5320 |

*Ribonucleotides

Figure 6B:
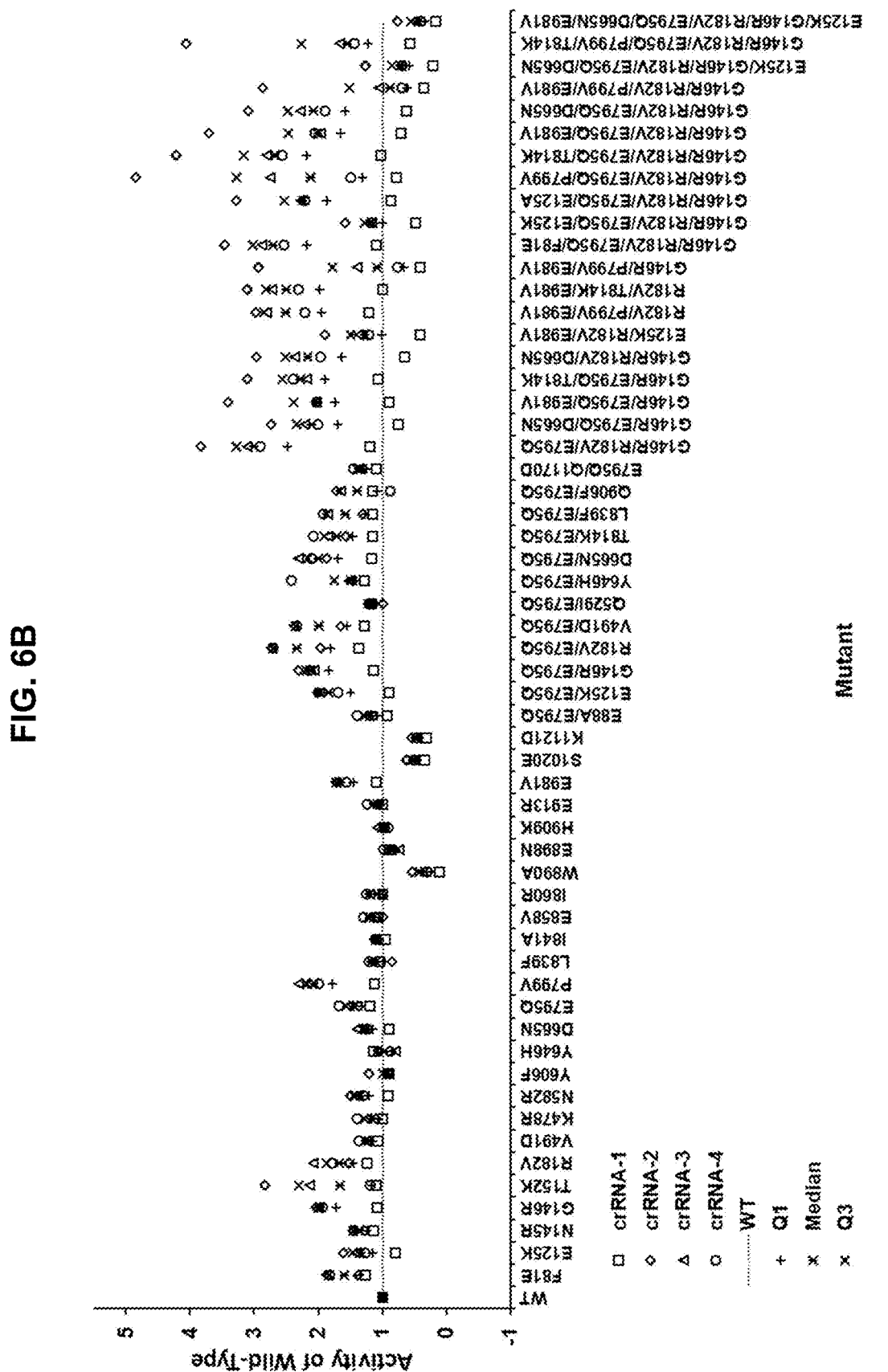

To facilitate comparison, the efficiency of variant at each target was normalized to WT LbCas12a and presented as fold-improvement over WT in Table 11 and FIG. 6B. Overall, 49 of the 57 purified variants containing single or multiple point mutations improved activity over WT at one or multiple sites (Tables 10-11). Triple mutant number 38 (SEQ ID NO: 3984), G146R/R182V/E795Q ("RVQ") had the best performance, with ~3-fold improvement over WT in this assay. Stacking other beneficial mutations on RVQ gradually reduced the activity (see mutants Nos. 47-57, Tables 10-11; FIG. 6A-B). Accordingly, the triple mutant RVQ (No. 38, SEQ ID NO: 3984) appears to be an optimal LbCas12a variant for genome editing.

TABLE 10

LbCas12a Mutant Activity in T7 Endonuclease I Assay with Four crRNAs

| No | Mutant | crRNA-1* | Std Dev | crRNA-2* | Std Dev | crRNA-3* | Std Dev | crRNA-4* | Std Dev |
|---|---|---|---|---|---|---|---|---|---|
| 0 | Wild-Type (WT) | 54.13 | 9.04 | 7.70 | 0.46 | 12.40 | 1.08 | 15.77 | 0.46 |
| 1 | F81E | 60.27 | 0.23 | 9.97 | 0.40 | 22.07 | 1.01 | 26.90 | 1.18 |
| 2 | E125K | 41.03 | 1.26 | 12.47 | 0.70 | 17.60 | 0.70 | 20.23 | 0.61 |
| 3 | N145R | 54.63 | 1.69 | 9.60 | 0.99 | 17.77 | 0.40 | 23.97 | 1.34 |
| 4 | G146R | 56.13 | 0.97 | 16.23 | 1.17 | 25.53 | 0.87 | 32.20 | 0.30 |
| 5 | T152K | 52.77 | 1.63 | 20.93 | 1.01 | 25.33 | 1.50 | 18.60 | 1.06 |
| 6 | R182V | 59.20 | 1.91 | 10.37 | 0.49 | 24.10 | 0.82 | 29.13 | 1.24 |
| 7 | V491D | 52.17 | 1.65 | 8.67 | 1.00 | 17.17 | 0.55 | 21.67 | 0.93 |
| 8 | K478R | 48.50 | 1.83 | 8.83 | 0.75 | 13.67 | 1.36 | 18.55 | 0.49 |
| 9 | N582R | 46.73 | 3.06 | 11.27 | 0.59 | 17.47 | 0.55 | 20.97 | 1.45 |
| 10 | Y606F | 45.43 | 2.04 | 9.33 | 0.95 | 12.97 | 1.36 | 14.87 | 1.86 |
| 11 | Y646H | 55.50 | 2.45 | 7.30 | 0.40 | 9.13 | 0.81 | 13.00 | 1.28 |
| 12 | D665N | 44.37 | 1.33 | 9.17 | 0.38 | 17.10 | 0.66 | 17.93 | 1.80 |
| 13 | E795Q | 59.03 | 1.77 | 9.77 | 1.25 | 18.00 | 0.61 | 26.80 | 1.06 |
| 14 | P799V | 55.27 | 1.07 | 16.70 | 1.25 | 28.47 | 0.45 | 30.70 | 1.57 |
| 15 | L839F | 49.63 | 1.39 | 6.57 | 1.02 | 13.77 | 0.96 | 19.20 | 0.62 |
| 16 | I841A | 46.10 | 1.01 | 8.03 | 1.10 | 12.43 | 1.15 | 16.73 | 0.21 |
| 17 | E858V | 52.13 | 1.31 | 7.30 | 0.82 | 13.63 | 1.04 | 19.63 | 1.16 |
| 18 | I860R | 48.67 | 2.43 | 7.27 | 1.23 | 13.20 | 1.11 | 18.90 | 0.75 |
| 19 | W890A | 4.63 | 2.64 | 3.80 | 0.00 | 4.03 | 0.42 | 4.27 | 0.64 |
| 20 | E898N | 43.27 | 0.45 | 6.00 | 1.31 | 8.33 | 0.40 | 15.10 | 1.11 |
| 21 | H909K | 47.77 | 1.17 | 7.47 | 0.67 | 13.37 | 0.51 | 15.40 | 0.26 |
| 22 | E913R | 52.50 | 1.14 | 8.80 | 0.26 | 14.67 | 0.61 | 20.90 | 0.87 |
| 23 | E981V | 58.03 | 0.71 | 13.80 | 0.10 | 21.77 | 0.55 | 26.37 | 0.99 |
| 24 | S1020E | 17.37 | 0.78 | 4.27 | 0.12 | 5.23 | 0.51 | 7.60 | 0.35 |
| 25 | K1121D | 15.37 | 0.55 | 3.65 | 0.64 | 5.20 | 0.17 | 6.87 | 1.07 |
| 26 | E88A/E795Q | 50.77 | 0.67 | 8.53 | 0.75 | 16.07 | 0.90 | 24.13 | 0.76 |
| 27 | E125K/E795Q | 50.37 | 0.38 | 16.73 | 1.47 | 24.03 | 0.31 | 30.80 | 1.18 |
| 28 | G146R/E795Q | 59.73 | 1.38 | 19.50 | 0.20 | 27.53 | 0.67 | 37.63 | 1.23 |
| 29 | R182V/E795Q | 66.67 | 0.21 | 15.83 | 1.61 | 34.87 | 0.42 | 42.77 | 0.15 |
| 30 | V491D/E795Q | 63.93 | 0.40 | 12.87 | 0.45 | 30.33 | 0.31 | 37.73 | 0.31 |
| 31 | Q529I/E795Q | 58.40 | 0.26 | 8.03 | 1.44 | 16.43 | 0.40 | 18.70 | 7.88 |
| 32 | Y646H/E795Q | 64.83 | 0.83 | 11.70 | 1.08 | 20.20 | 1.82 | 32.23 | 0.58 |
| 33 | D665N/E795Q | 62.70 | 3.29 | 15.17 | 0.98 | 32.10 | 4.81 | 37.67 | 1.55 |
| 34 | T814K/E795Q | 59.07 | 0.67 | 13.40 | 0.26 | 25.17 | 2.86 | 36.97 | 0.61 |
| 35 | L839F/E795Q | 61.00 | 0.28 | 10.93 | 0.15 | 24.63 | 1.42 | 33.93 | 0.65 |
| 36 | Q906F/E795Q | 60.97 | 0.60 | 14.27 | 0.49 | 23.07 | 1.27 | 16.00 | 1.87 |
| 37 | E795Q/Q1170D | 56.33 | 0.85 | 10.20 | 1.65 | 17.80 | 1.22 | 22.77 | 6.77 |
| 38 | G146R/R182V/E795Q | 63.10 | 1.10 | 32.80 | 0.95 | 42.03 | 1.81 | 51.53 | 0.21 |
| 39 | G146R/E795Q/D665N | 41.73 | 0.38 | 22.97 | 1.05 | 30.27 | 0.23 | 35.73 | 1.45 |
| 40 | G146R/E795Q/E981V | 50.70 | 5.98 | 29.33 | 1.81 | 26.63 | 1.01 | 36.00 | 0.95 |
| 41 | G146R/E795Q/T814K | 56.57 | 0.67 | 26.50 | 0.70 | 27.63 | 6.03 | 42.40 | 0.95 |
| 42 | G146R/R182V/D665N | 36.67 | 0.91 | 25.30 | 1.83 | 33.20 | 1.35 | 36.57 | 0.31 |

TABLE 10-continued

LbCas12a Mutant Activity in T7 Endonuclease I Assay with Four crRNAs

| No | Mutant | crRNA-1* | Std Dev | crRNA-2* | Std Dev | crRNA-3* | Std Dev | crRNA-4* | Std Dev |
|---|---|---|---|---|---|---|---|---|---|
| 43 | E125K/R182V/E981V | 22.43 | 1.62 | 15.93 | 0.81 | 19.33 | 0.91 | 21.50 | 0.61 |
| 44 | R182V/P799V/E981V | 63.57 | 0.25 | 25.67 | 0.64 | 39.40 | 1.80 | 37.60 | 9.09 |
| 45 | R182V/T814K/E981V | 52.93 | 0.55 | 27.93 | 0.58 | 36.97 | 0.81 | 40.50 | 1.13 |
| 46 | G146R/P799V/E981V | 23.27 | 5.63 | 27.33 | 0.76 | 20.43 | 0.80 | 13.60 | 0.70 |
| 47 | G146R/R182V/E795Q/F81E | 60.07 | 0.64 | 30.73 | 0.47 | 39.00 | 0.53 | 45.23 | 1.86 |
| 48 | G146R/R182V/E795Q/E125K | 27.90 | 0.79 | 14.03 | 1.00 | 16.33 | 0.23 | 21.97 | 0.78 |
| 49 | G146R/R182V/E795Q/E125A | 49.30 | 1.20 | 29.93 | 1.06 | 32.00 | 0.56 | 38.17 | 1.63 |
| 50 | G146R/R182V/E795Q/P799V | 44.93 | 0.61 | 44.50 | 0.36 | 38.83 | 0.59 | 27.87 | 0.59 |
| 51 | G146R/R182V/E795Q/T814K | 58.07 | 0.59 | 38.43 | 0.38 | 38.93 | 0.87 | 46.50 | 1.31 |
| 52 | G146R/R182V/E795Q/E981V | 41.60 | 2.07 | 33.23 | 0.57 | 27.13 | 0.25 | 37.63 | 0.90 |
| 53 | G146R/R182V/E795Q/D665N | 36.60 | 0.36 | 27.33 | 1.12 | 31.50 | 0.61 | 33.73 | 0.55 |
| 54 | G146R/R182V/P799V/E981V | 19.57 | 0.93 | 25.83 | 0.91 | 14.70 | 0.10 | 10.80 | 0.53 |
| 55 | E125K/G146R/R182V/E795Q/D665N | 10.50 | 1.04 | 11.13 | 0.55 | 8.67 | 0.76 | 10.67 | 1.22 |
| 56 | G146R/R182V/E795Q/P799V/T814K | 32.60 | 1.91 | 37.37 | 1.55 | 24.23 | 0.42 | 19.07 | 0.90 |
| 57 | E125K/G146R/R182V/E795Q/D665N/E981V | 7.50 | 2.51 | 5.87 | 2.32 | 6.00 | 0.46 | 5.97 | 0.92 |

*Activity is the mean of three replicates.

TABLE 11

LbCas12a Mutant Editing Activity Relative to Wild-Type with Four crRNAs

| No. | Mutant | crRNA-1 | crRNA-2 | crRNA-3 | crRNA-4 |
|---|---|---|---|---|---|
| 0 | Wild-Type (WT) | 1 | 1 | 1 | 1 |
| 1 | F81E | 1.27 | 1.38 | 1.88 | 1.82 |
| 2 | E125K | 0.8 | 1.61 | 1.41 | 1.26 |
| 3 | N145R | 1.13 | 1.28 | 1.46 | 1.45 |
| 4 | G146R | 1.08 | 2.03 | 1.99 | 1.93 |
| 5 | T152K | 1.09 | 2.83 | 2.13 | 1.2 |
| 6 | R182V | 1.24 | 1.52 | 2.08 | 1.8 |
| 7 | V491D | 1.06 | 1.19 | 1.25 | 1.36 |
| 8 | K478R | 0.99 | 1.09 | 1.24 | 1.4 |
| 9 | N582R | 0.91 | 1.5 | 1.41 | 1.3 |
| 10 | Y606F | 0.9 | 1.21 | 0.93 | 0.93 |
| 11 | Y646H | 1.14 | 1.06 | 0.79 | 0.88 |
| 12 | D665N | 0.9 | 1.27 | 1.4 | 1.24 |
| 13 | E795Q | 1.19 | 1.37 | 1.52 | 1.68 |
| 14 | P799V | 1.12 | 2.13 | 2.3 | 1.99 |
| 15 | L839F | 1.03 | 0.85 | 1.17 | 1.21 |
| 16 | I841A | 0.95 | 1.07 | 1.12 | 1.11 |
| 17 | E858V | 1.06 | 1 | 1.2 | 1.29 |
| 18 | I860R | 0.99 | 1 | 1.19 | 1.25 |
| 19 | W890A | 0.11 | 0.54 | 0.38 | 0.29 |
| 20 | E898N | 0.9 | 0.81 | 0.74 | 0.98 |
| 21 | H909K | 0.96 | 0.98 | 1.08 | 0.91 |
| 22 | E913R | 1 | 1.03 | 1.12 | 1.23 |
| 23 | E981V | 1.1 | 1.72 | 1.72 | 1.57 |
| 24 | S1020E | 0.34 | 0.62 | 0.49 | 0.51 |
| 25 | K1121D | 0.31 | 0.54 | 0.46 | 0.46 |
| 26 | E88A/E795Q | 0.92 | 1.14 | 1.25 | 1.39 |
| 27 | E125K/E795Q | 0.9 | 2.01 | 1.98 | 1.7 |
| 28 | G146R/E795Q | 1.14 | 2.31 | 2.07 | 2.14 |
| 29 | R182V/E795Q | 1.37 | 1.96 | 2.73 | 2.7 |
| 30 | V491D/E795Q | 1.28 | 1.65 | 2.38 | 2.34 |

TABLE 11-continued

LbCas12a Mutant Editing Activity Relative to Wild-Type with Four crRNAs

| No. | Mutant | crRNA-1 | crRNA-2 | crRNA-3 | crRNA-4 |
|---|---|---|---|---|---|
| 31 | Q529I/E795Q | 1.16 | 0.99 | 1.22 | 1.21 |
| 32 | Y646H/E795Q | 1.28 | 1.46 | 1.52 | 2.42 |
| 33 | D665N/E795Q | 1.16 | 1.87 | 2.3 | 2.11 |
| 34 | T814K/E795Q | 1.15 | 1.57 | 1.85 | 2.08 |
| 35 | L839F/E795Q | 1.15 | 1.31 | 1.85 | 1.92 |
| 36 | Q906F/E795Q | 1.15 | 1.72 | 1.65 | 0.88 |
| 37 | E795Q/Q1170D | 1.09 | 1.3 | 1.37 | 1.45 |
| 38 | G146R/R182V/E795Q | 1.19 | 3.83 | 3.1 | 2.91 |
| 39 | G146R/E795Q/D665N | 0.75 | 2.73 | 2.21 | 2.01 |
| 40 | G146R/E795Q/E981V | 0.9 | 3.41 | 2.03 | 2.02 |
| 41 | G146R/E795Q/T814K | 1.06 | 3.11 | 2.18 | 2.39 |
| 42 | G146R/R182V/D665N | 0.65 | 2.97 | 2.36 | 1.97 |
| 43 | E125K/R182V/E981V | 0.41 | 1.89 | 1.36 | 1.21 |
| 44 | R182V/P799V/E981V | 1.21 | 2.98 | 2.81 | 2.2 |
| 45 | R182V/T814K/E981V | 0.99 | 3.1 | 2.72 | 2.3 |
| 46 | G146R/P799V/E981V | 0.41 | 2.94 | 1.4 | 0.76 |
| 47 | G146R/R182V/E795Q/F81E | 1.1 | 3.46 | 2.88 | 2.53 |
| 48 | G146R/R182V/E795Q/E125K | 0.48 | 1.58 | 1.17 | 1.16 |
| 49 | G146R/R182V/E795Q/E125A | 0.86 | 3.28 | 2.28 | 2.2 |
| 50 | G146R/R182V/E795Q/P799V | 0.78 | 4.85 | 2.75 | 1.49 |
| 51 | G146R/R182V/E795Q/T814K | 1.02 | 4.22 | 2.81 | 2.56 |
| 52 | G146R/R182V/E795Q/E981V | 0.71 | 3.71 | 1.96 | 2.05 |
| 53 | G146R/R182V/E795Q/D665N | 0.62 | 3.09 | 2.28 | 1.89 |
| 54 | G146R/R182V/P799V/E981V | 0.35 | 2.86 | 1.05 | 0.7 |
| 55 | E125K/G146R/R182V/E795Q/D665N | 0.21 | 1.27 | 0.71 | 0.7 |
| 56 | G146R/R182V/E795Q/P799V/T814K | 0.56 | 4.06 | 1.67 | 1.44 |
| 57 | E125K/G146R/R182V/E795Q/D665N/E981V | 0.16 | 0.76 | 0.49 | 0.39 |

SEQUENCE LISTING

The patent contains a lengthy sequence listing. A copy of the sequence listing is available in electronic form from the USPTO web site (https://seqdata.uspto.gov/?pageRequest=docDetail&DocID=US11999979B2). An electronic copy of the sequence listing will also be available from the USPTO upon request and payment of the fee set forth in 37 CFR 1.19(b)(3).

What is claimed:

1. An isolated mutant *Lachnospiraceae bacterium* ND2006 Cas12a ("LbCas12a") polypeptide comprising the G146R/R182V/E795Q polypeptide sequence of SEQ ID NO: 39844.

2. An isolated polynucleotide sequence encoding the mutant LbCas12a polypeptide of claim 1, wherein the polynucleotide sequence comprises the sequence of SEQ ID NO: 3983.

* * * * *

UNITED STATES PATENT AND TRADEMARK OFFICE
CERTIFICATE OF CORRECTION

| | | |
|---|---|---|
| PATENT NO. | : 11,999,979 B2 | Page 1 of 1 |
| APPLICATION NO. | : 17/245401 | |
| DATED | : June 4, 2024 | |
| INVENTOR(S) | : Liyang Zhang and Christopher Anthony Vakulskas | |

It is certified that error appears in the above-identified patent and that said Letters Patent is hereby corrected as shown below:

In the Claims

In Column 187, Claim 1, Line 3, delete "SEQ ID NO: 39844" and insert -- SEQ ID NO: 3984 --

Signed and Sealed this
Fifteenth Day of April, 2025

Coke Morgan Stewart
*Acting Director of the United States Patent and Trademark Office*